United States Patent
Szyperski et al.

(10) Patent No.: US 8,248,071 B2
(45) Date of Patent: Aug. 21, 2012

(54) METHODS OF USING COMBINED FORWARD AND BACKWARD SAMPLING OF NUCLEAR MAGNETIC RESONANCE TIME DOMAIN FOR MEASUREMENT OF SECONDARY PHASE SHIFTS, DETECTION OF ABSORPTION MODE SIGNALS DEVOID OF DISPERSIVE COMPONENTS, AND/OR OPTIMIZATION OF NUCLEAR MAGNETIC RESONANCE EXPERIMENTS

(75) Inventors: Thomas Szyperski, Amherst, NY (US); Arindam Ghosh, North Tonawanda, NY (US); Yibing Wu, Snyder, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 531 days.

(21) Appl. No.: 12/370,303

(22) Filed: Feb. 12, 2009

(65) Prior Publication Data
US 2009/0230959 A1  Sep. 17, 2009

Related U.S. Application Data

(60) Provisional application No. 61/028,070, filed on Feb. 12, 2008, provisional application No. 61/092,901, filed on Aug. 29, 2008.

(51) Int. Cl.
G01V 3/00 (2006.01)
(52) U.S. Cl. ........................ 324/309; 324/307
(58) Field of Classification Search .......... 324/300–322; 382/128–131; 600/407–435; 356/451, 496
See application file for complete search history.

(56) References Cited

U.S. PATENT DOCUMENTS

| | | | | |
|---|---|---|---|---|
| 5,105,152 A * | 4/1992 | Pauly | ............................. | 324/309 |
| 5,204,625 A * | 4/1993 | Cline et al. | .................... | 324/306 |
| 5,233,298 A * | 8/1993 | Dumoulin | ..................... | 324/306 |
| 5,270,653 A * | 12/1993 | Pauly | ............................. | 324/309 |
| 5,650,723 A * | 7/1997 | Meyer | ............................ | 324/309 |
| 6,011,625 A * | 1/2000 | Glass | ............................. | 356/496 |
| 6,020,739 A * | 2/2000 | Meyer et al. | .................. | 324/309 |
| 6,133,736 A | 10/2000 | Pervushin et al. | | |
| 6,873,153 B2 * | 3/2005 | Frydman | ........................ | 324/307 |
| 7,206,073 B2 * | 4/2007 | Hajian et al. | .................. | 356/451 |
| 7,271,588 B2 * | 9/2007 | Frydman | ........................ | 324/318 |
| 7,408,345 B2 * | 8/2008 | Bammer et al. | .............. | 324/307 |
| 7,408,346 B2 * | 8/2008 | Szyperski et al. | ............. | 324/307 |

(Continued)

OTHER PUBLICATIONS

Atreya et al., "J-GFT NMR for Precise Measurement of Mutually Correlated Nuclear Spin—Spin Couplings," J.Am. Chem. Soc., 129:680-692 (2007).
Bachman et al., "Phase Separation in Two-Dimensional Spectroscopy," Journal of Magnetic Resonance, 28:29-39 (1977).

(Continued)

Primary Examiner — Melissa Koval
Assistant Examiner — Tiffany Fetzner
(74) Attorney, Agent, or Firm — LeClairRyan a Professional Corporation

(57) ABSTRACT

The present invention relates to a method of conducting an N-dimensional nuclear magnetic resonance (NMR) experiment in a phase-sensitive manner by the use of forward and backward sampling of time domain shifted by a primary phase shift under conditions effective to measure time domain amplitudes and secondary phase shifts. The present invention also relates to methods of conducting an N-dimensional NMR experiment in a phase-sensitive manner by the use of dual forward and backward sampling of time domain shifted by a primary phase shift under conditions effective to measure secondary phase shifts or at least partially cancel dispersive and quadrature image signal components arising in the frequency domain from secondary phase shifts.

67 Claims, 11 Drawing Sheets

U.S. PATENT DOCUMENTS

| | | | |
|---|---|---|---|
| 7,586,306 B2* | 9/2009 | Szyperski et al. | 324/309 |
| 7,920,972 B2* | 4/2011 | Szyperski et al. | 702/27 |
| 7,944,206 B2* | 5/2011 | Frydman et al. | 324/307 |
| 2004/0061497 A1 | 4/2004 | Szyperski et al. | |
| 2004/0201850 A1* | 10/2004 | Hajian et al. | 356/451 |
| 2005/0007111 A1* | 1/2005 | Frydman | 324/307 |
| 2005/0134275 A1* | 6/2005 | Frydman | 324/321 |
| 2006/0111846 A1* | 5/2006 | Szyperski et al. | 702/19 |
| 2007/0007959 A1* | 1/2007 | Szyperski et al. | 324/307 |
| 2007/0182411 A1* | 8/2007 | Bammer et al. | 324/307 |
| 2009/0033326 A1* | 2/2009 | Szyperski et al. | 324/307 |
| 2009/0230959 A1* | 9/2009 | Szyperski et al. | 324/309 |
| 2011/0044524 A1* | 2/2011 | Wang et al. | 382/131 |

OTHER PUBLICATIONS

States et al., "A Two-Dimensional Nuclear Overhauser Experiment with Pure Absorption Phase in Four Quadrants," Journal of Magnetic Resonance, 48:286-292 (1982).

Wu et al., "Clean Absorption-Mode NMR Data Acquisition," Angew. Chem. Int. Ed. Engl. 48:1479-1483. PMID: 19140147 (2009).

International Search Report for International Patent Application No. PCT/09/33932 (May 12, 2009).

Written Opinion of the International Searching Authority for International Patent Application No. PCT/US09/33932 (May 12, 2009).

Nagayama, "Four-Quadrant Pure-Phase Representation of Two-Dimensional Spectra with Time Reversal or Frequency Inversion," J. Mag. Reson. 66:240-249 (1986).

* cited by examiner

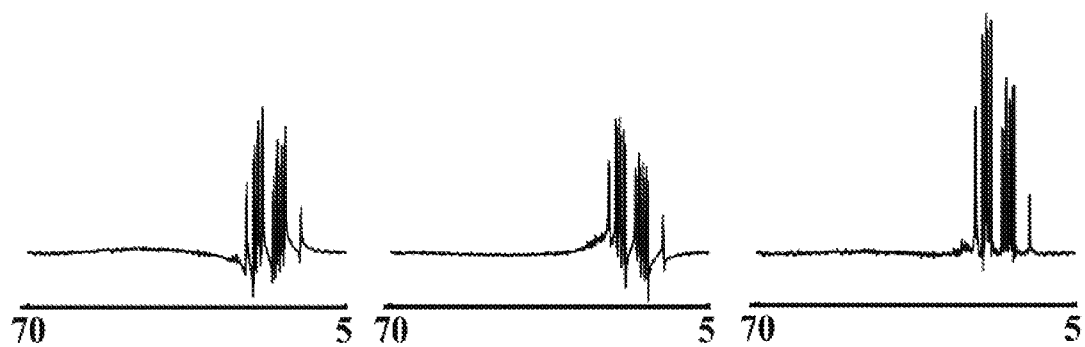
FIG. 4A  FIG. 4B  FIG. 4C
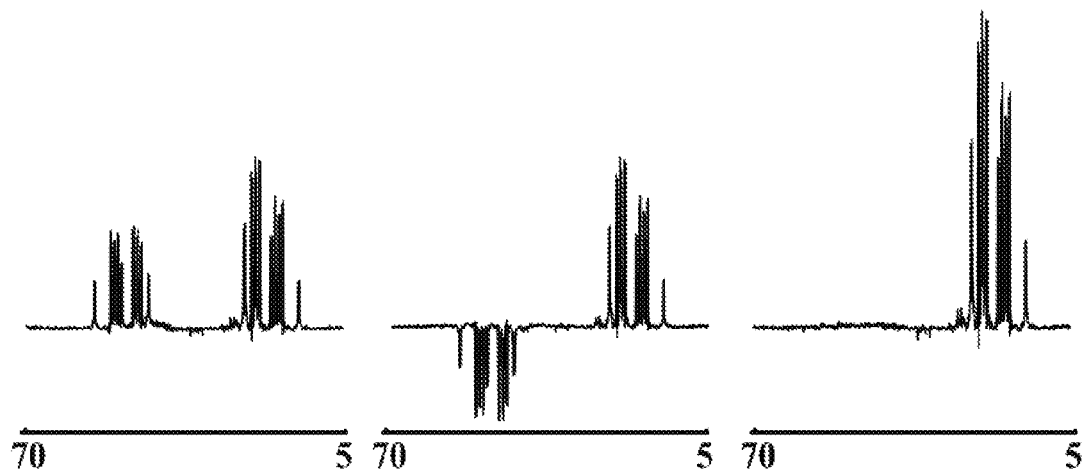
FIG. 4D  FIG. 4E  FIG. 4F
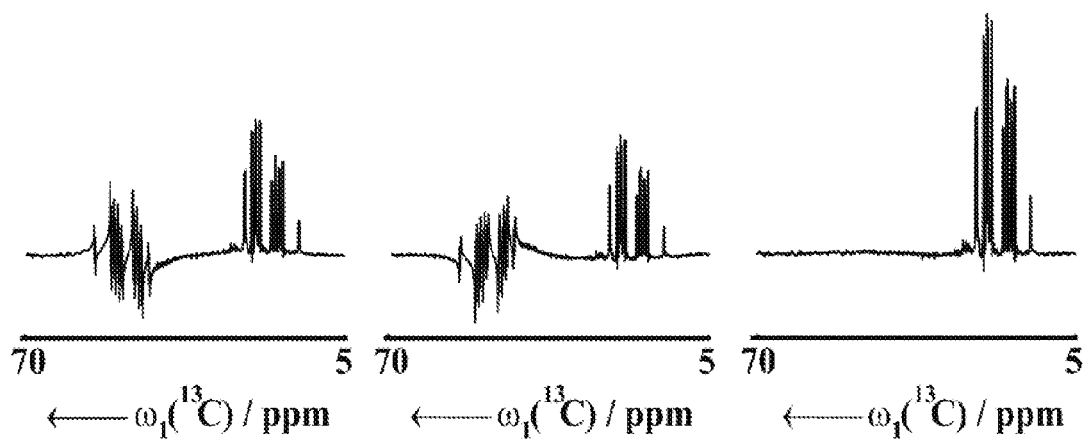
$\longleftarrow \omega_1(^{13}C)\,/\,\text{ppm}$    $\longleftarrow \omega_1(^{13}C)\,/\,\text{ppm}$    $\longleftarrow \omega_1(^{13}C)\,/\,\text{ppm}$
FIG. 4G  FIG. 4H  FIG. 4I

METHODS OF USING COMBINED FORWARD AND BACKWARD SAMPLING OF NUCLEAR MAGNETIC RESONANCE TIME DOMAIN FOR MEASUREMENT OF SECONDARY PHASE SHIFTS, DETECTION OF ABSORPTION MODE SIGNALS DEVOID OF DISPERSIVE COMPONENTS, AND/OR OPTIMIZATION OF NUCLEAR MAGNETIC RESONANCE EXPERIMENTS

This application claims the benefit of U.S. Provisional Patent Application Ser. No. 61/028,070, filed Feb. 12, 2008 and U.S. Provisional Patent Application Ser. No. 61/092,901, filed Aug. 29, 2008, which are hereby incorporated by reference in their entirety.

The subject matter of this application was made with support from the United States Government under The National Institutes of Health Grant No. U54 GM074958-01 and the National Science Foundation Grant Nos. MCB 0416899 and MCB 0817857. The government has certain rights in this invention.

FIELD OF THE INVENTION

The present invention relates to a method of conducting an N-dimensional nuclear magnetic resonance (NMR) experiment in a phase-sensitive manner by the use of forward and backward sampling of time domain shifted by a primary phase shift under conditions effective to measure time domain amplitudes and secondary phase shifts. The present invention also relates to methods of conducting an N-dimensional NMR experiment in a phase-sensitive manner by the use of dual forward and backward sampling of time domain shifted by a primary phase shift under conditions effective to at least partially cancel dispersive and quadrature image signal components arising in the frequency domain from secondary phase shifts.

BACKGROUND OF THE INVENTION

Multi-dimensional Fourier Transform (FT) NMR spectroscopy is broadly used in chemistry (Ernst et al., "Principles of Nuclear Magnetic Resonance in One and Two Dimensions," Oxford: Oxford University Press (1987); Jacobsen, N. E., "NMR Spectroscopy Explained," Wiley, New York (2007)) and spectral resolution is pivotal for its performance. The use of forward and backward sampling for pure absorption mode signal detection to obtain improved spectral resolution is described in Bachman et al., *J. Mag. Res.*, 28:29-39 (1977), however, this methodology does not allow phase-sensitive detection. In particular, Bachmann et al. teach the combined forward-backward sampling of a chemical shift evolution along one axis, the 'x-axis', only. This results in two cosine modulations which, after addition, yield a real time domain signal devoid of terms that lead to dispersive components in the frequency domain spectrum obtained after a cosine transformation. Hence, Bachmann et al. do not teach phase-sensitive detection of chemical shifts.

Phase-sensitive, pure absorption mode signal detection (Ernst et al., "Principles of Nuclear Magnetic Resonance in One and Two Dimensions," Oxford: Oxford University Press (1987); Cavanagh et al., "Protein NMR Spectroscopy," 2nd Ed., San Diego Academic Press (2007); Schmidt-Rohr et al., "Multidimensional Solid-State NMR and Polymers," New York: Academic Press (1994)) is required for achieving high spectral resolution since an absorptive signal at frequency $\Omega_0$ rapidly decays proportional to $1/(\Omega_0-\Omega)^2$ while a dispersive signal slowly decays proportional to $1/(\Omega_0-\Omega)$. Hence, a variety of approaches were developed to accomplish pure absorption mode signal detection (Ernst et al., "Principles of Nuclear Magnetic Resonance in One and Two Dimensions," Oxford: Oxford University Press (1987); Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994)). Moreover, by use of techniques such as spin-lock purge pulses (Messerle et al., *J. Magn. Reson.* 85:608-613 (1989)), phase cycling, (Ernst et al., "Principles of Nuclear Magnetic Resonance in One and Two Dimensions," Oxford: Oxford University Press (1987)) pulsed magnetic field gradients, (Keeler et al., *Methods Enzymol.* 239:145-207 (1994)) or z-filters (Sorensen et al., *J. Magn. Reson.* 56:527-534 (1984)), radio-frequency (r.f.) pulse sequences for phase-sensitive detection are designed to avoid 'mixed' phases, so that only phase errors remain which can then be removed by a zero-or first-order phase correction.

A limitation of the hitherto developed approaches (Ernst et al., "Principles of Nuclear Magnetic Resonance in One and Two Dimensions," Oxford: Oxford University Press (1987); Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994)) arises whenever signals exhibit phase errors which cannot be removed by a zero-or first-order correction, or when aliasing limits (Cavanagh et al., "Protein NMR Spectroscopy," 2nd Ed., San Diego: Academic Press (2007)) first-order phase corrections to 0° or 180°. Due to experimental imperfections, such phase errors inevitably accumulate to some degree during the execution of r.f. pulse sequences (Ernst et al., "Principles of Nuclear Magnetic Resonance in One and Two Dimensions," Oxford: Oxford University Press (1987); Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994)) which results in superposition of the desired absorptive signals with dispersive signals of varying relative intensity not linearly correlated with $\Omega_0$. This not only exacerbates peak identification, but also reduces the signal-to-noise (S/N) and shifts the peak maxima. In turn, this reduces the precision of chemical shift measurements and impedes spectral assignment based on matching of shifts.

Furthermore, phase-sensitive, pure absorption mode detection of signals encoding linear combinations of chemical shifts relies on joint sampling of chemical shifts as in Reduced-dimensionality (RD) NMR (Szyperski et al., *J. Am. Chem. Soc.* 115:9307-9308 (1993); Brutscher et al., *J. Magn. Reson.*, B109:238-242 (1995); Szyperski et al., *Proc. Natl. Acad. Sci. USA* 99:8009-8014 (2002)) and its generalization, G-matrix Fourier transform (GFT) projection NMR (Kim et al., *J. Am. Chem. Soc.* 125:1385-1393 (2003); Atreya et al., *Proc. Natl. Acad. Sci. USA* 101:9642-9647 (2004); Xia et al., *J. Biomol. NMR* 29:467-476 (2004); Eletsky et al., *J. Am. Chem. Soc.* 127, 14578-14579 (2005); Yang et al., *J. Am. Chem. Soc.* 127:9085-9099 (2005); Atreya et al., *Methods Enzymol.* 394:78-108 (2005); Liu et al., *Proc. Natl. Acad. Sci. U.S.A.* 102:10487-10492 (2005); Atreya et al., *J. Am. Chem. Soc.* 129:680-692 (2007)). The latter is broadly employed, in particular also (Szyperski et al., *Magn. Reson. Chem.* 44:51-60 (2006)) for projection-reconstruction (PR) (Kupce et al., *J. Am. Chem. Soc.* 126:6429-6440 (2004); Coggins et al., *J. Am. Chem. Soc.* 126:1000-1001 (2004)), high-resolution iterative frequency identification (HIFI) (Eghbalnia et al., *J. Am. Chem. Soc.* 127:12528-12536 (2005)), and automated projection (APSY) NMR (Hiller et al., *Proc. Natl. Acad. Sci.*

U.S.A. 102:10876-10881 (2005)). Importantly, the joint sampling of chemical shifts entangles phase errors from several shift evolution periods. Hence, zero-and first-order phase corrections cannot be applied in the GFT dimension (Atreya et al., *J. Am. Chem. Soc.* 129:680-692 (2007)), which further accentuates the need for approaches which are capable of eliminating (residual) dispersive components.

In Atreya et al., *J. Am. Chem. Soc.* 129:680-692 (2007), measurement of nuclear spin-spin coupling is taught. In particular, Atreya et al. teach transforming a secondary phase shift in the cosine J-modulation arising from 'J-mismatch', that is, variation of J by spins system requiring different $\Delta t = \frac{1}{2} J$ delays for each spin system, into an imbalance of amplitudes of sine and cosine modulation. This yields quadrature image peaks which are not removed. Atreya et al. teach combined forward and backward sampling of cosine modulations, since sine modulations are not affected by secondary phase shifts arising from J-mismatch.

The present invention is directed to overcoming these and other deficiencies in the art.

SUMMARY OF THE INVENTION

The present invention relates to a method of conducting an N-dimensional NMR experiment in a phase-sensitive manner by use of forward (from time 0 to +t) and backward (from time 0 to −t) sampling of time domain shifted by a primary phase shift under conditions effective to measure time domain amplitudes and secondary phase shifts. The method comprises providing a sample; applying radiofrequency pulses for an N-dimensional NMR experiment to said sample; selecting m dimensions of said NMR experiment, wherein $m \leq N$, sampling a time domain modulation in a phase-sensitive manner in each selected dimension $j \in [1, 2, \ldots, m]$ arising from time evolution of chemical shift $\alpha_j$ in both a forward and backward manner to obtain two interferograms for each time domain dimension $t_j$ defining the vector $$C_{j,\psi_j}(t_j) := \begin{bmatrix} I^+_{j,\psi_j} c^+_{\psi_j}(t_j) \\ I^-_{j,\psi_j,\delta_j} c^-_{\psi_j,\delta_j}(t_j) \end{bmatrix} = \begin{bmatrix} I^+_{j,\psi_j} \cos(\psi_j + \alpha_j t_j + \Phi^+_{j,\psi_j}) \\ I^-_{j,\psi_j,\delta_j} \cos(\psi_j + \delta_j - \alpha_j t_j + \Phi^-_{j,\psi_j,\delta_j}) \end{bmatrix},$$

wherein $I^+_{j,\psi_j}$ and $I^-_{j,\psi_j,\delta_j}$ are amplitudes, $\Psi_j$ and $\Psi_j + \delta_j$ are primary phase shifts with $\Psi_j, \delta_j \in [0, 2\pi[$ and the cases $\{\psi_j = n\pi/2$ and $\delta_j = m\pi\}$ with $n = 0, 1, 2, 3$ and $m = 0, 1$ being omitted, and $\Phi^+_{j,\psi_j}$ and $\Phi^-_{j,\psi_j,\delta_j}$ are secondary phase shifts; multiplying each said vectors $C_{j,\psi_j}(t_j)$ with a D-matrix defined as $$D_j = \begin{bmatrix} \sin(\psi_j + \delta_j) & \sin(\psi_j) \\ -\cos(\psi_j + \delta_j) & \cos(\psi_j) \end{bmatrix}$$

and a vector $Q = [1 \; i]$, wherein $i = \sqrt{-1}$, according to $Q \cdot D_j \cdot C_{j,\psi_j}(t_j)$ under conditions effective to create a complex time domain of said selected m dimensions according to $$\bigotimes_j Q \cdot D_j \cdot C_{j,\psi_j}(t_j);$$

and transforming said complex time domain into frequency domain by use of an operator O under conditions effective to measure the values of $I^+_{j,\psi_j}$, $I^-_{j,\psi_j}$, $\Phi^+_{j,\psi_j}$ and $\Phi^-_{j,\psi_j}$ in said frequency domain.

Another aspect of the present invention relates to a method of conducting an N-dimensional NMR experiment in a phase-sensitive manner by use of dual forward (from time 0 to +t) and backward (from time 0 to −t) sampling of time domain shifted by a primary phase shift under conditions effective to measure secondary phase shifts or at least partially cancel dispersive and quadrature image signal components arising in a frequency domain from secondary phase shifts. The method comprises providing a sample; applying radiofrequency pulses for an N-dimensional NMR experiment to said sample; selecting m dimensions of said NMR experiment, wherein $m \leq N$, sampling a time domain modulation in a phase-sensitive manner in each said selected dimension $j \in [1, 2, \ldots, m]$ arising from time evolution of chemical shift $\alpha_j$ in both a forward and backward manner to obtain two interferograms for each time domain dimension $t_j$ defining the vector $$C_{j,\psi_j}(t_j) := \begin{bmatrix} I^+_{j,\psi_j} c^+_{\psi_j}(t_j) \\ I^-_{j,\psi_j,\delta_j} c^-_{\psi_j,\delta_j}(t_j) \end{bmatrix} = \begin{bmatrix} I^+_{j,\psi_j} \cos(\psi_j + \alpha_j t_j + \Phi^+_{j,\psi_j}) \\ I^-_{j,\psi_j,\delta_j} \cos(\psi_j + \delta_j - \alpha_j t_j + \Phi^-_{j,\psi_j,\delta_j}) \end{bmatrix},$$

wherein $I^+_{j,\psi_j}$ and $I^-_{j,\psi_j}$ are amplitudes, $\Psi_j$ and $\Psi_j + \delta_j$ are primary phase shifts with $\Psi_j, \delta_j \in [0, 2\pi[$ and the cases $\{\psi_j = n\pi/2$ and $\delta_j = m\pi\}$ with $n = 0, 1, 2, 3$ and $m = 0, 1$ being omitted, and $\Phi^+_{j,\psi_j}$ and $\Phi^-_{j,\psi_j}$ are secondary phase shifts; multiplying each said vectors $C_{j,\psi_j}(t_j)$ with a D-matrix defined as $$D_j = \begin{bmatrix} \sin(\psi_j + \delta_j) & \sin(\psi_j) \\ -\cos(\psi_j + \delta_j) & \cos(\psi_j) \end{bmatrix}$$

and a vector $Q = [1 \; i]$, wherein $i = \sqrt{-1}$, according to $Q \cdot D_j \cdot C_{j,\psi_j}(t_j)$ under conditions effective to create a complex time domain of said selected m dimensions according to $$\bigotimes_j Q \cdot D_j \cdot C_{j,\psi_j}(t_j);$$

repeating said selecting, said sampling and said multiplying $(2^m)$-times, thereby sampling the m dimensions with all $2^m$ possible permutations resulting from selecting for each dimension j either $\Psi_j$ or $\Psi_j + \pi/2$, with $\delta_j$ being incremented by either 0 or $\pi$, thereby yielding $2^m$ complex time domains; linearly combining said $2^m$ complex time domains; and transforming said linearly combined complex time domain into frequency domain by use of an operator O, under conditions effective to at least partially cancel dispersive and quadrature image peak components arising from $\Phi^+_{j,\psi_j}$ and $\Phi^-_{j,\psi_j}$ in said frequency domain.

A further aspect of the present invention relates to a method of conducting an N-dimensional NMR experiment in a phase-sensitive manner by use of dual forward (from time 0 to +t) and backward (from time 0 to −t) sampling of time domain shifted by a primary phase shift under conditions effective to measure secondary phase shifts or at least partially cancel dispersive and quadrature image signal components arising in a frequency domain from secondary phase shifts. The method comprises providing a sample; applying radiofrequency pulses for an N-dimensional NMR experiment to said sample; selecting m dimensions of said NMR experiment, wherein $m \leq N$, sampling twice a time domain modulation in a phase-sensitive manner in each said selected dimension j∈[1,2, ..., m] arising from time evolution of chemical shift $\alpha_j$, once in a forward manner to obtain two interferograms for each time domain dimension $t_j$ defining the vector $$C_{j,\psi_j}^+(t_j) := \begin{bmatrix} I_{j,\psi_j}^+ c_{\psi_j}^+(t_j) \\ I_{j,\psi_j,\delta_j}^+ c_{\psi_j,\delta_j}^+(t_j) \end{bmatrix} = \begin{bmatrix} I_{j,\psi_j}^+ \cos(\psi_j + \alpha_j t_j + \Phi_{j,\psi_j}^+) \\ I_{j,\psi_j,\delta_j}^+ \cos(\psi_j + \delta_j + \alpha_j t_j + \Phi_{j,\psi_j,\delta_j}^+) \end{bmatrix},$$

and once in a backward manner to obtain two interferograms for each time domain dimension $t_j$ defining the vector $$C_{j,\psi_j}^-(t_j) := \begin{bmatrix} I_{j,\psi_j}^- c_{\psi_j}^-(t_j) \\ I_{j,\psi_j,\delta_j}^- c_{\psi_j,\delta_j}^-(t_j) \end{bmatrix} = \begin{bmatrix} I_{j,\psi_j}^- \cos(\psi_j - \alpha_j t_j + \Phi_{j,\psi_j}^-) \\ I_{j,\psi_j,\delta_j}^- \cos(\psi_j + \delta_j - \alpha_j t_j + \Phi_{j,\psi_j,\delta_j}^-) \end{bmatrix},$$

wherein $I_{j,\psi_j}^+$, $I_{j,\psi_j,\delta_j}^+$, $I_{j,\psi_j}^-$, and $I_{j,\psi_j,\delta_j}^-$ are amplitudes, $\Psi_j$ and $\Psi_j + \delta_j$ are primary phase shifts with $\Psi_j$, $\delta_j \in [0, 2\pi[$, and $\Phi_{j,\psi_j}^+$, $\Phi_{j,\psi_j,\delta_j}^+$, $\Phi_{j,\psi_j}^-$, and $\Phi_{j,\psi_j,\delta_j}^-$ are secondary phase shifts; multiplying each said vector $C_{j,\psi_j}^+(t_j)$ with a D-matrix defined as $$D_j^+ = \begin{bmatrix} \sin(\psi_j + \delta_j) & -\sin(\psi_j) \\ \cos(\psi_j + \delta_j) & -\cos(\psi_j) \end{bmatrix}$$

and each said vector $C_{j,\psi_j}^-(t_j)$ with a D-matrix defined as $$D_j^- = \begin{bmatrix} \sin(\psi_j + \delta_j) & -\sin(\psi_j) \\ -\cos(\psi_j + \delta_j) & \cos(\psi_j) \end{bmatrix};$$

multiplying the said products $D_j^+ \cdot C_{j,\psi_j}^+(t_j)$ and $D_j^- \cdot C_{j,\psi_j}^-(t_j)$ with a vector $Q=[1\ i]$, wherein $i=\sqrt{-1}$, according to $Q \cdot D_j^+ \cdot C_{j,\psi_j}^+(t_j)$ and $Q \cdot D_j^- \cdot C_{j,\psi_j}^-(t_j)$ under conditions effective to create a complex time domain of said selected m dimensions according to $$\bigotimes_j Q \cdot D_j^+ \cdot C_{j,\psi_j}^+(t_j) \text{ and } \bigotimes_j Q \cdot D_j^- \cdot C_{j,\psi_j}^-(t_j);$$

repeating said selecting, said phase-sensitive sampling twice and said multiplying ($2^m - 2$)-times, thereby sampling said m dimensions with all $2^m$ possible permutations resulting from selecting for each dimension j either phase-sensitive forward or backward sampling according to $C_{j,\psi_j}^+(t_j)$ or $C_{j,\psi_j}^-(t_j)$; linearly combining said $2^m$ complex time domains; and transforming said linearly combined complex time domain into frequency domain by use of an operator O, under conditions effective to at least partially cancel dispersive and quadrature image peak components arising from $\Phi_{j,\psi_j}^+$, $\Phi_{j,\psi_j,\delta_j}^+$, $\Phi_{j,\psi_j}^-$, and $\Phi_{j,\psi_j,\delta_j}^-$, in said frequency domain.

Pure absorption mode NMR spectra in accordance with the present invention are most amenable to automated (Moseley et al., *J. Magn. Reson.* 170:263-277 (2004); Lopez-Mendez et al., *J. Am. Chem. Soc.* 128:13112-13122 (2006), which are hereby incorporated by reference in their entirety) peak 'picking' and the resulting increased precision of shift measurements also increases the efficiency of automated resonance assignment of NMR spectra (Moseley et al., *Methods Enzymol.* 339:91-108 (2001), which is hereby incorporated by reference in its entirety). This is because chemical shift matching tolerances can be reduced (For the program AutoAssign (Moseley et al., *Methods Enzymol*, 339:91-108 (2001), which is hereby incorporated by reference in its entirety), a matching tolerance of 0.3 ppm is routinely used for $^{13}C^{\alpha/\beta}$ chemical shifts. Since shifts of peak maxima are up to about ±0.07 ppm, elimination of dispersive components enables one to reduce the tolerance significantly). Moreover, the enhanced spectral resolution promises to be of particular value for systems exhibiting very high chemical shift degeneracy such as (partially) unfolded or membrane proteins.

Pure absorption mode NMR data acquisition as set forth in the present invention enables one to also remove dispersive components arising from secondary phase shifts, such as phase errors, which cannot be removed by a zero-or first-order phase correction. Hence, such data acquisition resolves a long-standing challenge of both conventional (Ernst et al., "Principles of Nuclear Magnetic Resonance in One and Two Dimensions," Oxford: Oxford University Press (1987); Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994), which are hereby incorporated by reference in their entirety) and GFT-based projection NMR (Kim et al., *J. Am. Chem. Soc.* 125:1385-1393 (2003); Atreya et al., *Proc. Natl. Acad. Sci. USA* 101:9642-9647 (2004); Xia et al., *J. Biomol. NMR* 29:467-476 (2004); Eletsky et al., *J. Am. Chem. Soc.* 127, 14578-14579 (2005); Yang et al., *J. Am. Chem. Soc.* 127:9085-9099 (2005); Atreya et al., *Methods Enzymol.* 394:78-108 (2005); Liu et al., *Proc. Natl. Acad. Sci. U.S.A.* 102:10487-10492 (2005); Atreya et al., *J. Am. Chem. Soc.* 129:680-692 (2007); Szyperski et al., *Magn. Reson. Chem.* 44:51-60 (2006); Kupce et al., *J. Am. Chem. Soc.* 126:6429-6440 (2004); Coggins et al., *J. Am. Chem. Soc.* 126:1000-1001 (2004); Eghbalnia et al., *J. Am. Chem. Soc.* 127:12528-12536 (2005); Hiller et al., *Proc. Natl. Acad. Sci. U.S.A.* 102:10876-10881 (2005), which are hereby incorporated by reference in their entirety). Furthermore, the present invention promises to broadly impact NMR data acquisition protocols for science and engineering.

The present invention relates to phase-sensitive detection of chemical shifts, which is reflected by the fact that the cases $\{\psi_j = n\pi/2$ and $\delta_j = m\pi\}$ with $n=0, 1, 2, 3$ and $m=0, 1$ are omitted in the claims for conventional phase incrementation (TPPI) is used. This is in contrast to the prior art, for example, Bachmann et al. *J. Mag. Res.*, 28:29-39 (1977) (with $\psi_j = \delta_j = 0$), which does not relate to phase-sensitive detection of chemical shifts.

Moreover, in contrast to the prior art, the present invention teaches how secondary phase shifts can be measured in frequency domain spectra in which chemical shifts are measured, and how frequency domain signals or signal components arising from the secondary shifts can be partly or entirely canceled. Nuclear spin-spin couplings (as measured in Atreya et al., *J. Am. Chem. Soc.* 129:680-692 (2007), which is hereby incorporated by reference in its entirety) and chemical shifts (as measured in the present invention) result from fundamentally different interactions, that is, from interaction among nuclear spins and interaction of nuclear spins with the magnetic field, respectively, and thus result in a fundamentally different types of time evolution of spin systems. Considering a two-spin system containing spins I and S, time evolution can be conveniently described by use of corresponding Cartesian spin operators I and S (Cavanagh et al., "Protein NMR Spectroscopy," San Diego: Academic Press, $2^{nd}$ Ed., (2007), which is hereby incorporated by reference in its entirety). The time evolution of transverse magnetization $I_x$ present at time t=0 is given by:

$$I_x \xrightarrow{t} I_x \cos(\omega t) + I_y \sin(\omega t), \quad \text{(A1)}$$

revealing that magnetization aligned along the x-axis at time t=0 evolves into the magnetization pointing along the orthogonal y-axis. For $I_y$, one obtains:

$$I_y \xrightarrow{t} I_y \cos(\omega t) - I_x \sin(\omega t). \quad \text{(A2)}$$

In contrast, time evolution driven by nuclear spin-spin couplings, e.g. J-couplings, is given by $$I_x \xrightarrow{t} I_x \cos(\pi J t) + 2 I_y S_z \sin(\pi J t), \quad \text{(A3)}$$

where in-phase magnetization is converted into anti-phase magnetization, and $$I_y S_z \xrightarrow{t} I_y S_z \cos(\pi J t) - I_x \sin(\pi J t), \quad \text{(A4)}$$

where anti-phase magnetization is converted into in-phase magnetization.

Comparison of equations (A1) and (A2) with (A3) and (A4) reveals that a straightforward phase-sensitive detection of J-coupling evolution is not possible. Instead, sine modulation must obtained when starting with a type of spin state, that is, anti-phase magnetization which needs to be created during a delay $\Delta t = \frac{1}{2}J$.

As pointed out by Freeman and Kupce (Freeman et al., *Concepts in Mag. Res.* 23A:63-75 (2004), which is hereby incorporated by reference in its entirety), experiments measuring nuclear spin-spin couplings (as in Atreya et al., *J. Am. Chem. Soc.* 129:680-692 (2007), which is hereby incorporated by reference in its entirety) thus belong to the class of NMR experiments in which a 'real variable' is sampled, while chemical shift evolution, as in the present invention, is sampled in a complex manner when performed phase-sensitively.

The present invention teaches measurement of secondary phase shifts and/or partial or entire elimination of dispersive frequency domain components, quadrature image frequency domain peaks, as well as cross-talk peaks in GFT NMR spectra. In particular, the present invention teaches implementation of combined phase-shifted forward and backward sampling of chemical shifts. Due to the fundamental difference of time evolution of transverse magnetization under chemical shift and J-coupling, the implementation of sampling of corresponding time evolution in NMR experiments are different. This becomes apparent when inspecting the radio-frequency (r.f) pulse schemes effective to implement J-GFT NMR experiments or NMR experiments designed to measure chemical shifts. In order to phase-sensitively detect chemical shifts, phases of r.f. pulses creating transverse magnetization are incremented. In contrast, detection of cosine and sine J-modulations requires that 180° r.f. pulse, which can refocus the evolution arising from J-couplings, are shifted in time.

BRIEF DESCRIPTION OF THE DRAWINGS

FIG. 1A shows dual 'States' and FIG. 1B shows $(c_{-1}, c_{-1}, c_{+3}, c_{-3})$-dual phase shifted mirrored sampling (DPMS). The residual phase error $\Phi$ is assumed to be 15°. For comparison of the intensity and phase of the interferograms, the dashed grey lines represent time domain data of unit amplitude and $\Phi=0$. In FIG. 1A, the intensities of frequency domain peaks were calculated using the following equation:

$$\mathfrak{R}^{States} = \frac{I_0^{States}(\Phi)}{I_0^{States}(\Phi=0)} = \frac{\sin^2\Phi}{2R_2(1-\cos\Phi)} \bigg/ \frac{1}{R_2} = \frac{\sin^2\Phi}{2(1-\cos\Phi)}$$

Figure 2:
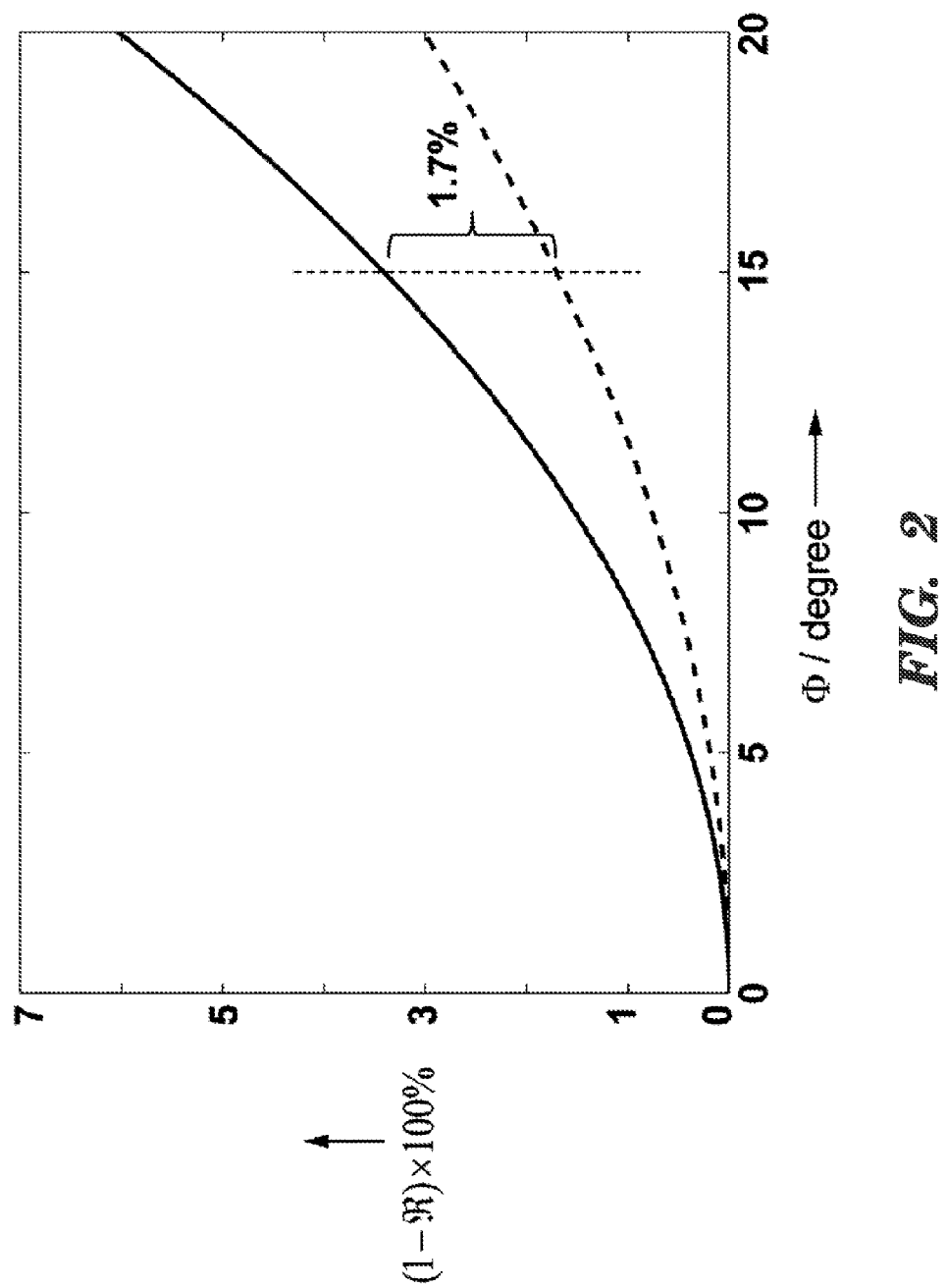

FIG. 2 illustrates percentage reduction of signals' maximum for 'States' (black upper line) and $(c_{+1}, c_{-1})$-PMS (phase-shifted mirrored time domain sampling) (dashed lower line) data acquisition versus $\Phi$. For $\Phi=15°$, the reduction arising from PMS is approximately 1.7% larger than for 'States'.

Figure 3B:
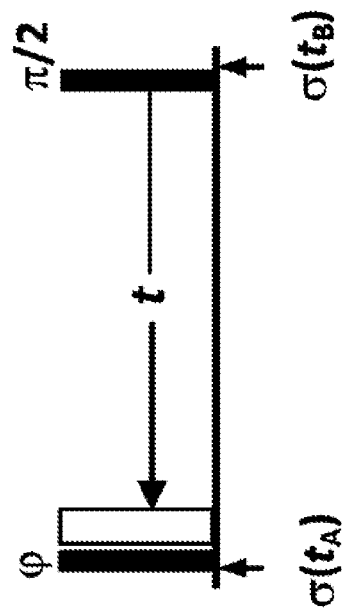
Figure 3A:
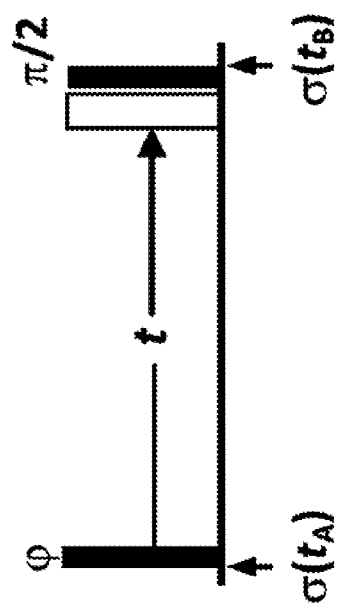

FIGS. 3A-B illustrate a $^{13}C$ r.f. pulse module enabling forward (FIG. 3A) and backward (FIG. 3B) sampling of the $^{13}C$ chemical shift evolution period in 2D [$^{13}C, ^1H$]-HSQC (Cavanagh et al., "Protein NMR Spectroscopy," 2nd Ed., San Diego: Academic Press (2007), which is hereby incorporated by reference in its entirety). Filled and open bars represent, respectively, 90° and 180° pulses. Pulse phases are indicated above the 90° pulses, and the phase of the 180° pulse is 0. The setting of $\phi$ defines the type of sampling. For $c_{+0}$ or $c_{-0}$-interferograms, $\phi=-\pi/2$; For $c_{+2}$ or $c_{-2}$-interferograms, $\phi=0$; For $c_{+0}$ or $c_{-0}$-interferograms, $\phi=-\pi/4$; For $c_{+3}$ or $c_{-3}$-interferograms, $\phi=\pi/4$ FIGS. 4A-I illustrate cross sections taken along $\omega_1(^{13}C)$ of 2D [$^{13}C, ^1H$]-HSQC spectra recorded with $(c_{+0}, c_{+2})$-sampling (FIG. 4A), $(c_{-0}, c_{-2})$-sampling (FIG. 4B), $(c_{+0}, c_{+2}, c_{-0}, c_{-2})$-sampling (FIG. 4C), $(c_{+1}, c_{-1})$-sampling (FIG. 4D), $(c_{+3}, c_{-3})$-sampling (FIG. 4E), $(c_{+1}, c_{-1}, c_{+3}, c_{-3})$-sampling (FIG. 4F), $(c_{+0}, c_{-2})$-sampling (FIG. 4G), $(c_{-0}, c_{+2})$-sampling (FIG. 4H), and $(c_{+0}, c_{-2}, c_{-0}, c_{+2})$-sampling (FIG. 4I). Note that delayed acquisition for $t_1(^{13}C)$ greatly amplifies the salient features of the various sampling schemes. All PMS and DPMS spectra were obtained without a phase correction. The measurement time for the PMS 2D [$^{13}C, ^1H$]-HSQC spectra was one hour resulting in measurement time of two hours for the DMPS spectrum. The respective measurement times were two hours invested for the 'States' and dual 'States' spectra.

Figure 5:
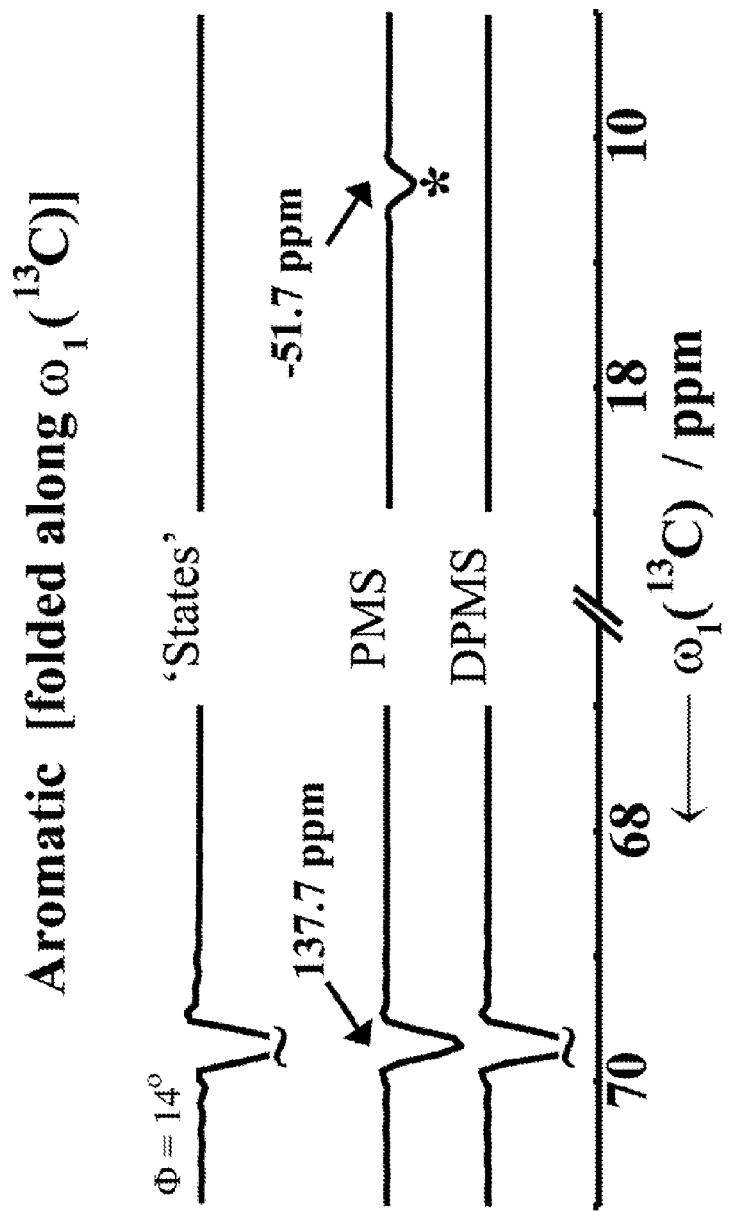

FIG. 5 illustrates cross sections along $\omega_1(^{13}C)$ taken from 2D [$^{13}C^{aliphatic}/^{13}C^{aromatic}, ^1H$]-HSQC acquired with States (Ernst et al., "Principles of Nuclear Magnetic Resonance in One and Two Dimensions," Oxford: Oxford University Press (1987), which is hereby incorporated by reference in its entirety), $(c_{+1}, c_{-1})$-PMS, or $(c_{+1}, c_{-1}, c_{+3}, c_{-3})$-DPMS. The States spectrum was phase-corrected such that aliphatic peaks are purely absorptive. This leads to a dispersive component in the aromatic peaks (top). The quad peak in the PMS spectra (middle) results from the dispersive component and is marked with (*). The quad peak is canceled in the clean absorption mode DPMS spectrum (bottom). The actual chemical shifts (detected without folding) are indicated. For data processing, see discussion in Example 1.

Figure 6:
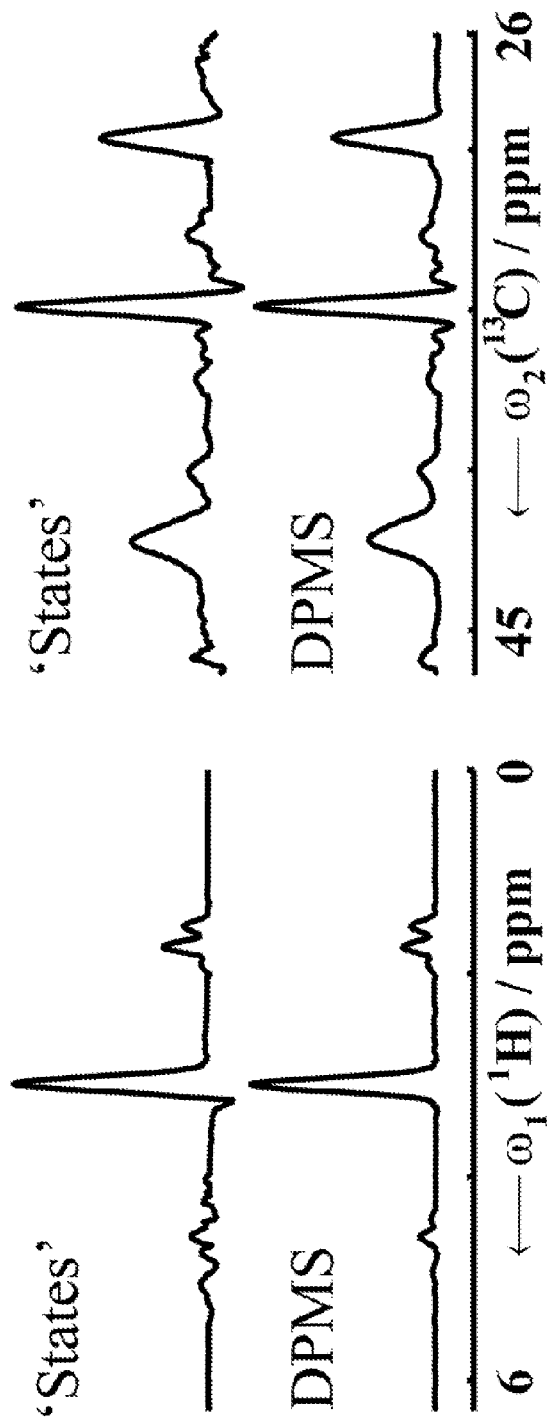

FIGS. 6A-B illustrate cross sections taken along $\omega_1(^1H)$ (FIG. 6A) and $\omega_2(^{13}C)$ (FIG. 6B) from 3D HC(C)H TOCSY spectra recorded with either 'States' quadrature (Ernst et al., "Principles of Nuclear Magnetic Resonance in One and Two Dimensions," Oxford: Oxford University Press (1987), which is hereby incorporated by reference in its entirety) detection or DPMS in both indirect dimensions. The latter yields a clean absorption mode spectrum without applying a phase correction. Note that the dispersive components of the peak located approximately in the middle of the selected spectral range cannot be removed by a first order phase correction: this would introduce dispersive components for other peaks located either up-or down-field. For data processing, see discussion in Example 1.

Figure 7:
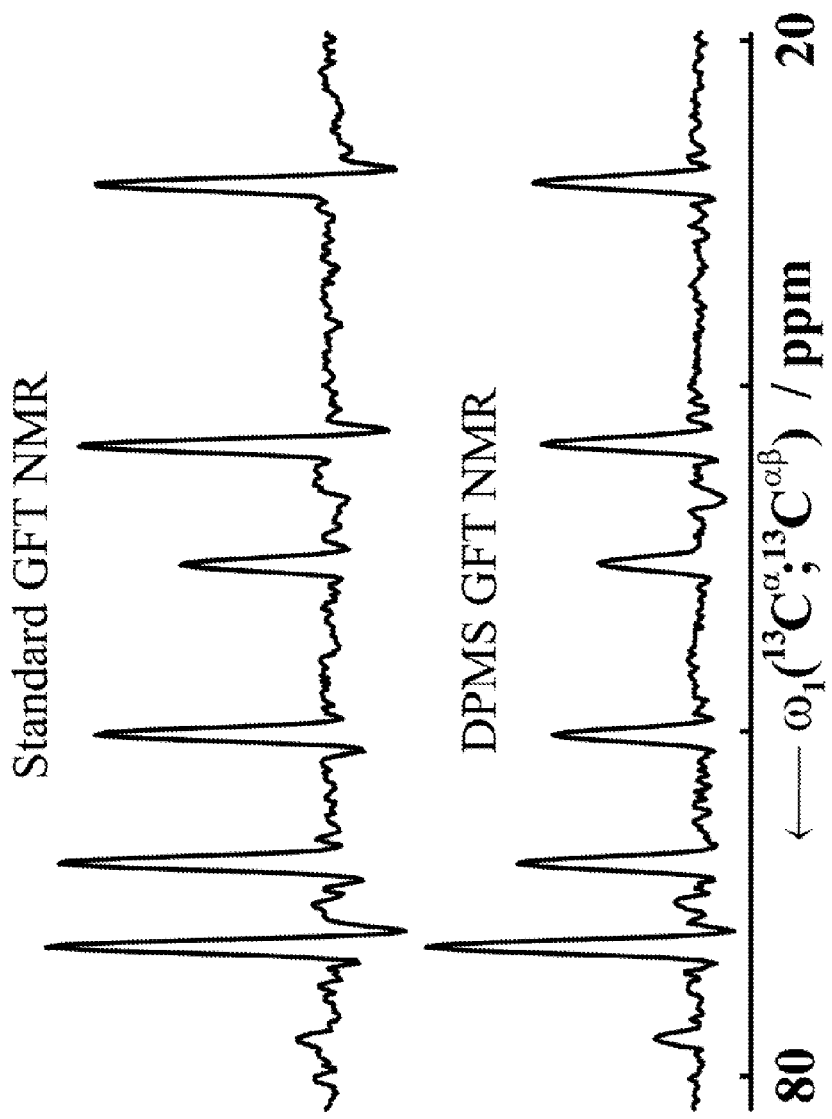

FIG. 7 illustrates cross sections along $\omega_1(^{13}C^\alpha;^{13}CU^{13})$ taken from the $\omega_2(^{15}N)$-projection of the (4,3)D $C^{\alpha\beta}C^\alpha(CO)NHN$ (Atreya et al., *Proc. Natl. Acad. Sci. USA*, $\overline{101}$: $\overline{9642}$-9647 (2004), which is hereby incorporated by reference in its entirety) sub-spectrum comprising signals at $\Omega(^{13}C^\alpha)+\Omega(^{13}C^{\alpha\beta})$, recorded with standard GFT NMR data acquisition (Atreya et al., *Proc. Natl. Acad. Sci. USA*, 101:9642-9647 (2004), which is hereby incorporated by reference in its entirety) or $(c_{+1},c_{-1},c_{+3},c_{-3})$-DPMS for the jointly sampled chemical shift evolution periods. The latter yields clean absorption mode GFT NMR sub-spectra. For data processing, see discussion in Example 1.

FIGS. 8A-D show cross sections taken along $\omega_1(^{13}C)$ of aliphatic ct-2D [$^{13}C$, $^1H$]-HSQC spectra recorded with ($c_{+1}$, $c_{-1}$)-sampling (FIG. 8A), ($c_{+3}$,$c_{-3}$)-sampling (FIG. 8B), ($c_{+0}$, $c_{-2}$)-sampling (FIG. 8C), and ($c_{-0}$,$c_{+2}$)-sampling (FIG. 8D) for a 5 mM aqueous solution of phenylalanine. The quadrature peaks for spectra recorded using ($c_{+0}$,$c_{-2}$)-and ($c_{-0}$,$c_{+2}$)-sampling (labeled with an asterisk) are shown after a $\pi/2$ zero-order phase correction was applied. The digital resolution after zero filling in the $\psi_2(^1H)$ and $\omega_1(^{13}C)$ dimensions are, respectively, 7.8 and 2.5 Hz/pt. The measurement time for each of the spectra was 40 minutes.

DETAILED DESCRIPTION OF THE INVENTION

The present invention relates to a method of conducting an N-dimensional NMR experiment in a phase-sensitive manner by use of forward (from time 0 to +t) and backward (from time 0 to −t) sampling of time domain shifted by a primary phase shift under conditions effective to measure time domain amplitudes and secondary phase shifts. The method comprises providing a sample; applying radiofrequency pulses for an N-dimensional NMR experiment to said sample; selecting m dimensions of said NMR experiment, wherein $m \leq N$, sampling a time domain modulation in a phase-sensitive manner in each selected dimension $j \in [1,2,\ldots,m]$ arising from time evolution of chemical shift $\alpha_j$ in both a forward and backward manner to obtain two interferograms for each time domain dimension $t_j$ defining the vector $$C_{j,\psi_j}(t_j) := \begin{bmatrix} I^+_{j,\psi_j} c^+_{\psi_j}(t_j) \\ I^-_{j,\psi_j,\delta_j} c^-_{\psi_j,\delta_j}(t_j) \end{bmatrix} = \begin{bmatrix} I^+_{j,\psi_j}\cos(\psi_j + \alpha_j t_j + \Phi^+_{j,\psi_j}) \\ I^-_{j,\psi_j,\delta_j}\cos(\psi_j + \delta_j - \alpha_j t_j + \Phi^-_{j,\psi_j,\delta_j}) \end{bmatrix},$$

wherein $I^+_{j,\psi_j}$ and $I^-_{j,\psi_j}$ are amplitudes, $\Psi_j$ and $\Psi_j+\delta_j$ are primary phase shifts with $\Psi_j$, $\delta_j \in [0,2\pi[$ and the cases $\{\psi_j=n\pi/2$ and $\delta_j=m\pi\}$ with n=0, 1, 2, 3 and m=0, 1 being omitted, and $\Phi^+_{j,\psi_j}$ and $\Phi^-_{j,\psi_j,\delta_j}$ are secondary phase shifts; multiplying each said vectors $C_{j,\psi_j}(t_j)$ with a D-matrix defined as $$D_j = \begin{bmatrix} \sin(\psi_j + \delta_j) & \sin(\psi_j) \\ -\cos(\psi_j + \delta_j) & \cos(\psi_j) \end{bmatrix}$$

and a vector Q=[1 i], wherein $i=\sqrt{-1}$, according to $Q \cdot D_j \cdot C_{j,\psi_j}(t_j)$ under conditions effective to create a complex time domain of said selected m dimensions according to $$\otimes_j Q \cdot D_j \cdot C_{j,\psi_j}(t_j);$$

and transforming said complex time domain into frequency domain by use of an operator O under conditions effective to measure the values of $I^+_{j,\psi_j}$, $I^-_{j,\psi_j,\delta_j}$, $\Phi^+_{j,\psi_j}$ and $\Phi^-_{j,\psi_j,\delta_j}$ in said frequency domain.

Another aspect of the present invention relates to a method of conducting an N-dimensional NMR experiment in a phase-sensitive manner by use of dual forward (from time 0 to +t) and backward (from time 0 to −t) sampling of time domain shifted by a primary phase shift under conditions effective to measure secondary phase shifts or at least partially cancel dispersive and quadrature image signal components arising in a frequency domain from secondary phase shifts. The method comprises providing a sample; applying radiofrequency pulses for an N-dimensional NMR experiment to said sample; selecting m dimensions of said NMR experiment, wherein $m \leq N$, sampling a time domain modulation in a phase-sensitive manner in each said selected dimension $j \in [1, 2, \ldots, m]$ arising from time evolution of chemical shift $\alpha_j$ in both a forward and backward manner to obtain two interferograms for each time domain dimension $t_j$ defining the vector $$C_{j,\psi_j}(t_j) := \begin{bmatrix} I^+_{j,\psi_j} c^+_{\psi_j}(t_j) \\ I^-_{j,\psi_j,\delta_j} c^-_{\psi_j,\delta_j}(t_j) \end{bmatrix} = \begin{bmatrix} I^+_{j,\psi_j}\cos(\psi_j + \alpha_j t_j + \Phi^+_{j,\psi_j}) \\ I^-_{j,\psi_j,\delta_j}\cos(\psi_j + \delta_j - \alpha_j t_j + \Phi^-_{j,\psi_j,\delta_j}) \end{bmatrix},$$

wherein $I^+_{j,\psi_j}$ and $I^-_{j,\psi_j,\delta_j}$ are amplitudes, $\Psi_j$ and $\Psi_j+\delta_j$ are primary phase shifts with $\Psi_j$, $\delta_j \in [0,2\pi[$ and the cases $\{\psi_j=n\pi/2$ and $\delta_j=m\pi\}$ with n=0, 1, 2, 3 and m=0, 1 being omitted, and $\Phi^+_{j,\psi_j}$ and $\Phi^-_{j,\psi_j,\delta_j}$ are secondary phase shifts; multiplying each said vectors $C_{j,\psi_j}(t_j)$ with a D-matrix defined as $$D_j = \begin{bmatrix} \sin(\psi_j + \delta_j) & \sin(\psi_j) \\ -\cos(\psi_j + \delta_j) & \cos(\psi_j) \end{bmatrix}$$

and a vector Q=[1 i], wherein $i=\sqrt{-1}$, according to $Q \cdot D_j \cdot C_{j,\psi_j}(t_j)$ under conditions effective to create a complex time domain of said selected m dimensions according to $$\otimes_j Q \cdot D_j \cdot C_{j,\psi_j}(t_j);$$

repeating said selecting, said sampling and said multiplying ($2^m$)-times, thereby sampling the m dimensions with all $2^m$ possible permutations resulting from selecting for each dimension j either $\Psi_j$ or $\Psi_j+\pi/2$, with $\delta_j$ being incremented by either 0 or $\pi$, thereby yielding $2^m$ complex time domains; linearly combining said $2^m$ complex time domains; and transforming said linearly combined complex time domain into frequency domain by use of an operator O, under conditions effective to at least partially cancel dispersive and quadrature image peak components arising from $\Phi_{j,\psi_j}^+$ and $\Phi_{j,\psi_j,\delta_j}^-$ in said frequency domain.

A further aspect of the present invention relates to a method of conducting an N-dimensional NMR experiment in a phase-sensitive manner by use of dual forward (from time 0 to +t) and backward (from time 0 to −t) sampling of time domain shifted by a primary phase shift under conditions effective to measure secondary phase shifts or at least partially cancel dispersive and quadrature image signal components arising in a frequency domain from secondary phase shifts. The method comprises providing a sample; applying radiofrequency pulses for an N-dimensional NMR experiment to said sample; selecting m dimensions of said NMR experiment, wherein m≤N; sampling twice a time domain modulation in a phase-sensitive manner in each said selected dimension j∈[1,2, . . . , m] arising from time evolution of chemical shift $\alpha_j$, once in a forward manner to obtain two interferograms for each time domain dimension $t_j$ defining the vector $$C_{j,\psi_j}^+(t_j) := \begin{bmatrix} I_{j,\psi_j}^+ c_{\psi_j}^+(t_j) \\ I_{j,\psi_j,\delta_j}^+ c_{\psi_j,\delta_j}^+(t_j) \end{bmatrix} = \begin{bmatrix} I_{j,\psi_j}^+ \cos(\psi_j + \alpha_j t_j + \Phi_{j,\psi_j}^+) \\ I_{j,\psi_j,\delta_j}^+ \cos(\psi_j + \delta_j + \alpha_j t_j + \Phi_{j,\psi_j,\delta_j}^+) \end{bmatrix},$$

and once in a backward manner to obtain two interferograms for each time domain dimension $t_j$ defining the vector $$C_{j,\psi_j}^-(t_j) := \begin{bmatrix} I_{j,\psi_j}^- c_{\psi_j}^-(t_j) \\ I_{j,\psi_j,\delta_j}^- c_{\psi_j,\delta_j}^-(t_j) \end{bmatrix} = \begin{bmatrix} I_{j,\psi_j}^- \cos(\psi_j - \alpha_j t_j + \Phi_{j,\psi_j}^-) \\ I_{j,\psi_j,\delta_j}^- \cos(\psi_j + \delta_j - \alpha_j t_j + \Phi_{j,\psi_j,\delta_j}^-) \end{bmatrix},$$

wherein $I_{j,\psi_j}^+, I_{j,\psi_j,\delta_j}^+, I_{j,\psi_j}^-,$ and $I_{j,\psi_j,\delta_j}^-$ are amplitudes, $\Psi_j$ and $\Psi_j+\delta_j$ are primary phase shifts with $\Psi_j, \delta_j \in [0,2\pi[$, and $\Phi_{j,\psi_j}^+, \Phi_{j,\psi_j,\delta_j}^+, \Phi_{j,\psi_j}^-,$ and $I_{j,\psi_j,\delta_j}^-$ are secondary phase shifts; multiplying each said vector $C_{j,\psi_j}^+ W(t_j)$ with a D-matrix defined as $$D_j^+ = \begin{bmatrix} \sin(\psi_j + \delta_j) & -\sin(\psi_j) \\ \cos(\psi_j + \delta_j) & -\cos(\psi_j) \end{bmatrix}$$

and each said vector $C_{j,\psi_j}^-(t_j)$ with a D-matrix defined as $$D_j^- = \begin{bmatrix} \sin(\psi_j + \delta_j) & -\sin(\psi_j) \\ -\cos(\psi_j + \delta_j) & \cos(\psi_j) \end{bmatrix};$$

multiplying the said products $D_j^+ \cdot C_{j,\psi_j}^+(t_j)$ and $D_j^- \cdot C_{j,\psi_j}^-(t_j)$ with a vector Q=[1 i], wherein i=$\sqrt{-1}$, according to $Q \cdot D_j^+ \cdot C_{j,\psi_j}^+(t_j)$ and $Q \cdot D_j^- \cdot C_{j,\psi_j}^-(t_j)$ under conditions effective to create a complex time domain of said selected m dimensions according to $$\bigotimes_j Q \cdot D_j^+ \cdot C_{j,\psi_j}^+(t_j) \text{ and } \bigotimes_j Q \cdot D_j^- \cdot C_{j,\psi_j}^-(t_j);$$

repeating said selecting, said phase-sensitive sampling twice and said multiplying ($2^m-2$)-times, thereby sampling the said m dimensions with all $2^m$ possible permutations resulting from selecting for each dimension j either phase-sensitive forward or backward sampling according to $C_{j,\psi_j}^+(t_j)$ or $C_{j,\psi_j}^-(t_j)$; linearly combining said $2^m$ complex time domains; and transforming said linearly combined complex time domain into frequency domain by use of an operator O, under conditions effective to at least partially cancel dispersive and quadrature image peak components arising from $\Phi_{j,\psi_j}^+$, $\Phi_{j,\psi_j,\delta_j}^+$, $\Phi_{j,\psi_j}^-$, and $\Phi_{j,\psi_j,\delta_j}^-$ in said frequency domain.

Suitable NMR experiments for the present invention include, but are not limited to, those described in U.S. Pat. Nos. 6,831,459, 7,141,432, 7,365,539, 7,396,685, and 7,408,346, which are hereby incorporated by reference in their entirety. Any desired sample suitable for NMR experiments may be used.

In the present invention, novel, generally applicable acquisition schemes for phase-sensitive detection of pure absorption mode signals devoid of dispersive components are described. They were established by generalizing mirrored time domain sampling (MS) to 'phase shifted MS' (PMS). MS was originally contemplated for absolute-value 2D resolved NMR spectroscopy (Bachmann et al., *J. Magn. Reson.*, 28:29-39 (1977), which is hereby incorporated by reference in its entirety) and was later introduced for measurement of spin-spin couplings in J-GFT NMR (Atreya et al., *J. Am Chem. Soc.* 129:680-692 (2007), which is hereby incorporated by reference in its entirety).

Phase-sensitive detection of a chemical shift a can be accomplished by sampling the time evolution ('precession') of transverse magnetization twice, under the condition that the two axes along which the time evolution is sampled and thus registered, which yields a time domain 'interferogram', are not collinear. When considering that the time domain can be sampled from time 0 to t ('forward sampling'), as well as from time 0 to −t (backward sampling), three cases can be considered:

(i) Both the interferograms are forward sampled from time 0 to t,
(ii) Both the interferograms are backward sampled from time 0 to −t and
(iii) Combined forward and backward sampling, where one of the two interferograms is forward sampled from time 0 to −t and the other is backward sampled from time 0 to −t (also referred to herein as "mirrored time domain sampling").

(i) Both Interferograms are Forward Sampled

The two interferograms for the $j^{th}$ time dimension in a multidimensional NMR experiment are given by $$C_{j,\psi_j}^+(t_j) = \begin{bmatrix} I_{j,\psi_j}^+ c_{\psi_j}^+(t_j) \\ I_{j,\psi_j,\delta_j}^+ c_{\psi_j,\delta_j}^+(t_j) \end{bmatrix} = \begin{bmatrix} I_{j,\psi_j}^+ \cos(\psi_j + \alpha_j t_j + \Phi_{j,\psi_j}^+) \\ I_{j,\psi_j,\delta_j}^+ \cos(\psi_j + \delta_j + \alpha_j t_j + \Phi_{j,\psi_j,\delta_j}^+) \end{bmatrix}, \quad (B1)$$

where $\psi_j$ is a primary phase shift, $\delta_j$ is the difference of primary phase shifts of the two interferograms, $I_{j,\psi_j}^+$ and $I_{j,\psi_j,\delta_j}^+$ are the amplitudes of the modulations, and $\Phi_{j,\psi_j}^+$, and $\Phi_{j,\psi_j,\delta_j}^+$ are defining secondary phase shifts. Orthogonal phase-sensitive forward sampling, requiring that $\delta_j=\pi/2$, represents known art in the field and is commonly referred to as 'States' sampling or 'quadrature detection' (States et al., *J. Magn. Reson.*, 48:286-292 (1982), which is hereby incorporated by reference in its entirety).

The complex time domain signal $S_{j,\psi_j}^+(t_j)$ resulting from signal detection along the two non-collinear axes is proportional to Addition of $S_{j,\psi_j}^+(t_j)$ and $S_{j,\psi_j}^-(t_j)$ then yields the complex time domain signal for 'dual States' sampling and is proportional to $$S_{j,\psi_j}^+(t_j) \propto QD_j^+ C_{j,\psi_j}^+(t_j) = [1 \quad i]\begin{bmatrix} \sin(\psi_j+\delta_j) & -\sin(\psi_j) \\ \cos(\psi_j+\delta_j) & -\cos(\psi_j) \end{bmatrix}\begin{bmatrix} I_{j,\psi_j}^+ c_{\psi_j}^+(t_j) \\ I_{j,\psi_j,\delta_j}^+ c_{\psi_j,\delta_j}^+(t_j) \end{bmatrix} = \tag{B2}$$

$$[1 \quad i]\begin{bmatrix} \sin(\psi_j+\delta_j) & -\sin(\psi_j) \\ \cos(\psi_j+\delta_j) & -\cos(\psi_j) \end{bmatrix}\begin{bmatrix} I_{j,\psi_j}^+\left(\cos\psi_j\cos(\alpha_j t_j+\Phi_{j,\psi_j}^+)-\sin\psi_j\sin(\alpha_j t_j+\Phi_{j,\psi_j}^+)\right) \\ I_{j,\psi_j,\delta_j}^+\left(\cos(\psi_j+\delta_j)\cos(\alpha_j t_j+\Phi_{j,\psi_j,\delta_j}^+)-\sin(\psi_j+\delta_j)\sin(\alpha_j t_j+\Phi_{j,\psi_j,\delta_j}^+)\right) \end{bmatrix} =$$

$$\sin\psi_j\cos\psi_j\cos\delta_j\left(I_{j,\psi_j}^+\cos\Phi_{j,\psi_j}^+ e^{-i\alpha t}-iI_{j,\psi_j}^+\sin\Phi_{j,\psi_j}^+ e^{-i\alpha t}-I_{j,\psi_j,\delta_j}^+\cos\Phi_{j,\psi_j,\delta_j}^+ e^{-i\alpha t}+iI_{j,\psi_j,\delta_j}^+\sin\Phi_{j,\psi_j,\delta_j}^+ e^{-i\alpha t}\right)-$$

$$\sin\psi_j\cos\psi_j\sin\delta_j\left(I_{j,\psi_j}^+\sin\Phi_{j,\psi_j}^+ e^{-i\alpha t}+iI_{j,\psi_j}^+\cos\Phi_{j,\psi_j}^+ e^{-i\alpha t}-I_{j,\psi_j,\delta_j}^+\sin\Phi_{j,\psi_j,\delta_j}^+ e^{-i\alpha t}-iI_{j,\psi_j,\delta_j}^+\cos\Phi_{j,\psi_j,\delta_j}^+ e^{-i\alpha t}\right)+$$

$$\cos^2\psi_j\sin\delta_j\left(I_{j,\psi_j,\delta_j}^+\cos(\alpha_j t_j+\Phi_{j,\psi_j,\delta_j}^+)+iI_{j,\psi_j,\delta_j}^+\sin(\alpha_j t_j+\Phi_{j,\psi_j,\delta_j}^+)\right)+$$

$$\sin^2\psi_j\sin\delta_j\left(I_{j,\psi_j,\delta_j}^+\cos(\alpha_j t_j+\Phi_{j,\psi_j,\delta_j}^+)+iI_{j,\psi_j}^+\sin(\alpha_j t_j+\Phi_{j,\psi_j}^+)\right)-$$

$$\sin^2\psi_j\cos\delta_j\left(I_{j,\psi_j}^+\sin(\alpha_j t_j+\Phi_{j,\psi_j}^+)-I_{j,\psi_j,\delta_j}^+\sin(\alpha_j t_j+\Phi_{j,\psi_j,\delta_j}^+)\right)+$$

$$\cos^2\psi_j\cos\delta_j\left(iI_{j,\psi_j}^+\cos(\alpha_j t_j+\Phi_{j,\psi_j}^+)-iI_{j,\psi_j,\delta_j}^+\cos(\alpha_j t_j+\Phi_{j,\psi_j,\delta_j}^+)\right)$$

(ii) Both Interferograms are Backward Sampled

The two interferograms for the $j^{th}$ time dimension in a multidimensional NMR experiment are given by $$C_{j,\psi_j}^-(t_j) = \begin{bmatrix} I_{j,\psi_j}^- c_{\psi_j}^-(t_j) \\ I_{j,\psi_j,\delta_j}^- c_{\psi_j,\delta_j}^-(t_j) \end{bmatrix} \tag{B3}$$

$$= \begin{bmatrix} I_{j,\psi_j}^-\cos(\psi_j-\alpha_j t_j+\Phi_{j,\psi_j}^-) \\ I_{j,\psi_j,\delta_j}^-\cos(\psi_j+\delta_j-\alpha_j t_j+\Phi_{j,\psi_j,\delta_j}^-) \end{bmatrix},$$

where $\psi_j$ is a primary phase shift, $\delta_j$ is the difference of primary phase shifts of the two interferograms, $I_{j,\psi_j}^-$ and $I_{j,\psi_j,\delta_j}^-$ are the amplitudes of the modulations, and $\Phi_{j,\psi_j}^-$ and $\Phi_{j,\psi_j,\delta_j}^-$ are defining secondary phase shifts. Orthogonal phase-sensitive backward sampling, requiring that $\delta_j=\pi/2$, represents known art in the field and is also commonly referred to as 'States' sampling or 'quadrature detection' (States et al., *J. Magn. Reson.*, 48:286-292 (1982), which is hereby incorporated by reference in its entirety).

The complex time domain signal $S_{j,\psi_j}^-(t_j)$ resulting from signal detection along the two non-collinear axes is proportional to $$S_{j,\psi_j}^+(t_j)+S_{j,\psi_j}^-(t_j) \propto \tag{B5}$$

$$\sin\psi_j\cos\psi_j\cos\delta_j\left(I_{j,\psi_j}^+\cos\Phi_{j,\psi_j}^+ e^{-i\alpha t}-iI_{j,\psi_j}^+\sin\Phi_{j,\psi_j}^+ e^{-i\alpha t}-\right.$$

$$I_{j,\psi_j,\delta_j}^+\cos\Phi_{j,\psi_j,\delta_j}^+ e^{-i\alpha t}+iI_{j,\psi_j,\delta_j}^+\sin\Phi_{j,\psi_j,\delta_j}^+ e^{-i\alpha t}+$$

$$I_{j,\psi_j}^-\cos\Phi_{j,\psi_j}^- e^{-i\alpha t}+iI_{j,\psi_j}^-\sin\Phi_{j,\psi_j}^- e^{-i\alpha t}-$$

$$I_{j,\psi_j,\delta_j}^-\cos\Phi_{j,\psi_j,\delta_j}^- e^{-i\alpha t}-iI_{j,\psi_j,\delta_j}^-\sin\Phi_{j,\psi_j,\delta_j}^- e^{-i\alpha t}\bigg)-$$

$$\sin\psi_j\cos\psi_j\sin\delta_j\left(I_{j,\psi_j}^+\sin\Phi_{j,\psi_j}^+ e^{-i\alpha t}+iI_{j,\psi_j}^+\cos\Phi_{j,\psi_j}^+ e^{-i\alpha t}-\right.$$

$$I_{j,\psi_j,\delta_j}^+\sin\Phi_{j,\psi_j,\delta_j}^+ e^{-i\alpha t}-iI_{j,\psi_j,\delta_j}^+\cos\Phi_{j,\psi_j,\delta_j}^+ e^{-i\alpha t}+$$

$$I_{j,\psi_j}^-\sin\Phi_{j,\psi_j}^- e^{-i\alpha t}-iI_{j,\psi_j}^-\cos\Phi_{j,\psi_j}^- e^{-i\alpha t}-$$

$$I_{j,\psi_j,\delta_j}^-\sin\Phi_{j,\psi_j,\delta_j}^- e^{-i\alpha t}+iI_{j,\psi_j,\delta_j}^-\cos\Phi_{j,\psi_j,\delta_j}^- e^{-i\alpha t}\bigg)+$$

$$\cos^2\psi_j\sin\delta_j\left(I_{j,\psi_j,\delta_j}^+\cos(\alpha_j t_j+\Phi_{j,\psi_j,\delta_j}^+)+iI_{j,\psi_j}^+\sin(\alpha_j t_j+\Phi_{j,\psi_j,\delta_j}^+)+\right.$$

$$I_{j,\psi_j,\delta_j}^-\cos(\alpha_j t_j-\Phi_{j,\psi_j,\delta_j}^-)+iI_{j,\psi_j,\delta_j}^-\sin(\alpha_j t_j-\Phi_{j,\psi_j,\delta_j}^-)\bigg)+$$

$$\sin^2\psi_j\sin\delta_j\left(I_{j,\psi_j,\delta_j}^+\cos(\alpha_j t_j+\Phi_{j,\psi_j,\delta_j}^+)+iI_{j,\psi_j}^+\sin(\alpha_j t_j+\Phi_{j,\psi_j}^+)+\right.$$

$$I_{j,\psi_j,\delta_j}^-\cos(\alpha_j t_j-\Phi_{j,\psi_j,\delta_j}^-)+iI_{j,\psi_j}^-\sin(\alpha_j t_j-\Phi_{j,\psi_j}^-)\bigg)-$$

$$S_{j,\psi_j}^-(t_j) \propto QD_j^- C_{j,\psi_j}^-(t_j) = [1 \quad i]\begin{bmatrix} \sin(\psi_j+\delta_j) & -\sin(\psi_j) \\ -\cos(\psi_j+\delta_j) & \cos(\psi_j) \end{bmatrix}\begin{bmatrix} I_{j,\psi_j}^- c_{\psi_j}^-(t_j) \\ I_{j,\psi_j,\delta_j}^- c_{\psi_j,\delta_j}^-(t_j) \end{bmatrix} = \tag{B4}$$

$$[1 \quad i]\begin{bmatrix} \sin(\psi_j+\delta_j) & -\sin(\psi_j) \\ -\cos(\psi_j+\delta_j) & \cos(\psi_j) \end{bmatrix}\begin{bmatrix} I_{j,\psi_j}^-\left(\cos\psi_j\cos(\alpha_j t_j-\Phi_{j,\psi_j}^-)+\sin\psi_j\sin(\alpha_j t_j-\Phi_{j,\psi_j}^-)\right) \\ I_{j,\psi_j,\delta_j}^-\left(\cos(\psi_j+\delta_j)\cos(\alpha_j t_j-\Phi_{j,\psi_j,\delta_j}^-)+\sin(\psi_j+\delta_j)\sin(\alpha_j t_j-\Phi_{j,\psi_j,\delta_j}^-)\right) \end{bmatrix} =$$

$$\sin\psi_j\cos\psi_j\cos\delta_j\left(I_{j,\psi_j}^-\cos\Phi_{j,\psi_j}^- e^{-i\alpha t}+iI_{j,\psi_j}^-\sin\Phi_{j,\psi_j}^- e^{-i\alpha t}-I_{j,\psi_j,\delta_j}^-\cos\Phi_{j,\psi_j,\delta_j}^- e^{-i\alpha t}-iI_{j,\psi_j,\delta_j}^-\sin\Phi_{j,\psi_j,\delta_j}^- e^{-i\alpha t}\right)-$$

$$\sin\psi_j\cos\psi_j\sin\delta_j\left(I_{j,\psi_j}^-\sin\Phi_{j,\psi_j}^- e^{-i\alpha t}-iI_{j,\psi_j}^-\cos\Phi_{j,\psi_j}^- e^{-i\alpha t}-I_{j,\psi_j,\delta_j}^-\sin\Phi_{j,\psi_j,\delta_j}^- e^{-i\alpha t}+iI_{j,\psi_j,\delta_j}^-\cos\Phi_{j,\psi_j,\delta_j}^- e^{-i\alpha t}\right)+$$

$$\cos^2\psi_j\sin\delta_j\left(I_{j,\psi_j,\delta_j}^-\cos(\alpha_j t_j-\Phi_{j,\psi_j,\delta_j}^-)+iI_{j,\psi_j,\delta_j}^-\sin(\alpha_j t_j-\Phi_{j,\psi_j,\delta_j}^-)\right)+$$

$$\sin^2\psi_j\sin\delta_j\left(I_{j,\psi_j,\delta_j}^-\cos(\alpha_j t_j-\Phi_{j,\psi_j,\delta_j}^-)+iI_{j,\psi_j}^-\sin(\alpha_j t_j-\Phi_{j,\psi_j}^-)\right)+$$

$$\sin^2\psi_j\cos\delta_j\left(I_{j,\psi_j}^-\sin(\alpha_j t_j-\Phi_{j,\psi_j}^-)-I_{j,\psi_j,\delta_j}^-\sin(\alpha_j t_j-\Phi_{j,\psi_j,\delta_j}^-)\right)-$$

$$\cos^2\psi_j\cos\delta_j\left(iI_{j,\psi_j}^-\cos(\alpha_j t_j-\Phi_{j,\psi_j}^-)-iI_{j,\psi_j,\delta_j}^-\cos(\alpha_j t_j+\Phi_{j,\psi_j,\delta_j}^-)\right)$$

-continued $$\sin^2\psi_j\cos\delta_j(I^+_{j,\psi_j}\sin(\alpha_j t_j + \Phi^+_{j,\psi_j}) - I^+_{j,\psi_j,\delta_j}\sin(\alpha_j t_j + \Phi^+_{j,\psi_j,\delta_j}) -$$

$$I^-_{j,\psi_j}\sin(\alpha_j t_j - \Phi^-_{j,\psi_j}) + I^-_{j,\psi_j,\delta_j}\sin(\alpha_j t_j - \Phi^-_{j,\psi_j,\delta_j})) + \cos^2\psi_j$$

$$\cos\delta_j(iI^+_{j,\psi_j}\cos(\alpha_j t_j + \Phi^+_{j,\psi_j}) - iI^+_{j,\psi_j,\delta_j}\cos(\alpha_j t_j + \Phi^+_{j,\psi_j,\delta_j}) -$$

$$iI^-_{j,\psi_j}\cos(\alpha_j t_j - \Phi^-_{j,\psi_j}) + iI^-_{j,\psi_j,\delta_j}\cos(\alpha_j t_j - \Phi^-_{j,\psi_j,\delta_j})).$$

For identical amplitudes, that is $I^+_{j,\psi_j}=I^+_{j,\psi_j,\delta_j}=I^-_{j,\psi_j}=I^-_{j,\psi_j,\delta_j}=I_j$, and identical secondary phases, that is $\Phi^+_{j,\psi_j}=\Phi_j$, $\Phi^+_{j,\psi_j,\delta_j}=\Phi^-_{j,\psi_j}=\Phi^-_{j,\psi_j,\delta_j}=\psi_j$, Eq. (B5) simplifies to $$S^+_{j,\psi_j}(t_j)+S^-_{j,\psi_j}(t_j)\propto 2\sin\delta_j I_j\cos\Phi_j e^{i\alpha t} \quad (B6).$$

Inspection of Eq. (B6) reveals that Fourier Transformation (FT) of signals acquired by use of 'dual States' yields absorptive spectrum. Furthermore, the intensity of the frequency domain peaks is maximum for orthogonal sampling ($\delta_j=\pi/2$ or $3\pi/2$).

(iii) One Interferogram is Forward and the Other Backward Sampled

The two interferograms for the $j^{th}$ time dimension in a multidimensional NMR experiment are given by $$C_{j,\psi_j}(t_j) = \begin{bmatrix} I^+_{j,\psi_j}c^+_{\psi_j}(t_j) \\ I^-_{j,\psi_j,\delta_j}c^-_{\psi_j,\delta_j}(t_j) \end{bmatrix} \quad (B7)$$

$$= \begin{bmatrix} I^+_{j,\psi_j}\cos(\psi_j + \alpha_j t_j + \Phi^+_{j,\psi_j}) \\ I^-_{j,\psi_j,\delta_j}\cos(\psi_j + \delta_j - \alpha_j t_j + \Phi^-_{j,\psi_j,\delta_j}) \end{bmatrix},$$

where $\psi_j$ is a primary phase shift, $\delta_j$ is the difference of primary phase shifts of the two interferograms, $I^+_{j,\psi_j}$ and $I^-_{j,\psi_j,\delta_j}$ are the amplitudes of the modulations, and $\Phi^+_{j,\psi_j}$ and $\Phi^-_{j,\psi_j,\delta_j}$ are defining secondary phase shifts. Phase-sensitive signal detection requires that $\psi_j \neq n\pi/2$ if $\delta_j=0$.

The resulting complex time domain signal $S_{j,\psi_j}(t_j)$ is proportional to $$S_{j,\psi_j}(t_j) \propto QD_j C_{j,\psi_j}(t_j) = [1\ i]\begin{bmatrix} \sin(\psi_j+\delta_j) & \sin(\psi_j) \\ -\cos(\psi_j+\delta_j) & \cos(\psi_j) \end{bmatrix}\begin{bmatrix} I_{j,\psi_j}c_{\psi_j}(t_j) \\ I_{j,\psi_j,\delta_j}c_{\psi_j,\delta_j}(t_j) \end{bmatrix} = \quad (B8)$$

$$[1\ i]\begin{bmatrix} \sin(\psi_j+\delta_j) & \sin(\psi_j) \\ -\cos(\psi_j+\delta_j) & \cos(\psi_j) \end{bmatrix}\begin{bmatrix} I_{j,\psi_j}(\cos\psi_j\cos(\alpha_j t_j+\Phi_{j,\psi_j})-\sin\psi_j\sin(\alpha_j t_j+\Phi_{j,\psi_j})) \\ I_{j,\psi_j,\delta_j}(\cos(\psi_j+\delta_j)\cos(\alpha_j t_j-\Phi_{j,\psi_j,\delta_j})+\sin(\psi_j+\delta_j)\sin(\alpha_j t_j-\Phi_{j,\psi_j,\delta_j})) \end{bmatrix} =$$

$$\sin\psi_j\cos\psi_j\cos\delta_j(I_{j,\psi_j}\cos\Phi_{j,\psi_j}e^{-i\alpha t}+iI_{j,\psi_j}\sin\Phi_{j,\psi_j}e^{i\alpha t}+I_{j,\psi_j,\delta_j}\cos\Phi_{j,\psi_j,\delta_j}e^{i\alpha t}-iI_{j,\psi_j,\delta_j}\sin\Phi_{j,\psi_j,\delta_j}e^{i\alpha t})-$$

$$\sin\psi_j\cos\psi_j\sin\delta_j(I_{j,\psi_j}\sin\Phi_{j,\psi_j}e^{i\alpha t}-iI_{j,\psi_j}\cos\Phi_{j,\psi_j}e^{i\alpha t}+I_{j,\psi_j,\delta_j}\sin\Phi_{j,\psi_j,\delta_j}e^{i\alpha t}+iI_{j,\psi_j,\delta_j}\cos\Phi_{j,\psi_j,\delta_j}e^{i\alpha t})+$$

$$\cos^2\psi_j\sin\delta_j(I_{j,\psi_j}\cos(\alpha_j t_j+\Phi_{j,\psi_j})+iI_{j,\psi_j,\delta_j}\sin(\alpha_j t_j-\Phi_{j,\psi_j,\delta_j}))-$$

$$\sin^2\psi_j\sin\delta_j(I_{j,\psi_j}\cos(\alpha_j t_j-\Phi_{j,\psi_j,\delta_j})+iI_{j,\psi_j}\sin(\alpha_j t_j+\Phi_{j,\psi_j}))-$$

$$\sin^2\psi_j\cos\delta_j(I_{j,\psi_j}\sin(\alpha_j t_j+\Phi_{j,\psi_j})-I_{j,\psi_j,\delta_j}\sin(\alpha_j t_j-\Phi_{j,\psi_j,\delta_j}))-$$

$$\cos^2\psi_j\cos\delta_j(iI_{j,\psi_j}\cos(\alpha_j t_j+\Phi_{j,\psi_j})-iI_{j,\psi_j,\delta_j}\cos(\alpha_j t_j-\Phi_{j,\psi_j,\delta_j})).$$

When increasing $\psi_j$ by $\pi/2$ while $\delta_j$ remains unchanged, $S_{j,\psi_j}(t_j)$ takes the form $$S_{j,\psi_j+\frac{\pi}{2}}(t_j) \propto \quad (B9)$$

$$-\sin\psi_j\cos\psi_j\cos\delta_j\left(I_{j,\psi_j+\frac{\pi}{2}}\cos\Phi_{j,\psi_j+\frac{\pi}{2}}e^{i\alpha t}+iI_{j,\psi_j+\frac{\pi}{2}}\sin\Phi_{j,\psi_j+\frac{\pi}{2}}e^{i\alpha t}+\right.$$

-continued $$I_{j,\psi_j+\frac{\pi}{2},\delta_j}\cos\Phi_{j,\psi_j+\frac{\pi}{2},\delta_j}e^{i\alpha t}-iI_{j,\psi_j+\frac{\pi}{2},\delta_j}\sin\Phi_{j,\psi_j+\frac{\pi}{2},\delta_j}e^{i\alpha t})+$$

$$\sin\psi_j\cos\psi_j\sin\delta_j\left(I_{j,\psi_j+\frac{\pi}{2}}\sin\Phi_{j,\psi_j+\frac{\pi}{2}}e^{i\alpha t}-iI_{j,\psi_j+\frac{\pi}{2}}\cos\Phi_{j,\psi_j+\frac{\pi}{2}}e^{i\alpha t}+\right.$$

$$I_{j,\psi_j+\frac{\pi}{2},\delta_j}\sin\Phi_{j,\psi_j+\frac{\pi}{2},\delta_j}e^{i\alpha t}+iI_{j,\psi_j+\frac{\pi}{2},\delta_j}\cos\Phi_{j,\psi_j+\frac{\pi}{2},\delta_j}e^{i\alpha t})+$$

$$\cos^2\psi_j\sin\delta_j\left(I_{j,\psi_j+\frac{\pi}{2}}\cos(\alpha_j t_j+\Phi_{j,\psi_j+\frac{\pi}{2}})+\right.$$

$$iI_{j,\psi_j+\frac{\pi}{2},\delta_j}\sin(\alpha_j t_j-\Phi_{j,\psi_j+\frac{\pi}{2},\delta_j}))-$$

$$\sin^2\psi_j\sin\delta_j\left(I_{j,\psi_j+\frac{\pi}{2},\delta_j}\cos(\alpha_j t_j-\Phi_{j,\psi_j+\frac{\pi}{2},\delta_j})+\right.$$

$$iI_{j,\psi_j+\frac{\pi}{2}}\sin(\alpha_j t_j+\Phi_{j,\psi_j+\frac{\pi}{2}}))-\sin^2\psi_j\cos\delta_j\left(\right.$$

$$I_{j,\psi_j+\frac{\pi}{2}}\sin(\alpha_j t_j+\Phi_{j,\psi_j+\frac{\pi}{2}})-I_{j,\psi_j+\frac{\pi}{2},\delta_j}\sin(\alpha_j t_j-\Phi_{j,\psi_j+\frac{\pi}{2},\delta_j}))-$$

$$\cos^2\psi_j\cos\delta_j(iI_{j,\psi_j+\frac{\pi}{2}}\cos(\alpha_j t_j+\Phi_{j,\psi_j+\frac{\pi}{2}})-$$

$$iI_{j,\psi_j+\frac{\pi}{2},\delta_j}\cos(\alpha_j t_j-\Phi_{j,\psi_j+\frac{\pi}{2},\delta_j})).$$

Subtraction of $$S_{j,\psi_j+\frac{\pi}{2}}(t_j)$$

from $S_{j,\psi_j}(t_j)$ yields the complex time domain signal for such 'dual combined forward and backward' sampling, which is proportional to $$S_{j,\psi_j}(t_j)+S_{j,\psi_j+\frac{\pi}{2}}(t_j) \propto \quad (B10)$$

$$\sin\psi_j\cos\psi_j\cos\delta_j(I_{j,\psi_j}\cos\Phi_{j,\psi_j}e^{i\alpha t}+iI_{j,\psi_j}\sin\Phi_{j,\psi_j}e^{i\alpha t}+$$

$$I_{j,\psi_j,\delta_j}\cos\Phi_{j,\psi_j,\delta_j}e^{i\alpha t}-iI_{j,\psi_j,\delta_j}\sin\Phi_{j,\psi_j,\delta_j}e^{i\alpha t}+$$

$$I_{j,\psi_j+\frac{\pi}{2}}\cos\Phi_{j,\psi_j+\frac{\pi}{2}}e^{i\alpha t}+iI_{j,\psi_j+\frac{\pi}{2},\delta_j}\sin\Phi_{j,\psi_j+\frac{\pi}{2},\delta_j}e^{i\alpha t}+$$

-continued $$I_{j,\psi_j+\frac{\pi}{2},\delta_j}\cos\Phi_{j,\psi_j+\frac{\pi}{2},\delta_j}e^{i\alpha t}-iI_{j,\psi_j+\frac{\pi}{2},\delta_j}\sin\Phi_{j,\psi_j+\frac{\pi}{2},\delta_j}e^{i\alpha t})-$$

$$\sin\psi_j\cos\psi_j\sin\delta_j(I_{j,\psi_j}\sin\Phi_{j,\psi_j}e^{i\alpha t}-iI_{j,\psi_j}\cos\Phi_{j,\psi_j}e^{i\alpha t}+$$

$$I_{j,\psi_j,\delta_j}\sin\Phi_{j,\psi_j,\delta_j}e^{i\alpha t}+iI_{j,\psi_j,\delta_j}\cos\Phi_{j,\psi_j,\delta_j}e^{i\alpha t}+$$

$$I_{j,\psi_j+\frac{\pi}{2}}\sin\Phi_{j,\psi_j+\frac{\pi}{2}}e^{i\alpha t}-iI_{j,\psi_j+\frac{\pi}{2}}\cos\Phi_{j,\psi_j+\frac{\pi}{2}}e^{i\alpha t}+$$

-continued $$I_{j,\psi_j+\frac{\pi}{2},\delta_j}\sin\Phi_{j,\psi_j+\frac{\pi}{2},\delta_j}e^{i\alpha t} + iI_{j,\psi_j+\frac{\pi}{2},\delta_j}\cos\Phi_{j,\psi_j+\frac{\pi}{2},\delta_j}e^{i\alpha t}) +$$

$$\sin\delta_j(\cos^2\psi_j(I_{j,\psi_j}\cos(\alpha_j t_j + \Phi_{j,\psi_j}) +$$

$$iI_{j,\psi_j,\delta_j}\sin(\alpha_j t_j - \Phi_{j,\psi_j,\delta_j})) -$$

$$\sin^2\psi_j(I_{j,\psi_j+\frac{\pi}{2}}\cos(\alpha_j t_j + \Phi_{j,\psi_j+\frac{\pi}{2}}) +$$

$$iI_{j,\psi_j+\frac{\pi}{2},\delta_j}\sin(\alpha_j t_j - \Phi_{j,\psi_j+\frac{\pi}{2},\delta_j}))) -$$

$$\sin\delta_j(\sin^2\psi_j(I_{j,\psi_j}^-\cos(\alpha_j t_j - \Phi_{j,\psi_j,\delta_j}) + iI_{j,\psi_j}\sin(\alpha_j t_j + \Phi_{j,\psi_j})) -$$

$$\cos^2\psi_j(I_{j,\psi_j+\frac{\pi}{2},\delta_j}^-\cos(\alpha_j t_j - \Phi_{j,\psi_j+\frac{\pi}{2},\delta_j}) +$$

$$iI_{j,\psi_j+\frac{\pi}{2}}\sin(\alpha_j t_j + \Phi_{j,\psi_j+\frac{\pi}{2}}))) -$$

$$\cos\delta_j(\sin^2\psi_j(I_{j,\psi_j}\sin(\alpha_j t_j + \Phi_{j,\psi_j}) -$$

$$I_{j,\psi_j,\delta_j}\sin(\alpha_j t_j - \Phi_{j,\psi_j,\delta_j})) -$$

$$\cos^2\psi_j(I_{j,\psi_j+\frac{\pi}{2}}\sin(\alpha_j t_j + \Phi_{j,\psi_j+\frac{\pi}{2}}) -$$

$$I_{j,\psi_j+\frac{\pi}{2},\delta_j}\sin(\alpha_j t_j - \Phi_{j,\psi_j+\frac{\pi}{2},\delta_j}))) -$$

$$\cos\delta_j(\cos^2\psi_j(iI_{j,\psi_j,\delta_j}\cos(\alpha_j t_j + \Phi_{j,\psi_j}) -$$

$$iI_{j,\psi_j,\delta_j}\cos(\alpha_j t_j - \Phi_{j,\psi_j,\delta_j})) -$$

$$\sin^2\psi_j(iI_{j,\psi_j+\frac{\pi}{2}}\cos(\alpha_j t_j + \Phi_{j,\psi_j+\frac{\pi}{2}}) -$$

$$iI_{j,\psi_j+\frac{\pi}{2},\delta_j}\cos(\alpha_j t_j - \Phi_{j,\psi_j+\frac{\pi}{2},\delta_j})))).$$

For identical amplitudes, that is $$I_{j,\psi_j} = I_{j,\psi_j,\delta_j} = I_{j,\psi_j+\frac{\pi}{2}} = I_{j,\psi_j+\frac{\pi}{2},\delta_j} = I_j, \text{ and}$$

identical secondary phases, that is $$\Phi_{j,\psi_j} = \Phi_{j,\psi_j,\delta_j} = \Phi_{j,\psi_j+\frac{\pi}{2}} = \Phi_{j,\psi_j+\frac{\pi}{2},\delta_j} = \Phi_j,$$

Eq. (B10) simplifies to $$S_{j,\psi_j}(t_j) - S_{j,\psi_j+\frac{\pi}{2}}(t_j) \propto 2I_j\sin(2\psi_j + \delta_j + \Phi_j)e^{i\alpha t}. \quad (B11)$$

Inspection of Eq. (B11) reveals that FT of dual combined forward and backward sampling yields absorption mode spectra for $|2\psi_j+\delta_j+\Phi_j|=(2n+1)*\pi/2$.

Alternatively, the time domain signal of Eq, (B9) can also be obtained with an increasing of $\psi_j$ by $3\pi/2$ and an unchanged $\delta_j$, followed by addition of the resulting signal with $S_{j,\psi_j}(t_j)$.

In the following, explicit calculations are performed for primary phase shifts which are integral multiples of $\pi/4$, that is $\psi_j=n\pi/4$ and $\psi_j+\delta_j=m\pi/4$ along with $I_{j,\psi_j}=I_{j,\psi_j,\delta_j}=1$, so that, for brevity, interferograms corresponding to the two integers (n,m) are denoted as $$C_{\pm n,\pm m}(t) = \begin{bmatrix} c_{\pm n}(t) \\ c_{\pm m}(t) \end{bmatrix} = \begin{bmatrix} \cos\left(\pm\alpha t + \frac{n\pi}{4} + \Phi_{\pm n}\right) \\ \cos\left(\pm\alpha t + \frac{m\pi}{4} + \Phi_{\pm m}\right) \end{bmatrix}, \quad (B12)$$

where '±' indicate forward ('+') and backward ('−') sampling. Table 1 provides a survey of the cases discussed in the following.

TABLE 1

Definition of interferograms

| $\psi_j$ | $\delta_j$ | n | m | Identities |
|---|---|---|---|---|
| 0 | $\pi/2$ | 0 | 2 | $c_0^+(t_j) \equiv c_{+0}(t_j)$ |
|  |  |  |  | $c_{0,\frac{\pi}{2}}^+(t_j) \equiv c_{+2}(t_j)$ |
| 0 | $\pi/2$ | 0 | 2 | $c_0^-(t_j) \equiv c_{-0}(t_j)$ |
|  |  |  |  | $c_{0,\frac{\pi}{2}}^-(t_j) \equiv c_{-2}(t_j)$ |
| $\pi/4$ | 0 | 1 | 1 | $c_{\frac{\pi}{4}}^+(t_j) \equiv c_{+1}(t_j)$ |
|  |  |  |  | $c_{\frac{\pi}{4},0}^-(t_j) \equiv c_{-1}(t_j)$ |
| $3\pi/4$ | 0 | 3 | 3 | $c_{\frac{3\pi}{4}}^+(t_j) \equiv c_{+3}(t_j)$ |
|  |  |  |  | $c_{\frac{3\pi}{4},0}^-(t_j) \equiv c_{-3}(t_j)$ |
| 0 | $\pi/2$ | 0 | 2 | $c_0^+(t_j) \equiv c_{+0}(t_j)$ |
|  |  |  |  | $c_{0,\frac{\pi}{2}}^-(t_j) \equiv c_{-2}(t_j)$ |
| $\pi/2$ | $3\pi/2$ | 2 | 0 | $c_{\frac{\pi}{2}}^+(t_j) \equiv c_{+2}(t_j)$ |
|  |  |  |  | $c_{\frac{\pi}{2},\frac{3\pi}{2}}^-(t_j) \equiv c_{-0}(t_j)$ |

Equations are thus derived for the complex time domain signal S(t), for a given chemical shift α assuming that the two secondary phase shifts are identical, that is $\phi_{\pm n}=\phi_{\pm m}=\phi$.

Figure 1A:
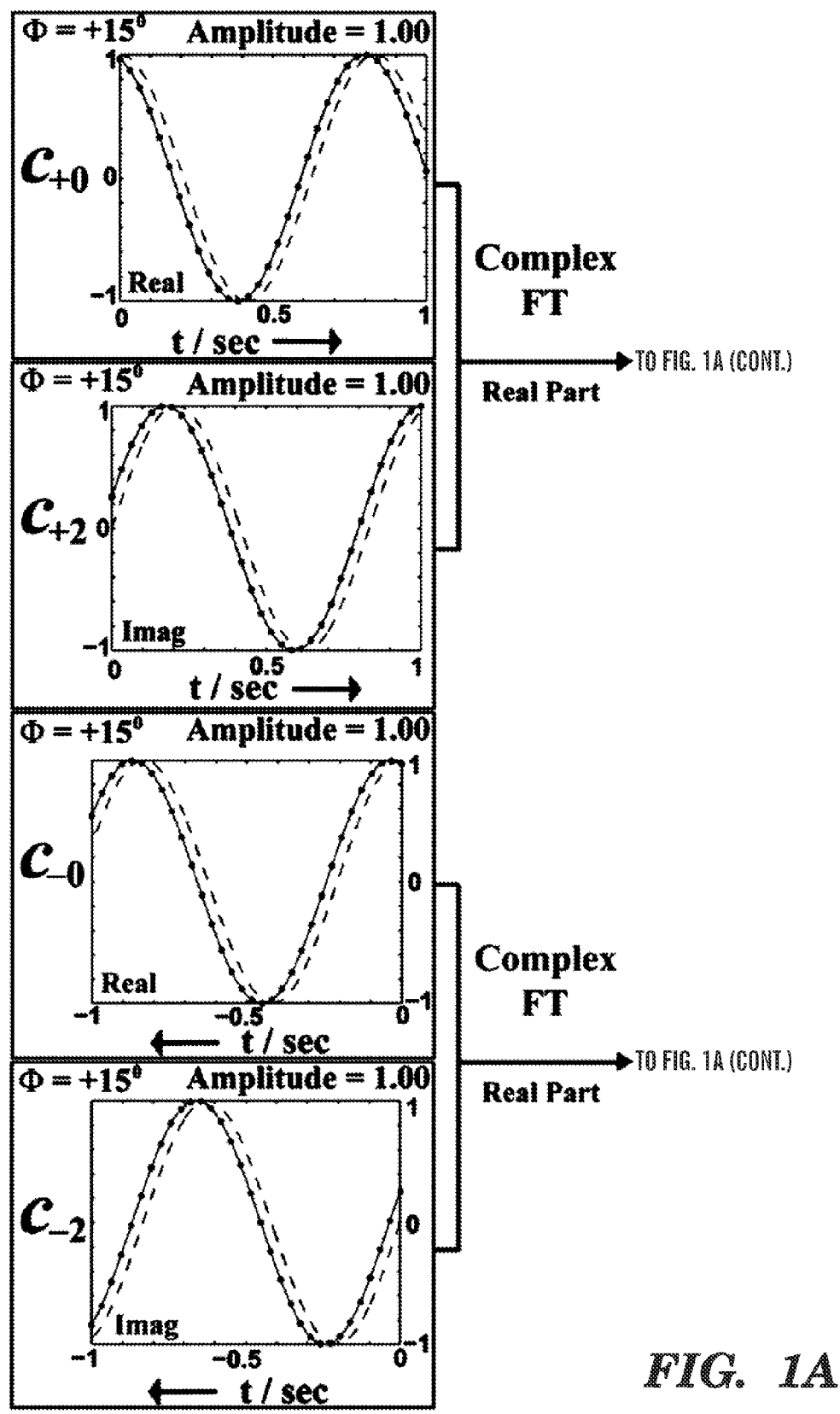
FIGS. 1A-B illustrate clean absorption mode NMR data acquisition.
Figure 1A:
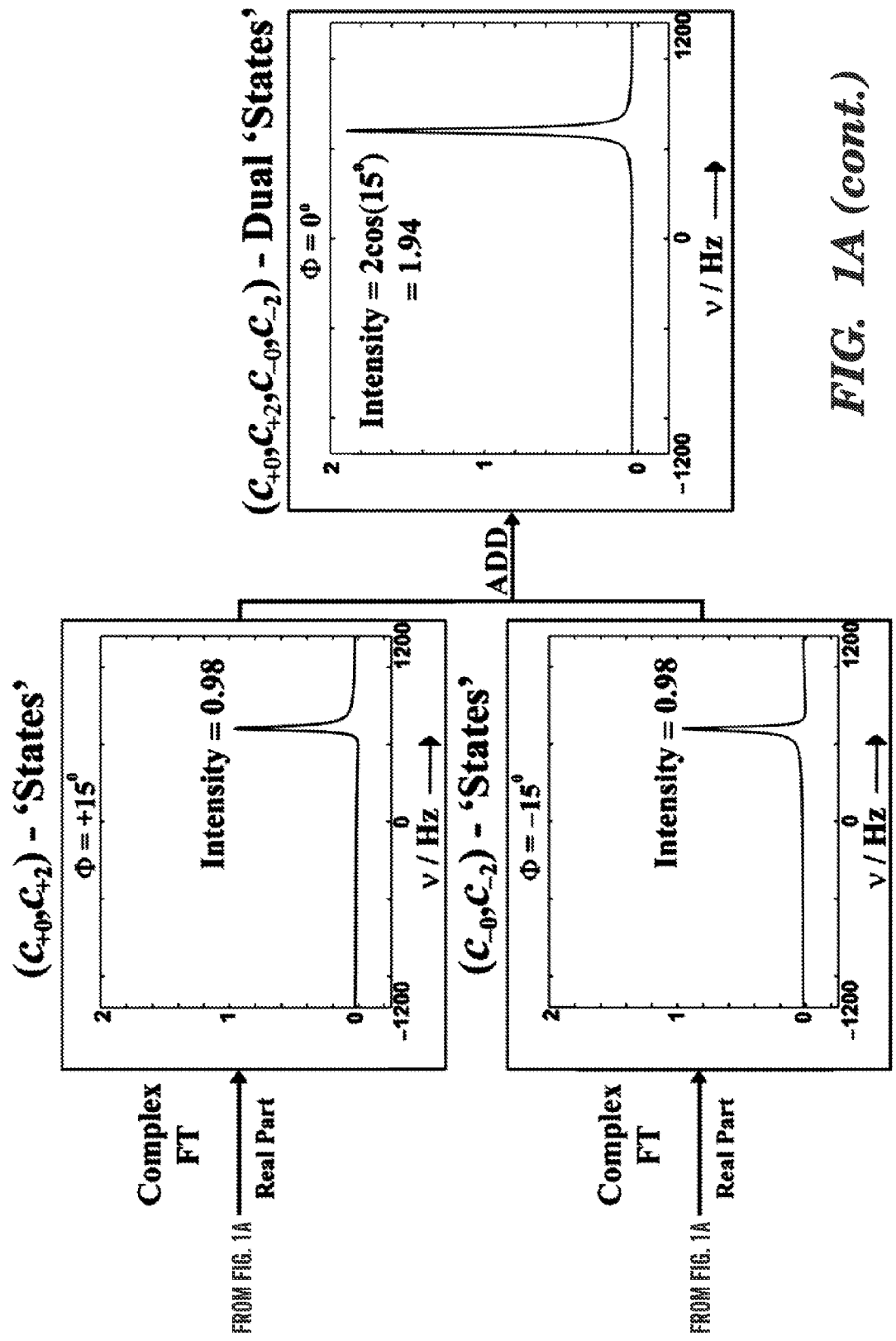
Figure 1B:
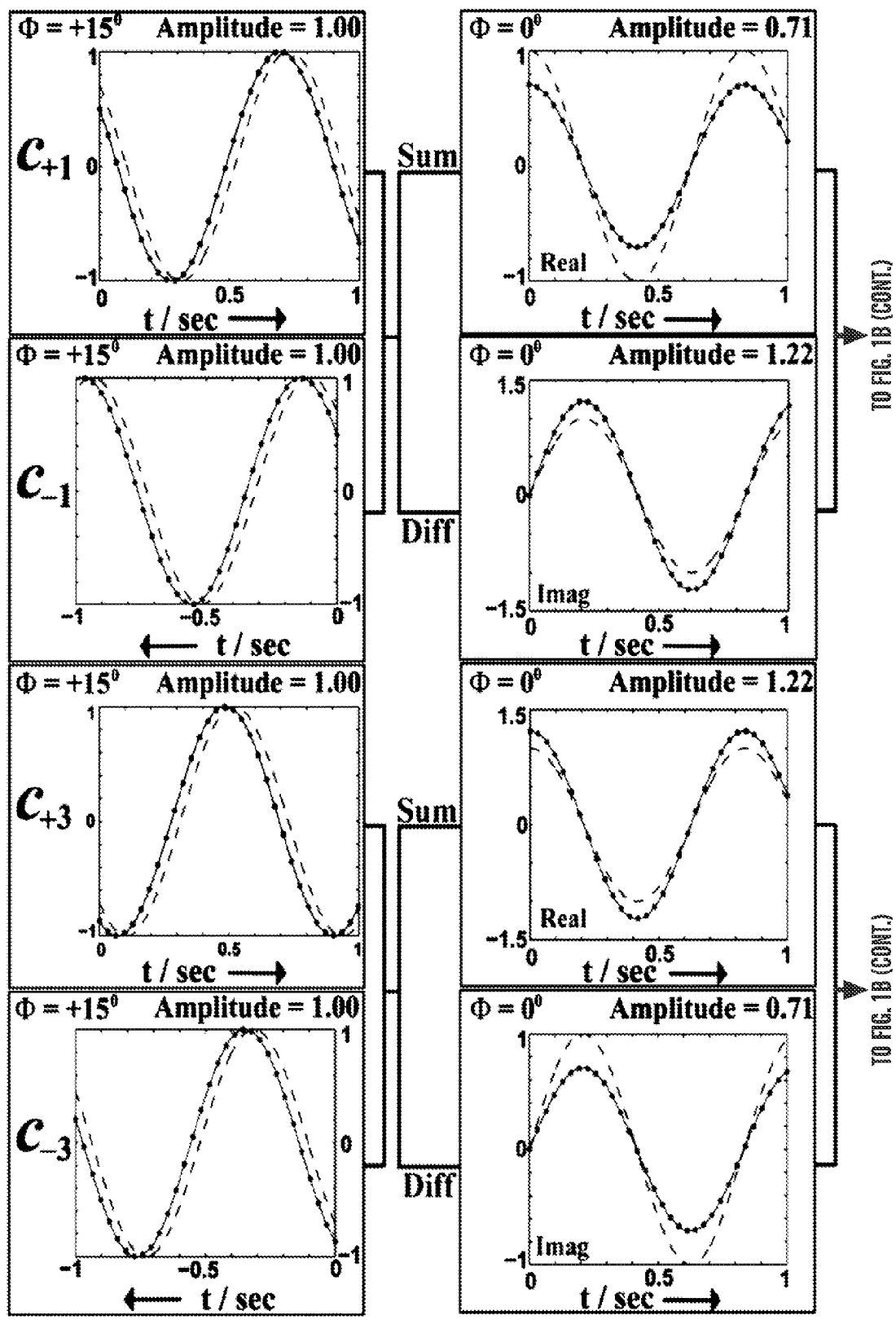
Figure 1B:
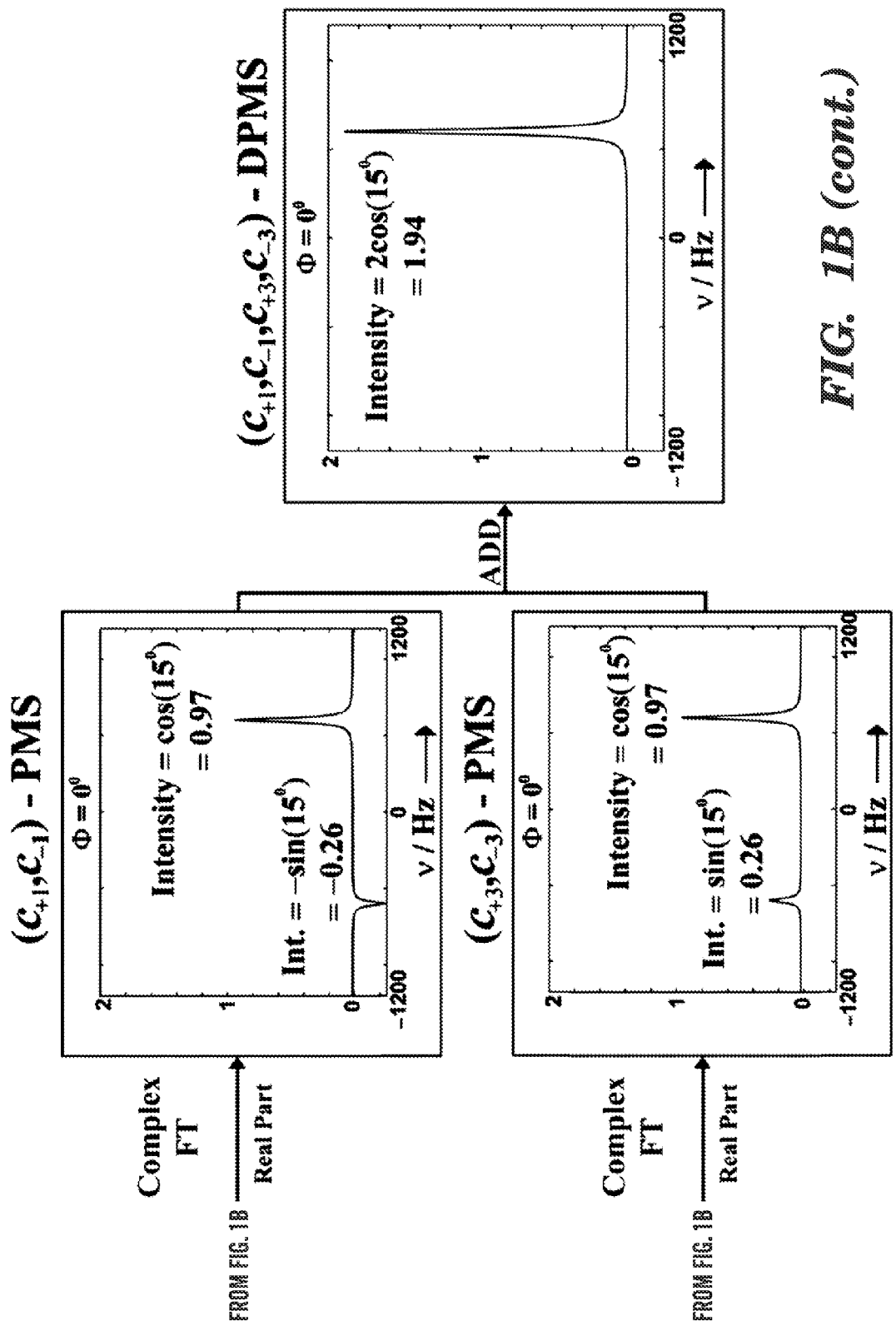

Forward sampling with n=0 and 2 results in 'States' quadrature detection, (Ernst et al., "Principles of Nuclear Magnetic Resonance in One and Two Dimensions," Oxford: Oxford University Press (1987); Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994), which are hereby incorporated by reference in their entirety) which is denoted ($c_{-0},c_{+2}$)-sampling here and yields a signal $S(t)\propto\cos\Phi e^{i\alpha t}+\sin\Phi e^{i\pi/2}e^{i\alpha t}$. Corresponding backward ($c_{-0}$, $c_{-2}$)-sampling yields $S(t)\propto\cos\Phi e^{i\alpha t}-\sin\Phi e^{i\pi/2}e^{i\alpha t}$, so that addition of the two spectra (corresponding to 'Dual States' ($c_{+0},c_{+2},c_{-0},c_{-2}$)-sampling) cancels the dispersive components. Thus, a clean absorption mode signal $S(t)\propto\cos\phi\ e^{i\alpha t}$ is detected (FIGS. 1A-B).

Forward sampling and backward sampling with n=1 results in ($c_{+1},c_{-1}$)-PMS, which yields $S(t)\propto\cos\Phi e^{i\alpha t}-\sin\Phi e^{-i\alpha t}$, i.e., two absorptive signals are detected: the desired signal at frequency α with relative intensity cos Φ, and a quadrature image ('quad') peak at frequency −α with intensity sin Φ. ($c_{+1},c_{-1}$)-PMS thus eliminates a dispersive component by transformation into an absorptive quad peak. Without phase correction, this results in clean absorption mode signals (FIGS. 1A-B). Corresponding ($c_{+3},c_{-3}$)-PMS sampling yields $S(t)\propto\cos\Phi e^{i\alpha t}+\sin\Phi e^{-i\alpha t}$, so that the quad peak is of opposite sign when compared with $(c_{+1},c_{-1})$-PMS. Addition of the two spectra cancels the quad peak (FIGS. 1A-B), and such combined $(c_{+1},c_{-1},c_{+3},c_{-3})$-sampling is named dual PMS (DPMS).

Forward sampling with n=0 and backward sampling with n=2 results in $(c_{-0},c_{-2})$-PMS yielding $S(t) \propto \cos \Phi e^{i\alpha t} - \sin \Phi e^{i\pi/2} e^{-i\alpha t}$, i.e., the quad peak is dispersive. This feature allows one to distinguish genuine and quad peaks if required. In $(c_{-0},c_{+2})$-PMS, the quad peak is of opposite sign when compared with $(C_{+0},c_{-2})$-PMS, i.e., $S(t) \propto \cos \Phi e^{i\alpha t} + \sin \Phi e^{i\pi/2} e^{-i\alpha t}$. Thus, $(c_{+0},c_{-2},c_{-0},c_{+2})$-DPMS likewise enables cancellation of the quad peak yielding solely clean absorption mode signals.

PMS can be applied to an arbitrary number of indirect dimensions of a multi-dimensional experiment. For example, $(c_{+1},c_{-1})$-PMS of K+1 chemical shifts $\alpha_0, \alpha_1, \ldots \alpha_K$ with phase errors $\Phi_0, \Phi_1, \ldots \Phi_K$ yields a purely absorptive peak at $(\alpha_0, \alpha_1, \ldots \alpha_K)$ with relative intensity $\pi^K_{j=0} \cos\Phi_j$, while the quad peak intensities are proportional to $\cos \Phi_j$ for every $+\alpha_j$ and to $\sin \Phi_j$ for every $-\alpha_j$ in the peak coordinates. PMS can likewise be applied to an arbitrary sub-set of the chemical shift evolution periods jointly sampled in GFT NMR. For example, joint $(c_{+1},c_{-1})$-PMS of K+1 chemical shifts $\alpha_0,\alpha_1, \ldots \alpha_K$ yields a peak at the desired linear combination of chemical shifts with relative intensity of $\pi^K_{j=0} \cos \Phi_j$, while peaks located at different linear combinations of shifts exhibit intensities proportional to $\cos \Phi_j$ for all $\alpha_j$ for which the sign of the chemical shift in the linear combination does not change, and proportional to $\sin \Phi_j$ for all $\alpha_j$ for which the sign in the linear combination does change. Hence, PMS converts dispersive GFT NMR peak components into both quad and 'cross-talk' peaks. For a given sub-spectrum, the latter peaks are located at linear combinations of chemical shifts which are detected in the other sub-spectra (Kim et al., *J. Am. Chem. Soc.* 125:1385-1393 (2003); Atreya et al., *Proc. Natl. Acad. Sci. USA* 101:9642-9647 (2004); Xia et al., *J. Biomol. NMR* 29:467-476 (2004); Eletsky et al., *J. Am. Chem. Soc.* 127, 14578-14579 (2005); Yang et al., *J. Am Chem. Soc.* 127:9085-9099 (2005); Atreya et al., *Methods Enzymol.* 394:78-108 (2005); Liu et al., *Proc. Natl. Acad. Sci. U.S.A.* 102:10487-10492 (2005); Atreya et al., *J. Am Chem. Soc.* 129:680-692 (2007), which are hereby incorporated by reference in their entirety). Furthermore, arbitrary combinations of time domain sampling schemes can be employed in multi-dimensional NMR, including GFT NMR.

Clean absorption mode data acquisition leads to a reduction of the signal maximum (and therefore the signal-to-noise ratio (S/N)) relative to a hypothetical absorptive signal by a factor of $\cos \Phi$ (see above). It is therefore advantageous to employ the commonly used repertoire (Ernst et al., "Principles of Nuclear Magnetic Resonance in One and Two Dimensions," Oxford: Oxford University Press (1987); Jacobsen, N. E., "NMR Spectroscopy Explained," Wiley, New York (2007); Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994); Messerle et al., *J. Magn. Reson.* 85:608-613 (1989); Keeler et al., *Methods Enzymol.* 239:145-207 (1994); Sorensen et al., *J. Magn. Reson.* 56:527-534 (1984), which are hereby incorporated by reference in their entirety) of techniques to avoid phase corrections, so that only residual dispersive components have to be removed. For routine applications, however, the reduction in S/N is then hardly significant: assuming that residual phase errors are $|\Phi|<15°$, one obtains a reduction of <3.4%. Moreover, the superposition of a dispersive component on an absorptive peak in a conventionally acquired spectrum likewise reduces the signal maximum. As a result, the actual loss for $|\Phi|<15°$ is <1.7% (FIG. 2).

$(c_{+1},c_{-1})$-PMS and $(c_{+3},c_{-3})$-PMS are unique since they yield clean absorption mode spectra (FIG. 1) with the same measurement time as is required for 'States' acquisition. Whenever the quad peaks (and cross talk peaks in GFT NMR), which exhibit a relative intensity proportional to $\sin \Phi$, emerge in otherwise empty spectral regions, they evidently do not interfere with spectral analysis and there is no need for their removal (when in doubt, $(c_{+0},c_{-2})$-PMS and $(c_{-0},c_{+2})$-PMS allows one to identify quad peaks since they are purely dispersive). Furthermore, sensitivity limited data acquisition (Szyperski et al., *Proc. Natl. Acad. Sci. USA* 99:8009-8014 (2002), which is hereby incorporated by reference in its entirety) is often desirable (e.g., with an average S/N 5). For $|\Phi|<15°$, $\sin \Phi<0.26$ implies that quad and cross-talk peaks exhibit intensities ~1.25 times the noise level, so that they are within the noise.

Suppression of axial peaks and residual solvent peaks is routinely accomplished using a two-step phase cycle (Ernst et al., "Principles of Nuclear Magnetic Resonance in One and Two Dimensions," Oxford: Oxford University Press (1987); Cavanagh et al., "Protein NMR Spectroscopy," 2nd Ed., San Diego: Academic Press (2007), which are hereby incorporated by reference in their entirety). In particular when studying molecules which exhibit resonances close those of the solvent line (e.g. $^1H^\alpha$ resonances of proteins dissolved in $^1H_2O$) such additional suppression of the solvent line is most often required. DPMS schemes can be readily concatenated with the two-step cycle (see discussion below), that is, DPMS spectra can be acquired with the same measurement as a conventional 2-step phase cycled NMR experiment. In solid state NMR relying on magic angle spinning of the sample (Schmidt-Rohr et al., "Multidimensional Solid-State NMR and Polymers," New York: Academic Press (1994), which is hereby incorporated by reference in its entirety), artifact suppression relies primarily on phase cycling, and such concatenation of (multiple) DPMS and phase cycles enables one to obtain clean absorption mode spectra without investment of additional spectrometer time.

Application for Non-Identical Secondary Phase Shifts

One aspect of the present invention relates to a general application for non-identical secondary phase shifts, where secondary phase shift associated with each interferogram is different from one another.

FT of S(t) yields, in general a frequency domain peak located at $+\alpha$ including an absorptive component and a dispersive component, and its frequency domain quadrature image peak ('quad peak') located at $-\alpha$, also including an absorptive component and a dispersive component. These four peak components can be written as components of a vector F. With A+ denoting the absorptive component of the peak at $+\alpha$,
D+ denoting the dispersive component of the peak at $+\alpha$,
A− denoting the absorptive component of the peak at $-\alpha$, and
D− denoting the dispersive component of the peak at $-\alpha$,
the frequency domain signal is then proportional to $$\text{Re}(F_C[S(t)]) \propto \lambda F = [\lambda^{A+} \quad \lambda^{D+} \quad \lambda^{A-} \quad \lambda^{D-}] \begin{bmatrix} A+ \\ D+ \\ A- \\ D- \end{bmatrix}. \quad (1)$$

$F_C$ denotes the complex FT and $\lambda=[\lambda^{A+}\lambda^{D+}\lambda^{A-}\lambda^{D-}]$ represents a 'coefficient vector' which provides the relative intensities of absorptive (A+) and dispersive (D+) components located at frequency +α, as well as the relative intensities of absorptive (A−) and dispersive (D−) components located at the quadrature image frequency −α.

Given the four coefficient vector components in Eq. 1, three figures of merit are defined to compare the sampling schemes:

1. Figure of Merit for elimination of the dispersive component, $$M^D = \frac{|\lambda^{A+}|}{|\lambda^{A+}| + |\lambda^{D+}|}$$

2. Figure of Merit for elimination of the quadrature image, $$M^Q = \frac{|\lambda^{A+}| + |\lambda^{D+}|}{|\lambda^{A+}| + |\lambda^{D+}| + |\lambda^{A-}| + |\lambda^{D-}|}$$

3. Figure of Merit for maximizing the intensity of the absorptive component, $$M^A = \frac{|\lambda^{A+}|}{|\lambda^{A+}(\Phi_{\pm n} = 0)|}$$

'States' Sampling $(c_{+0}, c_{+2})$-Sampling

The two interferograms acquired for 'States' quadrature detection (Ernst et al., "Principles of Nuclear Magnetic Resonance in One and Two Dimensions," Oxford: Oxford University Press (1987); Jacobsen, N. E., "NMR Spectroscopy Explained," Wiley, New York (2007), which are hereby incorporated by reference in their entirety) are given by $$C_{+0,+2}(t) = \begin{bmatrix} c_{+0}(t) \\ c_{+2}(t) \end{bmatrix} = \begin{bmatrix} \cos(+\alpha t + \Phi_{+0}) \\ \cos\left(+\alpha t + \frac{\pi}{2} + \Phi_{+2}\right) \end{bmatrix} = \begin{bmatrix} \cos(+\alpha t + \Phi_{+0}) \\ -\sin(+\alpha t + \Phi_{+2}) \end{bmatrix}. \quad (2)$$

The resulting complex time domain signal $S_{+0,+2}(t)$ is proportional to $$S_{+0,+2}(t) \propto [1 \; i] D_{+0,+2} C_{+0,+2}(t) = [1 \; i] \begin{bmatrix} 1 & 0 \\ 0 & -1 \end{bmatrix} \begin{bmatrix} c_{+0}(t) \\ c_{+2}(t) \end{bmatrix} = \quad (3)$$

$$[1 \; -i] \begin{bmatrix} \cos(+\alpha t + \Phi_{+0}) \\ -\sin(+\alpha t + \Phi_{+2}) \end{bmatrix} = (\cos\Phi_{+0}\cos(\alpha t) - \sin\Phi_{+0}\sin(\alpha t)) +$$

$$i(\cos\Phi_{+2}\sin(\alpha t) + \sin\Phi_{+2}\cos(\alpha t)) -$$

$$(\cos\Phi_{+0} + i\sin\Phi_{+2})\cos(\alpha t) - (\sin\Phi_{+0} - i\cos\Phi_{+2})\sin(\alpha t) =$$

$$(\cos\Phi_{+0} + i\sin\Phi_{+2})\frac{e^{i\alpha t} + e^{-i\alpha t}}{2} -$$

$$(\sin\Phi_{+0} - i\cos\Phi_{+2})\frac{e^{i\alpha t} - e^{-i\alpha t}}{2i} =$$

$$\frac{1}{2}(\cos\Phi_{+0} + \cos\Phi_{+2})e^{i\alpha t} + \frac{i}{2}(\sin\Phi_{+0} + \sin\Phi_{+2})e^{i\alpha t} +$$

$$\frac{1}{2}(\cos\Phi_{+0} - \cos\Phi_{+2})e^{-i\alpha t} - \frac{i}{2}(\sin\Phi_{+0} - \sin\Phi_{+2})e^{-i\alpha t} =$$

-continued $$\frac{1}{2}(\cos\Phi_{+0} + \cos\Phi_{+2})e^{i\alpha t} + \frac{1}{2}(\sin\Phi_{+0} + \sin\Phi_{+2})e^{i\frac{\pi}{2}}e^{i\alpha t} +$$

$$\frac{1}{2}(\cos\Phi_{+0} - \cos\Phi_{+2})e^{-i\alpha t} -$$

$$\frac{1}{2}(\sin\Phi_{+0} - \sin\Phi_{+2})e^{i\frac{\pi}{2}}e^{-i\alpha t}.$$

After FT, one obtains for $(c_{+0}, c_{+2})$-sampling:

$$\lambda^{A+}_{+0,+2} = \frac{1}{2}(\cos\Phi_{+0} + \cos\Phi_{+2}); \; \lambda^{D+}_{+0,+2} = \frac{1}{2}(\sin\Phi_{+0} + \sin\Phi_{+2}) \quad (4)$$

$$\lambda^{A-}_{+0,+2} = \frac{1}{2}(\cos\Phi_{+0} - \cos\Phi_{+2}); \; \lambda^{D-}_{+0,+2} = -\frac{1}{2}(\sin\Phi_{+0} - \sin\Phi_{+2})$$

or equivalently, $$\Phi_{+0} = \arccos(\lambda^{A+}_{+0,+2} + \lambda^{A-}_{+0,+2}) = \arcsin(\lambda^{D+}_{+0,+2} - \lambda^{D-}_{+0,+2})$$

$$\Phi_{+2} = \arccos(\lambda^{A+}_{+0,+2} - \lambda^{A-}_{+0,+2}) = \arcsin(\lambda^{D+}_{+0,+2} + \lambda^{D-}_{+0,+2}).$$

yielding superposition of absorptive and dispersive components at both the actual and the quadrature peak positions. These equations enable one to calculate the secondary phase shifts from the experimentally observed values for λ. The figures of merit for $(c_{+0}, c_{+2})$-sampling are then given by $$M^D_{+0,+2} = \frac{|\cos\Phi_{+0} + \cos\Phi_{+2}|}{|\cos\Phi_{+0} + \cos\Phi_{+2}| + |\sin\Phi_{+0} + \sin\Phi_{+2}|} \quad (5)$$

$$M^Q_{+0,+2} = \frac{|\cos\Phi_{+0} + \cos\Phi_{+2}| + |\sin\Phi_{+0} + \sin\Phi_{+2}|}{|\cos\Phi_{+0} + \cos\Phi_{+2}| + |\sin\Phi_{+0} + \sin\Phi_{+2}||\cos\Phi_{+0} - \cos\Phi_{+2}| + |\sin\Phi_{+0} - \sin\Phi_{+2}|}$$

$$M^A_{+0,+2} = \frac{1}{2}|\cos\Phi_{+0} + \cos\Phi_{+2}|.$$

$(c_{-0}, c_{-2})$-Sampling

For backward sampling the interferograms are given by $$C_{-0,-2}(t) = \begin{bmatrix} c_{-0}(t) \\ c_{-2}(t) \end{bmatrix} = \begin{bmatrix} \cos(-\alpha t + \Phi_{-0}) \\ \cos\left(-\alpha t + \frac{\pi}{2} + \Phi_{-2}\right) \end{bmatrix} = \quad (6)$$

$$\begin{bmatrix} \cos(-\alpha t + \Phi_{-0}) \\ -\sin(-\alpha t + \Phi_{-2}) \end{bmatrix} = \begin{bmatrix} \cos(\alpha t - \Phi_{-0}) \\ \sin(\alpha t - \Phi_{-2}) \end{bmatrix}.$$

so that the resulting signal $s_{-0,-2}(t)$ is proportional to $$S_{-0,-2}(t) \propto [1 \; i] \quad (7)$$

$$D_{-0,-2} C_{-0,-2}(t) = [1 \; i] \begin{bmatrix} 1 & 0 \\ 0 & 1 \end{bmatrix} \begin{bmatrix} c_{-0}(t) \\ c_{-2}(t) \end{bmatrix} = [1 \; i] \begin{bmatrix} c_{-0} \\ c_{-2} \end{bmatrix} =$$

$$[1 \; i] \begin{bmatrix} \cos(\alpha t - \Phi_{-0}) \\ \sin(\alpha t - \Phi_{-2}) \end{bmatrix} = (\cos\Phi_{-0}\cos(\alpha t) + \sin\Phi_{-0}\sin(\alpha t)) -$$

$$i(\sin\Phi_{-2}\cos(\alpha t) - \cos\Phi_{-2}\sin(\alpha t)) =$$

$$(\cos\Phi_{-0} - i\sin\Phi_{-2})\cos(\alpha t) + (\sin\Phi_{-0} + i\cos\Phi_{-2})\sin(\alpha t) =$$

$$(\cos\Phi_{-0} - i\sin\Phi_{-2})\frac{e^{i\alpha t} + e^{-i\alpha t}}{2} + (\sin\Phi_{-0} + i\cos\Phi_{-2})$$

$$\frac{e^{i\alpha t} - e^{-i\alpha t}}{2i} = \frac{1}{2}(\cos\Phi_{-0} + \cos\Phi_{-2})e^{i\alpha t} -$$

-continued $$\frac{i}{2}(\sin\Phi_{-0} + \sin\Phi_{-2})e^{i\alpha t} + \frac{1}{2}(\cos\Phi_{-0} - \cos\Phi_{-2})e^{-i\alpha t} +$$

$$\frac{i}{2}(\sin\Phi_{-0} - \sin\Phi_{-2})e^{-i\alpha t} =$$

$$\frac{1}{2}(\cos\Phi_{-0} + \cos\Phi_{-2})e^{i\alpha t} -$$

$$\frac{1}{2}(\sin\Phi_{-0} + \sin\Phi_{-2})e^{i\frac{\pi}{2}}e^{i\alpha t} + \frac{1}{2}(\cos\Phi_{-0} - \cos\Phi_{-2})e^{-i\alpha t} + \frac{1}{2}(\sin\Phi_{-0} - \sin\Phi_{-2})e^{i\frac{\pi}{2}}e^{-i\alpha t}.$$

After FT, one obtains for $(c_{-0}, c_{-2})$-sampling:

$$\lambda^{A+}_{-0,-2} = \frac{1}{2}(\cos\Phi_{-0} + \cos\Phi_{-2}); \quad \lambda^{D+}_{-0,-2} = -\frac{1}{2}(\sin\Phi_{-0} + \sin\Phi_{-2}) \quad (8)$$

$$\lambda^{A-}_{-0,-2} = \frac{1}{2}(\cos\Phi_{-0} - \cos\Phi_{-2}); \quad \lambda^{D-}_{-0,-2} = \frac{1}{2}(\sin\Phi_{-0} - \sin\Phi_{-2})$$

or equivalently, $$\Phi_{-0} = \arccos(\lambda^{A+}_{-0,-2} + \lambda^{A-}_{-0,-2}) = -\arcsin(\lambda^{D+}_{-0,-2} - \lambda^{D-}_{-0,-2})$$

$$\Phi_{-2} = \arccos(\lambda^{A+}_{-0,-2} - \lambda^{A-}_{-0,-2}) = -\arcsin(\lambda^{D+}_{-0,-2} + \lambda^{D-}_{-0,-2}).$$

so that the figures of merit are given by $$M^{D}_{-0,-2} = \frac{|\cos\Phi_{-0} + \cos\Phi_{-2}|}{|\cos\Phi_{-0} + \cos\Phi_{-2}| + |\sin\Phi_{-0} + \sin\Phi_{-2}|} \quad (9)$$

$$M^{Q}_{-0,-2} = \frac{|\cos\Phi_{-0} + \cos\Phi_{-2}| + |\sin\Phi_{-0} + \sin\Phi_{-2}|}{|\cos\Phi_{-0} + \cos\Phi_{-2}| + |\sin\Phi_{-0} + \sin\Phi_{-2}||\cos\Phi_{-0} - \cos\Phi_{-2}| + |\sin\Phi_{-0} - \sin\Phi_{-2}|}$$

$$M^{A}_{-0,-2} = \frac{1}{2}|\cos\Phi_{-0} + \cos\Phi_{-2}|.$$

$(c_{+0}, c_{+2}, c_{-0}, c_{-2})$-Sampling

Addition of $S_{+0,+2}(t)$ and $S_{-0,-2}(t)$ yields for such 'dual States sampling'

$$S_{+0,+2,-0,-2}(t) = \quad (10)$$

$$S_{+0,+2}(t) + S_{-0,-2}(t) \propto \frac{1}{2}(\cos\Phi_{+0} + \cos\Phi_{+2} + \cos\Phi_{-0} + \cos\Phi_{-2})e^{i\alpha t} +$$

$$\frac{1}{2}(\sin\Phi_{+0} + \sin\Phi_{+2} - \sin\Phi_{-0} - \sin\Phi_{-2})e^{i\frac{\pi}{2}}e^{i\alpha t} +$$

$$\frac{1}{2}(\cos\Phi_{+0} - \cos\Phi_{+2} + \cos\Phi_{-0} - \cos\Phi_{-2})e^{-i\alpha t} -$$

$$\frac{1}{2}(\sin\Phi_{+0} - \sin\Phi_{+2} - \sin\Phi_{-0} + \sin\Phi_{-2})e^{i\frac{\pi}{2}}e^{-i\alpha t}.$$

After FT, one obtains for $(c_{+0}, c_{+2}, c_{-0}, c_{-2})$-sampling:

$$\lambda^{A+}_{+0,+2,-0,-2} = \frac{1}{2}(\cos\Phi_{+0} + \cos\Phi_{+2} + \cos\Phi_{-0} + \cos\Phi_{-2}); \quad (11)$$

$$\lambda^{D+}_{+0,+2,-0,-2} = \frac{1}{2}(\sin\Phi_{+0} + \sin\Phi_{+2} - \sin\Phi_{-0} - \sin\Phi_{-2})$$

$$\lambda^{A-}_{+0,+2,-0,-2} = \frac{1}{2}(\cos\Phi_{+0} - \cos\Phi_{+2} + \cos\Phi_{-0} - \cos\Phi_{-2});$$

$$\lambda^{D-}_{+0,+2,-0,-2} = -\frac{1}{2}(\cos\Phi_{+0} - \sin\Phi_{+2} - \sin\Phi_{-0} + \sin\Phi_{-2}).$$

so that the figures of merit are given by $$M^{D}_{+0,+2,-0,-2} = \frac{|\cos\Phi_{+0} + \cos\Phi_{+2} + \cos\Phi_{-0} + \cos\Phi_{-2}|}{|\cos\Phi_{+0} + \cos\Phi_{+2} + \cos\Phi_{-0} + \cos\Phi_{-2}| + |\sin\Phi_{+0} + \sin\Phi_{+2} - \sin\Phi_{-0} - \sin\Phi_{-2}|} \quad (12)$$

$$M^{Q}_{+0,+2,-0,-2} = \frac{|\cos\Phi_{+0} + \cos\Phi_{+2} + \cos\Phi_{-0} + \cos\Phi_{-2}| + |\sin\Phi_{+0} + \sin\Phi_{+2} - \sin\Phi_{-0} - \sin\Phi_{-2}|}{|\cos\Phi_{+0} + \cos\Phi_{+2} + \cos\Phi_{-0} + \cos\Phi_{-2}| + |\sin\Phi_{+0} + \sin\Phi_{+2} - \sin\Phi_{-0} - \sin\Phi_{-2}| + |\cos\Phi_{+0} - \cos\Phi_{+2} + \cos\Phi_{-0} - \cos\Phi_{-2}| + |\sin\Phi_{+0} - \sin\Phi_{+2} - \sin\Phi_{-0} + \sin\Phi_{-2}|}$$

$$M^{A}_{+0,+2,-0,-2} = \frac{1}{4}|\cos\Phi_{+0} + \cos\Phi_{+2} + \cos\Phi_{-0} + \cos\Phi_{-2}|.$$

$\pi/4$ and $3\pi/4$-Shifted Mirrored Sampling
$(c_{+1}, c_{-1})$-Sampling (PMS)

The two interferograms for $(c_{+1}, c_{-1})$-PMS are given by $$C_{+1,-1}(t) = \begin{bmatrix} c_{+1}(t) \\ c_{-1}(t) \end{bmatrix} = \begin{bmatrix} \cos(+\alpha t + \frac{\pi}{4} + \Phi_{+1}) \\ \cos(-\alpha t + \frac{\pi}{4} + \Phi_{-1}) \end{bmatrix}. \quad (13)$$

so that the resulting signal $S_{+1,-1}(t)$ is proportional to $$S_{+1,-1}(t) \propto \begin{bmatrix} 1 & i \end{bmatrix} D_{+1,-1} C_{+1,-1}(t) = \frac{1}{\sqrt{2}} \begin{bmatrix} 1 & i \end{bmatrix} \begin{bmatrix} 1 & 1 \\ -1 & 1 \end{bmatrix} \begin{bmatrix} c_{+1}(t) \\ c_{-1}(t) \end{bmatrix} = \quad (14)$$

$$\frac{1}{\sqrt{2}} \begin{bmatrix} 1-i & 1+i \end{bmatrix} \begin{bmatrix} \cos(+\alpha t + \frac{\pi}{4} + \Phi_{+1}) \\ \cos(-\alpha t + \frac{\pi}{4} + \Phi_{-1}) \end{bmatrix} =$$

$$\frac{1}{\sqrt{2}}\left(\left(\cos(\frac{\pi}{4}+\Phi_{+1})+\cos(\frac{\pi}{4}+\Phi_{-1})\right)-\right.$$

$$i\left(\cos(\frac{\pi}{4}+\Phi_{+1})-\cos(\frac{\pi}{4}+\Phi_{-1})\right)\cos(\alpha t)-$$

$$\frac{1}{\sqrt{2}}\left(\left(\sin(\frac{\pi}{4}+\Phi_{+1})-\sin(\frac{\pi}{4}+\Phi_{-1})\right)-\right.$$

$$i\left(\sin(\frac{\pi}{4}+\Phi_{+1})+\sin(\frac{\pi}{4}+\Phi_{-1})\right)\sin(\alpha t)=$$

$$\frac{1}{\sqrt{2}}\left(\left(\cos(\frac{\pi}{4}+\Phi_{+1})+\cos(\frac{\pi}{4}+\Phi_{-1})\right)-\right.$$

$$i\left(\cos(\frac{\pi}{4}+\Phi_{+1})-\cos(\frac{\pi}{4}+\Phi_{-1})\right)\frac{e^{i\alpha t}+e^{-i\alpha t}}{2}-$$

$$\frac{1}{\sqrt{2}}\left(\left(\sin(\frac{\pi}{4}+\Phi_{+1})-\sin(\frac{\pi}{4}+\Phi_{-1})\right)-\right.$$

$$i\left(\sin(\frac{\pi}{4}+\Phi_{+1})+\sin(\frac{\pi}{4}+\Phi_{-1})\right)\frac{e^{i\alpha t}-e^{-i\alpha t}}{2i}=$$

$$\frac{1}{4}(\cos\Phi_{+1} - \sin\Phi_{+1} + \cos\Phi_{-1} - \sin\Phi_{-1} + \cos\Phi_{+1} +$$

$$\sin\Phi_{+1} + \cos\Phi_{-1} + \sin\Phi_{-1})e^{i\alpha t} +$$

-continued $$\frac{1}{4}(\cos\Phi_{+1} - \sin\Phi_{+1} + \cos\Phi_{-1} - \sin\Phi_{-1} - \cos\Phi_{+1} -$$

$$\sin\Phi_{+1} - \cos\Phi_{-1} - \sin\Phi_{-1})e^{-i\alpha t} -$$

$$\frac{i}{4}(\cos\Phi_{+1} - \sin\Phi_{+1} - \cos\Phi_{-1} + \sin\Phi_{-1} - \cos\Phi_{+1} -$$

$$\sin\Phi_{+1} + \cos\Phi_{-1} + \sin\Phi_{-1})e^{i\alpha t} -$$

$$\frac{i}{4}(\cos\Phi_{+1} - \sin\Phi_{+1} - \cos\Phi_{-1} + \sin\Phi_{-1} + \cos\Phi_{+1} +$$

$$\sin\Phi_{+1} - \cos\Phi_{-1} - \sin\Phi_{-1})e^{-i\alpha t} =$$

$$\frac{1}{2}(\cos\Phi_{+1} + \cos\Phi_{-1})e^{i\alpha t} + \frac{1}{2}(\sin\Phi_{+1} - \sin\Phi_{-1})e^{i\pi/2}e^{-i\alpha t} -$$

$$\frac{1}{2}(\sin\Phi_{+1} + \sin\Phi_{-1})e^{-i\alpha t} - \frac{1}{2}(\cos\Phi_{+1} - \cos\Phi_{-1})e^{i\pi/2}e^{-i\alpha t}.$$

After FT, one obtains for $(c_{+1}, c_{-1})$-sampling:

$$\lambda^{A+}_{+1,-1} = \frac{1}{2}(\cos\Phi_{+1} + \cos\Phi_{-1}); \lambda^{D+}_{+1,-1} = \frac{1}{2}(\sin\Phi_{+1} - \sin\Phi_{-1}) \quad (15)$$

$$\lambda^{A-}_{+1,-1} = -\frac{1}{2}(\sin\Phi_{+1} + \sin\Phi_{-1}); \lambda^{D-}_{+1,-1} = -\frac{1}{2}(\cos\Phi_{+1} - \cos\Phi_{-1})$$

or equivalently, $$\Phi_{+1} = \arccos(\lambda^{A+}_{+1,-1} - \lambda^{D-}_{+1,-1}) = \arcsin(\lambda^{D+}_{+1,-1} - \lambda^{A-}_{+1,-1})$$

$$\Phi_{-1} = \arccos(\lambda^{A+}_{+1,-1} + \lambda^{D-}_{+1,-1}) = -\arcsin(\lambda^{D+}_{+1,-1} + \lambda^{A-}_{+1,-1}).$$

so that the figures of merit are given by $$M^D_{+1,-1} = \frac{|\cos\Phi_{+1} + \cos\Phi_{-1}|}{|\cos\Phi_{+1} + \cos\Phi_{-1}| + |\sin\Phi_{+1} - \sin\Phi_{-1}|} \quad (16)$$

$$M^Q_{+1,-1} = \frac{|\cos\Phi_{+1} + \cos\Phi_{-1}| + |\sin\Phi_{+1} - \sin\Phi_{-1}|}{|\cos\Phi_{+1} + \cos\Phi_{-1}| + |\sin\Phi_{+1} - \sin\Phi_{-1}| +}$$
$$\phantom{M^Q_{+1,-1} =}{|\sin\Phi_{+1} + \sin\Phi_{-1}| + |\cos\Phi_{+1} - \cos\Phi_{-1}|}$$

$$M^A_{+1,-1} = \frac{1}{2}|\cos\Phi_{+1} + \cos\Phi_{-1}|.$$

$(c_{+3}, c_{-3})$-Sampling (PMS)

The two interferograms for $(c_{+3}, c_{-3})$-PMS are given by $$C_{+3,-3}(t) = \begin{bmatrix} c_{+3}(t) \\ c_{-3}(t) \end{bmatrix} = \begin{bmatrix} \cos\left(+\alpha t + \frac{3\pi}{4} + \Phi_{+3}\right) \\ \cos\left(-\alpha t + \frac{3\pi}{4} + \Phi_{-3}\right) \end{bmatrix} \quad (17)$$

$$= \begin{bmatrix} -\sin\left(+\alpha t + \frac{\pi}{4} + \Phi_{+3}\right) \\ -\sin\left(-\alpha t + \frac{\pi}{4} + \Phi_{-3}\right) \end{bmatrix}.$$

so that the resulting signal $S_{+3,-3}(t)$ is proportional to $$S_{+3,-3}(t) \propto [1 \ i]D_{+3,-3}C_{+3,-3}(t) = \frac{1}{\sqrt{2}}[1 \ i]\begin{bmatrix} -1 & -1 \\ -1 & 1 \end{bmatrix}\begin{bmatrix} c_{+3}(t) \\ c_{-3}(t) \end{bmatrix} = \quad (18)$$

$$\frac{1}{\sqrt{2}}[-1-i \ \ -1+i]\begin{bmatrix} -\sin\left(+\alpha t + \frac{\pi}{4} + \Phi_{+3}\right) \\ -\sin\left(-\alpha t + \frac{\pi}{4} + \Phi_{-3}\right) \end{bmatrix} =$$

$$\frac{1}{\sqrt{2}}\left((\sin\left(\frac{\pi}{4} + \Phi_{+3}\right) + \sin\left(\frac{\pi}{4} + \Phi_{-3}\right)\right) +$$

$$i\left(\sin\left(\frac{\pi}{4} + \Phi_{+3}\right) - \sin\left(\frac{\pi}{4} + \Phi_{-3}\right)\right))\cos(\alpha t) +$$

$$\frac{1}{\sqrt{2}}\left((\cos\left(\frac{\pi}{4} + \Phi_{+3}\right) - \cos\left(\frac{\pi}{4} + \Phi_{-3}\right)\right) +$$

$$i\left(\cos\left(\frac{\pi}{4} + \Phi_{+3}\right) + \cos\left(\frac{\pi}{4} + \Phi_{-3}\right)\right))\sin(\alpha t) =$$

$$\frac{1}{\sqrt{2}}\left((\sin\left(\frac{\pi}{4} + \Phi_{+3}\right) + \sin\left(\frac{\pi}{4} + \Phi_{-3}\right)\right) +$$

$$i\left(\sin\left(\frac{\pi}{4} + \Phi_{+3}\right) - \sin\left(\frac{\pi}{4} + \Phi_{-3}\right)\right))\frac{e^{i\alpha t} + e^{-i\alpha t}}{2} +$$

$$\frac{1}{\sqrt{2}}\left((\cos\left(\frac{\pi}{4} + \Phi_{+3}\right) - \cos\left(\frac{\pi}{4} + \Phi_{-3}\right)\right) +$$

$$i\left(\cos\left(\frac{\pi}{4} + \Phi_{+3}\right) + \cos\left(\frac{\pi}{4} + \Phi_{-3}\right)\right))\frac{e^{i\alpha t} - e^{-i\alpha t}}{2i} =$$

$$\frac{1}{4}(\cos\Phi_{+3} + \sin\Phi_{+3} + \cos\Phi_{-3} + \sin\Phi_{-3} + \cos\Phi_{+3} -$$

$$\sin\Phi_{+3} + \cos\Phi_{-3} - \sin\Phi_{-3})e^{i\alpha t} +$$

$$\frac{1}{4}(\cos\Phi_{+3} + \sin\Phi_{+3} + \cos\Phi_{-3} + \sin\Phi_{-3} - \cos\Phi_{+3} +$$

$$\sin\Phi_{+3} - \cos\Phi_{-3} + \sin\Phi_{-3})e^{-i\alpha t} +$$

$$\frac{i}{4}(\cos\Phi_{+3} + \sin\Phi_{+3} - \cos\Phi_{-3} - \sin\Phi_{-3} - \cos\Phi_{+3} +$$

$$\sin\Phi_{+3} + \cos\Phi_{-3} - \sin\Phi_{-3})e^{i\alpha t} +$$

$$\frac{i}{4}(\cos\Phi_{+3} + \sin\Phi_{+3} - \cos\Phi_{-3} - \sin\Phi_{-3} + \cos\Phi_{+3} -$$

$$\sin\Phi_{+3} - \cos\Phi_{-3} + \sin\Phi_{-3})e^{-i\alpha t} =$$

$$\frac{1}{2}(\cos\Phi_{+3} + \cos\Phi_{-3})e^{i\alpha t} + \frac{1}{2}(\sin\Phi_{+3} - \sin\Phi_{-3})e^{i\pi/2}e^{i\alpha t} +$$

$$\frac{1}{2}(\sin\Phi_{+3} + \sin\Phi_{-3})e^{-i\alpha t} + \frac{1}{2}(\cos\Phi_{+3} - \cos\Phi_{-3})e^{i\pi/2}e^{i\alpha t}.$$

After FT, one obtains for $(c_{+3}, c_{-3})$-sampling:

$$\lambda^{A+}_{+3,-3} = \frac{1}{2}(\cos\Phi_{+3} + \cos\Phi_{-3}); \lambda^{D+}_{+3,-3} = \frac{1}{2}(\sin\Phi_{+3} - \sin\Phi_{-3}) \quad (19)$$

$$\lambda^{A-}_{+3,-3} = \frac{1}{2}(\sin\Phi_{+3} + \sin\Phi_{-3}); \lambda^{D-}_{+3,-3} = \frac{1}{2}(\cos\Phi_{+3} - \cos\Phi_{-3})$$

or equivalently, $$\Phi_{+3} = \arccos(\lambda^{A+}_{+3,-3} + \lambda^{D-}_{+3,-3}) = \arcsin(\lambda^{D+}_{+3,-3} + \lambda^{A-}_{+3,-3})$$

$$\Phi_{-3} = \arccos(\lambda^{A+}_{+3,-3} - \lambda^{D-}_{+3,-3}) = -\arcsin(\lambda^{D+}_{+3,-3} - \lambda^{A-}_{+3,-3}).$$

so that the figures of merit are given by $$M^D_{+3,-3} = \frac{|\cos\Phi_{+3} + \cos\Phi_{-3}|}{|\cos\Phi_{+3} + \cos\Phi_{-3}| + |\sin\Phi_{+3} - \sin\Phi_{-3}|} \quad (20)$$

$$M^Q_{+3,-3} = \frac{|\cos\Phi_{+3} + \cos\Phi_{-3}| + |\sin\Phi_{+3} - \sin\Phi_{-3}|}{|\cos\Phi_{+3} + \cos\Phi_{-3}| + |\sin\Phi_{+3} - \sin\Phi_{-3}| +}$$
$$\phantom{M^Q_{+3,-3} =}{|\sin\Phi_{+3} + \sin\Phi_{-3}| + |\cos\Phi_{+3} - \cos\Phi_{-3}|}$$

$$M^A_{+3,-3} = \frac{1}{2}|\cos\Phi_{+3} + \cos\Phi_{-3}|.$$

($c_{+1}, c_{-1}, c_{+3}, c_{-3}$)-Sampling (DPMS)

Addition of $S_{+1,-1}(t)$ and $S_{+3,-3}(t)$ yields $$S_{+1,-1,+3,-3}(t) = \tag{21}$$

$$S_{+1,-1}(t) + S_{+3,-3}(t) \propto \frac{1}{2}(\cos\Phi_{+1} + \cos\Phi_{-1} + \cos\Phi_{+3} + \cos\Phi_{-3})e^{i\alpha t} +$$

$$\frac{1}{2}(\sin\Phi_{+1} - \sin\Phi_{-1} + \sin\Phi_{+3} - \sin\Phi_{-3})e^{i\pi/2}e^{i\alpha t} -$$

$$\frac{1}{2}(\sin\Phi_{+1} + \sin\Phi_{-1} - \sin\Phi_{+3} - \sin\Phi_{-3})e^{-i\alpha t} -$$

$$\frac{1}{2}(\cos\Phi_{+1} - \cos\Phi_{-1} - \cos\Phi_{+3} + \cos\Phi_{-3})e^{i\pi/2}e^{-i\alpha t}.$$

After FT, one obtains for ($c_{+1}, c_{-1}, c_{+3}, c_{-3}$)-sampling:

$$\lambda^{A+}_{+1,-1,+3,-3} = \frac{1}{2}(\cos\Phi_{+1} + \cos\Phi_{-1} + \cos\Phi_{+3} + \cos\Phi_{-3}); \tag{22}$$

$$\lambda^{D+}_{+1,-1,+3,-3} = \frac{1}{2}(\sin\Phi_{+1} - \sin\Phi_{-1} + \sin\Phi_{+3} - \sin\Phi_{-3})$$

$$\lambda^{A-}_{+1,-1,+3,-3} = -\frac{1}{2}(\sin\Phi_{+1} + \sin\Phi_{-1} - \sin\Phi_{+3} - \sin\Phi_{-3});$$

$$\lambda^{D-}_{+1,-1,+3,-3} = -\frac{1}{2}(\cos\Phi_{+1} - \cos\Phi_{-1} - \cos\Phi_{+3} + \cos\Phi_{-3}).$$

so that the figures of merit are given by $$M^{D}_{+1,-1,+3,-3} = \frac{|\cos\Phi_{+1} + \cos\Phi_{-1} + \cos\Phi_{+3} + \cos\Phi_{-3}|}{|\cos\Phi_{+1} + \cos\Phi_{-1} + \cos\Phi_{+3} + \cos\Phi_{-3}| + |\sin\Phi_{+1} - \sin\Phi_{-1} + \sin\Phi_{+3} - \sin\Phi_{-3}|} \tag{23}$$

$$M^{Q}_{+1,-1,+3,-3} = \frac{|\cos\Phi_{+1} + \cos\Phi_{-1} + \cos\Phi_{+3} + \cos\Phi_{-3}| + |\sin\Phi_{+1} - \sin\Phi_{-1} + \sin\Phi_{+3} - \sin\Phi_{-3}|}{|\cos\Phi_{+1} + \cos\Phi_{-1} + \cos\Phi_{+3} + \cos\Phi_{-3}| + |\sin\Phi_{+1} - \sin\Phi_{-1} + \sin\Phi_{+3} - \sin\Phi_{-3}| + |\sin\Phi_{+1} + \sin\Phi_{-1} - \sin\Phi_{+3} - \sin\Phi_{-3}| + |\cos\Phi_{+1} - \cos\Phi_{-1} - \cos\Phi_{+3} + \cos\Phi_{-3}|}$$

$$M^{A}_{+1,-1,+3,-3} = \frac{1}{4}|\cos\Phi_{+1} + \cos\Phi_{-1} + \cos\Phi_{+3} + \cos\Phi_{-3}|.$$

0 and $\pi/2$-Shifted Mirrored Sampling ($c_{+0}, c_{-2}$)-Sampling (PMS)

The two interferograms for ($c_{+0}, c_{-2}$)-PMS are given by $$C_{+0,-2}(t) = \begin{bmatrix} c_{+0}(t) \\ c_{-2}(t) \end{bmatrix} = \begin{bmatrix} \cos(+\alpha t + \Phi_{+0}) \\ \cos(-\alpha t + \frac{\pi}{2} + \Phi_{-2}) \end{bmatrix} \tag{24}$$

$$= \begin{bmatrix} \cos(+\alpha t + \Phi_{+0}) \\ -\sin(-\alpha t + \Phi_{-2}) \end{bmatrix} = \begin{bmatrix} \cos(+\alpha t + \Phi_{+0}) \\ \sin(+\alpha t - \Phi_{-2}) \end{bmatrix}.$$

so that the resulting signal $S_{+0,-2}(t)$ is proportional to $$S_{+0,-2}(t) \propto [1 \ i] D_{+0,-2} C_{+0,-2}(t) = [1 \ i] \begin{bmatrix} 1 & 0 \\ 0 & 1 \end{bmatrix} \begin{bmatrix} c_{+0}(t) \\ c_{-2}(t) \end{bmatrix} = \tag{25}$$

$$[1 \ i] \begin{bmatrix} c_{+0} \\ c_{-2} \end{bmatrix} = [1 \ i] \begin{bmatrix} \cos(\alpha t + \Phi_{+0}) \\ \sin(\alpha t - \Phi_{-2}) \end{bmatrix} =$$

-continued $$(\cos\Phi_{+0}\cos(\alpha t) - \sin\Phi_{+0}\sin(\alpha t)) -$$

$$i(\sin\Phi_{-2}\cos(\alpha t) - \cos\Phi_{-2}\sin(\alpha t)) =$$

$$(\cos\Phi_{+0} - i\sin\Phi_{-2})\cos(\alpha t) - (\sin\Phi_{+0} - i\cos\Phi_{-2})\sin(\alpha t) =$$

$$(\cos\Phi_{+0} - i\sin\Phi_{-2})\frac{e^{i\alpha t} + e^{-i\alpha t}}{2} -$$

$$(\sin\Phi_{+0} - i\cos\Phi_{-2})\frac{e^{i\alpha t} - e^{-i\alpha t}}{2i} =$$

$$\frac{1}{2}(\cos\Phi_{-0} + \cos\Phi_{-2})e^{i\alpha t} + \frac{i}{2}(\sin\Phi_{+0} - \sin\Phi_{-2})e^{i\alpha t} +$$

$$\frac{1}{2}(\cos\Phi_{+0} - \cos\Phi_{-2})e^{-i\alpha t} - \frac{i}{2}(\sin\Phi_{+0} + \sin\Phi_{-2})e^{i\alpha t} =$$

$$\frac{1}{2}(\cos\Phi_{+0} + \cos\Phi_{-2})e^{i\alpha t} + \frac{1}{2}(\sin\Phi_{+0} - \sin\Phi_{-2})$$

$$e^{i\frac{\pi}{2}}e^{i\alpha t} + \frac{1}{2}(\cos\Phi_{+0} - \cos\Phi_{-2})e^{-i\alpha t} -$$

$$\frac{1}{2}(\sin\Phi_{+0} + \sin\Phi_{-2})e^{i\frac{\pi}{2}}e^{-i\alpha t}.$$

After FT, one obtains for ($c_{+0}, c_{-2}$)-sampling:

$$\lambda^{A+}_{+0,-2} = \frac{1}{2}(\cos\Phi_{+0} + \cos\Phi_{-2}); \ \lambda^{D+}_{+0,-2} = \frac{1}{2}(\sin\Phi_{+0} - \sin\Phi_{-2}) \tag{26}$$

$$\lambda^{A-}_{+0,-2} = \frac{1}{2}(\cos\Phi_{+0} - \cos\Phi_{-2}); \ \lambda^{D-}_{+0,-2} = -\frac{1}{2}(\sin\Phi_{+0} + \sin\Phi_{-2})$$

or equivalently, $$\Phi_{+0} = \arccos(\lambda^{A+}_{+0,-2} + \lambda^{A-}_{+0,-2}) = \arcsin(\lambda^{D+}_{+0,-2} - \lambda^{D-}_{+0,-2})$$

$$\Phi_{-2} = \arccos(\lambda^{A+}_{+0,-2} - \lambda^{A-}_{+0,-2}) = -\arcsin(\lambda^{D+}_{+0,-2} + \lambda^{D-}_{+0,-2}),$$

so that the figures of merit are given by $$M^{D}_{+0,-2} = \frac{|\cos\Phi_{+0} + \cos\Phi_{-2}|}{|\cos\Phi_{+0} + \cos\Phi_{-2}| + |\sin\Phi_{+0} - \sin\Phi_{-2}|} \tag{27}$$

$$M^{Q}_{+0,-2} = \frac{|\cos\Phi_{+0} + \cos\Phi_{-2}| + |\sin\Phi_{+0} - \sin\Phi_{-2}|}{|\cos\Phi_{+0} + \cos\Phi_{-2}| + |\sin\Phi_{+0} - \sin\Phi_{-2}| + |\cos\Phi_{+0} - \cos\Phi_{-2}| + |\sin\Phi_{+0} + \sin\Phi_{-2}|}$$

$$M^{A}_{+0,-2} = \frac{1}{2}|\cos\Phi_{+0} + \cos\Phi_{-2}|.$$

($c_{-0}, c_{+2}$)-Sampling (PMS)

The two interferograms for ($c_{-0}, c_{+2}$)-PMS are given by $$C_{-0,+2}(t) = \begin{bmatrix} c_{-0} \\ c_{+2} \end{bmatrix} = \begin{bmatrix} \cos(-\alpha t + \Phi_{-0}) \\ \cos(+\alpha t + \frac{\pi}{2} + \Phi_{+2}) \end{bmatrix} \tag{28}$$

$$= \begin{bmatrix} \cos(-\alpha t + \Phi_{-0}) \\ -\sin(+\alpha t + \Phi_{+2}) \end{bmatrix} = \begin{bmatrix} \cos(+\alpha t - \Phi_{-0}) \\ \sin(+\alpha t + \Phi_{+2}) \end{bmatrix}.$$

so that the resulting signal $S_{-0,+2}(t)$ is proportional to $$S_{-0,+2}(t) \propto [1 \ i] D_{-0,+2} C_{-0,+2}(t) = [1 \ i] \begin{bmatrix} 1 & 0 \\ 0 & -1 \end{bmatrix} \begin{bmatrix} c_{-0}(t) \\ c_{+2}(t) \end{bmatrix} = \tag{29}$$

$$[1 \ -i] \begin{bmatrix} c_{-0} \\ c_{+2} \end{bmatrix} = [1 \ -i] \begin{bmatrix} \cos(\alpha t - \Phi_{-0}) \\ -\sin(\alpha t + \Phi_{+2}) \end{bmatrix} =$$

-continued $$(\cos\Phi_{-0}\cos(\alpha t) + \sin\Phi_{-0}\sin(\alpha t)) +$$

$$i(\sin\Phi_{+2}\cos(\alpha t) + \cos\Phi_{-2}\sin(\alpha t)) =$$

$$(\cos\Phi_{-0} + i\sin\Phi_{+2})\cos(\alpha t) + (\sin\Phi_{-0} + i\cos\Phi_{+2})\sin(\alpha t) =$$

$$(\cos\Phi_{-0} + i\sin\Phi_{+2})\frac{e^{i\alpha t} + e^{-i\alpha t}}{2} +$$

$$(\sin\Phi_{-0} + i\cos\Phi_{+2})\frac{e^{i\alpha t} - e^{-i\alpha t}}{2i} =$$

$$\frac{1}{2}(\cos\Phi_{-0} + \cos\Phi_{+2})e^{i\alpha t} - \frac{i}{2}(\sin\Phi_{-0} - \sin\Phi_{+2})e^{i\alpha t} +$$

$$\frac{1}{2}(\cos\Phi_{-0} - \cos\Phi_{+2})e^{-i\alpha t} +$$

$$\frac{i}{2}(\sin\Phi_{-0} + \sin\Phi_{+2})e^{-i\alpha t} = \frac{1}{2}(\cos\Phi_{-0} + \cos\Phi_{+2})e^{i\alpha t} -$$

$$\frac{1}{2}(\sin\Phi_{-0} - \sin\Phi_{+2})e^{i\frac{\pi}{2}}e^{i\alpha t} + \frac{1}{2}(\cos\Phi_{-0} - \cos\Phi_{+2})e^{-i\alpha t} +$$

$$\frac{1}{2}(\sin\Phi_{-0} + \sin\Phi_{+2})e^{i\frac{\pi}{2}}e^{-i\alpha t}.$$

After FT, one obtains for $(c_{-0}, c_{+2})$-sampling:

$$\lambda^{A+}_{-0,+2} = \frac{1}{2}(\cos\Phi_{-0} + \cos\Phi_{+2}); \lambda^{D+}_{-0,+2} = -\frac{1}{2}(\sin\Phi_{-0} - \sin\Phi_{+2}) \quad (30)$$

$$\lambda^{A-}_{-0,+2} = \frac{1}{2}(\cos\Phi_{-0} - \cos\Phi_{+2}); \lambda^{D-}_{-0,+2} = \frac{1}{2}(\sin\Phi_{-0} + \sin\Phi_{+2})$$

or equivalently, $$\Phi_{-0} = \arccos(\lambda^{A+}_{-0,+2} + \lambda^{A-}_{-0,+2}) = -\arcsin(\lambda^{D+}_{-0,+2} - \lambda^{D-}_{-0,+2})$$

$$\Phi_{+2} = \arccos(\lambda^{A+}_{-0,+2} - \lambda^{A-}_{-0,+2}) = \arcsin(\lambda^{D+}_{-0,+2} + \lambda^{D-}_{-0,+2}).$$

so that the figures of merit are given by $$M^D_{-0,+2} = \frac{|\cos\Phi_{-0} + \cos\Phi_{+2}|}{|\cos\Phi_{-0} + \cos\Phi_{+2}| + |\sin\Phi_{-0} - \sin\Phi_{+2}|} \quad (31)$$

$$M^Q_{-0,+2} = \frac{|\cos\Phi_{-0} + \cos\Phi_{+2}| + |\sin\Phi_{-0} - \sin\Phi_{+2}|}{|\cos\Phi_{-0} + \cos\Phi_{+2}| + |\sin\Phi_{-0} - \sin\Phi_{+2}| +}$$
$$\phantom{M^Q_{-0,+2} =} \frac{}{|\cos\Phi_{-0} - \cos\Phi_{+2}| + |\sin\Phi_{-0} + \sin\Phi_{+2}|}$$

$$M^A_{-0,+2} = \frac{1}{2}|\cos\Phi_{-0} + \cos\Phi_{+2}|.$$

$(c_{+0}, c_{-2}, c_{-0}, c_{+2})$-Sampling (DPMS)

Addition of $S_{+0,-2}(t)$ and $S_{-0,+2}(t)$ yields $$S_{+0,-2,-0,+2}(t) = \quad (32)$$

$$S_{+0,-2}(t) + S_{-0,+2}(t) \propto \frac{1}{2}(\cos\Phi_{+0} + \cos\Phi_{-2} + \cos\Phi_{-0} + \cos\Phi_{+2})e^{i\alpha t} +$$

$$\frac{1}{2}(\sin\Phi_{+0} - \sin\Phi_{-2} - \sin\Phi_{-0} + \sin\Phi_{+2})e^{i\frac{\pi}{2}}e^{i\alpha t} +$$

$$\frac{1}{2}(\cos\Phi_{+0} - \cos\Phi_{-2} + \cos\Phi_{-0} - \cos\Phi_{+2})e^{-i\alpha t} -$$

$$\frac{1}{2}(\sin\Phi_{+0} + \sin\Phi_{-2} - \sin\Phi_{-0} - \sin\Phi_{+2})e^{i\frac{\pi}{2}}e^{-i\alpha t}.$$

After FT, one obtains for $(c_{+0}, c_{-2}, c_{-0}, c_{+2})$-sampling:

$$\lambda^{A+}_{+0,-2,-0,+2} = \frac{1}{2}(\cos\Phi_{+0} + \cos\Phi_{-2} + \cos\Phi_{-0} + \cos\Phi_{+2}); \quad (33)$$

$$\lambda^{D+}_{+0,-2,-0,+2} = \frac{1}{2}(\sin\Phi_{+0} - \sin\Phi_{-2} - \sin\Phi_{-0} + \sin\Phi_{+2})$$

$$\lambda^{A-}_{+0,-2,-0,+2} = \frac{1}{2}(\cos\Phi_{+0} - \cos\Phi_{-2} + \cos\Phi_{-0} - \cos\Phi_{+2});$$

$$\lambda^{D-}_{+0,-2,-0,+2} = -\frac{1}{2}(\sin\Phi_{+0} + \sin\Phi_{-2} - \sin\Phi_{-0} - \sin\Phi_{+2}).$$

so that the figures of merit are given by $$M^D_{+0,-2,-0,+2} = \frac{|\cos\Phi_{+0} + \cos\Phi_{-2} + \cos\Phi_{-0} + \cos\Phi_{+2}|}{\substack{|\cos\Phi_{+0} + \cos\Phi_{-2} + \cos\Phi_{-0} + \cos\Phi_{+2}| + \\ |\sin\Phi_{+0} - \sin\Phi_{-2} - \sin\Phi_{-0} + \sin\Phi_{+2}|}} \quad (34)$$

$$M^Q_{+0,-2,-0,+2} = \frac{\substack{|\cos\Phi_{+0} + \cos\Phi_{-2} + \cos\Phi_{-0} + \cos\Phi_{+2}| + \\ |\sin\Phi_{+0} - \sin\Phi_{-2} - \sin\Phi_{-0} + \sin\Phi_{+2}|}}{\substack{|\cos\Phi_{+0} + \cos\Phi_{-2} + \cos\Phi_{-0} + \cos\Phi_{+2}| + \\ |\sin\Phi_{+0} - \sin\Phi_{-2} - \sin\Phi_{-0} + \sin\Phi_{+2}| + \\ |\cos\Phi_{+0} - \cos\Phi_{-2} + \cos\Phi_{-0} - \cos\Phi_{+2}| + \\ |\sin\Phi_{+0} + \sin\Phi_{-2} - \sin\Phi_{-0} - \sin\Phi_{+2}|}}$$

$$M^A_{+0,-2,-0,+2} = \frac{1}{4}|\cos\Phi_{+0} + \cos\Phi_{-2} + \cos\Phi_{-0} + \cos\Phi_{+2}|.$$

Application for Partially Identical Secondary Phase Shifts

Yet another embodiment of the present invention relates to clean absorption mode NMR data acquisition for partially identical secondary phase shifts.

In the embodiment described below, forward and backward sampling for given n are associated with the same secondary phase shift. If forward and backward sampling of the time domain for given n are associated with the same secondary phase shift, one can define $$\Phi_n = \Phi_{+n} = \Phi_{-n} \quad (35)$$

In the following, the coefficient vector elements and the figures of merit for the different sampling schemes described above are simplified using Equation 35.

'States' Sampling $(c_{+0}, c_{+2})$-Sampling

Given Eq. 4, one obtains for $(c_{+0}, c_{+2})$-sampling, under the condition of Eq. 35:

$$\lambda^{A+}_{+0,+2} = \frac{1}{2}(\cos\Phi_0 + \cos\Phi_2); \lambda^{D+}_{+0,+2} = \frac{1}{2}(\sin\Phi_0 + \sin\Phi_2) \quad (36)$$

$$\lambda^{A-}_{+0,+2} = \frac{1}{2}(\cos\Phi_0 - \cos\Phi_2); \lambda^{D-}_{+0,+2} = -\frac{1}{2}(\sin\Phi_0 - \sin\Phi_2).$$

so that the figures of merit are given by $$M^D_{+0,+2} = \frac{|\cos\Phi_0 + \cos\Phi_2|}{|\cos\Phi_0 + \cos\Phi_2| + |\sin\Phi_0 + \sin\Phi_2|} \quad (37)$$

$$M^Q_{+0,+2} = \frac{(|\cos\Phi_0 + \cos\Phi_2| + |\sin\Phi_0 + \sin\Phi_2|)}{\substack{|\cos\Phi_0 + \cos\Phi_2| + |\sin\Phi_0 + \sin\Phi_2| + \\ |\cos\Phi_0 - \cos\Phi_2| + |\sin\Phi_0 - \sin\Phi_2|}}$$

$$M^A_{+0,+2} = \frac{1}{2}|\cos\Phi_0 + \cos\Phi_2|.$$

One embodiment of this aspect of the present invention involves backward sampling which is described as follows:

$(c_{-0}, c_{-2})$-Sampling

Given Eq. 8, one obtains for $(c_{-0}, c_{-2})$-sampling, under the condition of Eq. 35:

$$\lambda_{-0,-2}^{A+} = \frac{1}{2}(\cos\Phi_0 + \cos\Phi_2); \lambda_{-0,-2}^{D+} = -\frac{1}{2}(\sin\Phi_0 + \sin\Phi_2) \quad (38)$$

$$\lambda_{-0,-2}^{A-} = \frac{1}{2}(\cos\Phi_0 - \cos\Phi_2); \lambda_{-0,-2}^{D-} = \frac{1}{2}(\sin\Phi_0 - \sin\Phi_2).$$

so that the figures of merit are given by $$M_{-0,-2}^{D} = \frac{|\cos\Phi_0 + \cos\Phi_2|}{|\cos\Phi_0 + \cos\Phi_2| + |\sin\Phi_0 + \sin\Phi_2|} \quad (39)$$

$$M_{-0,-2}^{Q} = \frac{|\cos\Phi_0 + \cos\Phi_2| + |\sin\Phi_0 + \sin\Phi_2|}{|\cos\Phi_0 + \cos\Phi_2| + |\sin\Phi_0 + \sin\Phi_2| + |\cos\Phi_0 - \cos\Phi_2| + |\sin\Phi_0 - \sin\Phi_2|}$$

$$M_{-0,-2}^{A} = \frac{1}{2}|\cos\Phi_0 + \cos\Phi_2|.$$

Dual 'States' Sampling $(c_{+0}, c_{+2}, c_{-0}, c_{-2})$-Sampling

Given Eq. 11, one obtains for $(c_{+0}, c_{+2}, c_{-0}, c_{-2})$-sampling, under the condition of Eq. 35:

$$\lambda_{+0,+2,-0,-2}^{A+} = (\cos\Phi_0 + \cos\Phi_2); \lambda_{+0,+2,-0,-2}^{D+} = 0 \quad (40)$$

$$\lambda_{+0,+2,-0,-2}^{A-} = (\cos\Phi_0 - \cos\Phi_2); \lambda_{+0,+2,-0,-2}^{D-} = 0.$$

so that the figures of merit are given by $$M_{+0,+2,-0,-2}^{D} = 1 \quad (41)$$

$$M_{+0,+2,-0,-2}^{Q} = \frac{|\cos\Phi_0 + \cos\Phi_2|}{|\cos\Phi_0 + \cos\Phi_2| + |\cos\Phi_0 - \cos\Phi_2|}$$

$$M_{+0,+2,-0,-2}^{A} = \frac{1}{2}|\cos\Phi_0 + \cos\Phi_2|.$$

$\pi/4$ and $3\pi/4$-Shifted Mirrored Sampling $(c_{+1}, c_{-1})$-Sampling (PMS)

Given Eq. 15, one obtains for $(c_{+1}, c_{-1})$-sampling, under the condition of Eq. 35:

$$\lambda_{+1,-1}^{A+} = \cos\Phi_1; \lambda_{+1,-1}^{D+} = 0$$

$$\lambda_{+1,-1}^{A-} = -\sin\Phi_1; \lambda_{+1,-1}^{D-} = 0 \quad (42).$$

so that the figures of merit are given by $$M_{+1,-1}^{D} = 1 \quad (43)$$

$$M_{+1,-1}^{Q} = \frac{|\cos\Phi_1|}{|\cos\Phi_1| + |\sin\Phi_1|}$$

$$M_{+1,-1}^{A} = |\cos\Phi_1|.$$

$(c_{+3}, c_{-3})$-Sampling (PMS)

Given Eq. 19, one obtains for $(c_{+3}, c_{-3})$-sampling, under the condition of Eq. 35:

$$\lambda_{+3,-3}^{A+} = \cos\Phi_3; \lambda_{+3,-3}^{D+} = 0$$

$$\lambda_{+3,-3}^{A-} = -\sin\Phi_3; \lambda_{+3,-3}^{D-} = 0 \quad (44).$$

so that the figures of merit are given by $$M_{+3,-3}^{D} = 1 \quad (45)$$

$$M_{+3,-3}^{Q} = \frac{|\cos\Phi_3|}{|\cos\Phi_3| + |\sin\Phi_3|}$$

$$M_{+3,-3}^{A} = |\cos\Phi_3|.$$

$(c_{+1}, c_{-1}, c_{+3}, c_{-3})$-Sampling (DPMS)

Given Eq. 22, one obtains for $(C_{+1}, c_{-1}, c_{+3}, c_{-3})$-sampling, under the condition of Eq. 35:

$$\lambda_{+1,-1,+3,-3}^{A+} = \cos\Phi_1 + \cos\Phi_3; \lambda_{+1,-1,+3,-3}^{D+} = 0$$

$$\lambda_{+1,-1,+3,-3}^{A-} = -(\sin\Phi_1 - \Phi_3); \lambda_{+1,-1,+3,-3}^{D-} = 0 \quad (46).$$

so that the figures of merit are given by $$M_{+1,-1,+3,-3}^{D} = 1 \quad (47)$$

$$M_{+1,-1,+3,-3}^{Q} = \frac{|\cos\Phi_1 + \cos\Phi_3|}{|\cos\Phi_1 + \cos\Phi_3| + |\sin\Phi_1 - \sin\Phi_3|}$$

$$M_{+1,-1,+3,-3}^{A} = \frac{1}{2}|\cos\Phi_1 + \cos\Phi_3|.$$

0 and $\pi/2$-Shifted Mirrored Sampling $(c_{+0}, c_{-2})$-Sampling (PMS)

Given Eq. 26, one obtains for $(c_{+0}, c_{-2})$-sampling, under the condition of Eq. 35:

$$\lambda_{+0,-2}^{A+} = \frac{1}{2}(\cos\Phi_0 + \cos\Phi_2); \lambda_{+0,-2}^{D+} = \frac{1}{2}(\sin\Phi_0 - \sin\Phi_2) \quad (48)$$

$$\lambda_{+0,-2}^{A-} = \frac{1}{2}(\cos\Phi_0 - \cos\Phi_2); \lambda_{+0,-2}^{D-} = -\frac{1}{2}(\sin\Phi_0 + \sin\Phi_2).$$

so that the figures of merit are given by $$M_{+0,-2}^{D} = \frac{|\cos\Phi_0 + \cos\Phi_2|}{|\cos\Phi_0 + \cos\Phi_2| + |\sin\Phi_0 - \sin\Phi_2|} \quad (49)$$

$$M_{+0,-2}^{Q} = \frac{|\cos\Phi_0 + \cos\Phi_2| + |\sin\Phi_0 - \sin\Phi_2|}{|\cos\Phi_0 + \cos\Phi_2| + |\sin\Phi_0 - \sin\Phi_2| + |\cos\Phi_0 - \cos\Phi_2| + |\sin\Phi_0 + \sin\Phi_2|}$$

$$M_{+0,-2}^{A} = \frac{1}{2}|\cos\Phi_0 + \cos\Phi_2|.$$

$(c_{-0}, c_{+2})$-Sampling (PMS)

Given Eq. 30, one obtains for $(c_{-0}, c_{+2})$-sampling, under the condition of Eq. 35:

$$\lambda_{-0,+2}^{A+} = \frac{1}{2}(\cos\Phi_0 + \cos\Phi_2); \lambda_{-0,+2}^{D+} = -\frac{1}{2}(\sin\Phi_0 - \sin\Phi_2) \quad (50)$$

$$\lambda_{-0,+2}^{A-} = \frac{1}{2}(\cos\Phi_0 - \cos\Phi_2); \lambda_{-0,+2}^{D-} = \frac{1}{2}(\sin\Phi_0 + \sin\Phi_2).$$

so that the figures of merit are given by $$M^D_{-0,+2} = \frac{|\cos\Phi_0 + \cos\Phi_2|}{|\cos\Phi_0 + \cos\Phi_2| + |\sin\Phi_0 - \sin\Phi_2|} \quad (51)$$

$$M^Q_{-0,+2} = \frac{|\cos\Phi_0 + \cos\Phi_2| + |\sin\Phi_0 - \sin\Phi_2|}{|\cos\Phi_0 + \cos\Phi_2| + |\sin\Phi_0 - \sin\Phi_2| + |\cos\Phi_0 - \cos\Phi_2| + |\sin\Phi_0 + \sin\Phi_2|}$$

$$M^A_{-0,+2} = \frac{1}{2}|\cos\Phi_0 + \cos\Phi_2|.$$

$(c_{+0}, c_{-2}, c_{-0}, c_{+2})$-Sampling (DPMS)

Given Eq. 33, one obtains for $(c_{+0}, c_{-2}, c_{-0}, c_{+2})$-sampling, under the condition of Eq. 35:

$$\lambda^{A+}_{+0,-2,-0,+2} = \cos\Phi_0 + \cos\Phi_2; \; \lambda^{D+}_{+0,-2,-0,+2} = 0$$

$$\lambda^{A-}_{+0,-2,-0,+2} = \cos\Phi_0 - \cos\Phi_2; \; \lambda^{D-}_{+0,-2,-0,+2} = 0 \quad (52)$$

so that the figures of merit are given by $$M^D_{+0,-2,-0,+2} = 1 \quad (53)$$

$$M^Q_{+0,-2,-0,+2} = \frac{|\cos\Phi_0 + \cos\Phi_2|}{|\cos\Phi_0 + \cos\Phi_2| + |\cos\Phi_0 - \cos\Phi_2|}$$

$$M^A_{+0,-2,-0,+2} = \frac{1}{2}|\cos\Phi_0 + \cos\Phi_2|.$$

Another aspect of the present invention relates to a general application for partly identical secondary phase shifts.

Given that two forward and two backward sampling are associated with secondary phase shifts independent of n, one can define $$\Phi_+ = \Phi_{+n}$$

$$\Phi_- = \Phi_{-n} \quad (54).$$

In the following, the coefficient vector elements and the figures of merit for the different sampling schemes of the above sections are simplified using Eq. 54.

'States' Sampling $(c_{+0}, c_{+2})$-Sampling

Given Eq. 4, one obtains for $(c_{+0}, c_{+2})$-sampling, under the condition of Eq. 54:

$$\lambda^{A+}_{+0,+2} = \cos\Phi_+; \; \lambda^{D+}_{+0,+2} = \sin\Phi_+$$

$$\lambda^{A-}_{+0,+2} = 0; \; \lambda^{D-}_{+0,+2} = 0 \quad (55),$$

so that the figures of merit are given by $$M^D_{+0,+2} = \frac{|\cos\Phi_+|}{|\cos\Phi_+| + |\sin\Phi_+|} \quad (56)$$

$$M^Q_{+0,+2} = 1$$

$$M^A_{+0,+2} = |\cos\Phi_+|.$$

$(c_{-0}, c_{-2})$-Sampling

Given Eq. 8, one obtains for $(c_{-0}, c_{-2})$-sampling, under the condition of Eq. 54:

$$\lambda^{A+}_{-0,-2} = \cos\Phi_-; \; \lambda^{D+}_{-0,-2} = -\sin\Phi_-$$

$$\lambda^{A-}_{-0,-2} = 0; \; \lambda^{D-}_{-0,-2} = 0 \quad (57).$$

so that the figures of merit are given by $$M^D_{-0,-2} = \frac{|\cos\Phi_-|}{|\cos\Phi_-| + |\sin\Phi_-|} \quad (58)$$

$$M^Q_{-0,-2} = 1$$

$$M^A_{-0,-2} = |\cos\Phi_-|.$$

$(c_{+0}, c_{+2}, c_{-0}, c_{-2})$-Sampling

Given Eq. 11, one obtains for $(c_{+0}, c_{+2}, c_{-0}, c_{-2})$-sampling, under the condition of Eq. 54:

$$\lambda^{A+}_{+0,+2,-0,-2} = \cos\Phi_+ + \cos\Phi_-; \; \lambda^{D+}_{+0,+2,-0,-2} = \sin\Phi_+ - \sin\Phi_-$$

$$\lambda^{A-}_{+0,+2,-0,-2} = 0; \; \lambda^{D-}_{+0,+2,-0,-2} = 0 \quad (59).$$

so that the figures of merit are given by $$M^D_{+0,+2,-0,-2} = \frac{|\cos\Phi_+ + \cos\Phi_-|}{|\cos\Phi_+ + \cos\Phi_-| + |\sin\Phi_+ - \sin\Phi_-|} \quad (60)$$

$$M^Q_{+0,+2,-0,-2} = 1$$

$$M^A_{+0,+2,-0,-2} = \frac{1}{2}|\cos\Phi_+ + \cos\Phi_-|.$$

$\pi/4$ and $3\pi/4$-Shifted Mirrored Sampling $(c_{+1}, c_{-1})$-Sampling (PMS)

Given Eq. 15, one obtains for $(c_{+1}, c_{-1})$-sampling, under the condition of Eq. 54:

$$\lambda^{A+}_{+1,-1} = \frac{1}{2}(\cos\Phi_+ + \cos\Phi_-); \; \lambda^{D+}_{+1,-1} = \frac{1}{2}(\sin\Phi_+ - \sin\Phi_-) \quad (61)$$

$$\lambda^{A-}_{+1,-1} = -\frac{1}{2}(\sin\Phi_+ + \sin\Phi_-); \; \lambda^{D-}_{+1,-1} = -\frac{1}{2}(\cos\Phi_+ - \cos\Phi_-).$$

so that the figures of merit are given by $$M^D_{+1,-1} = \frac{|\cos\Phi_+ + \cos\Phi_-|}{|\cos\Phi_+ + \cos\Phi_-| + |\sin\Phi_+ - \sin\Phi_-|} \quad (62)$$

$$M^Q_{+1,-1} = \frac{|\cos\Phi_+ + \cos\Phi_-| + |\sin\Phi_+ - \sin\Phi_-|}{|\cos\Phi_+ + \cos\Phi_-| + |\sin\Phi_+ - \sin\Phi_-| + |\sin\Phi_+ + \sin\Phi_-| + |\cos\Phi_+ - \cos\Phi_-|}$$

$$M^A_{+1,-1} = \frac{1}{2}|\cos\Phi_+ + \cos\Phi_-|.$$

$(c_{+3}, c_{-3})$-Sampling (PMS)

Given Eq. 19, one obtains for $(c_{+3}, c_{-3})$-sampling, under the condition of Eq. 54:

$$\lambda^{A+}_{+3,-3} = \frac{1}{2}(\cos\Phi_+ + \cos\Phi_-); \; \lambda^{D+}_{+3,-3} = \frac{1}{2}(\sin\Phi_+ - \sin\Phi_-) \quad (63)$$

$$\lambda^{A-}_{+3,-3} = \frac{1}{2}(\sin\Phi_+ + \sin\Phi_-); \; \lambda^{D-}_{+3,-3} = \frac{1}{2}(\cos\Phi_+ - \cos\Phi_-).$$

so that the figures of merit are given by $$M^D_{+3,-3} = \frac{|\cos\Phi_+ + \cos\Phi_-|}{|\cos\Phi_+ + \cos\Phi_-| + |\sin\Phi_+ - \sin\Phi_-|} \quad (64)$$

$$M^Q_{+3,-3} = \frac{|\cos\Phi_+ + \cos\Phi_-| + |\sin\Phi_+ - \sin\Phi_-|}{|\cos\Phi_+ + \cos\Phi_-| + |\sin\Phi_+ - \sin\Phi_-| + |\sin\Phi_+ + \sin\Phi_-| + |\cos\Phi_+ - \cos\Phi_-|}$$

$$M^A_{+3,-3} = \frac{1}{2}|\cos\Phi_+ + \cos\Phi_-|,$$

$(c_{+1}, c_{-1}, c_{+3}, c_{-3})$-Sampling (DPMS)

Given Eq. 22, one obtains for $(C+1, c_{-1}, C_{+3}, c_{-3})$-sampling, under the condition of Eq. 54:

$$\lambda^{A+}_{+1,-1,+3,-3} = \cos\Phi_+ + \cos\Phi_-; \lambda^{D+}_{+1,-1,+3,-3} = \sin\Phi_+ - \sin\Phi_-$$

$$\lambda^{A-}_{+1,-1,+3,-3} = 0; \lambda^{D-}_{+1,-1,+3,-3} = 0 \quad (65).$$

so that the figures of merit are given by $$M^D_{+1,-1,+3,-3} = \frac{|\cos\Phi_+ + \cos\Phi_-|}{|\cos\Phi_+ + \cos\Phi_-| + |\sin\Phi_+ - \sin\Phi_-|} \quad (66)$$

$$M^Q_{+1,-1,+3,-3} = 1$$

$$M^A_{+1,-1,+3,-3} = \frac{1}{2}|\cos\Phi_+ + \cos\Phi_-|.$$

0 and π/2-Shifted Mirrored Sampling $(c_{+0}, c_{-2})$-Sampling (PMS)

Given Eq. 26, one obtains for $(C_{+0}, c_{-2})$-sampling, under the condition of Eq. 54:

$$\lambda^{A+}_{+0,-2} = \frac{1}{2}(\cos\Phi_+ + \cos\Phi_-); \lambda^{D+}_{+0,-2} = \frac{1}{2}(\sin\Phi_+ - \sin\Phi_-) \quad (67)$$

$$\lambda^{A-}_{+0,-2} = \frac{1}{2}(\cos\Phi_+ - \cos\Phi_-); \lambda^{D-}_{+0,-2} = -\frac{1}{2}(\sin\Phi_+ + \sin\Phi_-).$$

so that the figures of merit are given by $$M^D_{+0,-2} = \frac{|\cos\Phi_+ + \cos\Phi_-|}{|\cos\Phi_+ + \cos\Phi_-| + |\sin\Phi_+ - \sin\Phi_-|} \quad (68)$$

$$M^Q_{+0,-2} = \frac{|\cos\Phi_+ + \cos\Phi_-| + |\sin\Phi_+ - \sin\Phi_-|}{|\cos\Phi_+ + \cos\Phi_-| + |\sin\Phi_+ - \sin\Phi_-| + |\cos\Phi_+ - \cos\Phi_-| + |\sin\Phi_+ + \sin\Phi_-|}$$

$$M^A_{+0,-2} = \frac{1}{2}|\cos\Phi_+ + \cos\Phi_-|.$$

$(c_{-0}, c_{+2})$-Sampling (PMS)

Given Eq. 30, one obtains for $(c_{-0}, c_{+2})$-sampling, under the condition of Eq. 54:

$$\lambda^{A+}_{-0,+2} = \frac{1}{2}(\cos\Phi_- + \cos\Phi_+); \lambda^{D+}_{-0,+2} = -\frac{1}{2}(\sin\Phi_- - \sin\Phi_+) \quad (69)$$

$$\lambda^{A-}_{-0,+2} = \frac{1}{2}(\cos\Phi_- - \cos\Phi_+); \lambda^{D-}_{-0,+2} = \frac{1}{2}(\sin\Phi_- + \sin\Phi_+).$$

so that the figures of merit are given by $$M^D_{-0,+2} = \frac{|\cos\Phi_- + \cos\Phi_+|}{|\cos\Phi_- + \cos\Phi_+| + |\sin\Phi_- - \sin\Phi_+|} \quad (70)$$

$$M^Q_{-0,+2} = \frac{|\cos\Phi_- + \cos\Phi_+| + |\sin\Phi_- - \sin\Phi_+|}{|\cos\Phi_- + \cos\Phi_+| + |\sin\Phi_- - \sin\Phi_+| + |\cos\Phi_- - \cos\Phi_+| + |\sin\Phi_- + \sin\Phi_+|}$$

$$M^A_{-0,+2} = \frac{1}{2}|\cos\Phi_- + \cos\Phi_+|.$$

$(c_{+0}, c_{-2}, c_{-0}, c_{+2})$-Sampling (DPMS)

Given Eq. 33, one obtains for $(c_{+0}, c_{-2}, c_{-0}, c_{+2})$-sampling, under the condition of Eq. 54:

$$\lambda^{A+}_{+0,-2,-0,+2} = \cos\Phi_+ + \cos\Phi_-; \lambda^{D+}_{+0,-2,-0,+2} = \sin\Phi_+ - \sin\Phi_-$$

$$\lambda^{A-}_{+0,-2,-0,+2} = 0; \lambda^{D-}_{+0,-2,-0,+2} = 0; \quad (71).$$

so that the figures of merit are given by $$M^D_{+0,-2,-0,+2} = \frac{|\cos\Phi_+ + \cos\Phi_-|}{|\cos\Phi_+ + \cos\Phi_-| + |\sin\Phi_+ - \sin\Phi_-|} \quad (72)$$

$$M^Q_{+0,-2,-0,+2} = 1$$

$$M^A_{+0,-2,-0,+2} = \frac{1}{2}|\cos\Phi_+ + \cos\Phi_-|.$$

Application for Identical Secondary Phase Shifts

One embodiment of the present invention relates to clean absorption mode NMR data acquisition for identical secondary phase shifts.

Given that secondary phase shifts of forward and backward sampling are the same and independent of n, one can define $$\Phi = \Phi_{\pm n} \quad (73).$$

In the following, the coefficient vector elements and the figures of merit for the different sampling schemes of the above sections are simplified using Eq. 73.

'States' Sampling $(c_{+0}, c_{+2})$-Sampling

Given Eq. 4, one obtains for $(c_{+0}, c_{+2})$-sampling, under the condition of Eq. 73:

$$\lambda^{A+}_{+0,+2} = \cos\Phi; \lambda^{D+}_{+0,+2} = \sin\Phi$$

$$\lambda^{A-}_{+0,+2} = 0; \lambda^{D-}_{+0,+2} = 0 \quad (74).$$

so that the figures of merit are given by $$M^D_{+0,+2} = \frac{|\cos\Phi|}{|\cos\Phi| + |\sin\Phi|} \quad (75)$$

$$M^Q_{+0,+2} = 1$$

$$M^A_{+0,+2} = |\cos\Phi|.$$

$(c_{-0}, c_{-2})$-Sampling

Given Eq. 8, one obtains for $(c_{-0}, c_{-2})$-sampling, under the condition of Eq. 73:

$$\lambda^{A+}_{-0,-2} = \cos\Phi; \lambda^{D+}_{-0,-2} = \sin\Phi$$

$$\lambda^{A-}_{-0,-2} = 0; \lambda^{D-}_{-0,-2} = 0 \quad (76).$$

so that the figures of merit are given by $$M_{-0,-2}^{D} = \frac{|\cos\Phi|}{|\cos\Phi| + |\sin\Phi|} \quad (77)$$

$$M_{-0,-2}^{Q} = 1$$

$$M_{-0,-2}^{A} = |\cos\Phi|.$$

$(c_{+0},c_{+2},c_{-0},c_{-2})$-Sampling

Given Eq. 11, one obtains for $(c_{+0},c_{+2},c_{-0},c_{-2})$-sampling, under the condition of Eq. 73:

$$\lambda_{+0,+2,-0,-2}^{A+} = 2\cos\Phi; \lambda_{+0,+2,-0,-2}^{D+} = 0$$

$$\lambda_{+0,+2,-0,-2}^{A-} = 0; \lambda_{+0,+2,-0,-2}^{D-} = 0 \quad (78).$$

so that the figures of merit are given by $$M_{+0,+2,-0,-2}^{D} = 1$$

$$M_{+0,+2,-0,-2}^{Q} = 1$$

$$M_{+0,+2,-0,-2}^{A} = |\cos\Phi| \quad (79).$$

$\pi/4$ and $3\pi/4$-Shifted Mirrored Sampling $(c_{+1},c_{-1})$-Sampling (PMS)

Given Eq. 15, one obtains for $(c_{+1},c_{-1})$-sampling, under the condition of Eq. 73:

$$\lambda_{+1,-1}^{A+} = \cos\Phi; \lambda_{+1,-1}^{D+} = 0$$

$$\lambda_{+1,-1}^{A-} = -\sin\Phi; \lambda_{+1,-1}^{D-} = 0 \quad (80).$$

so that the figures of merit are given by $$M_{+1,-1}^{D} = 1 \quad (81)$$

$$M_{+1,-1}^{Q} = \frac{|\cos\Phi|}{|\cos\Phi| + |\sin\Phi|}$$

$$M_{+1,-1}^{A} = |\cos\Phi|,$$

$(c_{+3},c_{-3})$-Sampling (PMS)

Given Eq. 19, one obtains for $(c_{+3},c_{-3})$-sampling, under the condition of Eq. 73:

$$\lambda_{+3,-3}^{A+} = \cos\Phi; \lambda_{+3,-3}^{D+} = 0$$

$$\lambda_{+3,-3}^{A-} = \sin\Phi; \lambda_{+3,-3}^{D-} = 0 \quad (82).$$

so that the figures of merit are given by $$M_{+3,-3}^{D} = 1 \quad (83)$$

$$M_{+3,-3}^{Q} = \frac{|\cos\Phi|}{|\cos\Phi| + |\sin\Phi|}$$

$$M_{+3,-3}^{A} = |\cos\Phi|,$$

$(c_{+1},c_{-1},c_{+3},C_{-3})$-Sampling (DPMS)

Given Eq. 22, one obtains for $(c_{+1},c_{-1},c_{+3},c_{-3})$-sampling, under the condition of Eq. 73:

$$\lambda_{+1,-1,+3,-3}^{A+} = 2\cos\Phi; \lambda_{+1,-1,+3,-3}^{D+} = 0$$

$$\lambda_{+1,-1,+3,-3}^{A-} = 0; \lambda_{+1,-1,+3,-3}^{D-} = 0 \quad (84).$$

so that the figures of merit are given by $$M_{+1,-1,+3,-3}^{D} = 1$$

$$M_{+1,-1,+3,-3}^{Q} = 1$$

$$M_{+1,-1,+3,-3}^{A} = |\cos\Phi| \quad (85).$$

0 and $\pi/2$-Shifted Mirrored Sampling $(c_{+0},c_{-2})$-Sampling (PMS)

Given Eq. 26, one obtains for $(c_{+0},c_{-2})$-sampling, under the condition of Eq. 73:

$$\lambda_{+0,-2}^{A+} = \cos\Phi; \lambda_{+0,-2}^{D+} = 0$$

$$\lambda_{+0,-2}^{A-} = 0; \lambda_{+0,-2}^{D-} = -\sin\Phi \quad (86).$$

so that the figures of merit are given by $$M_{+0,-2}^{D} = 1 \quad (87)$$

$$M_{+0,-2}^{Q} = \frac{|\cos\Phi|}{|\cos\Phi| + |\sin\Phi|}$$

$$M_{+0,-2}^{A} = |\cos\Phi|,$$

$(c_{-0},c_{+2})$-Sampling (PMS)

Given Eq. 30, one obtains for $(c_{-0},c_{+2})$-sampling, under the condition of Eq. 73:

$$\lambda_{-0,+2}^{A+} = \cos\Phi; \lambda_{-0,+2}^{D+} = 0$$

$$\lambda_{-0,+2}^{A-} = 0; \lambda_{-0,+2}^{D-} = \sin\Phi \quad (88).$$

so that the figures of merit are given by $$M_{-0,+2}^{D} = 1 \quad (89)$$

$$M_{-0,+2}^{Q} = \frac{|\cos\Phi|}{|\cos\Phi| + |\sin\Phi|}$$

$$M_{-0,+2}^{A} = |\cos\Phi|.$$

$(c_{+0},c_{-2},c_{-0},c_{+2})$-Sampling (DPMS)

Given Eq. 33, one obtains for $(c_{+0},c_{-2}, c_{-0},c_{+2})$-sampling, under the condition of Eq. 73:

$$\lambda_{+0,-2,-0,+2}^{A+} = 2\cos\Phi; \lambda_{+0,-2,-0,+2}^{D+} = 0;$$

$$\lambda_{+0,-2,-0,+2}^{A-} = 0; \lambda_{+0,-2,-0,+2}^{D-} = 0; \quad (90).$$

so that the figures of merit are given by $$M_{+0,-2,-0,+2}^{D} = 1$$

$$M_{+0,-2,-0,+2}^{Q} = 1$$

$$M_{+0,-2,-0,+2}^{A} = |\cos\Phi| \quad (91).$$

Extension to Multi-Dimensional NMR

Another aspect of the present invention relates to a general application for Extension to Multi-dimensional NMR.

The sections above introduce different $(c_p,c_q)$-samplings ($[p,q]=[+0,+2], [-0,-2]$ for 'States' sampling; $[+1,-1]$; $[+3,-3]$ for $\pi/4$ and $3\pi/4$-shifted mirrored sampling; $[+0,-2]$; $[-0,+2]$ for 0 and $\pi/2$-shifted mirrored sampling), the corresponding interferogram vectors $C_{p,q}$ of size 2×1 and the $D_{p,q}$ matrices of size 2×2, for a single indirect dimension. To summarize, the $D_{p,q}$ matrices defined thus far are:

$$D_{+0,+2} = D_{-0,+2} = \begin{bmatrix} 1 & 0 \\ 0 & -1 \end{bmatrix}; D_{-0,-2} = D_{+0,-2} = \begin{bmatrix} 1 & 0 \\ 0 & 1 \end{bmatrix} \quad (92)$$

$$D_{+1,-1} = \frac{1}{\sqrt{2}} \begin{bmatrix} 1 & 1 \\ -1 & 1 \end{bmatrix}; D_{+3,-3} = \frac{1}{\sqrt{2}} \begin{bmatrix} -1 & -1 \\ -1 & 1 \end{bmatrix}.$$

For the sake of brevity, we also define $$Q = [1 \; i] \quad (93)$$

and its conjugate $$Q^* = [1 \; -i] \quad (94).$$

The sampling schemes of the above sections, can readily be generalized to K+1 indirect dimensions of a multi-dimensional NMR experiment, where K+1 chemical shifts $\alpha_0$, $\alpha_1$, ... $\alpha_K$, that are associated with phase shifts $\Phi_{\pm n,0}$, $\Phi_{\pm n,1}$, ... $\Phi_{\pm n,K}$, are sampled using the same sampling scheme. For $(c_p, c_q)$-sampling, the corresponding interferogram vector $C_{p,q}(t_K, t_{K-1}, \ldots, t_0)$ of size $2^{K+1} \times 1$, the corresponding transformation matrix $D_{p,q}(K)$ of size $2^{K+1} \times 2^{K+1}$ and the vector $Q(K)$ of size $1 \times 2^{K+1}$ are obtained by K-fold tensor product formation:

$$C_{p,q}(t_K, \ldots, t_0) = \begin{bmatrix} c_p(t_K) \\ c_q(t_K) \end{bmatrix} \otimes \begin{bmatrix} c_p(t_{K-1}) \\ c_q(t_{K-1}) \end{bmatrix} \otimes \ldots \otimes \quad (95)$$

$$\begin{bmatrix} c_p(t_1) \\ c_q(t_1) \end{bmatrix} \otimes \begin{bmatrix} c_p(t_0) \\ c_q(t_0) \end{bmatrix} = \bigotimes_{j=0}^{K} C_{p,q}$$

$$D_{p,q}(K) = (D_{p,q})_K \otimes (D_{p,q})_{K-1} \otimes \ldots \otimes (D_{p,q})_1 \otimes (D_{p,q})_0 = \bigotimes_{j=0}^{K} D_{p,q}$$

$$Q(K) = (Q)_K \otimes (Q)_{K-1} \otimes \ldots \otimes (Q)_1 \otimes (Q)_0 = \bigotimes_{j=0}^{K} Q.$$

After FT, the frequency domain peaks of the K+1 dimensional spectrum can be obtained by an equivalent tensor product formation in the frequency domain using the description of Eq. 1

$$F(K) = (F)_K \otimes (F)_{K-1} \otimes \ldots \otimes (F)_1 \otimes (F)_0 = \bigotimes_{j=0}^{K} F \quad (96)$$

$$\lambda(K) = (\lambda)_K \otimes (\lambda)_{K-1} \otimes \ldots \otimes (\lambda)_1 \otimes (\lambda)_0 = \bigotimes_{j=0}^{K} \lambda.$$

In the following, the generalization of mirrored sampling (MS) for multidimensional NMR is derived in two stages. First, for $\pi/4$ and $3\pi/4$-shifted mirrored sampling of two indirect dimensions (K=1), and second, generalization to arbitrary K for all the sampling schemes.

Two Indirect Dimensions (K=1)

$(c_{+1}, c_{-1})$-Sampling (PMS)

Starting with Eq. 14, the complex signal for two indirect dimensions is proportional to $$S_{+1,-1}(t_1, t_0) \propto \bigotimes_{j=0}^{1} Q D_{+1,-1} C_{+1,1}(t_j) = \quad (97)$$

$$\frac{1}{\sqrt{2}} [1 \; i] \begin{bmatrix} 1 & 1 \\ -1 & 1 \end{bmatrix} \begin{bmatrix} c_{+1}(t_1) \\ c_{-1}(t_1) \end{bmatrix} \otimes \frac{1}{2} [1 \; i] \begin{bmatrix} 1 & 1 \\ -1 & 1 \end{bmatrix} \begin{bmatrix} c_{+1}(t_0) \\ c_{-1}(t_0) \end{bmatrix} =$$

$$\left( \frac{1}{2}(\cos\Phi_{+1,1} + \cos\Phi_{-1,1})e^{i\alpha_1 t_1} + \frac{1}{2}(\sin\Phi_{+1,1} - \sin\Phi_{-1,1}) \right)$$

$$e^{i\pi/2} e^{i\alpha_1 t_1} - \frac{1}{2}(\sin\Phi_{+1,1} + \sin\Phi_{-1,1})e^{-i\alpha_1 t_1} -$$

$$\frac{1}{2}(\cos\Phi_{+1,1} - \cos\Phi_{-1,1})e^{i\pi/2} e^{-i\alpha_1 t_1} \Big) \otimes$$

$$\left( \frac{1}{2}(\cos\Phi_{+1,0} + \cos\Phi_{-1,0})e^{i\alpha_0 t_0} + \frac{1}{2}(\sin\Phi_{+1,0} - \sin\Phi_{-1,0}) \right)$$

$$e^{i\pi/2} e^{i\alpha_0 t_0} - \frac{1}{2}(\sin\Phi_{+1,0} + \sin\Phi_{-1,0})e^{-i\alpha_0 t_0} -$$

$$\frac{1}{2}(\cos\Phi_{+1,0} - \cos\Phi_{-1,0})e^{i\pi/2} e^{-i\alpha_0 t_0} \Big).$$

Multidimensional FT reveals the peak components as $$\text{Re}(F_C(S_{+1,-1}(t_1, t_0))) \propto \quad (98)$$

$$\frac{1}{4}(\cos\Phi_{+1,1}\cos\Phi_{+1,0} + \cos\Phi_{+1,1}\cos\Phi_{-1,0} + \cos\Phi_{-1,1}\cos\Phi_{+1,0} +$$

$$\cos\Phi_{-1,1}\cos\Phi_{-1,0})(A_1 +)(A_0 +) +$$

$$\frac{1}{4}(\cos\Phi_{+1,1}\sin\Phi_{+1,0} - \cos\Phi_{+1,1}\sin\Phi_{-1,0} + \cos\Phi_{-1,1}\sin\Phi_{+1,0} -$$

$$\cos\Phi_{-1,1}\sin\Phi_{-1,0})(A_1 +)(D_0 +) -$$

$$\frac{1}{4}(\cos\Phi_{+1,1}\sin\Phi_{+1,0} + \cos\Phi_{+1,1}\sin\Phi_{-1,0} + \cos\Phi_{-1,1}\sin\Phi_{+1,0} +$$

$$\cos\Phi_{-1,1}\sin\Phi_{-1,0})(A_1 +)(A_0 -) -$$

$$\frac{1}{4}(\cos\Phi_{+1,1}\cos\Phi_{+1,0} - \cos\Phi_{+1,1}\cos\Phi_{-1,0} + \cos\Phi_{-1,1}\cos\Phi_{+1,0} -$$

$$\cos\Phi_{-1,1}\cos\Phi_{-1,0})(A_1 +)(D_0 -) +$$

$$\frac{1}{4}(\sin\Phi_{+1,1}\cos\Phi_{+1,0} + \sin\Phi_{+1,1}\cos\Phi_{-1,0} - \sin\Phi_{-1,1}\cos\Phi_{+1,0} -$$

$$\sin\Phi_{-1,1}\cos\Phi_{-1,0})(D_1 +)(A_0 +) +$$

$$\frac{1}{4}(\sin\Phi_{+1,1}\sin\Phi_{+1,0} - \sin\Phi_{+1,1}\sin\Phi_{-1,0} - \sin\Phi_{-1,1}\sin\Phi_{+1,0} +$$

$$\sin\Phi_{-1,1}\sin\Phi_{-1,0})(D_1 +)(D_0 +) -$$

$$\frac{1}{4}(\sin\Phi_{+1,1}\sin\Phi_{+1,0} + \sin\Phi_{+1,1}\sin\Phi_{-1,0} - \sin\Phi_{-1,1}\sin\Phi_{+1,0} -$$

$$\sin\Phi_{-1,1}\sin\Phi_{-1,0})(D_1 +)(A_0 -) -$$

$$\frac{1}{4}(\sin\Phi_{+1,1}\cos\Phi_{+1,0} - \sin\Phi_{+1,1}\cos\Phi_{-1,0} - \sin\Phi_{-1,1}\cos\Phi_{+1,0} +$$

$$\sin\Phi_{-1,1}\cos\Phi_{-1,0})(D_1 +)(D_0 -) -$$

$$\frac{1}{4}(\sin\Phi_{+1,1}\cos\Phi_{+1,0} + \sin\Phi_{+1,1}\cos\Phi_{-1,0} + \sin\Phi_{-1,1}\cos\Phi_{+1,0} +$$

$$\sin\Phi_{-1,1}\cos\Phi_{-1,0})(A_1 -)(A_0 +) -$$

$$\frac{1}{4}(\sin\Phi_{+1,1}\sin\Phi_{+1,0} - \sin\Phi_{+1,1}\sin\Phi_{-1,0} + \sin\Phi_{-1,1}\sin\Phi_{+1,0} -$$

$$\sin\Phi_{-1,1}\sin\Phi_{-1,0})(A_1 -)(D_0 +) +$$

$$\frac{1}{4}(\sin\Phi_{+1,1}\sin\Phi_{+1,0} + \sin\Phi_{+1,1}\sin\Phi_{-1,0} +$$

$$\sin\Phi_{-1,1}\sin\Phi_{+1,0} \sin\Phi_{-1,1}\sin\Phi_{-1,0})(A_1 -)(A_0 -) +$$

$$\frac{1}{4}(\sin\Phi_{+1,1}\cos\Phi_{+1,0} - \sin\Phi_{+1,1}\cos\Phi_{-1,0} + \sin\Phi_{-1,1}\cos\Phi_{+1,0} -$$

$$\sin\Phi_{-1,1}\cos\Phi_{-1,0})(A_1 -)(D_0 -) -$$

$$\frac{1}{4}(\cos\Phi_{+1,1}\cos\Phi_{+1,0} + \cos\Phi_{+1,1}\cos\Phi_{-1,0} - \cos\Phi_{-1,1}\cos\Phi_{+1,0} -$$

$$\cos\Phi_{-1,1}\cos\Phi_{-1,0})(D_1 -)(A_0 +) -$$

$$\frac{1}{4}(\cos\Phi_{+1,1}\sin\Phi_{+1,0} - \cos\Phi_{+1,1}\sin\Phi_{-1,0} - \cos\Phi_{-1,1}\sin\Phi_{+1,0} +$$

$$\cos\Phi_{-1,1}\sin\Phi_{-1,0})(D_1 -)(D_0 +) +$$

-continued $$\frac{1}{4}(\cos\Phi_{+1,1}\sin\Phi_{+1,0} + \cos\Phi_{+1,1}\sin\Phi_{-1,0} - \cos\Phi_{-1,1}\sin\Phi_{+1,0} -$$
$$\cos\Phi_{-1,1}\sin\Phi_{-1,0})(D_1 -)(A_0 -) +$$

$$\frac{1}{4}(\cos\Phi_{+1,1}\cos\Phi_{+1,0} - \cos\Phi_{+1,1}\cos\Phi_{-1,0} - \cos\Phi_{-1,1}\cos\Phi_{+1,0} +$$
$$\cos\Phi_{-1,1}\cos\Phi_{-1,0})(D_1 -)(D_0 -).$$

The desired peak component is given by $(A_1+)(A_0+)$, which is absorptive in both dimensions. Other terms in Eq. 98 represent mixed phase peak components at the desired or the quad peak location. Under the condition of identical secondary phase shifts for forward and backward samplings (Eq.35), Eq.98 simplifies to $$\text{Re}(F_C(S_{+1,-1}(t_1,t_0)))\propto_{(\cos\Phi_{1,1}}\cos\Phi_{1,0})(A_1+)(A_0+)-\\(\cos\Phi_{1,1}\sin\Phi_{1,0})(A_1+)(A_0-)-(\sin\Phi_{1,1}\cos\\\Phi_{1,0})(A_1-)(A_0+)+(\sin\Phi_{1,1}\sin\Phi_{1,0})(A_1-)(A_0-) \quad (99),$$

where, the dispersive peak components are eliminated and only the absorptive peak components at the desired and the quad positions remain. Under the condition of secondary phase shifts independent of n (Eq. 54), the peak components of Eq.98 remain unchanged. Under the condition of identical secondary phase shifts (Eq. 73), Eq. 98 simplifies to $$\text{Re}(F_C(S_{+1,-1}(t_1,t_0)))\propto_{(\cos\Phi_1}\cos\Phi_0)(A_1+)(A_0+)-(\cos\\\Phi_1\sin\Phi_0)(A_1+)(A_0-)-(\sin\Phi_1\cos\Phi_0)(A_1-)\\(A_0+)+(\sin\Phi_1\sin\Phi_0)(A_1-)(A_0-) \quad (100).$$

$(c_{+3}, c_{-3})$-Sampling (PMS)

Starting with Eq. 18, the complex signal for two indirect dimensions is proportional to $$S_{+3,-3}(t_1, t_0) \propto \bigotimes_{j=0}^{1} QD_{+3,-3} C_{3,3}(t_j) = \quad (101)$$

$$\frac{1}{\sqrt{2}}[1 \ i]\begin{bmatrix}-1 & -1\\-1 & 1\end{bmatrix}\begin{bmatrix}c_{+3}(t_1)\\c_{-3}(t_1)\end{bmatrix} \otimes \frac{1}{2}[1 \ i]\begin{bmatrix}-1 & -1\\-1 & 1\end{bmatrix}\begin{bmatrix}c_{+3}(t_0)\\c_{-3}(t_0)\end{bmatrix} =$$

$$\left(\frac{1}{2}(\cos\Phi_{+3,1} + \cos\Phi_{-3,1})e^{i\alpha t} + \frac{1}{2}(\sin\Phi_{+3,1} - \sin\Phi_{-3,1})e^{i\pi/2}e^{i\alpha t} +\right.$$
$$\frac{1}{2}(\sin\Phi_{+3,1} + \sin\Phi_{-3,1})e^{-i\alpha t} +$$
$$\left.\frac{1}{2}(\cos\Phi_{+3,1} - \cos\Phi_{-3,1})e^{i\pi/2}e^{-i\alpha t}\right) \otimes$$

$$\left(\frac{1}{2}(\cos\Phi_{+3,0} + \cos\Phi_{-3,0})e^{i\alpha t} + \frac{1}{2}(\sin\Phi_{+3,0} - \sin\Phi_{-3,0})e^{i\pi/2}e^{i\alpha t} +\right.$$
$$\frac{1}{2}(\sin\Phi_{+3,0} + \sin\Phi_{-3,0})e^{-i\alpha t} +$$
$$\left.\frac{1}{2}(\cos\Phi_{+3,0} - \cos\Phi_{-3,0})e^{i\pi/2}e^{-i\alpha t}\right).$$

Multidimensional FT reveals the peak components as $$\text{Re}(F_C(S_{+3,-3}(t_1,t_0))) \propto \quad (102)$$

$$\frac{1}{4}(\cos\Phi_{+3,1}\cos\Phi_{+3,0} + \cos\Phi_{+3,1}\cos\Phi_{-3,0} + \cos\Phi_{-3,1}\cos\Phi_{+3,0} +$$
$$\cos\Phi_{-3,1}\cos\Phi_{-3,0})(A_1 +)(A_0 +) +$$

$$\frac{1}{4}(\cos\Phi_{+3,1}\sin\Phi_{+3,0} - \cos\Phi_{+3,1}\sin\Phi_{-3,0} + \cos\Phi_{-3,1}\sin\Phi_{+3,0} -$$
$$\cos\Phi_{-3,1}\sin\Phi_{-3,0})(A_1 +)(D_0 +) +$$

$$\frac{1}{4}(\cos\Phi_{+3,1}\sin\Phi_{+3,0} + \cos\Phi_{+3,1}\sin\Phi_{-3,0} + \cos\Phi_{-3,1}\sin\Phi_{+3,0} +$$
$$\cos\Phi_{-3,1}\sin\Phi_{-3,0})(A_1 +)(A_0 -) +$$

$$\frac{1}{4}(\cos\Phi_{+3,1}\cos\Phi_{+3,0} - \cos\Phi_{+3,1}\cos\Phi_{-3,0} + \cos\Phi_{-3,1}\cos\Phi_{+3,0} -$$
$$\cos\Phi_{-3,1}\cos\Phi_{-3,0})(A_1 +)(D_0 -) +$$

$$\frac{1}{4}(\sin\Phi_{+3,1}\cos\Phi_{+3,0} + \sin\Phi_{+3,1}\cos\Phi_{-3,0} - \sin\Phi_{-3,1}\cos\Phi_{+3,0} -$$
$$\sin\Phi_{-3,1}\cos\Phi_{-3,0})(D_1 +)(A_0 +) +$$

$$\frac{1}{4}(\sin\Phi_{+3,1}\sin\Phi_{+3,0} - \sin\Phi_{+3,1}\sin\Phi_{-3,0} - \sin\Phi_{-3,1}\sin\Phi_{+3,0} +$$
$$\sin\Phi_{-3,1}\sin\Phi_{-3,0})(D_1 +)(D_0 +) +$$

$$\frac{1}{4}(\sin\Phi_{+3,1}\sin\Phi_{+3,0} + \sin\Phi_{+3,1}\sin\Phi_{-3,0} - \sin\Phi_{-3,1}\sin\Phi_{+3,0} -$$
$$\sin\Phi_{-3,1}\sin\Phi_{-3,0})(D_1 +)(A_0 -) +$$

$$\frac{1}{4}(\sin\Phi_{+3,1}\cos\Phi_{+3,0} - \sin\Phi_{+3,1}\cos\Phi_{-3,0} - \sin\Phi_{-3,1}\cos\Phi_{+3,0} +$$
$$\sin\Phi_{-3,1}\cos\Phi_{-3,0})(D_1 +)(D_0 -) +$$

$$\frac{1}{4}(\sin\Phi_{+3,1}\cos\Phi_{+3,0} + \sin\Phi_{+3,1}\cos\Phi_{-3,0} + \sin\Phi_{-3,1}\cos\Phi_{+3,0} +$$
$$\sin\Phi_{-3,1}\cos\Phi_{-3,0})(A_1 -)(A_0 +) +$$

$$\frac{1}{4}(\sin\Phi_{+3,1}\sin\Phi_{+3,0} - \sin\Phi_{+3,1}\sin\Phi_{-3,0} + \sin\Phi_{-3,1}\sin\Phi_{+3,0} -$$
$$\sin\Phi_{-3,1}\sin\Phi_{-3,0})(A_1 -)(D_0 +) +$$

$$\frac{1}{4}(\sin\Phi_{+3,1}\sin\Phi_{+3,0} + \sin\Phi_{+3,1}\sin\Phi_{-3,0} + \sin\Phi_{-3,1}\sin\Phi_{+3,0} +$$
$$\sin\Phi_{-3,1}\sin\Phi_{-3,0})(A_1 -)(A_0 -) +$$

$$\frac{1}{4}(\sin\Phi_{+3,1}\cos\Phi_{+3,0} - \sin\Phi_{+3,1}\cos\Phi_{-3,0} + \sin\Phi_{-3,1}\cos\Phi_{+3,0} -$$
$$\sin\Phi_{-3,1}\cos\Phi_{-3,0})(A_1 -)(D_0 -) +$$

$$\frac{1}{4}(\cos\Phi_{+3,1}\cos\Phi_{+3,0} + \cos\Phi_{+3,1}\cos\Phi_{-3,0} - \cos\Phi_{-3,1}\cos\Phi_{+3,0} -$$
$$\cos\Phi_{-3,1}\cos\Phi_{-3,0})(D_1 -)(A_0 +) +$$

$$\frac{1}{4}(\cos\Phi_{+3,1}\sin\Phi_{+3,0} - \cos\Phi_{+3,1}\sin\Phi_{-3,0} - \cos\Phi_{-3,1}\sin\Phi_{+3,0} +$$
$$\cos\Phi_{-3,1}\sin\Phi_{-3,0})(D_1 -)(D_0 +) +$$

$$\frac{1}{4}(\cos\Phi_{+3,1}\sin\Phi_{+3,0} + \cos\Phi_{+3,1}\sin\Phi_{-3,0} - \cos\Phi_{-3,1}\sin\Phi_{+3,0} -$$
$$\cos\Phi_{-3,1}\sin\Phi_{-3,0})(D_1 -)(A_0 -) +$$

$$\frac{1}{4}(\cos\Phi_{+3,1}\cos\Phi_{+3,0} - \cos\Phi_{+3,1}\cos\Phi_{-3,0} - \cos\Phi_{-3,1}\cos\Phi_{+3,0} +$$
$$\cos\Phi_{-3,1}\cos\Phi_{-3,0})(D_1 -)(D_0 -).$$

Under the condition of identical secondary phase shifts for forward and backward samplings (Eq. 35), Eq. 102 simplifies to $$\text{Re}(F_C(S_{+3,-3}(t_1,t_0)))\propto_{(\cos\Phi_{3,1}}\cos\Phi_{3,0})(A_1+)(A_0+)+\\(\cos\Phi_{3,1}\sin\Phi_{3,0})(A_1+)(A_0-)+(\sin\Phi_{3,1}\cos\\\Phi_{3,0})(A_1-)(A_0+)+(\sin\Phi_{3,1}\sin\Phi_{3,0})(A_1-)(A_0-) \quad (103).$$

Under the condition of secondary phase shifts independent of n (Eq. 54), the peak components of Eq. 102 remain unchanged. Under the condition of identical secondary phase shifts (Eq. 73), Eq. 102 simplifies to $$\text{Re}(F_C(S_{+3,-3}(t_1,t_0)))\propto_{(\cos\Phi_1}\cos\Phi_0)(A_1+)(A_0+)+(\cos\\\Phi_1\sin\Phi_0)(A_1+)(A_0-)+(\sin\Phi_1\cos\Phi_0)(A_1-)\\(A_0+)+(\sin\Phi_1\sin\Phi_0)(A_1-)(A_0-) \quad (104).$$

$(c_{+1}, c_{-1}, c_{+3}, C_{-3})$-Sampling (DPMS)

Starting with Eq. 21, the complex signal for two indirect dimensions is proportional to $$S_{+1,-1,+3,-3}(t_1,t_0)=[S_{+1,-1}(t_1)+S_{+3,-3}(t_1)]\otimes[S_{+1,-1}\\(t_0)+S_{+3,-3}(t_0)]\propto S_{+1,-1}(t_1)S_{+1,-1}(t_0)+\\S_{+1,-1}(t_1)S_{+3,-3}(t_0)+S_{+3,-3}(t_1)S_{+1,-1}(t_0)+S_{+3,-3}\\(t_1)S_{+3,-3}(t_0) \quad (105).$$

DPMS for two indirect dimensions requires all combinations of π/4 and 3π/4-shifted mirrored sampling of the time domains. The first and the last term in Eq. 105 are represented, respectively, by Eqs. 98 and 102. It is then straightforward to show that the signals of the spectrum corresponding to the second term in Eq. 105 is proportional to $$Re(F_C(S_{+1,-1}(t_1)S_{+3,-3}(t_0))) \propto \tag{106}$$

$$\frac{1}{4}(\cos\Phi_{+1,1}\cos\Phi_{+3,0} + \cos\Phi_{+1,1}\cos\Phi_{-3,0} +$$
$$\cos\Phi_{-1,1}\cos\Phi_{+3,0} + \cos\Phi_{-1,1}\cos\Phi_{-3,0})(A_1 +)(A_0 +) +$$

$$\frac{1}{4}(\cos\Phi_{+1,1}\sin\Phi_{+3,0} - \cos\Phi_{+1,1}\sin\Phi_{-3,0} + \cos\Phi_{-1,1}\sin\Phi_{+3,0} -$$
$$\cos\Phi_{-1,1}\sin\Phi_{-3,0})(A_1 +)(D_0 +) +$$

$$\frac{1}{4}(\cos\Phi_{+1,1}\sin\Phi_{+3,0} + \cos\Phi_{+1,1}\sin\Phi_{-3,0} + \cos\Phi_{-1,1}\sin\Phi_{+3,0} +$$
$$\cos\Phi_{-1,1}\sin\Phi_{-3,0})(A_1 +)(A_0 -) +$$

$$\frac{1}{4}(\cos\Phi_{+1,1}\cos\Phi_{+3,0} - \cos\Phi_{+1,1}\cos\Phi_{-3,0} + \cos\Phi_{-1,1}\cos\Phi_{+3,0} -$$
$$\cos\Phi_{-1,1}\cos\Phi_{-3,0})(A_1 +)(D_0 -) +$$

$$\frac{1}{4}(\sin\Phi_{+1,1}\cos\Phi_{+3,0} + \sin\Phi_{+1,1}\cos\Phi_{-3,0} - \sin_{-1,1}\cos\Phi_{+3,0} -$$
$$\sin s\Phi_{-1,1}\cos\Phi_{-3,0})(D_1 +)(A_0 +) +$$

$$\frac{1}{4}(\sin\Phi_{+1,1}\sin\Phi_{+3,0} - \sin\Phi_{+1,1}\sin\Phi_{-3,0} - \sin\Phi_{-1,1}\sin\Phi_{+3,0} +$$
$$\sin\Phi_{-1,1}\sin\Phi_{-3,0})(D_1 +)(D_0 +) +$$

$$\frac{1}{4}(\sin\Phi_{+1,1}\sin\Phi_{+3,0} + \sin\Phi_{+1,1}\sin\Phi_{-3,0} - \sin\Phi_{-1,1}\sin\Phi_{+3,0} -$$
$$\sin\Phi_{-1,1}\sin\Phi_{-3,0})(D_1 +)(A_0 -) +$$

$$\frac{1}{4}(\sin\Phi_{+1,1}\cos\Phi_{+3,0} - \sin\Phi_{+1,1}\cos\Phi_{-3,0} - \sin\Phi_{-1,1}\cos\Phi_{+3,0} +$$
$$\sin\Phi_{-1,1}\cos\Phi_{-3,0})(D_1 +)(D_0 -) -$$

$$\frac{1}{4}(\sin\Phi_{+1,1}\cos\Phi_{+3,0} + \sin\Phi_{+1,1}\cos\Phi_{-3,0} + \sin\Phi_{-1,1}\cos\Phi_{+3,0} +$$
$$\sin s\Phi_{-1,1}\cos\Phi_{-3,0})(A_1 -)(A_0 +) -$$

$$\frac{1}{4}(\sin\Phi_{+1,1}\sin\Phi_{+3,0} - \sin\Phi_{+1,1}\sin\Phi_{-3,0} + \sin\Phi_{-1,1}\sin\Phi_{+3,0} -$$
$$\sin\Phi_{-1,1}\sin\Phi_{-3,0})(A_1 -)(D_0 +) -$$

$$\frac{1}{4}(\sin\Phi_{+1,1}\sin\Phi_{+3,0} + \sin\Phi_{+1,1}\sin\Phi_{-3,0} + \sin\Phi_{-1,1}\sin\Phi_{+3,0} +$$
$$\sin\Phi_{-1,1}\sin\Phi_{-3,0})(A_1 -)(A_0 -) -$$

$$\frac{1}{4}(\sin\Phi_{+1,1}\cos\Phi_{+3,0} - \sin\Phi_{+1,1}\cos\Phi_{-3,0} + \sin\Phi_{-1,1}\cos\Phi_{+3,0} -$$
$$\sin\Phi_{-1,1}\cos\Phi_{-3,0})(A_1 -)(D_0 -) -$$

$$\frac{1}{4}(\cos\Phi_{+1,1}\cos\Phi_{+3,0} + \cos\Phi_{+1,1}\cos\Phi_{-3,0} - \cos\Phi_{-1,1}\cos\Phi_{+3,0} -$$
$$\cos\Phi_{-1,1}\cos\Phi_{-3,0})(D_1 -)(A_0 +) -$$

$$\frac{1}{4}(\cos\Phi_{+1,1}\sin\Phi_{+3,0} - \cos\Phi_{+1,1}\sin\Phi_{-3,0} - \cos\Phi_{-1,1}\sin\Phi_{+3,0} +$$
$$\cos\Phi_{-1,1}\sin\Phi_{-3,0})(D_1 -)(D_0 +) -$$

$$\frac{1}{4}(\cos\Phi_{+1,1}\sin\Phi_{+3,0} + \cos\Phi_{+1,1}\sin\Phi_{-3,0} - \cos\Phi_{-1,1}\sin\Phi_{+3,0} -$$
$$\cos\Phi_{-1,1}\sin\Phi_{-3,0})(D_1 -)(A_0 -) -$$

$$\frac{1}{4}(\cos\Phi_{+1,1}\cos\Phi_{+3,0} - \cos\Phi_{+1,1}\cos\Phi_{-3,0} - \cos\Phi_{-1,1}\cos\Phi_{+3,0} +$$
$$\cos\Phi_{-1,1}\cos\Phi_{-3,0})(D_1 -)(D_0 -).$$

Under the condition of identical secondary phase shifts for forward and backward samplings (Eq. 35), Eq.106 simplifies to $$Re(F_C(S_{+1,-1}(t_1)S_{+3,-3}(t_0))) \propto_{(cos\ \Phi_{1,1}\ cos\ \Phi_{3,0})}(A_1+)$$
$$(A_0+) + (\cos\Phi_{1,1}\sin\Phi_{3,0})(A_1+)(A_0-) - (\sin\Phi_{1,1}$$
$$\cos\Phi_{3,0})(A_1-)(A_0+) - (\sin\Phi_{1,1}\sin\Phi_{3,0})(A_1-)$$
$$(A_0-) \tag{107}.$$

Under the condition of secondary phase shifts independent of n (Eq. 54), the peak components of Eq. 106 remain unchanged. Under the condition of identical secondary phase shifts (Eq. 73), Eq. 106 simplifies to $$Re(F_C(S_{+1,-1}(t_1)S_{+3,-3}(t_0))) \propto_{(cos\ \Phi_1\ cos\ \Phi_0)}(A_1+)$$
$$(A_0+) + (\cos\Phi_1\sin\Phi_0)(A_1+)(A_0-) - (\sin\Phi_1\cos$$
$$\Phi_0)(A_1-)(A_0+) - (\sin\Phi_1\sin\Phi_0)(A_1-)(A_0-) \tag{108}.$$

The signals of the spectrum corresponding to the third term in Eq. 105 is proportional to $$Re(F_C(S_{+3,-3}(t_1)S_{+1,-1}(t_0))) \propto \tag{109}$$

$$\frac{1}{4}(\cos\Phi_{+3,1}\cos\Phi_{+1,0} + \cos\Phi_{+3,1}\cos\Phi_{-1,0} +$$
$$\cos\Phi_{-3,1}\cos\Phi_{+1,0} + \cos\Phi_{-3,1}\cos\Phi_{-1,0})(A_1 +)(A_0 +) +$$

$$\frac{1}{4}(\cos\Phi_{+3,1}\sin\Phi_{+1,0} - \cos\Phi_{+3,1}\sin\Phi_{-1,0} + \cos\Phi_{-3,1}\sin\Phi_{+1,0} -$$
$$\cos\Phi_{-3,1}\sin\Phi_{-1,0})(A_1 +)(D_0 +) -$$

$$\frac{1}{4}(\cos\Phi_{+3,1}\sin\Phi_{+1,0} + \cos\Phi_{+3,1}\sin\Phi_{-1,0} + \cos\Phi_{-3,1}\sin\Phi_{+1,0} +$$
$$\cos\Phi_{-3,1}\sin\Phi_{-1,0})(A_1 +)(A_0 -) -$$

$$\frac{1}{4}(\cos\Phi_{+3,1}\cos\Phi_{+1,0} - \cos\Phi_{+3,1}\cos\Phi_{-1,0} + \cos\Phi_{-3,1}\cos\Phi_{+1,0} -$$
$$\cos\Phi_{-3,1}\cos\Phi_{-1,0})(A_1 +)(D_0 -) +$$

$$\frac{1}{4}(\sin\Phi_{+3,1}\cos\Phi_{+1,0} + \sin\Phi_{+3,1}\cos\Phi_{-1,0} - \sin\Phi_{-3,1}\cos\Phi_{+1,0} -$$
$$\sin\Phi_{-3,1}\cos\Phi_{-1,0})(D_1 +)(A_0 +) +$$

$$\frac{1}{4}(\sin\Phi_{+3,1}\sin\Phi_{+1,0} - \sin\Phi_{+3,1}\sin\Phi_{-1,0} - \sin\Phi_{-3,1}\sin\Phi_{+1,0} +$$
$$\sin\Phi_{-3,1}\sin\Phi_{-1,0})(D_1 +)(D_0 +) -$$

$$\frac{1}{4}(\sin\Phi_{+3,1}\sin\Phi_{+1,0} + \sin\Phi_{+3,1}\sin\Phi_{-1,0} - \sin\Phi_{-3,1}\sin\Phi_{+1,0} -$$
$$\sin\Phi_{-3,1}\sin\Phi_{-1,0})(D_1 +)(A_0 -) -$$

$$\frac{1}{4}(\sin\Phi_{+3,1}\cos\Phi_{+1,0} - \sin\Phi_{+3,1}\cos\Phi_{-1,0} - \sin\Phi_{-3,1}\cos\Phi_{+1,0} +$$
$$\sin\Phi_{-3,1}\cos\Phi_{-1,0})(D_1 +)(D_0 -) +$$

$$\frac{1}{4}(\sin\Phi_{+3,1}\cos\Phi_{+1,0} + \sin\Phi_{+3,1}\cos\Phi_{-1,0} + \sin\Phi_{-3,1}\cos\Phi_{+1,0} +$$
$$\sin\Phi_{-3,1}\cos\Phi_{-1,0})(A_1 -)(A_0 +) +$$

$$\frac{1}{4}(\sin\Phi_{+3,1}\sin\Phi_{+1,0} - \sin\Phi_{+3,1}\sin\Phi_{-1,0} + \sin\Phi_{-3,1}\sin\Phi_{+1,0} -$$
$$\sin\Phi_{-3,1}\sin\Phi_{-1,0})(A_1 -)(D_0 +) -$$

$$\frac{1}{4}(\sin\Phi_{+3,1}\sin\Phi_{+1,0} + \sin\Phi_{+3,1}\sin\Phi_{-1,0} + \sin\Phi_{-3,1}\sin\Phi_{+1,0} +$$
$$\sin\Phi_{-3,1}\sin\Phi_{-1,0})(A_1 -)(A_0 -) -$$

$$\frac{1}{4}(\sin\Phi_{+3,1}\cos\Phi_{+1,0} - \sin\Phi_{+3,1}\cos\Phi_{-1,0} + \sin\Phi_{-3,1}\cos\Phi_{+1,0} -$$
$$\sin\Phi_{-3,1}\cos\Phi_{-1,0})(A_1 -)(D_0 -) +$$

$$\frac{1}{4}(\cos\Phi_{+3,1}\cos\Phi_{+1,0} + \cos\Phi_{+3,1}\cos\Phi_{-1,0} - \cos\Phi_{-3,1}\cos\Phi_{+1,0} -$$
$$\cos\Phi_{-3,1}\cos\Phi_{-1,0})(D_1 -)(A_0 +) +$$

-continued $$\frac{1}{4}(\cos\Phi_{+3,1}\sin\Phi_{+1,0} - \cos\Phi_{+3,1}\sin\Phi_{-1,0} - \cos\Phi_{-3,1}\sin\Phi_{+1,0} + \cos\Phi_{-3,1}\sin\Phi_{-1,0})(D_1-)(D_0+) -$$

$$\frac{1}{4}(\cos\Phi_{+3,1}\sin\Phi_{+1,0} + \cos\Phi_{+3,1}\sin\Phi_{-1,0} - \cos\Phi_{-3,1}\sin\Phi_{+1,0} - \cos\Phi_{-3,1}\sin\Phi_{-1,0})(D_1-)(A_0-) -$$

$$\frac{1}{4}(\cos\Phi_{+3,1}\cos\Phi_{+1,0} - \cos\Phi_{+3,1}\cos\Phi_{-1,0} - \cos\Phi_{-3,1}\cos\Phi_{+1,0} + \cos\Phi_{-3,1}\cos\Phi_{-1,0})(D_1-)(D_0-).$$

Under the condition of identical secondary phase shifts for forward and backward samplings (Eq. 35), Eq.109 simplifies to $$Re(F_C(S_{+3,-3}(t_1)S_{+1,-1}(t_0))) \propto (\cos\Phi_{3,1} \cos\Phi_{1,0})(A_1+)(A_0+) - (\cos\Phi_{3,1}\sin\Phi_{1,0})(A_1+)(A_0-) + (\sin\Phi_{3,1}\cos\Phi_{1,0})(A_1-)(A_0+) - (\sin\Phi_{3,1}\sin\Phi_{1,0})(A_1-)(A_0-)$$ (110).

Under the condition of secondary phase shifts independent of n (Eq. 54), the peak component pattern of the Eq. 109 does not change. Under the condition of identical secondary phase shifts (Eq. 73), Eq. 109 simplifies to $$Re(F_C(S_{+3,-3}(t_1)S_{+1,-1}(t_0))) \propto (\cos\Phi_1 \cos\Phi_0)(A_1+)(A_0+) - (\cos\Phi_1 \sin\Phi_0)(A_1+)(A_0-) + (\sin\Phi_1 \cos\Phi_0)(A_1-)(A_0+) - (\sin\Phi_1 \sin\Phi_0)(A_1-)(A_0-)$$ (111).

Addition of Eqs. 98, 102, 106 and 109 gives the complex signal for $(c_{+1}, c_{-1}, c_{+3}, c_{-3})$-sampling for two indirect dimensions and is proportional to $$Re(F_C(S_{+1,-1,-3,-3}(t_1, t_0))) \propto$$ (112)

$$\frac{1}{4}(\cos\Phi_{+1,1}\cos\Phi_{+1,0} + \cos\Phi_{+1,1}\cos\Phi_{-1,0} + \cos\Phi_{-1,1}\cos\Phi_{+1,0} + \cos\Phi_{-1,1}\cos\Phi_{-1,0} + \cos\Phi_{+1,1}\cos\Phi_{+3,0} + \cos\Phi_{+1,1}\cos\Phi_{-3,0} + \cos\Phi_{-1,1}\cos\Phi_{+3,0} + \cos\Phi_{-1,1}\cos\Phi_{-3,0} + \cos\Phi_{+3,1}\cos\Phi_{+1,0} + \cos\Phi_{+3,1}\cos\Phi_{-1,0} + \cos\Phi_{-3,1}\cos\Phi_{+1,0} + \cos\Phi_{-3,1}\cos\Phi_{-1,0} + \cos\Phi_{+3,1}\cos\Phi_{+3,0} + \cos\Phi_{+3,1}\cos\Phi_{-3,0} + \cos\Phi_{-3,1}\cos\Phi_{+3,0} + \cos\Phi_{-3,1}\cos\Phi_{-3,0})(A_1+)(A_0+) +$$

$$\frac{1}{4}(\cos\Phi_{+1,1}\sin\Phi_{+1,0} - \cos\Phi_{+1,1}\sin\Phi_{-1,0} + \cos\Phi_{-1,1}\sin\Phi_{+1,0} - \cos\Phi_{-1,1}\sin\Phi_{-1,0} + \cos\Phi_{+1,1}\sin\Phi_{+3,0} - \cos\Phi_{+1,1}\sin\Phi_{-3,0} + \cos\Phi_{-1,1}\sin\Phi_{+3,0} - \cos\Phi_{-1,1}\sin\Phi_{-3,0} + \cos\Phi_{+3,1}\sin + \cos\Phi_{+3,1}\sin\Phi_{+1,0} - \cos\Phi_{+3,1}\sin\Phi_{-1,0} + \cos\Phi_{-3,1}\sin\Phi_{+1,0} - \cos\Phi_{-3,1}\sin\Phi_{-1,0} + \cos\Phi_{+3,1}\sin\Phi_{+3,0} - \cos\Phi_{+3,1}\sin\Phi_{-3,0} + \cos\Phi_{-3,1}\sin\Phi_{+3,0} - \cos\Phi_{-3,1}\sin\Phi_{-3,0})(A_1+)(D_0+) -$$

$$\frac{1}{4}(\cos\Phi_{+1,1}\sin\Phi_{+1,0} + \cos\Phi_{+1,1}\sin\Phi_{-1,0} + \cos\Phi_{-1,1}\sin\Phi_{+1,0} + \cos\Phi_{-1,1}\sin\Phi_{-1,0} - \cos\Phi_{+1,1}\sin\Phi_{+3,0} - \cos\Phi_{+1,1}\sin\Phi_{-3,0} - \cos\Phi_{-1,1}\sin\Phi_{+3,0} - \cos\Phi_{-1,1}\sin\Phi_{-3,0} + \cos\Phi_{+3,1}\sin\Phi_{+1,0} + \cos\Phi_{+3,1}\sin\Phi_{-1,0} + \cos\Phi_{-3,1}\sin\Phi_{+1,0} + \cos\Phi_{-3,1}\sin\Phi_{-1,0} - \cos\Phi_{+3,1}\sin\Phi_{+3,0} - \cos\Phi_{-3,1}\sin\Phi_{-3,0})(A_1+)(A_0-) -$$

$$\frac{1}{4}(\cos\Phi_{+1,1}\cos\Phi_{+1,0} - \cos\Phi_{+1,1}\cos\Phi_{-1,0} + \cos\Phi_{-1,1}\cos\Phi_{+1,0} - \cos\Phi_{-1,1}\cos\Phi_{-1,0} - \cos\Phi_{+1,1}\cos\Phi_{+3,0} + \cos\Phi_{+1,1}\cos\Phi_{-3,0} - \cos\Phi_{-1,1}\cos\Phi_{+3,0} + \cos\Phi_{-1,1}\cos\Phi_{-3,0} + \cos\Phi_{+3,1}\cos\Phi_{+1,0} - \cos\Phi_{+3,1}\cos\Phi_{-1,0} + \cos\Phi_{-3,1}\cos\Phi_{+1,0} - \cos\Phi_{-3,1}\cos\Phi_{-1,0} - \cos\Phi_{+3,1}\cos\Phi_{+3,0} + \cos\Phi_{-3,1}\cos\Phi_{-3,0})(A_1+)(D_0-) +$$

$$\frac{1}{4}(\sin\Phi_{+1,1}\cos\Phi_{+1,0} + \sin\Phi_{+1,1}\cos\Phi_{-1,0} - \sin\Phi_{-1,1}\cos\Phi_{+1,0} - \sin\Phi_{-1,1}\cos\Phi_{-1,0} + \sin\Phi_{+1,1}\cos\Phi_{+3,0} + \sin\Phi_{+1,1}\cos\Phi_{-3,0} - \sin\Phi_{-1,1}\cos\Phi_{+3,0} - \sin\Phi_{-1,1}\cos\Phi_{-3,0} + \sin\Phi_{+3,1}\cos\Phi_{+1,0} + \sin\Phi_{+3,1}\cos\Phi_{-1,0} - \sin\Phi_{-3,1}\cos\Phi_{+1,0} - \sin\Phi_{-3,1}\cos\Phi_{-1,0} + \sin\Phi_{+3,1}\cos\Phi_{+3,0} + \sin\Phi_{+3,1}\cos\Phi_{-3,0} - \sin\Phi_{-3,1}\cos\Phi_{+3,0} - \sin\Phi_{-3,1}\cos\Phi_{-3,0})(D_1+)(A_0+) +$$

$$\frac{1}{4}(\sin\Phi_{+1,1}\sin\Phi_{+1,0} - \sin\Phi_{+1,1}\sin\Phi_{-1,0} - \sin\Phi_{-1,1}\sin\Phi_{+1,0} + \sin\Phi_{-1,1}\sin\Phi_{-1,0} + \sin\Phi_{+1,1}\sin\Phi_{+3,0} - \sin\Phi_{+1,1}\sin\Phi_{-3,0} - \sin\Phi_{-1,1}\sin\Phi_{+3,0} + \sin\Phi_{-1,1}\sin\Phi_{-3,0} + \sin\Phi_{+3,1}\sin\Phi_{+1,0} - \sin\Phi_{+3,1}\sin\Phi_{-1,0} - \sin\Phi_{-3,1}\sin\Phi_{+1,0} + \sin\Phi_{-3,1}\sin\Phi_{-1,0} + \sin\Phi_{+3,1}\sin\Phi_{+3,0} - \sin\Phi_{+3,1}\sin\Phi_{-3,0} - \sin\Phi_{-3,1}\sin\Phi_{+3,0} + \sin\Phi_{-3,1}\sin\Phi_{-3,0})(D_1+)(D_0+) -$$

$$\frac{1}{4}(\sin\Phi_{+1,1}\sin\Phi_{+1,0} + \sin\Phi_{+1,1}\sin\Phi_{-1,0} - \sin\Phi_{-1,1}\sin\Phi_{+1,0} - \sin\Phi_{-1,1}\sin\Phi_{-1,0} - \sin\Phi_{+1,1}\sin\Phi_{+3,0} - \sin\Phi_{+1,1}\sin\Phi_{-3,0} + \sin\Phi_{-1,1}\sin\Phi_{+3,0} + \sin\Phi_{-1,1}\sin\Phi_{-3,0} + \sin\Phi_{+3,1}\sin\Phi_{+1,0} + \sin\Phi_{+3,1}\sin\Phi_{-1,0} - \sin\Phi_{-3,1}\sin\Phi_{+1,0} - \sin\Phi_{-3,1}\sin\Phi_{-1,0} - \sin\Phi_{+3,1}\sin\Phi_{+3,0} - \sin\Phi_{+3,1}\sin\Phi_{-3,0} + \sin\Phi_{-3,1}\sin\Phi_{+3,0} + \sin\Phi_{-3,1}\sin\Phi_{-3,0})(D_1+)(A_0-) -$$

$$\frac{1}{4}(\sin\Phi_{+1,1}\cos\Phi_{+1,0} - \sin\Phi_{+1,1}\cos\Phi_{-1,0} - \sin\Phi_{-1,1}\cos\Phi_{+1,0} + \sin\Phi_{-1,1}\cos\Phi_{-1,0} - \sin\Phi_{+1,1}\cos\Phi_{+3,0} + \sin\Phi_{+1,1}\cos\Phi_{-3,0} - \sin\Phi_{-1,1}\cos\Phi_{+3,0} + \sin\Phi_{-1,1}\cos\Phi_{-3,0} + \sin\Phi_{+3,1}\cos\Phi_{+1,0} - \sin\Phi_{+3,1}\cos\Phi_{-1,0} - \sin\Phi_{-3,1}\cos\Phi_{+1,0} + \sin\Phi_{-3,1}\cos\Phi_{-1,0} - \sin\Phi_{+3,1}\cos\Phi_{+3,0} + \sin\Phi_{+3,1}\cos\Phi_{-3,0} - \sin\Phi_{-3,1}\cos\Phi_{+3,0} - \sin\Phi_{-3,1}\cos\Phi_{-3,0})(D_1+)(D_0-) -$$

$$\frac{1}{4}(\sin\Phi_{+1,1}\cos\Phi_{+1,0} + \sin\Phi_{+1,1}\cos\Phi_{-1,0} + \sin\Phi_{-1,1}\cos\Phi_{+1,0} + \sin\Phi_{-1,1}\cos\Phi_{-1,0} + \sin\Phi_{+1,1}\cos\Phi_{+3,0} + \sin\Phi_{+1,1}\cos\Phi_{-3,0} + \sin\Phi_{-1,1}\cos\Phi_{+3,0} + \sin\Phi_{-1,1}\cos\Phi_{-3,0} - \sin\Phi_{+3,1}\cos\Phi_{+1,0} - \sin\Phi_{+3,1}\cos\Phi_{-1,0} - \sin\Phi_{-3,1}\cos\Phi_{+1,0} - \sin\Phi_{-3,1}\cos\Phi_{-1,0} - \sin\Phi_{+3,1}\cos\Phi_{+3,0} - \sin\Phi_{+3,1}\cos\Phi_{-3,0} - \sin\Phi_{-3,1}\cos\Phi_{+3,0} - \sin\Phi_{-3,1}\cos\Phi_{-3,0})(A_1-)(A_0+) -$$

$$\frac{1}{4}(\sin\Phi_{+1,1}\sin\Phi_{+1,0} - \sin\Phi_{+1,1}\sin\Phi_{-1,0} + \sin\Phi_{-1,1}\sin\Phi_{+1,0} - \sin\Phi_{-1,1}\sin\Phi_{-1,0} + \sin\Phi_{+1,1}\sin\Phi_{+3,0} - \sin\Phi_{+1,1}\sin\Phi_{-3,0} + \sin\Phi_{-1,1}\sin\Phi_{+3,0} - \sin\Phi_{-1,1}\sin\Phi_{-3,0} -$$

-continued $$\sin\Phi_{+3,1}\sin\Phi_{+1,0} + \sin\Phi_{+3,1}\sin\Phi_{-1,0} - \sin\Phi_{-3,1}\sin\Phi_{+1,0} +$$
$$\sin\Phi_{-3,1}\sin\Phi_{-1,0} - \sin\Phi_{+3,1}\sin\Phi_{+3,0} + \sin\Phi_{+3,1}\sin\Phi_{-3,0} -$$
$$\sin\Phi_{-3,1}\sin\Phi_{+3,0} + \sin\Phi_{-3,1}\sin\Phi_{-3,0})(A_1-)(D_0+) +$$

$$\frac{1}{4}(\sin\Phi_{+1,1}\sin\Phi_{+1,0} + \sin\Phi_{+1,1}\sin\Phi_{-1,0} + \sin\Phi_{-1,1}\sin\Phi_{+1,0} +$$
$$\sin\Phi_{-1,1}\sin\Phi_{-1,0} - \sin\Phi_{+1,1}\sin\Phi_{+3,0} -$$
$$\sin\Phi_{+1,1}\sin\Phi_{-3,0} - \sin\Phi_{-1,1}\sin\Phi_{+3,0} - \sin\Phi_{-1,1}\sin\Phi_{-3,0} -$$
$$\sin\Phi_{+3,1}\sin\Phi_{+1,0} - \sin\Phi_{+3,1}\sin\Phi_{-1,0} - \sin\Phi_{-3,1}\sin\Phi_{+1,0} -$$
$$\sin\Phi_{-3,1}\sin\Phi_{-1,0} + \sin\Phi_{+3,1}\sin\Phi_{+3,0} + \sin\Phi_{+3,1}\sin\Phi_{-3,0} +$$
$$\sin\Phi_{-3,1}\sin\Phi_{+3,0} + \sin\Phi_{-3,1}\sin\Phi_{-3,0})(A_1-)(A_0-) +$$

$$\frac{1}{4}(\sin\Phi_{+1,1}\cos\Phi_{+1,0} - \sin\Phi_{+1,1}\cos\Phi_{-1,0} + \sin\Phi_{-1,1}\cos\Phi_{+1,0} -$$
$$\sin\Phi_{-1,1}\cos\Phi_{-1,0} - \sin\Phi_{+1,1}\cos\Phi_{+3,0} +$$
$$\sin\Phi_{+1,1}\cos\Phi_{-3,0} - \sin\Phi_{-1,1}\cos\Phi_{+3,0} + \sin\Phi_{-1,1}\cos\Phi_{-3,0} -$$
$$\sin\Phi_{+3,1}\cos\Phi_{+1,0} + \sin\Phi_{+3,1}\cos\Phi_{-1,0} - \sin\Phi_{-3,1}\cos\Phi_{+1,0} +$$
$$\sin\Phi_{-3,1}\cos\Phi_{-1,0} + \sin\Phi_{+3,1}\cos\Phi_{+3,0} - \sin\Phi_{+3,1}\cos\Phi_{-3,0} +$$
$$\sin\Phi_{-3,1}\cos\Phi_{+3,0} - \sin\Phi_{-3,1}\cos\Phi_{-3,0})(A_1-)(D_0-) -$$

$$\frac{1}{4}(\cos\Phi_{+1,1}\cos\Phi_{+1,0} + \cos\Phi_{+1,1}\cos\Phi_{-1,0} - \cos\Phi_{-1,1}\cos\Phi_{+1,0} -$$
$$\cos\Phi_{-1,1}\cos\Phi_{-1,0} + \cos\Phi_{+1,1}\cos\Phi_{+3,0} +$$
$$\cos\Phi_{+1,1}\cos\Phi_{-3,0} - \cos\Phi_{-1,1}\cos\Phi_{+3,0} - \cos\Phi_{-1,1}\cos\Phi_{-3,0} -$$
$$\cos\Phi_{+3,1}\cos\Phi_{+1,0} + \cos\Phi_{+3,1}\cos\Phi_{-1,0} + \cos\Phi_{-3,1}\cos\Phi_{+1,0} -$$
$$\cos\Phi_{-3,1}\cos\Phi_{-1,0} + \cos\Phi_{+3,1}\cos\Phi_{+3,0} - \cos\Phi_{+3,1}\cos\Phi_{-3,0} -$$
$$\cos\Phi_{-3,1}\cos\Phi_{+3,0} + \cos\Phi_{-3,1}\cos\Phi_{-3,0})(D_1-)(A_0+) -$$

$$\frac{1}{4}(\cos\Phi_{+1,1}\sin\Phi_{+1,0} - \cos\Phi_{+1,1}\sin\Phi_{-1,0} - \cos\Phi_{-1,1}\sin\Phi_{+1,0} +$$
$$\cos\Phi_{-1,1}\sin\Phi_{-1,0} + \cos\Phi_{+1,1}\sin\Phi_{+3,0} -$$
$$\cos\Phi_{+1,1}\sin\Phi_{-3,0} - \cos\Phi_{-1,1}\sin\Phi_{+3,0} + \cos\Phi_{-1,1}\sin\Phi_{-3,0} -$$
$$\cos\Phi_{+3,1}\sin\Phi_{+1,0} + \cos\Phi_{+3,1}\sin\Phi_{-1,0} + \cos\Phi_{-3,1}\sin\Phi_{+1,0} -$$
$$\cos\Phi_{-3,1}\sin\Phi_{-1,0} + \cos\Phi_{+3,1}\sin\Phi_{+3,0} - \cos\Phi_{+3,1}\sin\Phi_{-3,0} -$$
$$\cos\Phi_{-3,1}\sin\Phi_{+3,0} + \cos\Phi_{-3,1}\sin\Phi_{-3,0})(D_1-)(D_0+) +$$

$$\frac{1}{4}(\cos\Phi_{+1,1}\sin\Phi_{+1,0} + \cos\Phi_{+1,1}\sin\Phi_{-1,0} - \cos\Phi_{-1,1}\sin\Phi_{+1,0} -$$
$$\cos\Phi_{-1,1}\sin\Phi_{-1,0} - \cos\Phi_{+1,1}\sin\Phi_{+3,0} -$$
$$\cos\Phi_{+1,1}\sin\Phi_{-3,0} + \cos\Phi_{-1,1}\sin\Phi_{+3,0} + \cos\Phi_{-1,1}\sin\Phi_{-3,0} -$$
$$\cos\Phi_{+3,1}\sin\Phi_{+1,0} - \cos\Phi_{+3,1}\sin\Phi_{-1,0} + \cos\Phi_{-3,1}\sin\Phi_{+1,0} +$$
$$\cos\Phi_{-3,1}\sin\Phi_{-1,0} + \cos\Phi_{+3,1}\sin\Phi_{+3,0} + \cos\Phi_{+3,1}\sin\Phi_{-3,0} -$$
$$\cos\Phi_{-3,1}\sin\Phi_{+3,0} - \cos\Phi_{-3,1}\sin\Phi_{-3,0})(D_1-)(A_0-) +$$

$$\frac{1}{4}(\cos\Phi_{+1,1}\cos\Phi_{+1,0} - \cos\Phi_{+1,1}\cos\Phi_{-1,0} - \cos\Phi_{-1,1}\cos\Phi_{+1,0} +$$
$$\cos\Phi_{-1,1}\cos\Phi_{-1,0} - \cos\Phi_{+1,1}\cos\Phi_{+3,0} +$$
$$\cos\Phi_{+1,1}\cos\Phi_{-3,0} + \cos\Phi_{-1,1}\cos\Phi_{+3,0} - \cos\Phi_{-1,1}\cos\Phi_{-3,0} -$$
$$\cos\Phi_{+3,1}\cos\Phi_{+1,0} + \cos\Phi_{+3,1}\cos\Phi_{-1,0} + \cos\Phi_{-3,1}\cos\Phi_{+1,0} -$$
$$\cos\Phi_{-3,1}\cos\Phi_{-1,0} + \cos\Phi_{+3,1}\cos\Phi_{+3,0} - \cos\Phi_{+3,1}\cos\Phi_{-3,0} +$$
$$\cos\Phi_{-3,1}\cos\Phi_{+3,0} - \cos\Phi_{-3,1}\cos\Phi_{-3,0})(D_1-)(D_0-).$$

Under the condition of identical secondary phase shifts for forward and backward samplings (Eq. 35), Eq. 112 simplifies to $$Re(F_C(S_{+1,-1,+3,-3}(t_1, t_0))) \propto \qquad (113)$$
$$(\cos\Phi_{1,1}\cos\Phi_{1,0} + \cos\Phi_{1,1}\cos\Phi_{3,0} + \cos\Phi_{3,1}\cos\Phi_{1,0} +$$
$$\cos\Phi_{3,1}\cos\Phi_{3,0})(A_1+)(A_0+) -$$
$$(\cos\Phi_{1,1}\sin\Phi_{1,0} - \cos\Phi_{1,1}\sin\Phi_{3,0} + \cos\Phi_{3,1}\sin\Phi_{1,0} -$$
$$\cos\Phi_{3,1}\sin\Phi_{3,0})(A_1+)(A_0-) -$$
$$(\sin\Phi_{1,1}\cos\Phi_{1,0} + \sin\Phi_{1,1}\cos\Phi_{3,0} - \sin\Phi_{3,1}\cos\Phi_{1,0} -$$
$$\sin\Phi_{3,1}\cos\Phi_{3,0})(A_1-)(A_0+) +$$
$$(\sin\Phi_{1,1}\sin\Phi_{1,0} - \sin\Phi_{1,1}\sin\Phi_{3,0} - \sin\Phi_{3,1}\sin\Phi_{1,0} + \sin\Phi_{3,1}\sin\Phi_{3,0})$$
$$(A_1-)(A_0-).$$

Two dimensional FT reveals absorptive peaks at the desired and the quad positions. Under the condition of secondary phase shifts independent of n (Eq. 54), Eq. 112 simplifies to $$Re(F_C(S_{+1,-1,+3,-3}(t_1, t_0))) \propto \qquad (114)$$
$$(\cos\Phi_{+,1}\cos\Phi_{+,0} + \cos\Phi_{+,1}\cos\Phi_{-,0} + \cos\Phi_{-,1}\cos\Phi_{+,0} +$$
$$\cos\Phi_{-,1}\cos\Phi_{-,0})(A_1+)(A_0+) +$$
$$(\cos\Phi_{+,1}\sin\Phi_{+,0} - \cos\Phi_{+,1}\sin\Phi_{-,0} + \cos\Phi_{-,1}\sin\Phi_{+,0} -$$
$$\cos\Phi_{-,1}\sin\Phi_{-,0})(A_1+)(D_0+) +$$
$$(\sin\Phi_{+,1}\cos\Phi_{+,0} + \sin\Phi_{+,1}\cos\Phi_{-,0} - \sin\Phi_{-,1}\cos\Phi_{+,0} -$$
$$\sin\Phi_{-,1}\cos\Phi_{-,0})(D_1+)(A_0+) +$$
$$(\sin\Phi_{+,1}\sin\Phi_{+,0} - \sin\Phi_{+,1}\sin\Phi_{-,0} - \sin\Phi_{-,1}\sin\Phi_{+,0} +$$
$$\sin\Phi_{-,1}\sin\Phi_{-,0})(D_1+)(D_0+),$$

Two dimensional FT reveals a single mixed phase peak at the desired position. This proves that, imbalance between forward and backward samplings can not eliminate dispersive components. Under the condition of identical secondary phase shifts (Eq. 73), Eq. 112 simplifies to $$Re(F_C(S_{+1,-1,+3,-3}(t_1,t_0))) \propto 4\cos\Phi_1\cos\Phi_0(A_1+)(A_0+) \qquad (115).$$

Two dimensional FT reveals a single peak, $4\cos\Phi_1\cos\Phi_0(A_1+)(A_0+)$, which is purely absorptive in both dimensions.

Arbitrary Number of Indirect Dimensions

The complex time domain signal results in a sum over products of all possible permutations of $\cos\Phi_{\pm n,j}$ and $\sin\Phi_{\pm n,j}$.

$(c_{+0}, c_{+2})$-Sampling

Starting with Eq. 3, the complex signal for multiple States quadrature detection is proportional to $$S_{+0,+2}(t_K, \ldots, t_0) \propto \qquad (116)$$
$$\bigotimes_{j=0}^{K} QD_{+0,+2} C_{+0,+2}(t_j) = \begin{bmatrix} 1 & i \end{bmatrix} \begin{bmatrix} 1 & 0 \\ 0 & -1 \end{bmatrix} \begin{bmatrix} c_{+0}(t_K) \\ c_{+2}(t_K) \end{bmatrix} \otimes \begin{bmatrix} 1 & i \end{bmatrix}$$
$$\begin{bmatrix} 1 & 0 \\ 0 & -1 \end{bmatrix} \begin{bmatrix} c_{+0}(t_{K-1}) \\ c_{+2}(t_{K-1}) \end{bmatrix} \otimes \ldots \otimes \begin{bmatrix} 1 & i \end{bmatrix} \begin{bmatrix} 1 & 0 \\ 0 & -1 \end{bmatrix} \begin{bmatrix} c_{+0}(t_0) \\ c_{+2}(t_0) \end{bmatrix} =$$
$$\left( \frac{1}{2}(\cos\Phi_{+0,K} + \cos\Phi_{+2,K})e^{i\alpha_K t_K} + \frac{1}{2}(\sin\Phi_{+0,K} + \sin\Phi_{+2,K}) \right.$$
$$e^{i\frac{\pi}{2}} e^{i\alpha_K t_K} + \frac{1}{2}(\cos\Phi_{+0,K} - \cos\Phi_{+2,K})e^{-i\alpha_K t_K} -$$

-continued $$\frac{1}{2}(\sin\Phi_{+0,K} - \sin\Phi_{+2,K})e^{i\frac{\pi}{2}}e^{i\alpha_K t_K}\bigg)\otimes$$

$$\bigg(\frac{1}{2}(\cos\Phi_{+0,K-1} + \cos\Phi_{+2,K-1})e^{i\alpha_{K-1}t_{K-1}} +$$

$$\frac{1}{2}(\sin\Phi_{+0,K-1} + \sin\Phi_{+2,K-1})e^{i\frac{\pi}{2}}e^{i\alpha_{K-1}t_{K-1}} +$$

$$\frac{1}{2}(\cos\Phi_{+0,K-1} - \cos\Phi_{+2,K-1})e^{-i\alpha_{K-1}t_{K-1}} -$$

$$\frac{1}{2}(\sin\Phi_{+0,K-1} - \sin\Phi_{+2,K-1})e^{i\frac{\pi}{2}}e^{-i\alpha_{K-1}t_{K-1}}\bigg)\otimes\ldots\otimes$$

$$\bigg(\frac{1}{2}(\cos\Phi_{+0,0} + \cos\Phi_{+2,0})e^{i\alpha_0 t_0} + \frac{1}{2}(\sin\Phi_{+0,0} + \sin\Phi_{+2,0})$$

$$e^{i\frac{\pi}{2}}e^{i\alpha_0 t_0} + \frac{1}{2}(\cos\Phi_{+0,0} - \cos\Phi_{+2,0})e^{-i\alpha_0 t_0} -$$

$$\frac{1}{2}(\sin\Phi_{+0,0} - \sin\Phi_{+2,0})e^{i\frac{\pi}{2}}e^{-i\alpha_0 t_0}\bigg).$$

Multidimensional FT reveals the peak components as $$Re(F_C(S_{+0,+2}(t_K, \ldots, t_0))) \propto = \qquad (117)$$

$$\bigg(\frac{1}{2}(\cos\Phi_{+0,K} + \cos\Phi_{+2,K})(A_K +) + \frac{1}{2}(\sin\Phi_{+0,K} + \sin\Phi_{+2,K})$$

$$(D_K +) + \frac{1}{2}(\cos\Phi_{+0,K} - \cos\Phi_{+2,K})(A_K -) -$$

$$\frac{1}{2}(\sin\Phi_{+0,K} - \sin\Phi_{+2,K})(D_K -)\bigg)\otimes$$

$$\bigg(\frac{1}{2}(\cos\Phi_{+0,K-1} + \cos\Phi_{+2,K-1})(A_{K-1} +) +$$

$$\frac{1}{2}(\sin\Phi_{+0,K-1} + \sin\Phi_{+2,K-1})(D_{K-1} +) +$$

$$\frac{1}{2}(\cos\Phi_{+0,K-1} - \cos\Phi_{+2,K-1})(A_{K-1} -) -$$

$$\frac{1}{2}(\sin\Phi_{+0,K-1} - \sin\Phi_{+2,K-1})(D_{K-1} - 1)\bigg)\otimes\ldots\otimes$$

$$\bigg(\frac{1}{2}(\cos\Phi_{+0,0} + \cos\Phi_{+2,0})(A_0 +) + \frac{1}{2}(\sin\Phi_{+0,0} + \sin\Phi_{+2,0})(D_0 +) +$$

$$\frac{1}{2}(\cos\Phi_{+0,0} - \cos\Phi_{+2,0})(A_0 -) -$$

$$\frac{1}{2}(\sin\Phi_{+0,0} - \sin\Phi_{+2,0})(D_0 -)\bigg).$$

The term $(A_K+)(A_{K-1}+) \ldots (A_0+)$ and the term $(D_K+)(D_{K-1}+) \ldots (D_0+)$, respectively, represent an entirely absorptive and entirely dispersive components of the desired peak located at $(\alpha_0, \alpha_1, \ldots, \alpha_K)$, (ii) the term $(A_K-)(A_{K-1}-) \ldots (A_0-)$ and the term $(D_K-)(D_{K-1}-) \ldots (D_0-)$, respectively, represent an entirely absorptive and entirely dispersive components of the peak located at the quadrature position along all dimensions $(-\alpha_0, -\alpha_1, \ldots, -\alpha_K)$. All other terms represent mixed phase peak components at either the desired or any one of the quad positions.

($c_{-0}$, $c_{-2}$)-Sampling

Starting with Eq. 7, the complex signal for multiple backward States quadrature detection is proportional to $$S_{-0,-2}(t_K, \ldots, t_0) \propto \qquad (118)$$

$$\bigotimes_{j=0}^{K} QD_{-0,-2}C_{-0,-2}(t_j) = \begin{bmatrix} 1 & i \end{bmatrix}\begin{bmatrix} 1 & 0 \\ 0 & 1 \end{bmatrix}\begin{bmatrix} c_{-0}(t_K) \\ c_{-2}(t_K) \end{bmatrix}\otimes\begin{bmatrix} 1 & i \end{bmatrix}$$

$$\begin{bmatrix} 1 & 0 \\ 0 & 1 \end{bmatrix}\begin{bmatrix} c_{-0}(t_{K-1}) \\ c_{-2}(t_{K-1}) \end{bmatrix}\otimes\ldots\otimes\begin{bmatrix} 1 & i \end{bmatrix}\begin{bmatrix} 1 & 0 \\ 0 & 1 \end{bmatrix}\begin{bmatrix} c_{-0}(t_0) \\ c_{-2}(t_0) \end{bmatrix} =$$

$$\bigg(\frac{1}{2}(\cos\Phi_{-0,K} + \cos\Phi_{-2,K})e^{i\alpha_K t_K} - \frac{1}{2}(\sin\Phi_{-0,K} + \sin\Phi_{-2,K})$$

$$e^{i\frac{\pi}{2}}e^{i\alpha_K t_K} + \frac{1}{2}(\cos\Phi_{-0,K} - \cos\Phi_{-2,K})e^{-i\alpha_K t_K} +$$

$$\frac{1}{2}(\sin\Phi_{-0,K} - \sin\Phi_{-2,K})e^{i\frac{\pi}{2}}e^{-i\alpha_K t_K}\bigg)\otimes$$

$$\bigg(\frac{1}{2}(\cos\Phi_{-0,K-1} + \cos\Phi_{-2,K-1})e^{i\alpha_{K-1}t_{K-1}} -$$

$$\frac{1}{2}(\sin\Phi_{-0,K-1} + \sin\Phi_{-2,K-1})e^{i\frac{\pi}{2}}e^{i\alpha_{K-1}t_{K-1}} +$$

$$\frac{1}{2}(\cos\Phi_{-0,K-1} - \cos\Phi_{-2,K-1})e^{-i\alpha_{K-1}t_{K-1}} +$$

$$\frac{1}{2}(\sin\Phi_{-0,K-1} - \sin\Phi_{-2,K-1})e^{i\frac{\pi}{2}}e^{-i\alpha_{K-1}t_{K-1}}\bigg)\otimes\ldots\otimes$$

$$\bigg(\frac{1}{2}(\cos\Phi_{-0,0} + \cos\Phi_{-2,0})e^{i\alpha_0 t_0} - \frac{1}{2}(\sin\Phi_{-0,0} + \sin\Phi_{-2,0})$$

$$e^{i\frac{\pi}{2}}e^{i\alpha_0 t_0} + \frac{1}{2}(\cos\Phi_{-0,0} - \cos\Phi_{-2,0})e^{-i\alpha_0 t_0} +$$

$$\frac{1}{2}(\sin\Phi_{-0,0} - \sin\Phi_{-2,0})e^{i\frac{\pi}{2}}e^{-i\alpha_0 t_0}\bigg).$$

Multidimensional FT reveals the peak components as $$Re(F_C(S_{-0,-2}(t_K, \ldots, t_0))) \propto = \qquad (119)$$

$$\bigg(\frac{1}{2}(\cos\Phi_{-0,K} + \cos\Phi_{-2,K})(A_K +) - \frac{1}{2}(\sin\Phi_{-0,K} + \sin\Phi_{-2,K})$$

$$(D_K +) + \frac{1}{2}(\cos\Phi_{-0,K} - \cos\Phi_{-2,K})(A_K -) +$$

$$\frac{1}{2}(\sin\Phi_{-0,K} - \sin\Phi_{-2,K})(D_K -)\bigg)\otimes$$

$$\bigg(\frac{1}{2}(\cos\Phi_{-0,K-1} + \cos\Phi_{-2,K-1})(A_{K-1} +) -$$

$$\frac{1}{2}(\sin\Phi_{-0,K-1} + \sin\Phi_{-2,K-1})(D_{K-1} +) +$$

$$\frac{1}{2}(\cos\Phi_{-0,K-1} - \cos\Phi_{-2,K-1})(A_{K-1} -) +$$

$$\frac{1}{2}(\sin\Phi_{-0,K-1} - \sin\Phi_{-2,K-1})(D_{K-1} -)\bigg)\otimes\ldots\otimes$$

$$\bigg(\frac{1}{2}(\cos\Phi_{-0,0} + \cos\Phi_{-2,0})(A_0 +) - \frac{1}{2}(\sin\Phi_{-0,0} + \sin\Phi_{-2,0})(D_0 +) +$$

$$\frac{1}{2}(\cos\Phi_{-0,0} - \cos\Phi_{-2,0})(A_0 - 1) +$$

$$\frac{1}{2}(\sin\Phi_{-0,0} - \sin\Phi_{-2,0})(D_0 -)\bigg).$$

The peak component pattern is comparable to the one described for Eq. 117.

($c_{+0}, c_{+2}, c_{-0}, c_{-2}$)-Sampling

Starting with Eq. 10 the complex signal for multiple dual States quadrature detection is proportional to $$S_{+0,+2,-0,-2}(t_K, \ldots, t_0) \propto \qquad (120)$$

$$\bigg(\frac{1}{2}(\cos\Phi_{+0,K} + \cos\Phi_{+2,K} + \cos\Phi_{-0,K} + \cos\Phi_{-2,K})e^{i\alpha_K t_K} +$$

-continued $$\frac{1}{2}(\sin\Phi_{+0,K} + \sin\Phi_{+2,K} - \sin\Phi_{-0,K} - \sin\Phi_{-2,K})e^{\frac{\pi}{2}}e^{i\alpha_K t_K} +$$

$$\frac{1}{2}(\cos\Phi_{+0,K} - \cos\Phi_{+2,K} + \cos\Phi_{-0,K} - \cos\Phi_{-2,K})e^{-i\alpha_K t_K} -$$

$$\frac{1}{2}(\sin\Phi_{+0,K} - \sin\Phi_{-2,K} - \sin\Phi_{+0,K} + \sin\Phi_{-2,K})e^{\frac{\pi}{2}}e^{-i\alpha_K t_K}\Big) \otimes$$

$$\Big(\frac{1}{2}(\cos\Phi_{+0,K-1} + \cos\Phi_{+2,K-1} + \cos\Phi_{-0,K-1} + \cos\Phi_{2,K-1})$$

$$e^{i\alpha_{K-1} t_{K-1}} + \frac{1}{2}(\sin\Phi_{+0,K-1} + \sin\Phi_{+2,K-1} -$$

$$\sin\Phi_{-0,K-1} - \sin\Phi_{-2,K-1})e^{\frac{\pi}{2}}e^{i\alpha_{K-1} t_{K-1}} +$$

$$\frac{1}{2}(\cos\Phi_{+0,K-1} - \cos\Phi_{+2,K-1} + \cos\Phi_{-0,K-1} - \cos\Phi_{-2,K-1})$$

$$e^{-i\alpha_{K-1} t_{K-1}} -$$

$$\frac{1}{2}(\sin\Phi_{+0,K-1} - \sin\Phi_{+2,K-1} - \sin\Phi_{-0,K-1} + \sin\Phi_{-2,K-1})$$

$$e^{\frac{\pi}{2}}e^{-i\alpha_{K-1} t_{K-1}}\Big) \otimes \ldots \otimes$$

$$\Big(\frac{1}{2}(\cos\Phi_{+0,0} + \cos\Phi_{+2,0} + \cos\Phi_{-0,0} + \cos\Phi_{-2,0})e^{i\alpha_0 t_0} +$$

$$\frac{1}{2}(\sin\Phi_{+0,0} + \sin\Phi_{+2,0} - \sin\Phi_{-0,0} - \sin\Phi_{-2,0})e^{\frac{\pi}{2}}e^{i\alpha_0 t_0} +$$

$$\frac{1}{2}(\cos\Phi_{+0,0} - \cos\Phi_{+2,0} + \cos\Phi_{-0,0} - \cos\Phi_{-2,0})e^{-i\alpha_0 t_0} -$$

$$\frac{1}{2}(\sin\Phi_{+0,0} - \sin\Phi_{+2,0} - \sin\Phi_{-0,0} + \sin\Phi_{-2,0})e^{\frac{\pi}{2}}e^{-i\alpha_0 t_0}\Big),$$

Multidimensional FT reveals the peak components as $$Re(F_C(S_{+0,+2,-0,-2}(t_K, \ldots, t_0))) \propto \quad (121)$$

$$\Big(\frac{1}{2}(\cos\Phi_{+0,K} + \cos\Phi_{+2,K} + \cos\Phi_{-0,K} + \cos\Phi_{-2,K})(A_K +) +$$

$$\frac{1}{2}(\sin\Phi_{+0,K} + \sin\Phi_{+2,K} - \sin\Phi_{-0,K} - \sin\Phi_{-2,K})(D_K +) +$$

$$\frac{1}{2}(\cos\Phi_{+0,K} - \cos\Phi_{+2,K} + \cos\Phi_{-0,K} - \cos\Phi_{-2,K})(A_K -) -$$

$$\frac{1}{2}(\sin\Phi_{+0,K} - \sin\Phi_{+2,K} - \sin\Phi_{-0,K} + \sin\Phi_{-2,K})(D_K -)\Big) \otimes$$

$$\Big(\frac{1}{2}(\cos\Phi_{+0,K-1} + \cos\Phi_{+2,K-1} + \cos\Phi_{-0,K-1} + \cos\Phi_{-2,K-1})$$

$$(A_K +) + \frac{1}{2}(\sin\Phi_{+0,K-1} + \sin\Phi_{+2,K-1} -$$

$$\sin\Phi_{-0,K-1} - \sin\Phi_{-2,K-1})(D_{K-1} +) +$$

$$\frac{1}{2}(\cos\Phi_{+0,K-1} - \cos\Phi_{+2,K-1} + \cos\Phi_{-0,K-1} - \cos\Phi_{-2,K-1})$$

$$(A_{K-1} -) -$$

$$\frac{1}{2}(\sin\Phi_{+0,K-1} - \sin\Phi_{+2,K-1} - \sin\Phi_{-0,K-1} + \sin\Phi_{-2,K-1})$$

$$(D_{K-1} -)\Big) \otimes \ldots \otimes$$

$$\Big(\frac{1}{2}(\cos\Phi_{+0,0} + \cos\Phi_{+2,0} + \cos\Phi_{-0,0} + \cos\Phi_{-2,0})(A_0 +) +$$

$$\frac{1}{2}(\sin\Phi_{+0,0} + \sin\Phi_{+2,0} - \sin\Phi_{-0,0} - \sin\Phi_{-2,0})(D_0 +) +$$

$$\frac{1}{2}(\cos\Phi_{+0,0} - \cos\Phi_{+2,0} + \cos\Phi_{-0,0} - \cos\Phi_{-2,0})(A_0 -) -$$

$$\frac{1}{2}(\sin\Phi_{+0,0} - \sin\Phi_{+2,0} - \sin\Phi_{-0,0} + \sin\Phi_{-2,0})(D_0 -)\Big).$$

The peak component pattern is comparable to the one described for Eq. 117.

($c_{+1}, c_{-1}$)-Sampling (PMS)

Starting with Eq. 14, the complex signal for ($c_{+1}, c_{-1}$)-PMS is proportional to $$S_{+1,-1}(t_K, \ldots, t_0) \propto \bigotimes_{j=0}^{K} QD_{+1,-1} C_{+1,-1}(t_j) = \quad (122)$$

$$\frac{1}{\sqrt{2}}\begin{bmatrix} 1 & i \end{bmatrix}\begin{bmatrix} 1 & 1 \\ -1 & 1 \end{bmatrix}\begin{bmatrix} c_{+1}(t_K) \\ c_{-1}(t_K) \end{bmatrix} \otimes \frac{1}{\sqrt{2}}\begin{bmatrix} 1 & i \end{bmatrix}\begin{bmatrix} 1 & 1 \\ -1 & 1 \end{bmatrix}$$

$$\begin{bmatrix} c_{+1}(t_{K-1}) \\ c_{-1}(t_{K-1}) \end{bmatrix} \otimes \ldots \otimes \frac{1}{\sqrt{2}}\begin{bmatrix} 1 & i \end{bmatrix}\begin{bmatrix} 1 & 1 \\ -1 & 1 \end{bmatrix}\begin{bmatrix} c_{+1}(t_0) \\ c_{-1}(t_0) \end{bmatrix} =$$

$$\Big(\frac{1}{2}(\cos\Phi_{+1,K} + \cos\Phi_{-1,K})e^{i\alpha_K t_K} + \frac{1}{2}(\sin\Phi_{+1,K} - \sin\Phi_{-1,K})$$

$$e^{i\pi/2}e^{i\alpha_K t_K} - \frac{1}{2}(\sin\Phi_{+1,K} + \sin\Phi_{-1,K})e^{-i\alpha_K t_K} -$$

$$\frac{1}{2}(\cos\Phi_{+1,K} - \cos\Phi_{-1,K})e^{i\pi/2}e^{i\alpha_K t_K}\Big) \otimes$$

$$\Big(\frac{1}{2}(\cos\Phi_{+1,K-1} + \cos\Phi_{-1,K-1})e^{i\alpha_{K-1} t_{K-1}} +$$

$$\frac{1}{2}(\sin\Phi_{+1,K-1} - \sin\Phi_{-1,K-1}) \times^{i\pi/2} e^{i\alpha_{K-1} t_{K-1}} -$$

$$\frac{1}{2}(\sin\Phi_{+1,K-1} + \sin\Phi_{-1,K-1})e^{-i\alpha_{K-1} t_{K-1}} -$$

$$\frac{1}{2}(\cos\Phi_{+1,K-1} - \cos\Phi_{-1,K-1})e^{i\pi/2}e^{-i\alpha_{K-1} t_{K-1}}\Big) \otimes \ldots \otimes$$

$$\Big(\frac{1}{2}(\cos\Phi_{+0,0} + \cos\Phi_{-2,0})e^{i\alpha_0 t_0} + \frac{1}{2}(\sin\Phi_{+1,0} - \sin\Phi_{-1,0})$$

$$e^{i\pi/2}e^{i\alpha_0 t_0} - \frac{1}{2}(\sin\Phi_{+1,0} + \sin\Phi_{-3,0})e^{-i\alpha_0 t_0} -$$

$$\frac{1}{2}(\cos\Phi_{+1,0} - \cos\Phi_{-3,0})e^{i\pi/2}e^{-i\alpha_0 t_0}\Big).$$

Multidimensional FT reveals the peak components as $$Re(F_C(S_{+1,-1}(t_K, \ldots, t_0))) \propto = \quad (123)$$

$$\Big(\frac{1}{2}(\cos\Phi_{+1,K} + \cos\Phi_{-1,K})(A_K +) + \frac{1}{2}(\sin\Phi_{+1,K} - \sin\Phi_{-1,K})$$

$$(D_K +) - \frac{1}{2}(\sin\Phi_{+1,K} + \sin\Phi_{-1,K})(A_K -) -$$

$$\frac{1}{2}(\cos\Phi_{+1,K} - \cos\Phi_{-1,K})(D_K -)\Big) \otimes$$

$$\Big(\frac{1}{2}(\cos\Phi_{+1,K-1} + \cos\Phi_{-1,K-1})(A_{K-1} +) +$$

$$\frac{1}{2}(\sin\Phi_{+1,K-1} - \sin\Phi_{-1,K-1})(D_{K-1} +) -$$

$$\frac{1}{2}(\sin\Phi_{+1,K-1} + \sin\Phi_{-1,K-1})(A_{K-1} -) -$$

$$\frac{1}{2}(\cos\Phi_{+1,K-1} - \cos\Phi_{-1,K-1})(D_{K-1} -)\Big) \otimes \ldots \otimes$$

-continued $$\left(\frac{1}{2}(\cos\Phi_{+1,0} + \cos\Phi_{-1,0})(A_0 +) + \frac{1}{2}(\sin\Phi_{+1,0} - \sin\Phi_{-1,0})(D_0 +) - \right.$$
$$\frac{1}{2}(\sin\Phi_{+1,0} + \sin\Phi_{-1,0})(A_0 -) -$$
$$\left.\frac{1}{2}(\cos\Phi_{+1,0} - \cos\Phi_{-1,0})(D_0 -)\right).$$

The peak component pattern is comparable to the one described for Eq. 117.

$(c_{+3}, c_{-3})$-Sampling (PMS)

Starting with Eq. 18, the complex signal for $(c_{+3}, c_{-3})$-PMS is proportional to $$S_{+3,-3}(t_K, \ldots, t_0)) \propto \bigotimes_{j=0}^{K} QD_{+3,-3}C_{+3,-3}(t_j) = \quad (124)$$

$$\frac{1}{\sqrt{2}}\begin{bmatrix}1 & i\end{bmatrix}\begin{bmatrix}-1 & -1\\-1 & 1\end{bmatrix}\begin{bmatrix}c_{+3}(t_K)\\c_{-3}(t_K)\end{bmatrix} \otimes \frac{1}{\sqrt{2}}\begin{bmatrix}1 & i\end{bmatrix}\begin{bmatrix}-1 & -1\\-1 & 1\end{bmatrix}$$

$$\begin{bmatrix}c_{+3}(t_{K-1})\\c_{-3}(t_{K-1})\end{bmatrix} \otimes \ldots \otimes \frac{1}{\sqrt{2}}\begin{bmatrix}1 & i\end{bmatrix}\begin{bmatrix}-1 & -1\\-1 & 1\end{bmatrix}\begin{bmatrix}c_{+3}(t_0)\\c_{-3}(t_0)\end{bmatrix} =$$

$$\left(\frac{1}{2}(\cos\Phi_{+3,K} + \cos\Phi_{-3,K})e^{i\alpha_K t_K} + \frac{1}{2}(\sin\Phi_{+3,K} - \sin\Phi_{-3,K})\right.$$
$$e^{i\pi/2}e^{i\alpha_K t_K} + \frac{1}{2}(\sin\Phi_{+3,K} + \sin\Phi_{-3,K})e^{-i\alpha_K t_K} +$$
$$\left.\frac{1}{2}(\cos\Phi_{+3,K} - \cos\Phi_{-3,K})e^{i\pi/2}e^{-i\alpha_K t_K}\right) \otimes$$

$$\left(\frac{1}{2}(\cos\Phi_{+3,K-1} + \cos\Phi_{-3,K-1})e^{i\alpha_{K-1} t_{K-1}} + \right.$$
$$\frac{1}{2}(\sin\Phi_{+3,K-1} - \sin\Phi_{-3,K-1}) \times e^{i\pi/2} e^{i\alpha_{K-1} t_{K-1}} +$$
$$\frac{1}{2}(\sin\Phi_{+3,K-1} + \sin\Phi_{-3,K-1})e^{-i\alpha_{K-1} t_{K-1}} +$$
$$\left.\frac{1}{2}(\cos\Phi_{+3,K-1} - \cos\Phi_{-3,K-1})e^{i\pi/2}e^{-i\alpha_{K-1} t_{K-1}}\right) \otimes \ldots \otimes$$

$$\left(\frac{1}{2}(\cos\Phi_{+3,0} + \cos\Phi_{-3,0})e^{i\alpha_0 t_0} + \frac{1}{2}(\sin\Phi_{+3,0} - \sin\Phi_{-3,0})\right.$$
$$e^{i\pi/2}e^{i\alpha_0 t_0} + \frac{1}{2}(\sin\Phi_{+3,0} + \sin\Phi_{-3,0})e^{-i\alpha_0 t_0} +$$
$$\left.\frac{1}{2}(\cos\Phi_{+3,0} - \cos\Phi_{-3,0})e^{i\pi/2}e^{-i\alpha_0 t_0}\right).$$

Multidimensional FT reveals the peak components as $$Re(F_C(S_{+3,-3}(t_K, \ldots, t_0))) \propto = \quad (125)$$

$$\left(\frac{1}{2}(\cos\Phi_{+3,K} + \cos\Phi_{-3,K})(A_K +) + \frac{1}{2}(\sin\Phi_{+3,K} - \sin\Phi_{-3,K})\right.$$
$$(D_K +) + \frac{1}{2}(\sin\Phi_{+3,K} + \sin\Phi_{-3,K})(A_K -) +$$
$$\left.\frac{1}{2}(\cos\Phi_{+3,K} - \cos\Phi_{-3,K})(D_K -)\right) \otimes$$

$$\left(\frac{1}{2}(\cos\Phi_{+3,K-1} + \cos\Phi_{-3,K-1})(A_{K-1} +) + \right.$$
$$\frac{1}{2}(\sin\Phi_{+3,K-1} - \sin\Phi_{-3,K-1})(D_{K-1} +) +$$
$$\frac{1}{2}(\sin\Phi_{+3,K-1} + \sin\Phi_{-3,K-1})(A_{K-1} -) +$$
$$\left.\frac{1}{2}(\cos\Phi_{+3,K-1} - \cos\Phi_{-3,K-1})(D_{K-1} -)\right) \otimes \ldots \otimes$$

$$\left(\frac{1}{2}(\cos\Phi_{+3,0} + \cos\Phi_{-3,0})(A_0 +) + \frac{1}{2}(\sin\Phi_{+3,0} - \sin\Phi_{-3,0})(D_0 +) + \right.$$
$$\frac{1}{2}(\sin\Phi_{+3,0} + \sin\Phi_{-3,0})(A_0 -) +$$
$$\left.\frac{1}{2}(\cos\Phi_{+3,0} - \cos\Phi_{-3,0})(D_0 -)\right).$$

The peak component pattern is comparable to the one described for Eq. 117.

$(c_{+1}, c_{-1}, c_{+3}, c_{-3})$-Sampling (DPMS)

Starting with Eq. 21, the complex signal for $(c_{-1}, c_{-1}, c_{+3}, c_{-3})$-DPMS is proportional to $$S_{+1,-1,+3,-3}(t_K, \ldots, t_0) \propto \quad (126)$$

$$\left(\frac{1}{2}(\cos\Phi_{+1,K} + \cos\Phi_{-1,K} + \cos\Phi_{+3,K} + \cos\Phi_{-3,K})e^{i\alpha_K t_K} + \right.$$
$$\frac{1}{2}(\sin\Phi_{+1,K} - \sin\Phi_{-1,K} + \sin\Phi_{+3,K} - \sin\Phi_{-3,K})e^{i\frac{\pi}{2}}e^{i\alpha_K t_K} -$$
$$\frac{1}{2}(\sin\Phi_{+1,K} + \sin\Phi_{-1,K} - \sin\Phi_{+3,K} - \sin\Phi_{-3,K})e^{-i\alpha_K t_K} -$$
$$\left.\frac{1}{2}(\cos\Phi_{+1,K} - \cos\Phi_{-1,K} - \cos\Phi_{+3,K} + \cos\Phi_{-3,K})e^{i\frac{\pi}{2}}e^{-i\alpha_K t_K}\right) \otimes$$

$$\left(\frac{1}{2}(\cos\Phi_{+1,K-1} + \cos\Phi_{-1,K-1} + \cos\Phi_{+3,K-1} + \cos\Phi_{-3,K-1})\right.$$
$$e^{i\alpha_{K-1} t_{K-1}} + \frac{1}{2}(\sin\Phi_{+1,K-1} - \sin\Phi_{-1,K-1} +$$
$$\sin\Phi_{+3,K-1} - \sin\Phi_{-3,K-1})e^{i\frac{\pi}{2}}e^{i\alpha_{K-1} t_{K-1}} -$$
$$\frac{1}{2}(\sin\Phi_{+1,K-1} + \sin\Phi_{-1,K-1} - \sin\Phi_{+3,K-1} - \sin\Phi_{-3,K})$$
$$e^{-i\alpha_{K-1} t_{K-1}} -$$
$$\frac{1}{2}(\cos\Phi_{+1,K-1} - \cos\Phi_{-1,K-1} - \cos\Phi_{+3,K-1} + \cos\Phi_{-3,K-1})$$
$$\left.e^{i\frac{\pi}{2}}e^{-i\alpha_{K-1} t_{K-1}}\right) \otimes \ldots \otimes$$

$$\left(\frac{1}{2}(\cos\Phi_{+1,0} + \cos\Phi_{-1,0} + \cos\Phi_{+3,0} + \cos\Phi_{-3,0})e^{i\alpha_0 t_0} + \right.$$
$$\frac{1}{2}(\sin\Phi_{+1,0} - \sin\Phi_{-1,0} + \sin\Phi_{+3,0} - \sin\Phi_{-3,0})e^{i\frac{\pi}{2}}e^{i\alpha_0 t_0} -$$
$$\frac{1}{2}(\sin\Phi_{+1,0} + \sin\Phi_{-1,0} - \sin\Phi_{+3,0} - \sin\Phi_{-3,0})e^{-i\alpha_0 t_0} -$$
$$\left.\frac{1}{2}(\cos\Phi_{+1,0} - \cos\Phi_{-1,0} - \cos\Phi_{+3,0} + \cos\Phi_{-3,0})e^{i\frac{\pi}{2}}e^{-i\alpha_0 t_0}\right).$$

Multidimensional FT reveals the peak components as $$Re(F_C(S_{+0,+2,-0,-2}(t_K, \ldots, t_0))) \propto \quad (127)$$

$$\left(\frac{1}{2}(\cos\Phi_{+1,K} + \cos\Phi_{-1,K} + \cos\Phi_{+3,K} + \cos\Phi_{-3,K})(A_K +) + \right.$$
$$\frac{1}{2}(\sin\Phi_{+1,K} - \sin\Phi_{-1,K} + \sin\Phi_{+3,K} - \sin\Phi_{-3,K})(D_K +) -$$
$$\frac{1}{2}(\sin\Phi_{+1,K} + \sin\Phi_{-1,K} - \sin\Phi_{+3,K} - \sin\Phi_{-3,K})(A_K -) -$$
$$\left.\frac{1}{2}(\cos\Phi_{+1,K} - \cos\Phi_{-1,K} - \cos\Phi_{+3,K} + \cos\Phi_{-3,K})(D_K -)\right) \otimes$$

$$\left(\frac{1}{2}(\cos\Phi_{+1,K-1} + \cos\Phi_{-1,K-1} + \cos\Phi_{+3,K-1} + \cos\Phi_{-3,K-1})\right.$$

-continued $$(A_{K-1}+)+\frac{1}{2}(\sin\Phi_{+1,K-1}-\sin\Phi_{-1,K-1}+$$
$$\sin\Phi_{+3,K-1}-\sin\Phi_{-3,K-1})(D_{K-1}+)-$$
$$\frac{1}{2}(\sin\Phi_{+1,K-1}+\sin\Phi_{-1,K-1}-\sin\Phi_{+3,K-1}-\sin\Phi_{-3,K})$$
$$(A_{K-1}-)-\frac{1}{2}(\cos\Phi_{+1,K-1}-\cos\Phi_{-1,K-1}-$$
$$\cos\Phi_{+3,K-1}+\cos\Phi_{-3,K-1})(D_{K-1}-)\Big)\otimes\dots\otimes$$
$$\Big(\frac{1}{2}(\cos\Phi_{+1,0}+\cos\Phi_{-1,0}+\cos\Phi_{+3,0}+\cos\Phi_{-3,0})(A_0+)+$$
$$\frac{1}{2}(\sin\Phi_{+1,0}-\sin\Phi_{-1,0}+\sin\Phi_{+3,0}-\sin\Phi_{-3,0})(D_0+)-$$
$$\frac{1}{2}(\sin\Phi_{+1,0}+\sin\Phi_{-1,0}-\sin\Phi_{+3,0}-\sin\Phi_{-3,0})(A_0-)-$$
$$\frac{1}{2}(\cos\Phi_{+1,0}-\cos\Phi_{-1,0}-\cos\Phi_{+3,0}+\cos\Phi_{-3,0})(D_0-)\Big).$$

The peak component pattern is comparable to the one described for Eq. 117.

($c_{+0}$,$c_{-2}$)-Sampling (PMS)

Starting with Eq. 25, the complex signal for ($c_{+0}$,$c_{-2}$)-PMS is proportional to $$S_{+0,-2}(t_K,\dots,t_0)\propto\bigotimes_{j=0}^{K}QD_{+0,-2}C_{+0,-2}(t_j)= \qquad(128)$$

$$[1\ i]\begin{bmatrix}1&0\\0&1\end{bmatrix}\begin{bmatrix}c_{+0}(t_K)\\c_{-2}(t_K)\end{bmatrix}\otimes[1\ i]\begin{bmatrix}1&0\\0&1\end{bmatrix}\begin{bmatrix}c_{+0}(t_{K-1})\\c_{-2}(t_{K-1})\end{bmatrix}\otimes$$

$$\dots\otimes[1\ i]\begin{bmatrix}1&0\\0&1\end{bmatrix}\begin{bmatrix}c_{+0}(t_0)\\c_{-2}(t_0)\end{bmatrix}=$$

$$\Big(\frac{1}{2}(\cos\Phi_{+0,K}+\cos\Phi_{-2,K})e^{i\alpha_K t_K}+\frac{1}{2}(\sin\Phi_{+0,K}-\sin\Phi_{-2,K})$$
$$e^{i\frac{\pi}{2}}e^{i\alpha_K t_K}+\frac{1}{2}(\cos\Phi_{+0,K}-\cos\Phi_{-2,K})e^{-i\alpha_K t_K}-$$
$$\frac{1}{2}(\sin\Phi_{+0,K}+\sin\Phi_{-2,K})e^{i\frac{\pi}{2}}e^{-i\alpha_K t_K}\Big)\otimes$$
$$\Big(\frac{1}{2}(\cos\Phi_{+0,K-1}+\cos\Phi_{-2,K-1})e^{i\alpha_{K-1} t_{K-1}}+$$
$$\frac{1}{2}(\sin\Phi_{+0,K-1}-\sin\Phi_{-2,K-1})e^{i\frac{\pi}{2}}e^{i\alpha_{K-1} t_{K-1}}+$$
$$\frac{1}{2}(\cos\Phi_{+0,K-1}-\cos\Phi_{-2,K-1})e^{-i\alpha_{K-1} t_{K-1}}-$$
$$\frac{1}{2}(\sin\Phi_{+0,K-1}+\sin\Phi_{-2,K-1})e^{i\frac{\pi}{2}}e^{-i\alpha_{K-1} t_{K-1}}\Big)\otimes\dots\otimes$$
$$\Big(\frac{1}{2}(\cos\Phi_{+0,0}+\cos\Phi_{-2,0})e^{i\alpha_0 t_0}+\frac{1}{2}(\sin\Phi_{+0,0}-\sin\Phi_{-2,0})$$
$$e^{i\frac{\pi}{2}}e^{i\alpha_0 t_0}+\frac{1}{2}(\cos\Phi_{+0,0}-\cos\Phi_{-2,0})e^{-i\alpha_0 t_0}-$$
$$\frac{1}{2}(\sin\Phi_{+0,0}+\sin\Phi_{-2,0})e^{i\frac{\pi}{2}}e^{-i\alpha_0 t_0}\Big).$$

Multidimensional FT reveals the peak components as $$\mathrm{Re}(F_C(S_{+0,-2}(t_K,\dots,t_0)))\propto= \qquad(129)$$

$$\Big(\frac{1}{2}(\cos\Phi_{+0,K}+\cos\Phi_{-2,K})(A_K+)+\frac{1}{2}(\sin\Phi_{+0,K}-\sin\Phi_{-2,K})$$

-continued $$(D_K+)+\frac{1}{2}(\cos\Phi_{+0,K}-\cos\Phi_{-2,K})(A_K-)-$$
$$\frac{1}{2}(\sin\Phi_{+0,K}+\sin\Phi_{-2,K})(D_K-)\Big)\otimes$$
$$\Big(\frac{1}{2}(\cos\Phi_{+0,K-1}+\cos\Phi_{-2,K-1})(A_{K-1}+)+$$
$$\frac{1}{2}(\sin\Phi_{+0,K-1}-\sin\Phi_{-2,K-1})(D_{K-1}+)+$$
$$\frac{1}{2}(\cos\Phi_{+0,K-1}-\cos\Phi_{-2,K-1})(A_{K-1}-)-$$
$$\frac{1}{2}(\sin\Phi_{+0,K-1}+\sin\Phi_{-2,K-1})(D_{K-1}-)\Big)\otimes\dots\otimes$$
$$\Big(\frac{1}{2}(\cos\Phi_{+0,0}+\cos\Phi_{-2,0})(A_0+)+\frac{1}{2}(\sin\Phi_{+0,0}-\sin\Phi_{-2,0})(D_0+)+$$
$$\frac{1}{2}(\cos\Phi_{+0,0}+\cos\Phi_{-2,0})(A_0-)-$$
$$\frac{1}{2}(\sin\Phi_{+0,0}+\sin\Phi_{-2,0})(D_0-)\Big).$$

The peak component pattern is comparable to the one described for Eq. 117.

($c_{-0}$,$c_{+2}$)-Sampling (PMS)

Starting with Eq. 29, the complex signal for ($c_{-0}$,$c_{+2}$)-PMS is proportional to $$S_{-0,+2}(t_K,\dots,t_0)\propto\bigotimes_{j=0}^{K}QD_{-0,+2}C_{-0,+2}(t_j)= \qquad(130)$$

$$[1\ i]\begin{bmatrix}1&0\\0&-1\end{bmatrix}\begin{bmatrix}c_{-0}(t_K)\\c_{+2}(t_K)\end{bmatrix}\otimes[1\ i]\begin{bmatrix}1&0\\0&-1\end{bmatrix}\begin{bmatrix}c_{-0}(t_{K-1})\\c_{+2}(t_{K-1})\end{bmatrix}\otimes\dots\otimes$$

$$[1\ i]\begin{bmatrix}1&0\\0&-1\end{bmatrix}\begin{bmatrix}c_{-0}(t_0)\\c_{+2}(t_0)\end{bmatrix}=$$

$$\Big(\frac{1}{2}(\cos\Phi_{-0,K}+\cos\Phi_{+2,K})e^{i\alpha_K t_K}-\frac{1}{2}(\sin\Phi_{-0,K}-\sin\Phi_{+2,K})$$
$$e^{i\frac{\pi}{2}}e^{i\alpha_K t_K}+\frac{1}{2}(\cos\Phi_{-0,K}-\cos\Phi_{+2,K})e^{i\alpha_K t_K}+$$
$$\frac{1}{2}(\sin\Phi_{-0,K}-\sin\Phi_{+2,K})e^{i\frac{\pi}{2}}e^{-i\alpha_K t_K}\Big)\otimes$$
$$\Big(\frac{1}{2}(\cos\Phi_{-0,K-1}+\cos\Phi_{+2,K-1})e^{i\alpha_{K-1} t_{K-1}}-$$
$$\frac{1}{2}(\sin\Phi_{-0,K-1}-\sin\Phi_{+2,K-1})e^{i\frac{\pi}{2}}e^{i\alpha_{K-1} t_{K-1}}+$$
$$\frac{1}{2}(\cos\Phi_{-0,K-1}-\cos\Phi_{+2,K-1})e^{-i\alpha_{K-1} t_{K-1}}+$$
$$\frac{1}{2}(\sin\Phi_{-0,K-1}+\sin\Phi_{+2,K-1})e^{i\frac{\pi}{2}}e^{-i\alpha_{K-1} t_{K-1}}\Big)\otimes\dots\otimes$$
$$\Big(\frac{1}{2}(\cos\Phi_{-0,0}+\cos\Phi_{+2,0})e^{i\alpha_0 t_0}-\frac{1}{2}(\sin\Phi_{-0,0}-\sin\Phi_{+2,0})$$
$$e^{i\frac{\pi}{2}}e^{i\alpha_0 t_0}+\frac{1}{2}(\cos\Phi_{-0,0}-\cos\Phi_{+2,0})e^{-i\alpha_0 t_0}+$$
$$\frac{1}{2}(\sin\Phi_{-0,0}+\sin\Phi_{+2,0})e^{i\frac{\pi}{2}}e^{-i\alpha_0 t_0}\Big).$$

Multidimensional FT reveals the peak components as $$\mathrm{Re}(F_C(S_{-0,+2}(t_K,\dots,t_0)))\propto= \qquad(131)$$

$$\Big(\frac{1}{2}(\cos\Phi_{-0,K}+\cos\Phi_{+2,K})(A_K+)-\frac{1}{2}(\sin\Phi_{-0,K}-\sin\Phi_{+2,K})$$

-continued $$(D_K +) + \frac{1}{2}(\cos\Phi_{-0,K} - \cos\Phi_{+2,K})(A_K -) +$$

$$\frac{1}{2}(\sin\Phi_{-0,K} + \sin\Phi_{+2,K})(D_K -)\bigg) \otimes$$

$$\bigg(\frac{1}{2}(\cos\Phi_{-0,K-1} + \cos\Phi_{+2,K-1})(A_{K-1} +) -$$

$$\frac{1}{2}(\sin\Phi_{-0,K-1} - \sin\Phi_{+2,K-1})(D_{K-1} +) +$$

$$\frac{1}{2}(\cos\Phi_{-0,K-1} - \cos\Phi_{+2,K-1})(A_{K-1} -) +$$

$$\frac{1}{2}(\sin\Phi_{-0,K-1} + \sin\Phi_{+2,K-1})(D_{K-1} -)\bigg) \otimes \ldots \otimes$$

$$\bigg(\frac{1}{2}(\cos\Phi_{-0,0} + \cos\Phi_{+2,0})(A_0 +) - \frac{1}{2}(\sin\Phi_{-0,0} - \sin\Phi_{+2,0})(D_0 +) +$$

$$\frac{1}{2}(\cos\Phi_{-0,0} - \cos\Phi_{+2,0})(A_0 -) +$$

$$\frac{1}{2}(\sin\Phi_{-0,0} + \sin\Phi_{+2,0})(D_0 -)\bigg).$$

Multidimensional FT reveals a peak component pattern comparable to the one described for Eq. 117.

($c_{+0}, c_{-2}, c_{-0}, c_{+2}$)-Sampling (DPMS)

Starting with Eq. 32, the complex signal for ($c_{+0}, c_{-2}, c_{-0}, c_{+2}$)-DPMS is proportional to $$S_{+0,+2,-0,-2}(t_K, \ldots, t_0) \propto \tag{132}$$

$$\bigg(\frac{1}{2}(\cos\Phi_{+0,K} + \cos\Phi_{-2,K} + \cos\Phi_{-0,K} + \cos\Phi_{+2,K})e^{i\alpha_K t_K} +$$

$$\frac{1}{2}(\sin\Phi_{+0,K} - \sin\Phi_{-2,K} - \sin\Phi_{-0,K} + \sin\Phi_{+2,K})e^{i\frac{\pi}{2}}e^{i\alpha_K t_K} +$$

$$\frac{1}{2}(\cos\Phi_{+0,K} - \cos\Phi_{-2,K} + \cos\Phi_{-0,K} - \cos\Phi_{+2,K})e^{-i\alpha_K t_K} -$$

$$\frac{1}{2}(\sin\Phi_{+0,K} + \sin\Phi_{-2,K} - \sin\Phi_{-0,K} - \sin\Phi_{+2,K})e^{i\frac{\pi}{2}}e^{-i\alpha_K t_K}\bigg) \otimes$$

$$\bigg(\frac{1}{2}(\cos\Phi_{+0,K-1} + \cos\Phi_{-2,K-1} + \cos\Phi_{-0,K-1} + \cos\Phi_{+2,K-1})$$

$$e^{i\alpha_{K-1} t_{K-1}} +$$

$$\frac{1}{2}(\sin\Phi_{+0,K-1} - \sin\Phi_{-2,K-1} - \sin\Phi_{-0,K-1} + \sin\Phi_{+2,K-1})$$

$$e^{i\frac{\pi}{2}}e^{i\alpha_{K-1} t_{K-1}} + \frac{1}{2}(\cos\Phi_{+0,K-1} - \cos\Phi_{-2,K-1} +$$

$$\cos\Phi_{-0,K-1} - \cos\Phi_{+2,K-1})e^{-i\alpha_{K-1} t_{K-1}} -$$

$$\frac{1}{2}(\sin\Phi_{+0,K-1} + \sin\Phi_{-2,K-1} - \sin\Phi_{-0,K-1} - \sin\Phi_{+2,K-1})$$

$$e^{i\frac{\pi}{2}}e^{-i\alpha_{K-1} t_{K-1}}\bigg) \otimes \ldots \otimes$$

$$\bigg(\frac{1}{2}(\cos\Phi_{+0,0} + \cos\Phi_{-2,0} + \cos\Phi_{-0,0} + \cos\Phi_{+2,0})e^{i\alpha_0 t_0} +$$

$$\frac{1}{2}(\sin\Phi_{+0,0} - \sin\Phi_{-2,0} - \sin\Phi_{-0,0} - \sin\Phi_{+2,0})e^{i\frac{\pi}{2}}e^{i\alpha_0 t_0} +$$

$$\frac{1}{2}(\cos\Phi_{+0,0} - \cos\Phi_{-2,0} + \cos\Phi_{-0,0} - \cos\Phi_{+2,K})e^{-i\alpha_0 t_0} -$$

$$\frac{1}{2}(\sin\Phi_{+0,0} + \sin\Phi_{-2,0} - \sin\Phi_{-0,0} - \sin\Phi_{+2,0})e^{i\frac{\pi}{2}}e^{-i\alpha_0 t_0}\bigg).$$

Multidimensional FT reveals the peak components as $$\text{Re}(F_C(S_{+0,+2,-0,-2}(t_K, \ldots, t_0))) \propto \tag{133}$$

$$\bigg(\frac{1}{2}(\cos\Phi_{+0,K} + \cos\Phi_{-2,K} + \cos\Phi_{-0,K} + \cos\Phi_{+2,K})(A_K +) +$$

$$\frac{1}{2}(\sin\Phi_{+0,K} - \sin\Phi_{-2,K} - \sin\Phi_{-0,K} + \sin\Phi_{+2,K})(D_K +) +$$

$$\frac{1}{2}(\cos\Phi_{+0,K} - \cos\Phi_{-2,K} + \cos\Phi_{-0,K} - \cos\Phi_{+2,K})(A_K -) -$$

$$\frac{1}{2}(\sin\Phi_{+0,K} + \sin\Phi_{-2,K} - \sin\Phi_{-0,K} - \sin\Phi_{+2,K})(D_K -)\bigg) \otimes$$

$$\bigg(\frac{1}{2}(\cos\Phi_{+0,K-1} + \cos\Phi_{-2,K-1} + \cos\Phi_{-0,K-1} + \cos\Phi_{+2,K-1})$$

$$(A_{K-1} +) +$$

$$\frac{1}{2}(\sin\Phi_{+0,K-1} - \sin\Phi_{-2,K-1} - \sin\Phi_{-0,K-1} + \sin\Phi_{+2,K-1})$$

$$(D_{K-1} +) + \frac{1}{2}(\cos\Phi_{+0,K-1} - \cos\Phi_{-2,K-1} +$$

$$\cos\Phi_{-0,K-1} - \cos\Phi_{+2,K-1})(A_{K-1} -) -$$

$$\frac{1}{2}(\sin\Phi_{+0,K-1} + \sin\Phi_{-2,K-1} - \sin\Phi_{-0,K-1} - \sin\Phi_{+2,K-1})$$

$$(D_{K-1} -)\bigg) \otimes \ldots \otimes$$

$$\bigg(\frac{1}{2}(\cos\Phi_{+0,0} + \cos\Phi_{-2,0} + \cos\Phi_{-0,0} + \cos\Phi_{+2,0})(A_0 +) +$$

$$\frac{1}{2}(\sin\Phi_{+0,0} - \sin\Phi_{-2,0} - \sin\Phi_{-0,0} + \sin\Phi_{+2,0})(D_0 +) +$$

$$\frac{1}{2}(\cos\Phi_{+0,0} - \cos\Phi_{-2,0} + \cos\Phi_{-0,0} - \cos\Phi_{+2,K})(A_0 -) -$$

$$\frac{1}{2}(\sin\Phi_{+0,0} + \sin\Phi_{-2,0} - \sin\Phi_{-0,0} - \sin\Phi_{+2,0})(D_0 -)\bigg).$$

The peak component pattern is comparable to the one described for Eq. 117.

Extension to G-Matrix FT NMR

The sampling schemes introduced above can be applied to an arbitrary sub-set of K+1 chemical shift evolution periods which are jointly sampled in G-matrix FT (GFT) NMR (Kim et al., *J. Am. Chem. Soc.* 125:1385-1393 (2003); Atreya et al., *Proc. Natl. Acad. Sci. USA* 101:9642-9647 (2004); Xia et al., *J. Biomol. NMR* 29:467-476 (2004); Eletsky et al., *J. Am. Chem. Soc.* 127, 14578-14579 (2005); Yang et al., *J. Am. Chem. Soc.* 127:9085-9099 (2005); Atreya et al., *Methods Enzymol.* 394:78-108 (2005); Liu et al., *Proc. Natl. Acad. Sci. U.S.A.* 102:10487-10492 (2005); Atreya et al., *J. Am. Chem. Soc.* 129:680-692 (2007), which are hereby incorporated by reference in their entirety), where the K+1 chemical shifts $\alpha_0, \alpha_1, \ldots \alpha_K$ are associated with phase shifts $\Phi_{\pm n,0}, \Phi_{\pm n,1}, \ldots)$ $\Phi_{\pm n,K}$ depending on the sampling schemes chosen and measured as linear combinations $\alpha_0 \pm \kappa_1 \alpha_1 \pm \ldots \pm \kappa_K \alpha_K$ edited into $2^K$ sub-spectra. The scaling factors $\kappa_j$ enable one to achieve different maximal evolution times for the different jointly sampled shifts (see below).

The complex signal corresponding to the $2^K$ edited sub-spectra obtained after G matrix transformation can be written as $$T_{+0,+2}(t_K, \ldots, t_0) = G(K)D_{+0,+2}(K)C_{+0,+2}(t_K, \ldots, t_0) \tag{134}$$

where, $$G(K) = \begin{bmatrix} 1 & i \\ 1 & -i \end{bmatrix}_K \otimes \begin{bmatrix} 1 & i \\ 1 & -i \end{bmatrix}_{K-1} \otimes \ldots \otimes \begin{bmatrix} 1 & i \\ 1 & -i \end{bmatrix}_1 \otimes [1 \ i]_0$$

$$= \begin{bmatrix} Q \\ Q^* \end{bmatrix}_K \otimes \begin{bmatrix} Q \\ Q^* \end{bmatrix}_{K-1} \otimes \ldots \otimes \begin{bmatrix} Q \\ Q^* \end{bmatrix}_1 \otimes [Q]_0$$

$$D_{+0,+2}(K) = \begin{bmatrix} 1 & 0 \\ 0 & -1 \end{bmatrix}_K \otimes \begin{bmatrix} 1 & 0 \\ 0 & -1 \end{bmatrix}_{K-1} \otimes \ldots \otimes \begin{bmatrix} 1 & 0 \\ 0 & -1 \end{bmatrix}_1 \otimes \begin{bmatrix} 1 & 0 \\ 0 & -1 \end{bmatrix}_0$$

$$C_{+0,+2}(t_K, \ldots, t_0) = \begin{bmatrix} c_{+0}(t_K) \\ c_{+2}(t_K) \end{bmatrix} \otimes \begin{bmatrix} c_{+0}(t_{K-1}) \\ c_{+2}(t_{K-1}) \end{bmatrix} \otimes \ldots \otimes \begin{bmatrix} c_{+0}(t_1) \\ c_{+2}(t_1) \end{bmatrix} \otimes \begin{bmatrix} c_{+0}(t_0) \\ c_{+2}(t_0) \end{bmatrix}.$$

The time domain signal $S_{+0,+2}(t)$ given in Eq. 3 encodes $+\alpha$:

$$S_{+0,+2}(t) \propto QD_{+0,+2}C_{+0,+2}(t) = [1 \ i] \begin{bmatrix} 1 & 0 \\ 0 & -1 \end{bmatrix} \begin{bmatrix} c_{+0}(t) \\ c_{+2}(t) \end{bmatrix} = \tag{135}$$

$$[1 \ -i] \begin{bmatrix} \cos(+\alpha t + \Phi) \\ -\sin(+\alpha t + \Phi) \end{bmatrix} = \cos\Phi e^{i\alpha t} + \sin\Phi e^{i\frac{\pi}{2}} e^{i\alpha t},$$

The complex conjugate of $S_{+0,+2}(t)$, denoted as $S^*_{+0,+2}(t)$, encodes $-\alpha$:

$$S^*_{+0,+2}(t) \propto Q^* D_{+0,+2} C_{+0,+2}(t) \propto [1 \ -i] \begin{bmatrix} 1 & 0 \\ 0 & -1 \end{bmatrix} \begin{bmatrix} c_{+0}(t) \\ c_{+2}(t) \end{bmatrix} = \tag{136}$$

$$[1 \ i] \begin{bmatrix} \cos(+\alpha t + \Phi) \\ -\sin(+\alpha t + \Phi) \end{bmatrix} = \cos\Phi e^{-i\alpha t} - \sin\Phi e^{i\frac{\pi}{2}} e^{-i\alpha t}.$$

In GFT NMR, t is coupled to the increment of all jointly sampled evolution periods $t_K$ by $$t = t_0 = t_1/\kappa_1 = t_2/\kappa_2 = \ldots = t_j/\kappa_j = \ldots = t_K/\kappa_K \tag{137},$$

that is, $t_1 \ldots t_K$ are scaled with respect $t_0$. Hence, for the $j^{th}$ chemical shift $\alpha_j$, one has that $t = t_j/\kappa_j$.

With Eqs. 134-137, the vector $T_{+0,+2}$ can be written as $$T_{+0,+2}(t) = \begin{bmatrix} S_{+0,+2}(t) \\ S^*_{+0,+2}(t) \end{bmatrix}_K \otimes \begin{bmatrix} S_{+0,+2}(t) \\ S^*_{+0,+2}(t) \end{bmatrix}_{K-1} \otimes \ldots \otimes \begin{bmatrix} S_{+0,+2}(t) \\ S^*_{+0,+2}(t) \end{bmatrix}_1 \otimes \tag{138}$$

$$[S_{+0,+2}(t)]_0 \propto \begin{bmatrix} e^{i\alpha_K t} \\ e^{-i\alpha_K t} \end{bmatrix} \otimes \begin{bmatrix} e^{i\alpha_{K-1} t} \\ e^{-i\alpha_{K-1} t} \end{bmatrix} \otimes \ldots \otimes \begin{bmatrix} e^{i\alpha_1 t} \\ e^{-i\alpha_1 t} \end{bmatrix} \otimes e^{i\alpha_0 t}.$$

A specific element of $T_{+0,+2}(t)$, denoted here as $T_{+0,+2}(t,M)$, represents a sub-spectrum in which a particular linear combination of the jointly sampled chemical shifts is measured, that is, one linear combination out of the set $\{\alpha_0 \pm \kappa_1 \alpha_1 \pm \ldots \pm \kappa_K \alpha_K\}$ is selected. This particular linear combination can be identified with a sign vector $M = [M_K M_{K-1} \ldots M_0]$, where $M_j = 1$ for $+\alpha_j$ or $M_j = -1$ for $-\alpha_j$, so that $$T_{+0,+2}(t, M) \propto e^{iM_K \alpha_K t} \otimes e^{iM_{K-1} \alpha_{K-1} t} \otimes \ldots \otimes e^{iM_0 \alpha_0 t} = \bigotimes_{j=0}^{K} e^{iM_j \alpha_j t}. \tag{139}$$

Given M, $S_{+0,\pm 2}(t)$ defined in Eq. 135 and encoding $+\alpha_j$, and $S^*_{+0,+2}(t)$ defined in Eq. 136 and encoding $-\alpha_j$, results in $$T_{+0,+2}(t, M) \propto \bigotimes_{j=0}^{K} \left( \cos\Phi_j e^{iM_j \alpha_j t} + M_j \sin\Phi_j e^{i\frac{\pi}{2}} e^{iM_j \alpha_j t} \right). \tag{140}$$

For $(c_p, c_q)$-sampling, the time domain signal for the sub-spectrum, $T_{p,q}(t, M)$, can be obtained using the respective complex time domain signal $S_{p,q}(t)$ given in the section above and the corresponding conjugate $S^*_{p,q}(t)$.

In the following, the generalization of mirrored sampling (MS) in GFT projection NMR is derived in two steps. First, for $\pi/4$ and $3\pi/4$-shifted mirrored sampling of two jointly sampled chemical shifts (K=1) and second for arbitrary K for all sampling schemes.

Two Jointly Sampled Chemical Shifts (K=1)

For two jointly sampled chemical shifts, one has two edited sub-spectra, corresponding to M=[1 1], where the sum of the chemical shifts is recorded, and to M=[−1 1], where the difference of the chemical shifts is recorded. The following derivations consider only the sub-spectrum M=[1 1]. The derivations for the other sub-spectrum are analogous.

$(c_{+1}, c_{-1})$-Sampling (PMS)

With $S_{+1,-1}(t)$ of Eq. 14 the complex conjugate is proportional to $$S^*_{+1,-2}(t) \propto [1 \ -i] D_{+1,-1} C_{+1,-1}(t) = \tag{141}$$

$$\frac{1}{\sqrt{2}} [1 \ -i] \begin{bmatrix} 1 & 1 \\ -1 & 1 \end{bmatrix} \begin{bmatrix} c_{+1}(t) \\ c_{-1}(t) \end{bmatrix} =$$

$$\frac{1}{\sqrt{2}} [1+i \ 1-i] \begin{bmatrix} \cos(+\alpha t + \frac{\pi}{4} + \Phi_{+1}) \\ \cos(-\alpha t + \frac{\pi}{4} + \Phi_{-1}) \end{bmatrix} =$$

$$\frac{1}{\sqrt{2}} \left( \left( \cos(\frac{\pi}{4} + \Phi_{+1}) + \cos(\frac{\pi}{4} + \Phi_{-1}) \right) + \right.$$

$$i \left( \cos(\frac{\pi}{4} + \Phi_{+1}) - \cos(\frac{\pi}{4} + \Phi_{-1}) \right) \cos(\alpha t) -$$

$$\frac{1}{\sqrt{2}} \left( \left( \sin(\frac{\pi}{4} + \Phi_{+1}) - \sin(\frac{\pi}{4} + \Phi_{-1}) \right) + \right.$$

$$i \left( \sin(\frac{\pi}{4} + \Phi_{+1}) + \sin(\frac{\pi}{4} + \Phi_{-1}) \right) \sin(\alpha t) =$$

$$\frac{1}{\sqrt{2}} \left( \left( \cos(\frac{\pi}{4} + \Phi_{+1}) + \cos(\frac{\pi}{4} + \Phi_{-1}) \right) + \right.$$

$$i \left( \cos(\frac{\pi}{4} + \Phi_{+1}) - \cos(\frac{\pi}{4} + \Phi_{-1}) \right) \frac{e^{i\alpha t} + e^{-i\alpha t}}{2} -$$

$$\frac{1}{\sqrt{2}} \left( \left( \sin(\frac{\pi}{4} + \Phi_{+1}) - \sin(\frac{\pi}{4} + \Phi_{-1}) \right) + \right.$$

$$i \left( \sin(\frac{\pi}{4} + \Phi_{+1}) + \sin(\frac{\pi}{4} + \Phi_{-1}) \right) \frac{e^{i\alpha t} - e^{-i\alpha t}}{2i} =$$

$$\frac{1}{4}(\cos\Phi_{+1} - \sin\Phi_{+1} + \cos\Phi_{-1} - \sin\Phi_{-1} - \cos\Phi_{+1} -$$

$$\sin\Phi_{+1} - \cos\Phi_{-1} - \sin\Phi_{-1})e^{i\alpha t} +$$

$$\frac{1}{4}(\cos\Phi_{+1} - \sin\Phi_{+1} + \cos\Phi_{-1} - \sin\Phi_{-1} +$$

$$\cos\Phi_{+1} + \sin\Phi_{+1} + \cos\Phi_{-1} + \sin\Phi_{-1})e^{-i\alpha t} +$$

$$\frac{i}{4}(\cos\Phi_{+1} - \sin\Phi_{+1} - \cos\Phi_{-1} + \sin\Phi_{-1} +$$

$$\cos\Phi_{+1} + \sin\Phi_{+1} - \cos\Phi_{-1} - \sin\Phi_{-1})e^{i\alpha t} +$$

$$\frac{i}{4}(\cos\Phi_{+1} - \sin\Phi_{+1} - \cos\Phi_{-1} + \sin\Phi_{-1} -$$

$$\cos\Phi_{+1} - \sin\Phi_{+1} + \cos\Phi_{-1} + \sin\Phi_{-1})e^{-i\alpha t} =$$

$$\frac{1}{2}(\cos\Phi_{+1} + \cos\Phi_{-1})e^{-i\alpha t} - \frac{1}{2}(\sin\Phi_{+1} - \sin\Phi_{-1})$$

$$e^{i\pi/2}e^{-i\alpha t} - \frac{1}{2}(\sin\Phi_{+1} + \sin\Phi_{-1})e^{i\alpha t} +$$

$$\frac{1}{2}(\cos\Phi_{+1} - \cos\Phi_{-1})e^{i\pi/2}e^{i\alpha t}$$

Combining $S_{-1,-1}(t)$ of Eq. 14 and $S^*_{+1,-1}(t)$ of Eq. 141 one obtains $$T_{+1,-1}(t, M) \propto \tag{142}$$

$$\bigotimes_{j=0}^{K} \left( \frac{1}{2}(\cos\Phi_{+1,j} + \cos\Phi_{-1,j})e^{iM_j\alpha_j t} + \frac{M_j}{2}(\sin\Phi_{+1,j} - \sin\Phi_{-1,j}) \right.$$

$$e^{i\pi/2}e^{iM_j\alpha_j t} - \frac{1}{2}(\sin\Phi_{+1,j} + \sin\Phi_{-1,j})e^{-iM_j\alpha_j t} -$$

$$\left. \frac{M_j}{2}(\cos\Phi_{+1,j} - \cos\Phi_{-1,j})e^{i\pi/2}e^{iM_j\alpha_j t} \right).$$

With Eq. 142, the complex time domain signal for the edited sub spectrum represented by M=[1 1], is proportional to $$T_{+1,-1}(t, M) \propto \tag{143}$$

$$\left( \frac{1}{2}(\cos\Phi_{+1,1} + \cos\Phi_{-1,1})e^{i\alpha_1 t} + \frac{1}{2}(\sin\Phi_{+1,1} - \sin\Phi_{-1,1})e^{i\pi/2}e^{i\alpha_1 t} - \right.$$

$$\frac{1}{2}(\sin\Phi_{+1,1} + \sin\Phi_{-1,1})e^{-i\alpha_1 t} -$$

$$\left. \frac{1}{2}(\cos\Phi_{+1,1} - \cos\Phi_{-1,1})e^{i\pi/2}e^{-i\alpha_1 t} \right) \otimes$$

$$\left( \frac{1}{2}(\cos\Phi_{+1,0} + \cos\Phi_{-1,0})e^{i\alpha_0 t} + \frac{1}{2}(\sin\Phi_{+1,0} - \sin\Phi_{-1,0})e^{i\pi/2}e^{i\alpha_0 t} - \right.$$

$$\frac{1}{2}(\sin\Phi_{+1,0} + \sin\Phi_{-1,0})e^{-i\alpha_0 t} -$$

$$\left. \frac{1}{2}(\cos\Phi_{+1,0} - \cos\Phi_{-1,0})e^{i\pi/2}e^{-i\alpha_0 t} \right),$$

which is equivalent to $$T_{+1,-1}(t, M) \propto \tag{144}$$

$$\frac{1}{4}(\cos\Phi_{+1,1}\cos\Phi_{+1,0} + \cos\Phi_{+1,1}\cos\Phi_{-1,0} + \cos\Phi_{-1,1}\cos\Phi_{+1,0} +$$

$$\cos\Phi_{-1,1}\cos\Phi_{-1,0})e^{i(\alpha_1+\alpha_0)t} +$$

$$\frac{1}{4}(\cos\Phi_{+1,1}\sin\Phi_{+1,0} - \cos\Phi_{+1,1}\sin\Phi_{-1,0} + \cos\Phi_{-1,1}\sin\Phi_{+1,0} -$$

$$\cos\Phi_{-1,1}\sin\Phi_{-1,0})e^{i\pi/2}e^{i(\alpha_1+\alpha_0)t} -$$

$$\frac{1}{4}(\cos\Phi_{+1,1}\sin\Phi_{+1,0} + \cos\Phi_{+1,1}\sin\Phi_{-1,0} + \cos\Phi_{-1,1}\sin\Phi_{+1,0} +$$

$$\cos\Phi_{-1,1}\sin\Phi_{-1,0})e^{i(\alpha_1-\alpha_0)t} -$$

$$\frac{1}{4}(\cos\Phi_{+1,1}\cos\Phi_{+1,0} - \cos\Phi_{+1,1}\cos\Phi_{-1,0} + \cos\Phi_{-1,1}\cos\Phi_{+1,0} -$$

$$\cos\Phi_{-1,1}\cos\Phi_{-1,0})e^{i\pi/2}e^{i(\alpha_1-\alpha_0)t} +$$

$$\frac{1}{4}(\sin\Phi_{+1,1}\cos\Phi_{+1,0} + \sin\Phi_{+1,1}\cos\Phi_{-1,0} - \sin\Phi_{-1,1}\cos\Phi_{+1,0} -$$

$$\sin\Phi_{-1,1}\cos\Phi_{-1,0})e^{i\pi/2}e^{i(\alpha_1+\alpha_0)t} +$$

$$\frac{1}{4}(\sin\Phi_{+1,1}\sin\Phi_{+1,0} - \sin\Phi_{+1,1}\sin\Phi_{-1,0} - \sin\Phi_{-1,1}\sin\Phi_{+1,0} +$$

$$\sin\Phi_{-1,1}\sin\Phi_{-1,0})e^{i\pi}e^{i(\alpha_1+\alpha_0)t} -$$

$$\frac{1}{4}(\sin\Phi_{+1,1}\sin\Phi_{+1,0} + \sin\Phi_{+1,1}\sin\Phi_{-1,0} - \sin\Phi_{-1,1}\sin\Phi_{+1,0} -$$

$$\sin\Phi_{-1,1}\sin\Phi_{-1,0})e^{i\pi/2}e^{i(\alpha_1-\alpha_0)t} -$$

$$\frac{1}{4}(\sin\Phi_{+1,1}\cos\Phi_{+1,0} - \sin\Phi_{+1,1}\cos\Phi_{-1,0} - \sin\Phi_{-1,1}\cos\Phi_{+1,0} +$$

$$\sin\Phi_{-1,1}\cos\Phi_{-1,0})e^{i\pi}e^{i(\alpha_1-\alpha_0)t} -$$

$$\frac{1}{4}(\sin\Phi_{+1,1}\cos\Phi_{+1,0} + \sin\Phi_{+1,1}\cos\Phi_{-1,0} + \sin\Phi_{-1,1}\cos\Phi_{+1,0} +$$

$$\sin\Phi_{-1,1}\cos\Phi_{-1,0})e^{i(-\alpha_1+\alpha_0)t} -$$

$$\frac{1}{4}(\sin\Phi_{+1,1}\sin\Phi_{+1,0} - \sin\Phi_{+1,1}\sin\Phi_{-1,0} + \sin\Phi_{-1,1}\sin\Phi_{+1,0} -$$

$$\sin\Phi_{-1,1}\sin\Phi_{-1,0})e^{i\pi/2}e^{i(-\alpha_1+\alpha_0)t} +$$

$$\frac{1}{4}(\sin\Phi_{+1,1}\sin\Phi_{+1,0} + \sin\Phi_{+1,1}\sin\Phi_{-1,0} + \sin\Phi_{-1,1}\sin\Phi_{+1,0} +$$

$$\sin\Phi_{-1,1}\sin\Phi_{-1,0})e^{-i(\alpha_1+\alpha_0)t} +$$

$$\frac{1}{4}(\sin\Phi_{+1,1}\cos\Phi_{+1,0} - \sin\Phi_{+1,1}\cos\Phi_{-1,0} + \sin\Phi_{-1,1}\cos\Phi_{+1,0} -$$

$$\sin\Phi_{-1,1}\cos\Phi_{-1,0})e^{i\pi/2}e^{-i(\alpha_1+\alpha_0)t} -$$

$$\frac{1}{4}(\cos\Phi_{+1,1}\cos\Phi_{+1,0} + \cos\Phi_{+1,1}\cos\Phi_{-1,0} - \cos\Phi_{-1,1}\cos\Phi_{+1,0} -$$

$$\cos\Phi_{-1,1}\cos\Phi_{-1,0})e^{i(-\alpha_1+\alpha_0)t} -$$

$$\frac{1}{4}(\cos\Phi_{+1,1}\sin\Phi_{+1,0} - \cos\Phi_{+1,1}\sin\Phi_{-1,0} - \cos\Phi_{-1,1}\sin\Phi_{+1,0} +$$

$$\cos\Phi_{-1,1}\sin\Phi_{-1,0})e^{i\pi}e^{i(-\alpha_1+\alpha_0)t} +$$

$$\frac{1}{4}(\cos\Phi_{+1,1}\sin\Phi_{+1,0} + \cos\Phi_{+1,1}\sin\Phi_{-1,0} - \cos\Phi_{-1,1}\sin\Phi_{+1,0} -$$

$$\cos\Phi_{-1,1}\sin\Phi_{-1,0})e^{i\pi/2}e^{-i(\alpha_1+\alpha_0)t} +$$

$$\frac{1}{4}(\cos\Phi_{+1,1}\cos\Phi_{+1,0} - \cos\Phi_{+1,1}\cos\Phi_{-1,0} - \cos\Phi_{-1,1}\cos\Phi_{+1,0} +$$

$$\cos\Phi_{-1,1}\cos\Phi_{-1,0})e^{i\pi}e^{-i(\alpha_1+\alpha_0)t}.$$

FT along the GFT dimension reveals mixed phase peaks at (i) the desired position $(\alpha_1+\alpha_0)$, (ii) the quad position $-(\alpha_1+\alpha_0)$ of the desired peak, (iii) the 'cross-talk' position $(-\alpha_1+\alpha_0)$ and the quad position $(\alpha_1-\alpha_0)$ of the cross-talk peak. The 'cross talk' between GFT NMR sub-spectra results in peaks that are located at linear combinations of chemical shifts other than the desired one. Under the condition of identical secondary phase shifts for forward and backward samplings (Eq. 35), Eq. 144 simplifies to $$T_{+1,-1}(t,M) \propto (\cos\Phi_{1,1}\cos\Phi_{1,0})e^{i(\alpha_1+\alpha_0)t} - (\cos\Phi_{1,1}\sin\Phi_{1,0})e^{i(\alpha_1-\alpha_0)t} - (\sin\Phi_{1,1}\cos\Phi_{1,0})e^{i(-\alpha_1+\alpha_0)t} - (\sin\Phi_{1,1}\cos\Phi_{1,0})e^{i(-\alpha_1+\alpha_0)t} + (\sin\Phi_{1,1}\sin\Phi_{1,0})e^{-i(\alpha_1+\alpha_0)t} \tag{145}$$

FT along the GFT dimension reveals absorptive peaks at (i) the desired position $-(\alpha_1+\alpha_0)$, (ii) the quad position $-(\alpha_1+\alpha_0)$ of the desired peak, (iii) the cross-talk position $(-\alpha_1+\alpha_0)$ and the quad position $(\alpha_1-\alpha_0)$ of the cross-talk peak. Under the condition of secondary phase shifts independent of n (Eq. 54), the peak components of Eq. 144 does not change. Under the condition of identical secondary phase shifts (Eq. 73), Eq. 144 simplifies to $$T_{+1,-1}(t,M) \propto \cos\Phi_1 \cos\Phi_0 e^{i(\alpha_1+\alpha_0)t} - (\cos\Phi_1 \sin\Phi_0)e^{i(\alpha_1-\alpha_0)t} - (\sin\Phi_1 \cos\Phi_0)e^{i(-\alpha_1+\alpha_0)t} + (\sin\Phi_1 \cos\Phi_0)e^{i(-\alpha_1+\alpha_0)t} + (\sin\Phi_1 \sin\Phi_0)e^{-i(\alpha_1+\alpha_0)t} \quad (146).$$

$(c_{+3},c_{-3})$-Sampling (PMS)

With $S_{+3,-3}(t)$ of Eq. 18 the complex conjugate is proportional to $$S^*_{+3,-3}(t) \propto [\,1\ \ -i\,]D_{+3,-3}C_{+3,-3}(t) = \qquad (147)$$

$$\frac{1}{\sqrt{2}}[\,1\ \ -i\,]\begin{bmatrix}-1 & -1\\ -1 & 1\end{bmatrix}\begin{bmatrix}c_{+3}(t)\\ c_{-3}(t)\end{bmatrix}=$$

$$\frac{1}{\sqrt{2}}[-1+i\ \ -1-i\,]\begin{bmatrix}-\sin\!\left(+\alpha t+\frac{\pi}{4}+\Phi_{+3}\right)\\ -\sin\!\left(-\alpha t+\frac{\pi}{4}+\Phi_{-3}\right)\end{bmatrix}=$$

$$\frac{1}{\sqrt{2}}\Big(\!\Big(\sin\!\big(\tfrac{\pi}{4}+\Phi_{+3}\big)+\sin\!\big(\tfrac{\pi}{4}+\Phi_{-3}\big)\Big)-$$

$$i\Big(\sin\!\big(\tfrac{\pi}{4}+\Phi_{+3}\big)-\sin\!\big(\tfrac{\pi}{4}+\Phi_{-3}\big)\Big)\!\Big)\cos(\alpha t)+$$

$$\frac{1}{\sqrt{2}}\Big(\!\Big(\cos\!\big(\tfrac{\pi}{4}+\Phi_{+3}\big)-\cos\!\big(\tfrac{\pi}{4}+\Phi_{-3}\big)\Big)-$$

$$i\Big(\cos\!\big(\tfrac{\pi}{4}+\Phi_{+3}\big)+\cos\!\big(\tfrac{\pi}{4}+\Phi_{-3}\big)\Big)\!\Big)\sin(\alpha t)=$$

$$\frac{1}{\sqrt{2}}\Big(\!\Big(\sin\!\big(\tfrac{\pi}{4}+\Phi_{+3}\big)+\sin\!\big(\tfrac{\pi}{4}+\Phi_{-3}\big)\Big)-$$

$$i\Big(\sin\!\big(\tfrac{\pi}{4}+\Phi_{+3}\big)-\sin\!\big(\tfrac{\pi}{4}+\Phi_{-3}\big)\Big)\!\Big)\frac{e^{i\alpha t}+e^{-i\alpha t}}{2}+$$

$$\frac{1}{\sqrt{2}}\Big(\!\Big(\cos\!\big(\tfrac{\pi}{4}+\Phi_{+3}\big)-\cos\!\big(\tfrac{\pi}{4}+\Phi_{-3}\big)\Big)-$$

$$i\Big(\cos\!\big(\tfrac{\pi}{4}+\Phi_{+3}\big)+\cos\!\big(\tfrac{\pi}{4}+\Phi_{-3}\big)\Big)\!\Big)\frac{e^{i\alpha t}-e^{-i\alpha t}}{2i}=$$

$$\frac{1}{4}(\cos\Phi_{+3}+\sin\Phi_{+3}+\cos\Phi_{-3}+\sin\Phi_{-3}+\cos\Phi_{+3}-\sin\Phi_{+3}+\cos\Phi_{-3}-\sin\Phi_{-3})e^{-i\alpha t}+$$

$$\frac{1}{4}(\cos\Phi_{+3}+\sin\Phi_{+3}+\cos\Phi_{-3}+\sin\Phi_{-3}-\cos\Phi_{+3}+\sin\Phi_{+3}-\cos\Phi_{-3}+\sin\Phi_{-3})e^{i\alpha t}+$$

$$\frac{i}{4}(\cos\Phi_{+3}+\sin\Phi_{+3}-\cos\Phi_{-3}-\sin\Phi_{-3}-\cos\Phi_{+3}+\sin\Phi_{+3}+\cos\Phi_{-3}-\sin\Phi_{-3})e^{-i\alpha t}+$$

$$\frac{i}{4}(\cos\Phi_{+3}+\sin\Phi_{+3}-\cos\Phi_{-3}-\sin\Phi_{-3}+\cos\Phi_{+3}-\sin\Phi_{+3}-\cos\Phi_{-3}+\sin\Phi_{-3})e^{i\alpha t}=$$

$$\frac{1}{2}(\cos\Phi_{+3}+\cos\Phi_{-3})e^{-i\alpha t}-\frac{1}{2}(\sin\Phi_{+3}-\sin\Phi_{-3})e^{i\pi/2}e^{-i\alpha t}+\frac{1}{2}(\sin\Phi_{+3}+\sin\Phi_{-3})e^{i\alpha t}-$$

$$\frac{1}{2}(\cos\Phi_{+3}-\cos\Phi_{-3})e^{i\pi/2}e^{i\alpha t}.$$

Combining $S_{+3,-3}(t)$ of Eq. 18 and $S^*_{+3,-3}(t)$ of Eq. 147 one obtains $$T_{+3,-3}(t,M) \propto \qquad (148)$$

$$\bigotimes_{j=0}^{K}\Big(\tfrac{1}{2}(\cos\Phi_{+1,j}+\cos\Phi_{-1,j})e^{iM_j\alpha_j t}+\tfrac{M_j}{2}(\sin\Phi_{+1,j}-\sin\Phi_{-1,j})$$

$$e^{i\pi/2}e^{iM_j\alpha_j t}+\tfrac{1}{2}(\sin\Phi_{+1,j}+\sin\Phi_{-1,j})e^{-iM_j\alpha_j t}+$$

$$\tfrac{M_j}{2}(\cos\Phi_{+1,j}-\cos\Phi_{-1,j})e^{i\pi/2}e^{-iM_j\alpha_j t}\Big).$$

With Eq. 148, the complex time domain signal for the edited sub spectrum represented by M=[1 1], is proportional to $$T_{+3,-3}(t,M) \propto \qquad (149)$$

$$\Big(\tfrac{1}{2}(\cos\Phi_{+1,1}+\cos\Phi_{-1,1})e^{i\alpha_1 t}+\tfrac{1}{2}(\sin\Phi_{+1,1}-\sin\Phi_{-1,1})e^{i\pi/2}e^{i\alpha_1 t}+$$

$$\tfrac{1}{2}(\sin\Phi_{+1,1}+\sin\Phi_{-1,1})e^{-i\alpha_1 t}+$$

$$\tfrac{1}{2}(\cos\Phi_{+1,1}-\cos\Phi_{-1,1})e^{i\pi/2}e^{-i\alpha_1 t}\Big)\otimes$$

$$\Big(\tfrac{1}{2}(\cos\Phi_{+1,0}+\cos\Phi_{-1,0})e^{i\alpha_0 t}+\tfrac{1}{2}(\sin\Phi_{+1,0}-\sin\Phi_{-1,0})e^{i\pi/2}e^{i\alpha_0 t}+$$

$$\tfrac{1}{2}(\sin\Phi_{+1,0}+\sin\Phi_{-1,0})e^{-i\alpha_0 t}+$$

$$\tfrac{1}{2}(\cos\Phi_{+1,0}-\cos\Phi_{-1,0})e^{i\pi/2}e^{-i\alpha_0 t}\Big),$$

which is equivalent to $$T_{+3,-3}(t,M) \propto \qquad (150)$$

$$\tfrac{1}{4}(\cos\Phi_{+3,1}\cos\Phi_{+3,0}+\cos\Phi_{+3,1}\cos\Phi_{-3,0}+\cos\Phi_{-3,1}\cos\Phi_{+3,0}+$$

$$\cos\Phi_{-3,1}\cos\Phi_{-3,0})e^{i(\alpha_1+\alpha_0)t}+$$

$$\tfrac{1}{4}(\cos\Phi_{+3,1}\sin\Phi_{+3,0}-\cos\Phi_{+3,1}\sin\Phi_{-3,0}+\cos\Phi_{-3,1}\sin\Phi_{+3,0}-$$

$$\cos\Phi_{-3,1}\sin\Phi_{-3,0})e^{i\pi/2}e^{i(\alpha_1+\alpha_0)t}+$$

$$\tfrac{1}{4}(\cos\Phi_{+3,1}\sin\Phi_{+3,0}+\cos\Phi_{+3,1}\sin\Phi_{-3,0}+\cos\Phi_{-3,1}\sin\Phi_{+3,0}+$$

$$\cos\Phi_{-3,1}\sin\Phi_{-3,0})e^{i(\alpha_1-\alpha_0)t}+$$

$$\tfrac{1}{4}(\cos\Phi_{+3,1}\cos\Phi_{+3,0}-\cos\Phi_{+3,1}\cos\Phi_{-3,0}+\cos\Phi_{-3,1}\cos\Phi_{+3,0}-$$

$$\cos\Phi_{-3,1}\cos\Phi_{-3,0})e^{i\pi/2}e^{i(\alpha_1-\alpha_0)t}+$$

$$\tfrac{1}{4}(\sin\Phi_{+3,1}\cos\Phi_{+3,0}+\sin\Phi_{+3,1}\cos\Phi_{-3,0}-\sin\Phi_{-3,1}\cos\Phi_{+3,0}-$$

$$\sin\Phi_{-3,1}\cos\Phi_{-3,0})e^{i\pi/2}e^{i(\alpha_1+\alpha_0)t}+$$

$$\tfrac{1}{4}(\sin\Phi_{+3,1}\sin\Phi_{+3,0}-\sin\Phi_{+3,1}\sin\Phi_{-3,0}-\sin\Phi_{-3,1}\sin\Phi_{+3,0}+$$

$$\sin\Phi_{-3,1}\sin\Phi_{-3,0})e^{i\pi}e^{i(\alpha_1+\alpha_0)t}+$$

$$\tfrac{1}{4}(\sin\Phi_{+3,1}\sin\Phi_{+3,0}+\sin\Phi_{+3,1}\sin\Phi_{-3,0}-\sin\Phi_{-3,1}\sin\Phi_{+3,0}-$$

$$\sin\Phi_{-3,1}\sin\Phi_{-3,0})e^{i\pi/2}e^{i(\alpha_1-\alpha_0)t}+$$

$$\tfrac{1}{4}(\sin\Phi_{+3,1}\cos\Phi_{+3,0}-\sin\Phi_{+3,1}\cos\Phi_{-3,0}-\sin\Phi_{-3,1}\cos\Phi_{+3,0}+$$

$$\sin\Phi_{-3,1}\cos\Phi_{-3,0})e^{i\pi}e^{i(\alpha_1-\alpha_0)t}+$$

$$\tfrac{1}{4}(\sin\Phi_{+3,1}\cos\Phi_{+3,0}+\sin\Phi_{+3,1}\cos\Phi_{-3,0}+\sin\Phi_{-3,1}\cos\Phi_{+3,0}+$$

$$\sin\Phi_{-3,1}\cos\Phi_{-3,0})e^{i(-\alpha_1+\alpha_0)t}+$$

-continued $$\frac{1}{4}(\sin\Phi_{+3,1}\sin\Phi_{+3,0} - \sin\Phi_{+3,1}\sin\Phi_{-3,0} + \sin\Phi_{-3,1}\sin\Phi_{+3,0} - \sin\Phi_{-3,1}\sin\Phi_{-3,0})e^{i\pi/2}e^{i(-\alpha_1+\alpha_0)t} +$$

$$\frac{1}{4}(\sin\Phi_{+3,1}\sin\Phi_{+3,0} + \sin\Phi_{+3,1}\sin\Phi_{-3,0} + \sin\Phi_{-3,1}\sin\Phi_{+3,0} + \sin\Phi_{-3,1}\sin\Phi_{-3,0})e^{-i(\alpha_1+\alpha_0)t} +$$

$$\frac{1}{4}(\sin\Phi_{+3,1}\cos\Phi_{+3,0} - \sin\Phi_{+3,1}\cos\Phi_{-3,0} + \sin\Phi_{-3,1}\cos\Phi_{+3,0} - \sin\Phi_{-3,1}\cos\Phi_{-3,0})e^{i\pi/2}e^{-i(\alpha_1+\alpha_0)t} +$$

$$\frac{1}{4}(\cos\Phi_{+3,1}\cos\Phi_{+3,0} + \cos\Phi_{+3,1}\cos\Phi_{-3,0} - \cos\Phi_{-3,1}\cos\Phi_{+3,0} - \cos\Phi_{-3,1}\cos\Phi_{-3,0})e^{i\pi/2}e^{i(-\alpha_1+\alpha_0)t} +$$

$$\frac{1}{4}(\cos\Phi_{+3,1}\sin\Phi_{+3,0} - \cos\Phi_{+3,1}\sin\Phi_{-3,0} - \cos\Phi_{-3,1}\sin\Phi_{+3,0} + \cos\Phi_{-3,1}\sin\Phi_{-3,0})e^{i\pi}e^{i(-\alpha_1+\alpha_0)t} +$$

$$\frac{1}{4}(\cos\Phi_{+3,1}\sin\Phi_{+3,0} + \cos\Phi_{+3,1}\sin\Phi_{-3,0} - \cos\Phi_{-3,1}\sin\Phi_{+3,0} - \cos\Phi_{-3,1}\sin\Phi_{-3,0})e^{i\pi/2}e^{-i(\alpha_1+\alpha_0)t} +$$

$$\frac{1}{4}(\cos\Phi_{+3,1}\cos\Phi_{+3,0} - \cos\Phi_{+3,1}\cos\Phi_{-3,0} - \cos\Phi_{-3,1}\cos\Phi_{+3,0} + \cos\Phi_{-3,1}\cos\Phi_{-3,0})e^{i\pi}e^{-i(\alpha_1+\alpha_0)t}.$$

FT along the GFT dimension reveals the same peak components as $T_{+1,-1}(t,M)$. Under the condition of identical secondary phase shifts for forward and backward samplings (Eq. 35), Eq.150 simplifies to $$T_{+3,-3}(t,M) \propto (\cos\Phi_{3,1}\cos\Phi_{3,0})e^{i(\alpha_1+\alpha_0)t} + (\cos\Phi_{3,1}\sin\Phi_{3,0})e^{i(\alpha_1-\alpha_0)t} + (\sin\Phi_{3,1}\cos\Phi_{3,0})e^{i(-\alpha_1+\alpha_0)t} + (\sin\Phi_{3,1}\cos\Phi_{3,0})e^{-i(\alpha_1+\alpha_0)t} \quad (151).$$

and under the condition of identical secondary phase shifts (Eq. 35), Eq. 150 simplifies to $$T_{+3,-3}(t,M) \propto \cos\Phi_1\cos\Phi_0 e^{i(\alpha_1+\alpha_0)t} + (\cos\Phi_1\sin\Phi_0)e^{i(\alpha_1-\alpha_0)t} + (\sin\Phi_1\cos\Phi_0)e^{i(-\alpha_1+\alpha_0)t} + (\sin\Phi_1\cos\Phi_0)e^{-i(\alpha_1+\alpha_0)t} \quad (152).$$

$(c_{+1},c_{-1},c_{+3},c_{-3})$-sampling (DPMS)

Starting with Eq. 21, the complex signal for two indirect dimensions is proportional to $$S_{+1,-1,+3,-3}(t_1,t_0) = [S_{+1,-1}(t_1) + S_{+3,-3}(t_1)] \otimes [S_{+1,-1}(t_0) + S_{+3,-3}(t_0)] \propto S_{+1,-1}(t_1)S_{+1,-1}(t_0) + S_{+1,-1}(t_1)S_{+3,-3}(t_0) + S_{+3,-3}(t_1)S_{+1,-1}(t_0) + S_{+3,-3}(t_1)S_{+3,-3}(t_0) \quad (153).$$

DPMS for two jointly sampled chemical shifts requires all combinations of $\pi/4$ and $\pi/4$-shifted mirrored sampling of the two chemical shifts. The first and the last term in Eq. 153 are represented, respectively, by Eqs. 144 and 150. It is then straightforward to show that the signals of the spectrum corresponding to the second term in Eq. 153 where $\alpha_0$ is sampled as $(C_{+3},c_{-3})$ and $\alpha_1$ as $(c_{+1},c_{-1})$, is proportional to $$T_{+1,-1}(t,M) \otimes T_{+3,-3}(t,M) \propto \quad (154)$$

$$\frac{1}{4}(\cos\Phi_{+1,1}\cos\Phi_{+3,0} + \cos\Phi_{+1,1}\cos\Phi_{-3,0} + \cos\Phi_{-1,1}\cos\Phi_{+3,0} + \cos\Phi_{-1,1}\cos\Phi_{-3,0})e^{i(\alpha_1+\alpha_0)t} +$$

$$\frac{1}{4}(\cos\Phi_{+1,1}\sin\Phi_{+3,0} - \cos\Phi_{+1,1}\sin\Phi_{-3,0} + \cos\Phi_{-1,1}\sin\Phi_{+3,0} - \cos\Phi_{-1,1}\sin\Phi_{-3,0})e^{i\pi/2}e^{i(\alpha_1+\alpha_0)t} +$$

$$\frac{1}{4}(\cos\Phi_{+1,1}\sin\Phi_{+3,0} + \cos\Phi_{+1,1}\sin\Phi_{-3,0} + \cos\Phi_{-1,1}\sin\Phi_{+3,0} + \cos\Phi_{-1,1}\sin\Phi_{-3,0})e^{i(\alpha_1-\alpha_0)t} +$$

$$\frac{1}{4}(\cos\Phi_{+1,1}\cos\Phi_{+3,0} - \cos\Phi_{+1,1}\cos\Phi_{-3,0} + \cos\Phi_{-1,1}\cos\Phi_{+3,0} - \cos\Phi_{-1,1}\cos\Phi_{-3,0})e^{i\pi/2}e^{i(\alpha_1-\alpha_0)t} +$$

$$\frac{1}{4}(\sin\Phi_{+1,1}\cos\Phi_{+3,0} + \sin\Phi_{+1,1}\cos\Phi_{-3,0} - \sin\Phi_{-1,1}\cos\Phi_{+3,0} - \sin s\Phi_{-1,1}\cos\Phi_{-3,0})e^{i\pi/2}e^{i(\alpha_1+\alpha_0)t} +$$

$$\frac{1}{4}(\sin\Phi_{+1,1}\sin\Phi_{+3,0} - \sin\Phi_{+1,1}\sin\Phi_{-3,0} - \sin\Phi_{-1,1}\sin\Phi_{+3,0} + \sin\Phi_{-1,1}\sin\Phi_{-3,0})e^{i\pi}e^{i(\alpha_1+\alpha_0)t} +$$

$$\frac{1}{4}(\sin\Phi_{+1,1}\sin\Phi_{+3,0} + \sin\Phi_{+1,1}\sin\Phi_{-3,0} - \sin\Phi_{-1,1}\sin\Phi_{+3,0} - \sin\Phi_{-1,1}\sin\Phi_{-3,0})e^{i\pi/2}e^{i(\alpha_1-\alpha_0)t} +$$

$$\frac{1}{4}(\sin\Phi_{+1,1}\cos\Phi_{+3,0} - \sin\Phi_{+1,1}\cos\Phi_{-3,0} - \sin\Phi_{-1,1}\cos\Phi_{+3,0} + \sin\Phi_{-1,1}\cos\Phi_{-3,0})e^{i\pi}e^{i(\alpha_1-\alpha_0)t} -$$

$$\frac{1}{4}(\sin\Phi_{+1,1}\cos\Phi_{+3,0} + \sin\Phi_{+1,1}\cos\Phi_{-3,0} + \sin\Phi_{-1,1}\cos\Phi_{+3,0} + \sin s\Phi_{-1,1}\cos\Phi_{-3,0})e^{i(-\alpha_1+\alpha_0)t} -$$

$$\frac{1}{4}(\sin\Phi_{+1,1}\sin\Phi_{+3,0} - \sin\Phi_{+1,1}\sin\Phi_{-3,0} + \sin\Phi_{-1,1}\sin\Phi_{+3,0} - \sin\Phi_{-1,1}\sin\Phi_{-3,0})e^{i\pi/2}e^{i(-\alpha_1+\alpha_0)t} -$$

$$\frac{1}{4}(\sin\Phi_{+1,1}\sin\Phi_{+3,0} + \sin\Phi_{+1,1}\sin\Phi_{-3,0} + \sin\Phi_{-1,1}\sin\Phi_{+3,0} + \sin\Phi_{-1,1}\sin\Phi_{-3,0})e^{-i(\alpha_1+\alpha_0)t} -$$

$$\frac{1}{4}(\sin\Phi_{+1,1}\cos\Phi_{+3,0} - \sin\Phi_{+1,1}\cos\Phi_{-3,0} + \sin\Phi_{-1,1}\cos\Phi_{+3,0} - \sin\Phi_{-1,1}\cos\Phi_{-3,0})e^{i\pi/2}e^{-i(\alpha_1+\alpha_0)t} -$$

$$\frac{1}{4}(\cos\Phi_{+1,1}\cos\Phi_{+3,0} + \cos\Phi_{+1,1}\cos\Phi_{-3,0} - \cos\Phi_{-1,1}\cos\Phi_{+3,0} - \cos\Phi_{-1,1}\cos\Phi_{-3,0})e^{i\pi/2}e^{i(-\alpha_1+\alpha_0)t} -$$

$$\frac{1}{4}(\cos\Phi_{+1,1}\sin\Phi_{+3,0} - \cos\Phi_{+1,1}\sin\Phi_{-3,0} - \cos\Phi_{-1,1}\sin\Phi_{+3,0} + \cos\Phi_{-1,1}\sin\Phi_{-3,0})e^{i\pi}e^{i(-\alpha_1+\alpha_0)t} -$$

$$\frac{1}{4}(\cos\Phi_{+1,1}\sin\Phi_{+3,0} + \cos\Phi_{+1,1}\sin\Phi_{-3,0} - \cos\Phi_{-1,1}\sin\Phi_{+3,0} - \cos\Phi_{-1,1}\sin\Phi_{-3,0})e^{i\pi/2}e^{-i(\alpha_1+\alpha_0)t} -$$

$$\frac{1}{4}(\cos\Phi_{+1,1}\cos\Phi_{+3,0} - \cos\Phi_{+1,1}\cos\Phi_{-3,0} - \cos\Phi_{-1,1}\cos\Phi_{+3,0} + \cos\Phi_{-1,1}\cos\Phi_{-3,0})e^{i\pi}e^{-i(\alpha_1+\alpha_0)t}.$$

Under the condition of identical secondary phase shifts for forward and backward samplings (Eq. 35), Eq.154 simplifies to $$T_{+1,-1}(t,M) \otimes T_{+3,-3}(t,M) \propto (\cos\Phi_{1,1}\cos\Phi_{3,0})e^{i(\alpha_1+\alpha_0)t} + (\cos\Phi_{1,1}\sin\Phi_{3,0})e^{i(\alpha_1-\alpha_0)t} - (\sin\Phi_{1,1}\cos\Phi_{3,0})e^{i(-\alpha_1+\alpha_0)t} - (\sin\Phi_{1,1}\cos\Phi_{3,0})e^{-i(\alpha_1+\alpha_0)t} \quad (155).$$

Under the condition of secondary phase shifts independent of n (Eq. 54), the peak components of Eq. 154 remain unchanged. Under the condition of identical secondary phase shifts (Eq. 73), Eq. 154 simplifies to $$T_{+1,-1}(t,M) \otimes T_{+3,-3}(t,M) \propto \cos^2\Phi e^{i(\alpha_1+\alpha_0)t} + (\cos\Phi\sin\Phi)e^{i(\alpha_1-\alpha_0)t} - (\sin\Phi\cos\Phi)e^{i(-\alpha_1+\alpha_0)t} - (\sin^2\Phi)e^{-i(\alpha_1+\alpha_0)t} \quad (156).$$

The signals of the spectrum corresponding to the third term in Eq. 153 is proportional to $$T_{+3,-3}(t,M) \otimes T_{+1,-1}(t,M) \propto \quad (157)$$

$$\frac{1}{4}(\cos\Phi_{+3,1}\cos\Phi_{+1,0} + \cos\Phi_{+3,1}\cos\Phi_{-1,0} +$$
$$\cos\Phi_{-3,1}\cos\Phi_{+1,0} + \cos\Phi_{-3,1}\cos\Phi_{-1,0})e^{i(\alpha_1+\alpha_0)t} +$$

$$\frac{1}{4}(\cos\Phi_{+3,1}\sin\Phi_{+1,0} - \cos\Phi_{+3,1}\sin\Phi_{-1,0} + \cos\Phi_{-3,1}\sin\Phi_{+1,0} -$$
$$\cos\Phi_{-3,1}\sin\Phi_{-1,0})e^{i\pi/2}e^{i(\alpha_1+\alpha_0)t} -$$

$$\frac{1}{4}(\cos\Phi_{+3,1}\sin\Phi_{+1,0} + \cos\Phi_{+3,1}\sin\Phi_{-1,0} + \cos\Phi_{-3,1}\sin\Phi_{+1,0} +$$
$$\cos\Phi_{-3,1}\sin\Phi_{-1,0})e^{i(\alpha_1-\alpha_0)t} -$$

$$\frac{1}{4}(\cos\Phi_{+3,1}\cos\Phi_{+1,0} - \cos\Phi_{+3,1}\cos\Phi_{-1,0} + \cos\Phi_{-3,1}\cos\Phi_{+1,0} -$$
$$\cos\Phi_{-3,1}\cos\Phi_{-1,0})e^{i\pi/2}e^{i(\alpha_1-\alpha_0)t} +$$

$$\frac{1}{4}(\sin\Phi_{+3,1}\cos\Phi_{+1,0} + \sin\Phi_{+3,1}\cos\Phi_{-1,0} - \sin\Phi_{-3,1}\cos\Phi_{+1,0} -$$
$$\sin\Phi_{-3,1}\cos\Phi_{-1,0})e^{i\pi/2}e^{i(\alpha_1+\alpha_0)t} +$$

$$\frac{1}{4}(\sin\Phi_{+3,1}\sin\Phi_{+1,0} - \sin\Phi_{+3,1}\sin\Phi_{-1,0} - \sin\Phi_{-3,1}\sin\Phi_{+1,0} +$$
$$\sin\Phi_{-3,1}\sin\Phi_{-1,0})e^{i\pi}e^{i(\alpha_1+\alpha_0)t} -$$

$$\frac{1}{4}(\sin\Phi_{+3,1}\sin\Phi_{+1,0} + \sin\Phi_{+3,1}\sin\Phi_{-1,0} - \sin\Phi_{-3,1}\sin\Phi_{+1,0} -$$
$$\sin\Phi_{-3,1}\sin\Phi_{-1,0})e^{i\pi/2}e^{i(\alpha_1-\alpha_0)t} -$$

$$\frac{1}{4}(\sin\Phi_{+3,1}\cos\Phi_{+1,0} - \sin\Phi_{+3,1}\cos\Phi_{-1,0} - \sin\Phi_{-3,1}\cos\Phi_{+1,0} +$$
$$\sin\Phi_{-3,1}\cos\Phi_{-1,0})e^{i\pi}e^{i(\alpha_1-\alpha_0)t} +$$

$$\frac{1}{4}(\sin\Phi_{+3,1}\cos\Phi_{+1,0} + \sin\Phi_{+3,1}\cos\Phi_{-1,0} + \sin\Phi_{-3,1}\cos\Phi_{+1,0} +$$
$$\sin\Phi_{-3,1}\cos\Phi_{-1,0})e^{i(-\alpha_1+\alpha_0)t} +$$

$$\frac{1}{4}(\sin\Phi_{+3,1}\sin\Phi_{+1,0} - \sin\Phi_{+3,1}\sin\Phi_{-1,0} + \sin\Phi_{-3,1}\sin\Phi_{+1,0} -$$
$$\sin\Phi_{-3,1}\sin\Phi_{-1,0})e^{i\pi/2}e^{i(-\alpha_1+\alpha_0)t} -$$

$$\frac{1}{4}(\sin\Phi_{+3,1}\sin\Phi_{+1,0} + \sin\Phi_{+3,1}\sin\Phi_{-1,0} + \sin\Phi_{-3,1}\sin\Phi_{+1,0} +$$
$$\sin\Phi_{-3,1}\sin\Phi_{-1,0})e^{-i(\alpha_1+\alpha_0)t} -$$

$$\frac{1}{4}(\sin\Phi_{-3,1}\cos\Phi_{+1,0} - \sin\Phi_{+3,1}\cos\Phi_{-1,0} + \sin\Phi_{-3,1}\cos\Phi_{+1,0} -$$
$$\sin\Phi_{-3,1}\cos\Phi_{-1,0})e^{i\pi/2}e^{-i(\alpha_1+\alpha_0)t} +$$

$$\frac{1}{4}(\cos\Phi_{+3,1}\cos\Phi_{+1,0} + \cos\Phi_{+3,1}\cos\Phi_{-1,0} - \cos\Phi_{-3,1}\cos\Phi_{+1,0} -$$
$$\cos\Phi_{-3,1}\cos\Phi_{-1,0})e^{i\pi/2}e^{i(-\alpha_1+\alpha_0)t} +$$

$$\frac{1}{4}(\cos\Phi_{+3,1}\sin\Phi_{+1,0} - \cos\Phi_{+3,1}\sin\Phi_{-1,0} - \cos\Phi_{-3,1}\sin\Phi_{+1,0} +$$
$$\cos\Phi_{-3,1}\sin\Phi_{-1,0})e^{i\pi}e^{i(-\alpha_1+\alpha_0)t} -$$

$$\frac{1}{4}(\cos\Phi_{+3,1}\sin\Phi_{+1,0} + \cos\Phi_{+3,1}\sin\Phi_{-1,0} - \cos\Phi_{-3,1}\sin\Phi_{+1,0} -$$
$$\cos\Phi_{-3,1}\sin\Phi_{-1,0})e^{i\pi/2}e^{-i(\alpha_1+\alpha_0)t} -$$

$$\frac{1}{4}(\cos\Phi_{+3,1}\cos\Phi_{+1,0} - \cos\Phi_{+3,1}\cos\Phi_{-1,0} - \cos\Phi_{-3,1}\cos\Phi_{+1,0} +$$
$$\cos\Phi_{-3,1}\cos\Phi_{-1,0})e^{i\pi}e^{-i(\alpha_1+\alpha_0)t}.$$

Under the condition of identical secondary phase shifts for forward and backward samplings (Eq. 35), Eq.157 simplifies to $$T_{+3,-3}(t,M) \otimes T_{+1,-1}(t,M) \propto (\cos\Phi_{3,1}\cos\Phi_{1,0})e^{i(\alpha_1+\alpha_0)t}$$
$$-(\cos\Phi_{3,1}\sin\Phi_{1,0})e^{i(\alpha_1-\alpha_0)t} + (\sin\Phi_{3,1}\cos\Phi_{1,0})e^{i(-\alpha_1+\alpha_0)t} - (\sin\Phi_{3,1}\cos\Phi_{1,0})e^{-i(\alpha_1+\alpha_0)t} \quad (158).$$

Under the condition of secondary phase shifts independent of n (Eq. 54), the peak components of Eq. 157 remain unchanged. Under the condition of identical secondary phase shifts (Eq. 73), Eq. 157 simplifies to $$T_{+3,-3}(t,M) \otimes T_{+1,-1}(t,M) \propto \cos\Phi_1\cos\Phi_0 e^{i(\alpha_1+\alpha_0)t} -$$
$$(\cos\Phi_1\sin\Phi_0)e^{i(\alpha_1-\alpha_0)t} + (\sin\Phi_1$$
$$\cos\Phi_0)e^{i(-\alpha_1+\alpha_0)t} - (\sin\Phi_1\cos\Phi_0)e^{-i(\alpha_1+\alpha_0)t} \quad (159).$$

Addition of Eqs. 144, 150, 154 and 157 gives the complex signal for $(c_{+1},c_{-1},c_{+3},c_{-3})$-sampling for two jointly sampled chemical shifts and is proportional to $$T_{+1,-1,+3,-3}(t,M) \propto \quad (160)$$

$$\frac{1}{4}(\cos\Phi_{+1,1}\cos\Phi_{+1,0} + \cos\Phi_{+1,1}\cos\Phi_{-1,0} + \cos\Phi_{-1,1}\cos\Phi_{+1,0} +$$
$$\cos\Phi_{-1,1}\cos\Phi_{-1,0} + \cos\Phi_{+1,1}\cos\Phi_{+3,0} +$$
$$\cos\Phi_{+1,1}\cos\Phi_{-3,0} + \cos\Phi_{-1,1}\cos\Phi_{+3,0} + \cos\Phi_{-1,1}\cos\Phi_{-3,0} +$$
$$\cos\Phi_{+3,1}\cos\Phi_{+1,0} + \cos\Phi_{+3,1}\cos\Phi_{-1,0} + \cos\Phi_{-3,1}\cos\Phi_{+1,0} +$$
$$\cos\Phi_{-3,1}\cos\Phi_{-1,0} + \cos\Phi_{+3,1}\cos\Phi_{+3,0} + \cos\Phi_{+3,1}\cos\Phi_{-3,0} +$$
$$\cos\Phi_{-3,1}\cos\Phi_{+3,0} + \cos\Phi_{-3,1}\cos\Phi_{-3,0})e^{i(\alpha_1+\alpha_0)t} +$$

$$\frac{1}{4}(\cos\Phi_{+1,1}\sin\Phi_{+1,0} - \cos\Phi_{+1,1}\sin\Phi_{-1,0} + \cos\Phi_{-1,1}\sin\Phi_{+1,0} -$$
$$\cos\Phi_{-1,1}\sin\Phi_{-1,0} + \cos\Phi_{+1,1}\sin\Phi_{+3,0} -$$
$$\cos\Phi_{+1,1}\sin\Phi_{-3,0} + \cos\Phi_{-1,1}\sin\Phi_{+3,0} - \cos\Phi_{-1,1}\sin\Phi_{-3,0} +$$
$$\cos\Phi_{+3,1}\sin\Phi_{+1,0} - \cos\Phi_{+3,1}\sin\Phi_{-1,0} + \cos\Phi_{-3,1}\sin\Phi_{+1,0} -$$
$$\cos\Phi_{-3,1}\sin\Phi_{-1,0} + \cos\Phi_{+3,1}\sin\Phi_{+3,0} - \cos\Phi_{+3,1}\sin\Phi_{-3,0} +$$
$$\cos\Phi_{-3,1}\sin\Phi_{+3,0} - \cos\Phi_{-3,1}\sin\Phi_{-3,0})e^{i\pi/2}e^{i(\alpha_1+\alpha_0)t} -$$

$$\frac{1}{4}(\cos\Phi_{+1,1}\sin\Phi_{+1,0} + \cos\Phi_{+1,1}\sin\Phi_{-1,0} + \cos\Phi_{-1,1}\sin\Phi_{+1,0} +$$
$$\cos\Phi_{-1,1}\sin\Phi_{-1,0} - \cos\Phi_{+1,1}\sin\Phi_{+3,0} -$$
$$\cos\Phi_{+1,1}\sin\Phi_{-3,0} - \cos\Phi_{-1,1}\sin\Phi_{+3,0} - \cos\Phi_{-1,1}\sin\Phi_{-3,0} +$$
$$\cos\Phi_{+3,1}\sin\Phi_{+1,0} + \cos\Phi_{+3,1}\sin\Phi_{-1,0} + \cos\Phi_{-3,1}\sin\Phi_{+1,0} +$$
$$\cos\Phi_{-3,1}\sin\Phi_{-1,0} - \cos\Phi_{+3,1}\sin\Phi_{+3,0} - \cos\Phi_{+3,1}\sin\Phi_{-3,0} -$$
$$\cos\Phi_{-3,1}\sin\Phi_{+3,0} - \cos\Phi_{-3,1}\sin\Phi_{-3,0})e^{i(\alpha_1-\alpha_0)t} -$$

$$\frac{1}{4}(\cos\Phi_{+1,1}\cos\Phi_{+1,0} - \cos\Phi_{+1,1}\cos\Phi_{-1,0} + \cos\Phi_{-1,1}\cos\Phi_{+1,0} -$$
$$\cos\Phi_{-1,1}\cos\Phi_{-1,0} - \cos\Phi_{+1,1}\cos\Phi_{+3,0} +$$
$$\cos\Phi_{+1,1}\cos\Phi_{-3,0} - \cos\Phi_{-1,1}\cos\Phi_{+3,0} + \cos\Phi_{-1,1}\cos\Phi_{-3,0} +$$
$$\cos\Phi_{+3,1}\cos\Phi_{+1,0} - \cos\Phi_{+3,1}\cos\Phi_{-1,0} + \cos\Phi_{-3,1}\cos\Phi_{+1,0} -$$
$$\cos\Phi_{-3,1}\cos\Phi_{-1,0} - \cos\Phi_{+3,1}\cos\Phi_{+3,0} + \cos\Phi_{+3,1}\cos\Phi_{-3,0} -$$
$$\cos\Phi_{-3,1}\cos\Phi_{+3,0} + \cos\Phi_{-3,1}\cos\Phi_{-3,0})e^{i\pi/2}e^{i(\alpha_1-\alpha_0)t} +$$

$$\frac{1}{4}(\sin\Phi_{+1,1}\cos\Phi_{+1,0} + \sin\Phi_{+1,1}\cos\Phi_{-1,0} - \sin\Phi_{-1,1}\cos\Phi_{+1,0} -$$
$$\sin\Phi_{-1,1}\cos\Phi_{-1,0} + \sin\Phi_{+1,1}\cos\Phi_{+3,0} + \sin\Phi_{+1,1}\cos\Phi_{-3,0} -$$
$$\sin\Phi_{-1,1}\cos\Phi_{+3,0} - \sin\Phi_{-1,1}\cos\Phi_{-3,0} +$$
$$\sin\Phi_{+3,1}\cos\Phi_{+1,0} + \sin\Phi_{+3,1}\cos\Phi_{-1,0} - \sin\Phi_{-3,1}\cos\Phi_{+1,0} -$$
$$\sin\Phi_{-3,1}\cos\Phi_{-1,0} + \sin\Phi_{+3,1}\cos\Phi_{+3,0} + \sin\Phi_{+3,1}\cos\Phi_{-3,0} -$$
$$\sin\Phi_{-3,1}\cos\Phi_{+3,0} - \sin\Phi_{-3,1}\cos\Phi_{-3,0})e^{i\pi/2}e^{i(\alpha_1+\alpha_0)t} +$$

$$\frac{1}{4}(\sin\Phi_{+1,1}\sin\Phi_{+1,0} - \sin\Phi_{+1,1}\sin\Phi_{-1,0} - \sin\Phi_{-1,1}\sin\Phi_{+1,0} +$$
$$\sin\Phi_{-1,1}\sin\Phi_{-1,0} + \sin\Phi_{+1,1}\sin\Phi_{+3,0} -$$
$$\sin\Phi_{+1,1}\sin\Phi_{-3,0} - \sin\Phi_{-1,1}\sin\Phi_{+3,0} + \sin\Phi_{-1,1}\sin\Phi_{-3,0} +$$

-continued $$\sin\Phi_{+3,1}\sin\Phi_{+1,0} - \sin\Phi_{+3,1}\sin\Phi_{-1,0} - \sin\Phi_{-3,1}\sin\Phi_{+1,0} +$$
$$\sin\Phi_{-3,1}\sin\Phi_{-1,0} + \sin\Phi_{+3,1}\sin\Phi_{+3,0} - \sin\Phi_{+3,1}\sin\Phi_{-3,0} -$$
$$\sin\Phi_{-3,1}\sin\Phi_{+3,0} + \sin\Phi_{-3,1}\sin\Phi_{-3,0})e^{i\pi}e^{i(\alpha_1+\alpha_0)t} -$$
$$\frac{1}{4}(\sin\Phi_{+1,1}\sin\Phi_{+1,0} + \sin\Phi_{+1,1}\sin\Phi_{-1,0} - \sin\Phi_{-1,1}\sin\Phi_{+1,0} -$$
$$\sin\Phi_{-1,1}\sin\Phi_{-1,0} - \sin\Phi_{+1,1}\sin\Phi_{+3,0} -$$
$$\sin\Phi_{+1,1}\sin\Phi_{-3,0} + \sin\Phi_{-1,1}\sin\Phi_{+3,0} + \sin\Phi_{-1,1}\sin\Phi_{-3,0} +$$
$$\sin\Phi_{+3,1}\sin\Phi_{+1,0} + \sin\Phi_{+3,1}\sin\Phi_{-1,0} - \sin\Phi_{-3,1}\sin\Phi_{+1,0} -$$
$$\sin\Phi_{-3,1}\sin\Phi_{-1,0} - \sin\Phi_{+3,1}\sin\Phi_{+3,0} - \sin\Phi_{+3,1}\sin\Phi_{-3,0} +$$
$$\sin\Phi_{-3,1}\sin\Phi_{+3,0} + \sin\Phi_{-3,1}\sin\Phi_{-3,0})e^{i\pi/2}e^{i(\alpha_1-\alpha_0)t} -$$
$$\frac{1}{4}(\sin\Phi_{+1,1}\cos\Phi_{+1,0} - \sin\Phi_{+1,1}\cos\Phi_{-1,0} - \sin\Phi_{-1,1}\cos\Phi_{+1,0} +$$
$$\sin\Phi_{-1,1}\cos\Phi_{-1,0} - \sin\Phi_{+1,1}\cos\Phi_{+3,0} +$$
$$\sin\Phi_{+1,1}\cos\Phi_{-3,0} + \sin\Phi_{-1,1}\cos\Phi_{+3,0} - \sin\Phi_{-1,1}\cos\Phi_{-3,0} +$$
$$\sin\Phi_{+3,1}\cos\Phi_{+1,0} - \sin\Phi_{+3,1}\cos\Phi_{-1,0} - \sin\Phi_{-3,1}\cos\Phi_{+1,0} +$$
$$\sin\Phi_{-3,1}\cos\Phi_{-1,0} - \sin\Phi_{+3,1}\cos\Phi_{+3,0} + \sin\Phi_{+3,1}\cos\Phi_{-3,0} +$$
$$\sin\Phi_{-3,1}\cos\Phi_{+3,0} - \sin\Phi_{-3,1}\cos\Phi_{-3,0})e^{i\pi}e^{i(\alpha_1-\alpha_0)t} -$$
$$\frac{1}{4}(\sin\Phi_{+1,1}\cos\Phi_{+1,0} + \sin\Phi_{+1,1}\cos\Phi_{-1,0} + \sin\Phi_{-1,1}\cos\Phi_{+1,0} +$$
$$\sin\Phi_{-1,1}\cos\Phi_{-1,0} + \sin\Phi_{+1,1}\cos\Phi_{+3,0} + \sin\Phi_{+1,1}\cos\Phi_{-3,0} +$$
$$\sin\Phi_{-1,1}\cos\Phi_{+3,0} + \sin\Phi_{-1,1}\cos\Phi_{-3,0} -$$
$$\sin\Phi_{+3,1}\cos\Phi_{+1,0} - \sin\Phi_{+3,1}\cos\Phi_{-1,0} - \sin\Phi_{-3,1}\cos\Phi_{+1,0} -$$
$$\sin\Phi_{-3,1}\cos\Phi_{-1,0} - \sin\Phi_{+3,1}\cos\Phi_{+3,0} - \sin\Phi_{+3,1}\cos\Phi_{-3,0} -$$
$$\sin\Phi_{-3,1}\cos\Phi_{+3,0} - \sin\Phi_{-3,1}\cos\Phi_{-3,0})e^{i(-\alpha_1+\alpha_0)t} -$$
$$\frac{1}{4}(\sin\Phi_{+1,1}\sin\Phi_{+1,0} - \sin\Phi_{+1,1}\sin\Phi_{-1,0} + \sin\Phi_{-1,1}\sin\Phi_{+1,0} -$$
$$\sin\Phi_{-1,1}\sin\Phi_{-1,0} + \sin\Phi_{+1,1}\sin\Phi_{+3,0} -$$
$$\sin\Phi_{+1,1}\sin\Phi_{-3,0} + \sin\Phi_{-1,1}\sin\Phi_{+3,0} - \sin\Phi_{-1,1}\sin\Phi_{-3,0} -$$
$$\sin\Phi_{+3,1}\sin\Phi_{+1,0} + \sin\Phi_{+3,1}\sin\Phi_{-1,0} - \sin\Phi_{-3,1}\sin\Phi_{+1,0} +$$
$$\sin\Phi_{-3,1}\sin\Phi_{-1,0} - \sin\Phi_{+3,1}\sin\Phi_{+3,0} + \sin\Phi_{+3,1}\sin\Phi_{-3,0} -$$
$$\sin\Phi_{-3,1}\sin\Phi_{+3,0} + \sin\Phi_{-3,1}\sin\Phi_{-3,0})e^{i\pi/2}e^{i(-\alpha_1+\alpha_0)t} +$$
$$\frac{1}{4}(\sin\Phi_{+1,1}\sin\Phi_{+1,0} + \sin\Phi_{+1,1}\sin\Phi_{-1,0} + \sin\Phi_{-1,1}\sin\Phi_{+1,0} +$$
$$\sin\Phi_{-1,1}\sin\Phi_{-1,0} - \sin\Phi_{+1,1}\sin\Phi_{+3,0} -$$
$$\sin\Phi_{+1,1}\sin\Phi_{-3,0} - \sin\Phi_{-1,1}\sin\Phi_{+3,0} - \sin\Phi_{-1,1}\sin\Phi_{-3,0} -$$
$$\sin\Phi_{+3,1}\sin\Phi_{+1,0} - \sin\Phi_{+3,1}\sin\Phi_{-1,0} - \sin\Phi_{-3,1}\sin\Phi_{+1,0} -$$
$$\sin\Phi_{-3,1}\sin\Phi_{-1,0} + \sin\Phi_{+3,1}\sin\Phi_{+3,0} + \sin\Phi_{+3,1}\sin\Phi_{-3,0} +$$
$$\sin\Phi_{-3,1}\sin\Phi_{+3,0} + \sin\Phi_{-3,1}\sin\Phi_{-3,0})e^{-i(\alpha_1+\alpha_0)t} +$$
$$\frac{1}{4}(\sin\Phi_{+1,1}\cos\Phi_{+1,0} - \sin\Phi_{+1,1}\cos\Phi_{-1,0} + \sin\Phi_{-1,1}\cos\Phi_{+1,0} -$$
$$\sin\Phi_{-1,1}\cos\Phi_{-1,0} - \sin\Phi_{+1,1}\cos\Phi_{+3,0} +$$
$$\sin\Phi_{+1,1}\cos\Phi_{-3,0} - \sin\Phi_{-1,1}\cos\Phi_{+3,0} + \sin\Phi_{-1,1}\cos\Phi_{-3,0} -$$
$$\sin\Phi_{+3,1}\cos\Phi_{+1,0} + \sin\Phi_{+3,1}\cos\Phi_{-1,0} - \sin\Phi_{-3,1}\cos\Phi_{+1,0} +$$
$$\sin\Phi_{-3,1}\cos\Phi_{-1,0} + \sin\Phi_{+3,1}\cos\Phi_{+3,0} - \sin\Phi_{+3,1}\cos\Phi_{-3,0} +$$
$$\sin\Phi_{-3,1}\cos\Phi_{+3,0} - \sin\Phi_{-3,1}\cos\Phi_{-3,0})e^{i\pi/2}e^{-i(\alpha_1+\alpha_0)t} -$$
$$\frac{1}{4}(\cos\Phi_{+1,1}\cos\Phi_{+1,0} + \cos\Phi_{+1,1}\cos\Phi_{-1,0} - \cos\Phi_{-1,1}\cos\Phi_{+1,0} -$$
$$\cos\Phi_{-1,1}\cos\Phi_{-1,0} + \cos\Phi_{+1,1}\cos\Phi_{+3,0} +$$

-continued $$\cos\Phi_{+1,1}\cos\Phi_{-3,0} - \cos\Phi_{-1,1}\cos\Phi_{+3,0} - \cos\Phi_{-1,1}\cos\Phi_{-3,0} -$$
$$\cos\Phi_{+3,1}\cos\Phi_{+1,0} - \cos\Phi_{+3,1}\cos\Phi_{-1,0} + \cos\Phi_{-3,1}\cos\Phi_{+1,0} +$$
$$\cos\Phi_{-3,1}\cos\Phi_{-1,0} - \cos\Phi_{+3,1}\cos\Phi_{+3,0} - \cos\Phi_{+3,1}\cos\Phi_{-3,0} +$$
$$\cos\Phi_{-3,1}\cos\Phi_{+3,0} + \cos\Phi_{-3,1}\cos\Phi_{-3,0})e^{i\pi/2}e^{i(-\alpha_1+\alpha_0)t} -$$
$$\frac{1}{4}(\cos\Phi_{+1,1}\sin\Phi_{+1,0} - \cos\Phi_{+1,1}\sin\Phi_{-1,0} - \cos\Phi_{-1,1}\sin\Phi_{+1,0} +$$
$$\cos\Phi_{-1,1}\sin\Phi_{-1,0} + \cos\Phi_{+1,1}\sin\Phi_{+3,0} -$$
$$\cos\Phi_{+1,1}\sin\Phi_{-3,0} - \cos\Phi_{-1,1}\sin\Phi_{+3,0} + \cos\Phi_{-1,1}\sin\Phi_{-3,0} -$$
$$\cos\Phi_{+3,1}\sin\Phi_{+1,0} + \cos\Phi_{+3,1}\sin\Phi_{-1,0} + \cos\Phi_{-3,1}\sin\Phi_{+1,0} -$$
$$\cos\Phi_{-3,1}\sin\Phi_{-1,0} - \cos\Phi_{+3,1}\sin\Phi_{+3,0} + \cos\Phi_{+3,1}\sin\Phi_{-3,0} +$$
$$\cos\Phi_{-3,1}\sin\Phi_{+3,0} - \cos\Phi_{-3,1}\sin\Phi_{-3,0})e^{i\pi}e^{i(-\alpha_1+\alpha_0)t} +$$
$$\frac{1}{4}(\cos\Phi_{+1,1}\sin\Phi_{+1,0} + \cos\Phi_{+1,1}\sin\Phi_{-1,0} - \cos\Phi_{-1,1}\sin\Phi_{+1,0} -$$
$$\cos\Phi_{-1,1}\sin\Phi_{-1,0} - \cos\Phi_{+1,1}\sin\Phi_{+3,0} -$$
$$\cos\Phi_{+1,1}\sin\Phi_{-3,0} + \cos\Phi_{-1,1}\sin\Phi_{+3,0} + \cos\Phi_{-1,1}\sin\Phi_{-3,0} -$$
$$\cos\Phi_{+3,1}\sin\Phi_{+1,0} - \cos\Phi_{+3,1}\sin\Phi_{-1,0} + \cos\Phi_{-3,1}\sin\Phi_{+1,0} +$$
$$\cos\Phi_{-3,1}\sin\Phi_{-1,0} + \cos\Phi_{+3,1}\sin\Phi_{+3,0} + \cos\Phi_{+3,1}\sin\Phi_{-3,0} -$$
$$\cos\Phi_{-3,1}\sin\Phi_{+3,0} - \cos\Phi_{-3,1}\sin\Phi_{-3,0})e^{i\pi/2}e^{-i(\alpha_1+\alpha_0)t} +$$
$$\frac{1}{4}(\cos\Phi_{+1,1}\cos\Phi_{+1,0} - \cos\Phi_{+1,1}\cos\Phi_{-1,0} - \cos\Phi_{-1,1}\cos\Phi_{+1,0} +$$
$$\cos\Phi_{-1,1}\cos\Phi_{-1,0} - \cos\Phi_{+1,1}\cos\Phi_{+3,0} +$$
$$\cos\Phi_{+1,1}\cos\Phi_{-3,0} + \cos\Phi_{-1,1}\cos\Phi_{+3,0} - \cos\Phi_{-1,1}\cos\Phi_{-3,0} -$$
$$\cos\Phi_{+3,1}\cos\Phi_{+1,0} + \cos\Phi_{+3,1}\cos\Phi_{-1,0} + \cos\Phi_{-3,1}\cos\Phi_{+1,0} -$$
$$\cos\Phi_{-3,1}\cos\Phi_{-1,0} + \cos\Phi_{+3,1}\cos\Phi_{+3,0} - \cos\Phi_{+3,1}\cos\Phi_{-3,0} -$$
$$\cos\Phi_{-3,1}\cos\Phi_{+3,0} + \cos\Phi_{-3,1}\cos\Phi_{-3,0})e^{i\pi}e^{-i(\alpha_1+\alpha_0)t}.$$

Under the condition of identical secondary phase shifts for forward and backward samplings (Eq. 35), Eq.160 simplifies to $$T_{+1,-1,+3,-3}(t, M) \propto \qquad (161)$$
$$(\cos\Phi_{1,1}\cos\Phi_{1,0} + \cos\Phi_{1,1}\cos\Phi_{3,0} + \cos\Phi_{3,1}\cos\Phi_{1,0} +$$
$$\cos\Phi_{3,1}\cos\Phi_{3,0})e^{i(\alpha_1+\alpha_0)t} -$$
$$(\cos\Phi_{1,1}\sin\Phi_{1,0} - \cos\Phi_{1,1}\sin\Phi_{3,0} + \cos\Phi_{3,1}\sin\Phi_{1,0} -$$
$$\cos\Phi_{3,1}\sin\Phi_{3,0})e^{i(\alpha_1-\alpha_0)t} -$$
$$(\sin\Phi_{1,1}\cos\Phi_{1,0} + \sin\Phi_{1,1}\cos\Phi_{3,0} - \sin\Phi_{3,1}\cos\Phi_{1,0} -$$
$$\sin\Phi_{3,1}\cos\Phi_{3,0})e^{i(-\alpha_1+\alpha_0)t} +$$
$$(\sin\Phi_{1,1}\sin\Phi_{1,0} - \sin\Phi_{1,1}\sin\Phi_{3,0} - \sin\Phi_{3,1}\sin\Phi_{1,0} + \sin\Phi_{3,1}\sin\Phi_{3,0})$$
$$e^{-i(\alpha_1+\alpha_0)t}.$$

Two dimensional FT reveals absorptive peaks at the desired, cross-talk and the quad positions. Under the condition of secondary phase shifts independent of n (Eq. 54), Eq.160 simplifies to $$F_C(S_{+1,-1,+3,-3}(t_1, t_0)) \propto \qquad (162)$$
$$(\cos\Phi_{+,1}\cos\Phi_{+,0} + \cos\Phi_{+,1}\cos\Phi_{-,0} + \cos\Phi_{-,1}\cos\Phi_{+,0} +$$
$$\cos\Phi_{-,1}\cos\Phi_{-,0})e^{i(\alpha_1+\alpha_0)t} +$$

-continued $(\cos\Phi_{+,1}\sin\Phi_{+,0} - \cos\Phi_{+,1}\sin\Phi_{-,0} + \cos\Phi_{-,1}\sin\Phi_{+,0} -$ $\cos\Phi_{-,1}\sin\Phi_{-,0})e^{i\pi/2}e^{i(\alpha_1+\alpha_0)t} +$ $(\sin\Phi_{+,1}\cos\Phi_{+,0} + \sin\Phi_{+,1}\cos\Phi_{-,0} - \sin\Phi_{-,1}\cos\Phi_{+,0} -$ $\sin\Phi_{-,1}\cos\Phi_{-,0})e^{i\pi/2}e^{i(\alpha_1+\alpha_0)t} +$ $(\sin\Phi_{+,1}\sin\Phi_{+,0} - \sin\Phi_{+,1}\sin\Phi_{-,0} - \sin\Phi_{-,1}\sin\Phi_{+,0} +$ $\sin\Phi_{-,1}\sin\Phi_{-,0})e^{i\pi}e^{i(\alpha_1+\alpha_0)t},$ Two dimensional FT reveals a single mixed phase peak at the desired position. This proves that, imbalance between forward and backward samplings can not eliminate dispersive components. Under the condition of identical secondary phase shifts (Eq. 73), Eq. 160 simplifies to $$F_C(S_{+1,\,-1,+3,-3}(t_1,t_0)) \propto 4\cos\Phi_1\cos\Phi_0 e^{i(\alpha_1+\alpha_0)t} \quad (163).$$

Two dimensional FT reveals a single peak, $4\cos\Phi_1\cos\Phi_0 e^{i(\alpha_1+\alpha_0)t}$, which is purely absorptive and located at the desired linear combination of chemical shift $(\alpha_1+\alpha_0)$.

Arbitrary Subset of Jointly Sampled Chemical Shifts

As in multi-dimensional NMR, multiple PMS in GFT results for the complex time domain signal in a sum over products of all possible permutations of $\cos\Phi_{\pm n,j}$ and $\sin\Phi_{\pm n,j}$.

$(c_{+0}, c_{+2})$-Sampling

Combining $S_{+0,+2}(t)$ of Eq. 3 and $S^*_{+0,+2}(t)$ of Eq. 136 one obtains $$T_{+0,+2}(t, M) = \quad (164)$$

$$\left(\frac{1}{2}(\cos\Phi_{+0,K} + \cos\Phi_{+2,K})e^{iM_K\alpha_Kt} + \frac{M_K}{2}(\sin\Phi_{+0,K} + \sin\Phi_{+2,K})\right.$$

$$e^{i\frac{\pi}{2}}e^{iM_K\alpha_Kt} + \frac{1}{2}(\cos\Phi_{+0,K} - \cos\Phi_{+2,K})e^{-iM_K\alpha_Kt} -$$

$$\left.\frac{M_K}{2}(\sin\Phi_{+0,K} - \sin\Phi_{+2,K})e^{i\frac{\pi}{2}}e^{-iM_K\alpha_Kt}\right)\otimes$$

$$\left(\frac{1}{2}(\cos\Phi_{+0,K-1} + \cos\Phi_{+2,K-1})e^{iM_{K-1}\alpha_{K-1}t} +\right.$$

$$\frac{M_{K-1}}{2}(\sin\Phi_{+0,K-1} + \sin\Phi_{+2,K-1})e^{i\frac{\pi}{2}}e^{iM_{K-1}\alpha_{K-1}t} +$$

$$\frac{1}{2}(\cos\Phi_{+0,K-1} - \cos\Phi_{+2,K-1})e^{-iM_{K-1}\alpha_{K-1}t} -$$

$$\left.\frac{M_{K-1}}{2}(\sin\Phi_{+0,K-1} - \sin\Phi_{+2,K-1})e^{i\frac{\pi}{2}}e^{-iM_{K-1}\alpha_{K-1}t}\right)\otimes\ldots\otimes$$

$$\left(\frac{1}{2}(\cos\Phi_{+0,0} + \cos\Phi_{+2,0})e^{iM_0\alpha_0t} + \frac{M_0}{2}(\sin\Phi_{+0,0} + \sin\Phi_{+2,0})\right.$$

$$e^{i\frac{\pi}{2}}e^{iM_0\alpha_0t} + \frac{1}{2}(\cos\Phi_{+0,0} - \cos\Phi_{+2,0})e^{-iM_0\alpha_0t} -$$

$$\left.\frac{M_0}{2}(\sin\Phi_{+0,0} - \sin\Phi_{+2,0})e^{i\frac{\pi}{2}}e^{-iM_0\alpha_0t}\right),$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

$(c_{-0}, c_{-2})$-Sampling

With $S_{-0,-2}(t)$ of Eq. 7, the complex conjugate is proportional to $$S^*_{-0,-2}(t) \propto Q^*D_{-0,-2}C_{-0,-2}(t) = [1 \;\; -i]\begin{bmatrix}1 & 0\\ 0 & 1\end{bmatrix} \quad (165)$$

$$\begin{bmatrix}c_{-0}(t)\\ c_{-2}(t)\end{bmatrix} = [1\;\; -i]\begin{bmatrix}c_{-0}\\ c_{-2}\end{bmatrix} = [1\;\; -i]\begin{bmatrix}\cos(\alpha t - \Phi_{-0})\\ \sin(\alpha t - \Phi_{-2})\end{bmatrix} =$$

$$(\cos\Phi_{-0}\cos(\alpha t) + \sin\Phi_{-0}\sin(\alpha t)) +$$

$$i(\sin\Phi_{-2}\cos(\alpha t) - \cos\Phi_{-2}\sin(\alpha t)) =$$

$$(\cos\Phi_{-0} + i\sin\Phi_{-2})\cos(\alpha t) + (\sin\Phi_{-0} - i\cos\Phi_{-2})\sin(\alpha t) =$$

$$(\cos\Phi_{-0} + i\sin\Phi_{-2})\frac{e^{i\alpha t} + e^{-i\alpha t}}{2} +$$

$$(\sin\Phi_{-0} - i\cos\Phi_{-2})\frac{e^{i\alpha t} - e^{-i\alpha t}}{2i} =$$

$$\frac{1}{2}(\cos\Phi_{-0} - \cos\Phi_{-2})e^{i\alpha t} - \frac{i}{2}(\sin\Phi_{-0} - \sin\Phi_{-2})e^{i\alpha t} +$$

$$\frac{1}{2}(\cos\Phi_{-0} + \cos\Phi_{-2})e^{-i\alpha t} + \frac{i}{2}(\sin\Phi_{-0} + \sin\Phi_{-2})$$

$$e^{-i\alpha t} = \frac{1}{2}(\cos\Phi_{-0} - \cos\Phi_{-2})e^{i\alpha t} -$$

$$\frac{1}{2}(\sin\Phi_{-0} - \sin\Phi_{-2})e^{\frac{\pi}{2}}e^{i\alpha t} + \frac{1}{2}(\cos\Phi_{-0} +$$

$$\cos\Phi_{-2})e^{-i\alpha t} + \frac{1}{2}(\sin\Phi_{-0} + \sin\Phi_{-2})e^{\frac{\pi}{2}}e^{-i\alpha t}.$$

Combining $S_{-0,-2}(t)$ of Eq. 7 and $S^*_{-0,-2}(t)$ of Eq. 165 one obtains $$T_{-0,-2}(t, M) = \quad (166)$$

$$\left(\frac{1}{2}(\cos\Phi_{-0,K} + \cos\Phi_{-2,K})e^{iM_K\alpha_Kt} - \frac{M_K}{2}(\sin\Phi_{-0,K} + \sin\Phi_{-2,K})\right.$$

$$e^{i\frac{\pi}{2}}e^{iM_K\alpha_Kt} + \frac{1}{2}(\cos\Phi_{-0,K} - \cos\Phi_{-2,K})e^{-iM_K\alpha_Kt} +$$

$$\left.\frac{M_K}{2}(\sin\Phi_{-0,K} - \sin\Phi_{-2,K})e^{i\frac{\pi}{2}}e^{-iM_K\alpha_Kt}\right)\otimes$$

$$\left(\frac{1}{2}(\cos\Phi_{-0,K-1} + \cos\Phi_{-2,K-1})e^{iM_{K-1}\alpha_{K-1}t} -\right.$$

$$\frac{M_{K-1}}{2}(\sin\Phi_{-0,K-1} + \sin\Phi_{-2,K-1})e^{i\frac{\pi}{2}}e^{iM_{K-1}\alpha_{K-1}t} +$$

$$\frac{1}{2}(\cos\Phi_{-0,K-1} - \cos\Phi_{-2,K-1})e^{-iM_{K-1}\alpha_{K-1}t} +$$

$$\left.\frac{M_{K-1}}{2}(\sin\Phi_{-0,K-1} - \sin\Phi_{-2,K-1})e^{i\frac{\pi}{2}}e^{-iM_{K-1}\alpha_{K-1}t}\right)\otimes\ldots\otimes$$

$$\left(\frac{1}{2}(\cos\Phi_{-0,0} + \cos\Phi_{-2,0})e^{iM_0\alpha_0t} - \frac{M_0}{2}(\sin\Phi_{-0,0} + \sin\Phi_{-2,0})\right.$$

$$e^{i\frac{\pi}{2}}e^{iM_0\alpha_0t} + \frac{1}{2}(\cos\Phi_{-0,0} - \cos\Phi_{-2,0})e^{-iM_0\alpha_0t} +$$

$$\left.\frac{M_0}{2}(\sin\Phi_{-0,0} - \sin\Phi_{-2,0})e^{i\frac{\pi}{2}}e^{-iM_0\alpha_0t}\right).$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

($c_{+0}, c_{+2}, c_{-0}, c_{-2}$)-Sampling

As for Eq. 10, addition of $S^*_{+0,+2}(t)$ and $S^*_{-0,-2}(t)$ yields $$S^*_{+0,+2,-0,-2}(t) = S^*_{+0,+2}(t) + S^*_{-0,-2}(t) \propto \quad (167)$$

$$\frac{1}{2}(\cos\Phi_{+0} - \cos\Phi_{+2} + \cos\Phi_{-0} - \cos\Phi_{-2})e^{i\alpha t} +$$

$$\frac{1}{2}(\sin\Phi_{+0} - \sin\Phi_{+2} - \sin\Phi_{-0} + \sin\Phi_{-2})e^{i\frac{\pi}{2}}e^{i\alpha t} +$$

$$\frac{1}{2}(\cos\Phi_{+0} + \cos\Phi_{+2} + \cos\Phi_{-0} + \cos\Phi_{-2})e^{-i\alpha t} -$$

$$\frac{1}{2}(\sin\Phi_{+0} + \sin\Phi_{+2} - \sin\Phi_{-0} - \sin\Phi_{-2})e^{i\frac{\pi}{2}}e^{-i\alpha t}.$$

Combining $S_{+0,+2,-0,-2}(t)$ of Eq.10 and $S^*_{+0,+2,-0,-2}(t)$ of Eq. 167 one obtains $$T_{+0,+2,-0,-2}(t) \propto \quad (168)$$

$$\left(\frac{1}{2}(\cos\Phi_{+0,K} + \cos\Phi_{+2,K} + \cos\Phi_{-0,K} + \cos\Phi_{-2,K})e^{iM_K\alpha_K t} + \right.$$

$$\frac{M_K}{2}(\sin\Phi_{+0,K} + \sin\Phi_{+2,K} - \sin\Phi_{-0,K} - \sin\Phi_{-2,K})e^{i\frac{\pi}{2}}e^{iM_K\alpha_K t} +$$

$$\frac{1}{2}(\cos\Phi_{+0,K} - \cos\Phi_{+2,K} + \cos\Phi_{-0,K} - \cos\Phi_{-2,K})$$

$$e^{-iM_K\alpha_K t} - \frac{M_K}{2}(\sin\Phi_{+0,K} - \sin\Phi_{+2,K} -$$

$$\left. \sin\Phi_{-0,K} + \sin\Phi_{-2,K})e^{i\frac{\pi}{2}}e^{-iM_K\alpha_K t}\right) \otimes$$

$$\left(\frac{1}{2}(\cos\Phi_{+0,K-1} + \cos\Phi_{+2,K-1} + \cos\Phi_{-0,K-1} + \cos\Phi_{-2,K-1})\right.$$

$$e^{iM_{K-1}\alpha_{K-1} t} + \frac{M_{K-1}}{2}(\sin\Phi_{+0,K-1} + \sin\Phi_{+2,K-1} -$$

$$\sin\Phi_{-0,K-1} - \sin\Phi_{-2,K-1})e^{i\frac{\pi}{2}}e^{iM_{K-1}\alpha_{K-1} t} +$$

$$\frac{1}{2}(\cos\Phi_{+0,K-1} - \cos\Phi_{+2,K-1} + \cos\Phi_{-0,K-1} - \cos\Phi_{-2,K})$$

$$e^{-iM_{K-1}\alpha_{K-1} t} - \frac{M_{K-1}}{2}(\sin\Phi_{+0,K-1} - \sin\Phi_{+2,K-1} -$$

$$\left. \sin\Phi_{-0,K-1} + \sin\Phi_{-2,K-1})e^{i\frac{\pi}{2}}e^{-iM_{K-1}\alpha_{K-1} t}\right) \otimes \dots \otimes$$

$$\left(\frac{1}{2}(\cos\Phi_{+0,0} + \cos\Phi_{+2,0} + \cos\Phi_{-0,0} + \cos\Phi_{-2,0})e^{iM_0\alpha_0 t} + \right.$$

$$\frac{M_0}{2}(\sin\Phi_{+0,0} + \sin\Phi_{+2,0} - \sin\Phi_{-0,0} - \sin\Phi_{-2,0})e^{i\frac{\pi}{2}}$$

$$e^{iM_0\alpha_0 t} + \frac{1}{2}(\cos\Phi_{+0,0} - \cos\Phi_{+2,0} + \cos\Phi_{-0,0} -$$

$$\cos\Phi_{-2,0})e^{-iM_0\alpha_0 t} - \frac{M_0}{2}(\sin\Phi_{+0,0} -$$

$$\left. \sin\Phi_{+2,0} - \sin\Phi_{-0,0} + \sin\Phi_{-2,0})e^{i\frac{\pi}{2}}e^{-iM_0\alpha_0 t}\right),$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

($c_{+1}, c_{-1}$)-Sampling (PMS)

Combining $S_{+1,-1}(t)$ of Eq. 14 and $S^*_{+1,-1}(t)$ of Eq. 141 one obtains $$T_{+1,-1}(t, M) = \quad (169)$$

$$\left(\frac{1}{2}(\cos\Phi_{+1,K} + \cos\Phi_{-1,K})e^{iM_K\alpha_K t} + \frac{M_K}{2}(\sin\Phi_{+1,K} - \sin\Phi_{-1,K})\right.$$

$$e^{i\frac{\pi}{2}}e^{iM_K\alpha_K t} - \frac{1}{2}(\sin\Phi_{+1,K} + \sin\Phi_{-1,K})e^{-iM_K\alpha_K t} -$$

$$\left. \frac{M_K}{2}(\cos\Phi_{+1,K} - \cos\Phi_{-1,K})e^{i\frac{\pi}{2}}e^{-iM_K\alpha_K t}\right) \otimes$$

$$\left(\frac{1}{2}(\cos\Phi_{+1,K-1} + \cos\Phi_{-1,K-1})e^{iM_{K-1}\alpha_{K-1} t} + \right.$$

$$\frac{M_{K-1}}{2}(\sin\Phi_{+1,K-1} - \sin\Phi_{-1,K-1})e^{i\frac{\pi}{2}}e^{iM_{K-1}\alpha_{K-1} t} -$$

$$\frac{1}{2}(\sin\Phi_{+1,K-1} + \sin\Phi_{-1,K-1})e^{-iM_{K-1}\alpha_{K-1} t} -$$

$$\left. \frac{M_{K-1}}{2}(\cos\Phi_{+1,K-1} - \cos\Phi_{-1,K-1})e^{i\frac{\pi}{2}}e^{-iM_{K-1}\alpha_{K-1} t}\right) \otimes \dots \otimes$$

$$\left(\frac{1}{2}(\cos\Phi_{+1,0} + \cos\Phi_{-1,0})e^{iM_0\alpha_0 t} + \frac{M_0}{2}(\sin\Phi_{+1,0} - \sin\Phi_{-1,0})\right.$$

$$e^{i\frac{\pi}{2}}e^{iM_0\alpha_0 t} - \frac{1}{2}(\sin\Phi_{+1,0} + \sin\Phi_{-1,0})e^{-iM_0\alpha_0 t} -$$

$$\left. \frac{M_0}{2}(\cos\Phi_{+1,0} - \cos\Phi_{-1,0})e^{i\frac{\pi}{2}}e^{-iM_0\alpha_0 t}\right).$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

($c_{+3}, c_{-3}$)-Sampling (PMS)

Combining $S_{+3,-3}(t)$ of Eq. 18 and $S^*_{+3,-3}(t)$ of Eq. 147 one obtains $$T_{+3,-3}(t, M) = \quad (170)$$

$$\left(\frac{1}{2}(\cos\Phi_{+3,K} + \cos\Phi_{-3,K})e^{iM_K\alpha_K t} + \frac{M_K}{2}(\sin\Phi_{+3,K} - \sin\Phi_{-3,K})\right.$$

$$e^{i\frac{\pi}{2}}e^{iM_K\alpha_K t} + \frac{1}{2}(\sin\Phi_{+3,K} + \sin\Phi_{-3,K})e^{-iM_K\alpha_K t} +$$

$$\left. \frac{M_K}{2}(\cos\Phi_{+3,K} - \cos\Phi_{-3,K})e^{i\frac{\pi}{2}}e^{-iM_K\alpha_K t}\right) \otimes$$

$$\left(\frac{1}{2}(\cos\Phi_{+3,K-1} + \cos\Phi_{-3,K-1})e^{iM_{K-1}\alpha_{K-1} t} + \right.$$

$$\frac{M_{K-1}}{2}(\sin\Phi_{+3,K-1} - \sin\Phi_{-1,K-1})e^{i\frac{\pi}{2}}e^{iM_{K-1}\alpha_{K-1} t} +$$

$$\frac{1}{2}(\sin\Phi_{+3,K-1} + \sin\Phi_{-1,K-1})e^{-iM_{K-1}\alpha_{K-1} t} +$$

$$\left. \frac{M_{K-1}}{2}(\cos\Phi_{+3,K-1} - \cos\Phi_{-1,K-1})e^{i\frac{\pi}{2}}e^{-iM_{K-1}\alpha_{K-1} t}\right) \otimes \dots \otimes$$

-continued $$\left(\frac{1}{2}(\cos\Phi_{+3,0} + \cos\Phi_{-3,0})e^{iM_0\alpha_0 t} + \frac{M_0}{2}(\sin\Phi_{+3,0} - \sin\Phi_{-3,0})\right.$$
$$e^{i\frac{\pi}{2}}e^{iM_0\alpha_0 t} + \frac{1}{2}(\sin\Phi_{+3,0} + \sin\Phi_{-3,0})e^{-iM_0\alpha_0 t} +$$
$$\left.\frac{M_0}{2}(\cos\Phi_{+3,0} - \cos\Phi_{-3,0})e^{i\frac{\pi}{2}}e^{-iM_0\alpha_0 t}\right).$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

($c_{+1}, c_{-1}, c_{+3}, C_{-3}$)-Sampling (DPMS)

As for Eq. 21, addition of $S^*_{+1,-1}(t)$ and $S^*_{+3,-3}(t)$ yields $$S^*_{+1,-1,+3,-3}(t) = S^*_{+1,-1}(t) + S^*_{+3,-3}(t) \propto \qquad (171)$$
$$-\frac{1}{2}(\sin\Phi_{+1} + \sin\Phi_{-1} - \sin\Phi_{+3} - \sin\Phi_{-3})e^{i\alpha t} +$$
$$\frac{1}{2}(\cos\Phi_{+1} - \cos\Phi_{-1} - \cos\Phi_{+3} + \cos\Phi_{-3})e^{i\frac{\pi}{2}}e^{i\alpha t} +$$
$$\frac{1}{2}(\cos\Phi_{+1} + \cos\Phi_{-1} + \cos\Phi_{+3} + \cos\Phi_{-3})e^{-i\alpha t} -$$
$$\frac{1}{2}(\sin\Phi_{+1} - \sin\Phi_{-1} + \sin\Phi_{+3} - \sin\Phi_{-3})e^{i\frac{\pi}{2}}e^{-i\alpha t}.$$

Combining $S_{+1,-1,+3,-3}(t)$ of Eq. 21 and $S^*_{+1,-1,+3,-3}(t)$ of Eq. 171 one obtains $$T_{+1,-1,+3,-3}(t) \propto \qquad (172)$$
$$\left(\frac{1}{2}(\cos\Phi_{+1,K} + \cos\Phi_{-1,K} + \cos\Phi_{+3,K} + \cos\Phi_{-3,K})e^{iM_K\alpha_K t} + \right.$$
$$\frac{M_K}{2}(\sin\Phi_{+1,K} - \sin\Phi_{-1,K} + \sin\Phi_{+3,K} - \sin\Phi_{-3,K})e^{i\frac{\pi}{2}}e^{iM_K\alpha_K t} -$$
$$\frac{1}{2}(\sin\Phi_{+1,K} + \sin\Phi_{-1,K} - \sin\Phi_{+3,K} - \sin\Phi_{-3,K})e^{-iM_K\alpha_K t} -$$
$$\left.\frac{M_K}{2}(\cos\Phi_{+1,K} - \cos\Phi_{-1,K} - \cos\Phi_{+3,K} + \cos\Phi_{-3,K})\right.$$
$$\left.e^{i\frac{\pi}{2}}e^{-iM_K\alpha_K t}\right) \otimes$$
$$\left(\frac{1}{2}(\cos\Phi_{+1,K-1} + \cos\Phi_{-1,K-1} + \cos\Phi_{+3,K-1} + \cos\Phi_{-3,K-1})\right.$$
$$e^{iM_{K-1}\alpha_{K-1}t} + \frac{M_K}{2}(\sin\Phi_{+1,K-1} - \sin\Phi_{-1,K-1} +$$
$$\sin\Phi_{+3,K-1} - \sin\Phi_{-3,K-1})e^{i\frac{\pi}{2}}e^{iM_{K-1}\alpha_{K-1}t} -$$
$$\frac{1}{2}(\sin\Phi_{+1,K-1} + \sin\Phi_{-1,K-1} - \sin\Phi_{+3,K-1} - \sin\Phi_{-3,K-1})$$
$$e^{-iM_{K-1}\alpha_{K-1}t} -$$
$$\left.\frac{M_K}{2}(\cos\Phi_{+1,K-1} - \cos\Phi_{-1,K-1} - \cos\Phi_{+3,K-1} + \cos\Phi_{-3,K-1})\right.$$
$$\left.e^{i\frac{\pi}{2}}e^{-iM_{K-1}\alpha_{K-1}t}\right) \ldots \otimes$$
$$\left(\frac{1}{2}(\cos\Phi_{+1,0} + \cos\Phi_{-1,0} + \cos\Phi_{+3,0} + \cos\Phi_{-3,0})e^{iM_0\alpha_0 t} + \right.$$
$$\frac{M_K}{2}(\sin\Phi_{+1,0} - \sin\Phi_{-1,0} + \sin\Phi_{+3,0} - \sin\Phi_{-3,0})$$
$$e^{i\frac{\pi}{2}}e^{-iM_0\alpha_0 t} -$$

-continued $$\frac{1}{2}(\sin\Phi_{+1,0} + \sin\Phi_{-1,0} - \sin\Phi_{+3,0} - \sin\Phi_{-3,0})e^{-iM_0\alpha_0 t} -$$
$$\frac{M_K}{2}(\cos\Phi_{+1,0} - \cos\Phi_{-1,0} - \cos\Phi_{+3,0} + \cos\Phi_{-3,0})$$
$$e^{i\frac{\pi}{2}}e^{-iM_0\alpha_0 t}\biggr),$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

($c_{+0}, c_{-2}$)-Sampling (PMS)

With $S_{+0,-2}(t)$ of Eq. 25, the complex conjugate is proportional to $$S^*_{+0,-2}(t) \propto Q^* D_{+0,-2} C_{+0,-2}(t) = \begin{bmatrix} 1 & i \end{bmatrix} \begin{bmatrix} 1 & 0 \\ 0 & 1 \end{bmatrix} \begin{bmatrix} c_{+0}(t) \\ c_{-2}(t) \end{bmatrix} = \qquad (173)$$
$$\begin{bmatrix} 1 & i \end{bmatrix} \begin{bmatrix} c_{+0} \\ c_{-2} \end{bmatrix} = \begin{bmatrix} 1 & i \end{bmatrix} \begin{bmatrix} \cos(\alpha t + \Phi_{+0}) \\ \sin(\alpha t - \Phi_{-2}) \end{bmatrix} =$$
$$(\cos\Phi_{+0}\cos(\alpha t) - \sin\Phi_{+0}\sin(\alpha t)) +$$
$$i(\sin\Phi_{-2}\cos(\alpha t) - \cos\Phi_{-2}\sin(\alpha t)) =$$
$$(\cos\Phi_{+0} + i\sin\Phi_{-2})\cos(\alpha t) - (\sin\Phi_{+0} + i\cos\Phi_{-2})\sin(\alpha t) =$$
$$(\cos\Phi_{+0} + i\sin\Phi_{-2})\frac{e^{i\alpha t} + e^{-i\alpha t}}{2} -$$
$$(\sin\Phi_{+0} + i\cos\Phi_{-2})\frac{e^{i\alpha t} + e^{-i\alpha t}}{2i} =$$
$$\frac{1}{2}(\cos\Phi_{+0} - \cos\Phi_{-2})e^{i\alpha t} + \frac{i}{2}(\sin\Phi_{+0} + \sin\Phi_{-2})e^{i\alpha t} +$$
$$\frac{1}{2}(\cos\Phi_{+0} + \cos\Phi_{-2})e^{-i\alpha t} - \frac{i}{2}(\sin\Phi_{+0} - \sin\Phi_{-2})$$
$$e^{-i\alpha t} = \frac{1}{2}(\cos\Phi_{+0} - \cos\Phi_{-2})e^{i\alpha t} +$$
$$\frac{1}{2}(\sin\Phi_{+0} + \sin\Phi_{-2})e^{i\frac{\pi}{2}}e^{i\alpha t} + \frac{1}{2}(\cos\Phi_{+0} + \cos\Phi_{-2})$$
$$e^{-i\alpha t} - \frac{1}{2}(\sin\Phi_{+0} - \sin\Phi_{-2})e^{i\frac{\pi}{2}}e^{-i\alpha t}.$$

Combining $S_{+0,-2}(t)$ of Eq. 25 and $S^*_{+0,-2}(t)$ of Eq. 173 one obtains $$T_{+0,-2}(t, M) = \qquad (174)$$
$$\left(\frac{1}{2}(\cos\Phi_{+0,K} + \cos\Phi_{-2,K})e^{iM_K\alpha_K t} + \frac{M_K}{2}(\sin\Phi_{+0,K} - \sin\Phi_{-2,K})\right.$$
$$e^{i\frac{\pi}{2}}e^{iM_K\alpha_K t} + \frac{1}{2}(\cos\Phi_{+0,K} - \cos\Phi_{-2,K})e^{-iM_K\alpha_K t} -$$
$$\left.\frac{M_K}{2}(\sin\Phi_{+0,K} + \sin\Phi_{-2,K})e^{i\frac{\pi}{2}}e^{-iM_K\alpha_K t}\right) \otimes$$
$$\left(\frac{1}{2}(\cos\Phi_{+0,K-1} + \cos\Phi_{-2,K-1})e^{iM_{K-1}\alpha_{K-1}t} + \right.$$
$$\frac{M_{K-1}}{2}(\sin\Phi_{+0,K-1} - \sin\Phi_{-2,K-1})e^{i\frac{\pi}{2}}e^{iM_{K-1}\alpha_{K-1}t} +$$
$$\frac{1}{2}(\cos\Phi_{+0,K-1} - \cos\Phi_{-2,K-1})e^{-iM_{K-1}\alpha_{K-1}t} -$$
$$\left.\frac{M_{K-1}}{2}(\sin\Phi_{+0,K-1} + \sin\Phi_{-2,K-1})e^{i\frac{\pi}{2}}e^{-iM_{K-1}\alpha_{K-1}t}\right) \otimes \ldots \otimes$$

$$\left(\frac{1}{2}(\cos\Phi_{+0,0} + \cos\Phi_{-2,0})e^{iM_0\alpha_0 t} + \frac{M_0}{2}(\sin\Phi_{+0,0} - \sin\Phi_{-2,0})\right.$$

$$e^{i\frac{\pi}{2}}e^{iM_0\alpha_0 t} + \frac{1}{2}(\cos\Phi_{+0,0} - \cos\Phi_{-2,0})e^{-iM_0\alpha_0 t} -$$

$$\left.\frac{M_0}{2}(\sin\Phi_{+0,0} + \sin\Phi_{-2,0})e^{i\frac{\pi}{2}}e^{-iM_0\alpha_0 t}\right).$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

($c_{-0}$,$c_{+2}$)-Sampling (PMS)

With $S_{-0,+2}(t)$ of Eq. 29, the complex conjugate is proportional to $$S^*_{-0,+2}(t) \propto Q^* D_{-0,+2} C_{-0,+2}(t) = [1 \ \ i]\begin{bmatrix}1 & 0 \\ 0 & -1\end{bmatrix} \qquad (175)$$

$$\begin{bmatrix}c_{-0}(t) \\ c_{+2}(t)\end{bmatrix} = [1 \ \ i]\begin{bmatrix}c_{-0} \\ c_{+2}\end{bmatrix} = [1 \ \ i]\begin{bmatrix}\cos(\alpha t - \Phi_{-0}) \\ -\sin(\alpha t + \Phi_{+2})\end{bmatrix} =$$

$$(\cos\Phi_{-0}\cos(\alpha t) + \sin\Phi_{-0}\sin(\alpha t)) -$$

$$i(\sin\Phi_{+2}\cos(\alpha t) + \cos\Phi_{+2}\sin(\alpha t)) =$$

$$(\cos\Phi_{-0} - i\sin\Phi_{+2})\cos(\alpha t) + (\sin\Phi_{-0} - i\cos\Phi_{+2})\sin(\alpha t) =$$

$$(\cos\Phi_{-0} - i\sin\Phi_{+2})\frac{e^{i\alpha t} + e^{-i\alpha t}}{2} +$$

$$(\sin\Phi_{-0} - i\cos\Phi_{+2})\frac{e^{i\alpha t} - e^{-i\alpha t}}{2i} =$$

$$\frac{1}{2}(\cos\Phi_{-0} - \cos\Phi_{+2})e^{i\alpha t} - \frac{i}{2}(\sin\Phi_{-0} + \sin\Phi_{+2})e^{i\alpha t} +$$

$$\frac{1}{2}(\cos\Phi_{-0} + \cos\Phi_{+2})e^{-i\alpha t} + \frac{i}{2}(\sin\Phi_{-0} - \sin\Phi_{+2})$$

$$e^{-i\alpha t} = \frac{1}{2}(\cos\Phi_{-0} - \cos\Phi_{+2})e^{i\alpha t} -$$

$$\frac{1}{2}(\sin\Phi_{-0} + \sin\Phi_{+2})e^{i\frac{\pi}{2}}e^{i\alpha t} + \frac{1}{2}(\cos\Phi_{-0} + \cos\Phi_{+2})$$

$$e^{-i\alpha t} + \frac{1}{2}(\sin\Phi_{-0} - \sin\Phi_{+2})e^{i\frac{\pi}{2}}e^{-i\alpha t}.$$

Combining $S_{-0,+2}(t)$ of Eq. 29 and $S^*_{-0,+2}(t)$ of Eq. 175 one obtains $$T_{-0,+2}(t, M) = \qquad (176)$$

$$\left(\frac{1}{2}(\cos\Phi_{-0,K} + \cos\Phi_{+2,K})e^{iM_K\alpha_K t} - \frac{M_K}{2}(\sin\Phi_{-0,K} - \sin\Phi_{+2,K})\right.$$

$$e^{i\frac{\pi}{2}}e^{iM_K\alpha_K t} + \frac{1}{2}(\cos\Phi_{-0,K} - \cos\Phi_{+2,K})e^{-iM_K\alpha_K t} +$$

$$\left.\frac{M_K}{2}(\sin\Phi_{-0,K} + \sin\Phi_{+2,K})e^{i\frac{\pi}{2}}e^{-iM_K\alpha_K t}\right) \otimes$$

$$\left(\frac{1}{2}(\cos\Phi_{-0,K-1} + \cos\Phi_{+2,K-1})e^{iM_{K-1}\alpha_{K-1} t} - \right.$$

$$\frac{M_{K-1}}{2}(\sin\Phi_{-0,K-1} - \sin\Phi_{+2,K-1})e^{i\frac{\pi}{2}}e^{iM_{K-1}\alpha_{K-1} t} +$$

$$\frac{1}{2}(\cos\Phi_{-0,K-1} - \cos\Phi_{+2,K-1})e^{-iM_{K-1}\alpha_{K-1} t} +$$

$$\left.\frac{M_{K-1}}{2}(\sin\Phi_{-0,K-1} + \sin\Phi_{+2,K-1})e^{i\frac{\pi}{2}}e^{-iM_{K-1}\alpha_{K-1} t}\right) \otimes \ldots \otimes$$

$$\left(\frac{1}{2}(\cos\Phi_{-0,0} + \cos\Phi_{+2,0})e^{iM_0\alpha_0 t} - \frac{M_0}{2}(\sin\Phi_{-0,0} - \sin\Phi_{+2,0})\right.$$

$$e^{i\frac{\pi}{2}}e^{iM_0\alpha_0 t} + \frac{1}{2}(\cos\Phi_{-0,0} - \cos\Phi_{+2,0})e^{-iM_0\alpha_0 t} +$$

$$\left.\frac{M_0}{2}(\sin\Phi_{-0,0} + \sin\Phi_{+2,0})e^{i\frac{\pi}{2}}e^{-iM_0\alpha_0 t}\right).$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

($c_{+0}$,$c_{-2}$,$c_{-0}$,$c_{+2}$)-Sampling (DPMS)

As for Eq. 32, addition of $S^*_{+0,-2}(t)$ and $S^*_{-0,+2}(t)$ yields $$S^*_{+0,-2,-0,+2}(t) = S^*_{+0,-2}(t) + S^*_{-0,+2}(t) \propto \qquad (177)$$

$$-\frac{1}{2}(\cos\Phi_{+0} - \cos\Phi_{-2} + \cos\Phi_{-0} - \cos\Phi_{+2})e^{i\alpha t} +$$

$$\frac{1}{2}(\sin\Phi_{+0} + \sin\Phi_{-2} - \sin\Phi_{-0} - \sin\Phi_{+2})e^{i\frac{\pi}{2}}e^{i\alpha t} +$$

$$\frac{1}{2}(\cos\Phi_{+0} + \cos\Phi_{-2} + \cos\Phi_{-0} + \cos\Phi_{+2})e^{-i\alpha t} -$$

$$\frac{1}{2}(\sin\Phi_{+0} - \sin\Phi_{-2} - \sin\Phi_{-0} + \sin\Phi_{+2})e^{i\frac{\pi}{2}}e^{-i\alpha t}.$$

Combining $S_{+0,-2,-0,+2}(t)$ of Eq. 32 and $S^*_{+0,-2,-0,+2}(t)$ of Eq. 177 one obtains $$T_{+0,-2,-0,+2}(t) \propto \qquad (178)$$

$$\left(\frac{1}{2}(\cos\Phi_{+0,K} + \cos\Phi_{-2,K} + \cos\Phi_{-0,K} + \cos\Phi_{+2,K})e^{iM_K\alpha_K t} + \right.$$

$$\frac{M_K}{2}(\sin\Phi_{+0,K} - \sin\Phi_{-2,K} - \sin\Phi_{-0,K} + \sin\Phi_{+2,K})e^{i\frac{\pi}{2}}e^{iM_K\alpha_K t} +$$

$$\frac{1}{2}(\cos\Phi_{+0,K} - \cos\Phi_{-2,K} + \cos\Phi_{-0,K} - \cos\Phi_{+2,K})$$

$$e^{-iM_K\alpha_K t} - \frac{M_K}{2}(\sin\Phi_{+0,K} + \sin\Phi_{-2,K} -$$

$$\left.\sin\Phi_{-0,K} + \sin\Phi_{+2,K})e^{i\frac{\pi}{2}}e^{-iM_K\alpha_K t}\right) \otimes$$

$$\left(\frac{1}{2}(\cos\Phi_{+0,K-1} + \cos\Phi_{-2,K-1} + \cos\Phi_{-0,K-1} + \cos\Phi_{+2,K-1})\right.$$

$$e^{iM_{K-1}\alpha_{K-1} t} +$$

$$\frac{M_K}{2}(\sin\Phi_{+0,K-1} - \sin\Phi_{-2,K-1} - \sin\Phi_{-0,K-1} + \sin\Phi_{+2,K-1})$$

$$e^{i\frac{\pi}{2}}e^{iM_{K-1}\alpha_{K-1} t} + \frac{1}{2}(\cos\Phi_{+0,K-1} - \cos\Phi_{-2,K-1} +$$

$$\cos\Phi_{-0,K-1} - \cos\Phi_{+2,K-1})e^{-iM_{K-1}\alpha_{K-1} t} -$$

$$\frac{M_K}{2}(\sin\Phi_{+0,K-1} + \sin\Phi_{-2,K-1} - \sin\Phi_{-0,K-1} - \sin\Phi_{+2,K-1})$$

$$\left.e^{i\frac{\pi}{2}}e^{-iM_{K-1}\alpha_{K-1} t}\right) \otimes \ldots \otimes$$

$$\left(\frac{1}{2}(\cos\Phi_{+0,0} + \cos\Phi_{-2,0} + \cos\Phi_{-0,0} + \cos\Phi_{+2,0})e^{iM_0\alpha_0 t} +\right.$$

$$\frac{M_K}{2}(\sin\Phi_{+0,0} - \sin\Phi_{-2,0} - \sin\Phi_{-0,0} + \sin\Phi_{+2,0})e^{i\frac{\pi}{2}}$$

-continued $$e^{iM_0\alpha_0 t} + \frac{1}{2}(\cos\Phi_{+0,0} - \cos\Phi_{-2,0} + \cos\Phi_{-0,0} -$$

$$\cos\Phi_{+2,0})e^{-iM_0\alpha_0 t} - \frac{M_K}{2}(\sin\Phi_{+0,0} +$$

$$\sin\Phi_{-2,0} - \sin\Phi_{-0,0} - \sin\Phi_{+2,0})e^{i\frac{\pi}{2}}e^{-iM_0\alpha_0 t}\Big),$$

FT along the GFT dimension reveals mixed phase peak components at the desired linear combination of chemical shifts, as well as at its quadrature position. It also reveals 'cross talk' between GFT NMR sub-spectra, that is, the resulting peaks are located at linear combinations of chemical shifts other than the desired one.

Combination of Different Sampling Schemes

Another aspect of the present invention relates to the generalization of PMS and DPMS schemes for multiple indirect evolution times. In the sections above the discussion is based on the assumption that the same sampling scheme is employed for all evolution periods. Here it is shown that it is readily possible to choose different sampling scheme for each of the evolution periods.

With $(c_p, c_q, c_r, c_s)$-sampling scheme being employed for the $j^{th}$ dimension of an (K+1)D experiment one has $$S_{p,q,r,s}(t_j) \propto QD_{p,q,r,s}C_{p,q,r,s}(t_j) \tag{179},$$

where $\{[p,q], [r,s]\} = \{[+0,+2], [-0,-2]\}$ for 'States'-sampling, $\{[p,q], [r,s]\} = \{[+1,-1], [+3,-3]\}$ for $\pi/4, 3\pi/4$-shifted mirrored sampling and $\{[p,q], [r,s]\} = \{[+0,-2], [-0,+2]\}$ for $0, \pi/2$-shifted mirrored sampling. The signal detected in the multi-dimensional NMR experiment is then proportional to $$S(t_K, t_{K-1}, \ldots, t_0) = \bigotimes_{j=0}^{K} S_{p,q,r,s}(t_j) \propto \bigotimes_{j=0}^{K} Q \bigotimes_{j=0}^{K} D_{p,q,r,s} \bigotimes_{j=0}^{K} C_{p,q,r,s}(t_j) = \tag{180}$$

$$Q(K)D(K)C(t_K, t_{K-1}, \ldots, t_0),$$

and one obtains for (K+1) jointly sampled chemical shifts in GFT NMR $$T_{p,q,r,s}(t) \propto \bigotimes_{j=0}^{K} G \bigotimes_{j=0}^{K} D_{p,q,r,s} \bigotimes_{j=0}^{K} C_{p,q,r,s}(t) = G(K)D(K)C(t) \tag{181}$$

where, $$t = t_0 = t_1/\kappa_1 = t_2/\kappa_2 = \ldots = t_3/\kappa_3.$$

Inspection of Eqs. 180 and 181 shows that with the choice of a particular sampling scheme for each shift evolution period, the resulting D matrix and C vector are constructed by straightforward tensor product formation.

Applications in NMR Spectroscopy

Another aspect of the present invention relates to general applications of acquisition schemes in NMR spectroscopy.

Measurement of NMR Parameters

With Eqs. 4, 8, 15, 19, 26 and 30, one can calculate the secondary phase shifts $\Phi_{\pm n}$ from the elements of the coefficient vector $\lambda_{\pm n}$. Hence, one can design NMR experiments in which a parameter $\beta$, for example associated with a short-lived nuclear spin state, is encoded into the secondary phase shift. Then, measurement of the coefficient vector $\lambda_{\pm n}$ enables measurement of $\beta$. Parameter $\beta$ can also be, for example, a nuclear spin-spin coupling.

Optimization and (re-)Design of Radio-Frequency (r.f.) Pulse Schemes

Imperfections of r.f. pulse schemes introduce secondary phase shifts which are then considered to be 'phase errors'. Optimization of r.f. pulse schemes requires minimization of phase errors to obtain pure absorption mode NMR spectra. Measurement of the coefficient vector $\lambda$ enables measurement of phase errors. In turn, this allows one to derive hypotheses regarding the origin of these phase errors and corresponding (re-)design of the pulse sequence.

Concatenation of Two Step Phase Cycle for Solvent/Axial Peak Suppression with Dual 'States' and DPMS One embodiment of the present invention involves concatenation of two step phase cycle for solvent/axial peak suppression with dual 'States' and DPMS The residual solvent and axial peaks are not frequency labeled in all indirect dimensions. This feature enables one to concatenate dual 'States' or DPMS acquisition with solvent/axial peak cancellation.

Hence, it is assumed in the following that the detected solvent/axial peak time domain signal is independent of indirect evolution periods.

Dual 'States' Sampling

The solvent/axial peak signal is detected for each of $c_{+0}$ and $c_{+2}$ interferograms. After transformation with D matrix and Q vector given in Eq. 3, one thus obtains for the solvent signal:

$$S_{-0,-2}^w(t) \propto [1 \ \ i]\begin{bmatrix} 1 & 0 \\ 0 & -1 \end{bmatrix}\begin{bmatrix} I_w(t)e^{i\alpha_w t_{aq}} \\ I_w(t)e^{i\alpha_w t_{aq}} \end{bmatrix} = (1-i)I_w(t)e^{i\alpha_w t_{aq}}, \tag{182}$$

where, $I_w, \alpha_w$ and $t_{aq}$ represent, respectively, the amplitude and frequency of the time domain solvent/axial peak signal and the direct acquisition time.

The $c_{-0}$-interferogram can be acquired by shifting both the first 90° r.f pulse generating transverse magnetization for frequency labeling and the receiver phase by $\pi$, so that the sign of the desired signal remains unchanged. Hence, after transformations with D matrix and Q vector given in Eq. 7, one obtains:

$$S_{-0,-2}^w(t) \propto [1 \ \ i]\begin{bmatrix} 1 & 0 \\ 0 & 1 \end{bmatrix}\begin{bmatrix} -I_w(t)e^{i\alpha_w t_{aq}} \\ I_w(t)e^{i\alpha_w t_{aq}} \end{bmatrix} = -(1-i)I_w(t)e^{i\alpha_w t_{aq}}. \tag{183}$$

Addition of $S_{+0,+2}^w(t_{aq})$ in Eq. 182 and $S_{-0,-2}^w(t_{aq})$ in Eq. 183 then results in cancelation of the residual solvent/axial peak signal.

$\pi/4$ and $3\pi/4$-Shifted Mirrored Sampling

For $c_{+1}$ and $c_{-1}$ interferograms, one obtains after the transformations with D matrix and Q vector given in Eq. 14:

$$S_{+1,-1}^w(t) \propto \frac{1}{\sqrt{2}}[1 \ \ i]\begin{bmatrix} 1 & 1 \\ -1 & 1 \end{bmatrix}\begin{bmatrix} I_w(t)e^{i\alpha_w t_{aq}} \\ I_w(t)e^{i\alpha_w t_{aq}} \end{bmatrix} = \sqrt{2}\,I_w(t)e^{i\alpha_w t_{aq}}. \tag{184}$$

For the corresponding $C_{+3}$ and $c_{-3}$ interferograms one obtains after transformations with D matrix and Q vector given in Eq. 18:

$$S_{+3,-3}^w(t) \propto \frac{1}{\sqrt{2}}[1 \ \ i]\begin{bmatrix} -1 & -1 \\ -1 & 1 \end{bmatrix}\begin{bmatrix} I_w(t)e^{i\alpha_w t_{aq}} \\ I_w(t)e^{i\alpha_w t_{aq}} \end{bmatrix} = -\sqrt{2}\,I_w(t)e^{i\alpha_w t_{aq}}. \tag{185}$$

Addition of $S^w_{+1,-1}(t_{aq})$ in Eq. 184 and $S^w_{+3,-3}(t_{aq})$ in Eq. 185 results in cancellation of the residual solvent/axial peak signal and r.f pulse or receiver phase shifts are not required.

0 and $\pi/2$-Shifted Mirrored Sampling

For $c_{+0}$ and $c_{-2}$ interferograms, one obtains after the transformations with D matrix and Q vector given in Eq. 25:

$$S^w_{+0,-2}(t) \propto [1 \ i] \begin{bmatrix} 1 & 0 \\ 0 & 1 \end{bmatrix} \begin{bmatrix} I_w(t)e^{i\alpha_w t_{aq}} \\ I_w(t)e^{i\alpha_w t_{aq}} \end{bmatrix} = (1+i)I_w(t)e^{i\alpha_w t_{aq}}. \quad (186)$$

The $c_{-0}$-interferogram can be acquired by shifting both the first 90° r.f pulse generating transverse magnetization for frequency labeling and the receiver phase by $\pi$. Hence, after transformations with D matrix and Q vector given in Eq. 29, one obtains:

$$S^w_{-0,+2}(t) \propto [1 \ i] \begin{bmatrix} 1 & 0 \\ 0 & -1 \end{bmatrix} \begin{bmatrix} -I_w(t)e^{i\alpha_w t_{aq}} \\ I_w(t)e^{i\alpha_w t_{aq}} \end{bmatrix} = -(1+i)I_w(t)e^{i\alpha_w t_{aq}}. \quad (187)$$

Addition of $S^w_{+0,-2}(t_{aq})$ in Eq. 186 and $S^w_{-0,+2}(t_{aq})$ in Eq. 187 results in cancellation of the residual solvent/axial peak signal.

Shift in Peak Position and Reduction of Peak Intensity as a Function of Phase Error Another aspect of the present invention relates to a shift in peak position and reduction of peak intensity as a function of phase error.

With a time domain signal S(t) given by $$S(t) = \exp(i\alpha t) \cdot \exp(-R_2 t) \cdot \exp(i\Phi) \quad (188),$$

where $\alpha$ denotes the chemical shift, $R_2$ represents the transverse relaxation rate constant and $\Phi$ is the phase error, one obtains (Cavanagh et al., "Protein NMR Spectroscopy," 2nd Ed., San Diego: Academic Press (2007), which is hereby incorporated by reference in its entirety) after FT for the real part $$Re(\mathcal{F}[S(t)]) = A(\omega)\cos\Phi - D(\omega)\sin\Phi \quad (189),$$

with $A(\omega) = R_2/[R_2^2 + (\alpha-\omega)^2]$ and $D(\omega) = (\alpha-\omega)/[R_2^2 + (\alpha-\omega)^2]$ representing the absorptive and dispersive peak components. For a given $\Phi$, the signal maximum, $I_0^{States}(\Phi)$ and its position $\omega'$ can be calculated by solving $$\frac{d}{d\omega}(A(\omega)\cos\Phi - D(\omega)\sin\Phi) = 0, \quad (190)$$

which yields $$\omega' = \alpha - R_2\left(\frac{\cos\Phi - 1}{\sin\Phi}\right) = \alpha - \frac{\omega_{FWHH}}{2}\left(\frac{\cos\Phi - 1}{\sin\Phi}\right) = tg^2\frac{\Phi}{2} \quad (191)$$

or $$\nu' = \nu_0 - \frac{\nu_{FWHH}}{2}\left(\frac{\cos\Phi - 1}{\sin\Phi}\right) = tg^2\frac{\Phi}{2},$$

where $\nu_0 = \alpha/2\pi$ and $2R_2 = \omega_{FWHH} = 2\pi\nu_{FWHH}$ denotes the full width at half height. With $\nu_{FWHH} \sim 140$ Hz and $\Phi = \pm 15°$, the shift $\alpha - \omega'$ in the position of the maximum according to Eq. 191 thus amounts to be ~10 Hz.

Substituting into the expression of $A(\omega)$ the value of $\omega'$ one obtains the maximum intensity of a mixed phase signal with phase error $\Phi$:

$$I_0^{States}(\Phi) = \cos\Phi \frac{R_2}{R_2^2 + R_2^2\left(\frac{\cos\Phi - 1}{\sin\Phi}\right)^2} - \sin\Phi \frac{R_2\left(\frac{\cos\Phi - 1}{\sin\Phi}\right)}{R_2^2 + R_2^2\left(\frac{\cos\Phi - 1}{\sin\Phi}\right)^2} = \frac{\sin^2\Phi}{2R_2(1-\cos\Phi)} = \frac{\cos^2\frac{\Phi}{2}}{R_2}. \quad (192)$$

The maximum intensity, $I_0^{States}(\Phi=0)$, of an absorptive Lorentzian line is calculated by substituting $\omega=\alpha$ in the expression of $A(\omega)$ given above, yielding $I_0^{States}(\Phi=0)=1/R_2$. Hence, the ratio of the intensities of the signal with phase error and the absorptive Lorenstzian line is given by $$\Re^{States} = \frac{I_0^{States}(\Phi)}{I_0^{States}(\Phi=0)} = \frac{\sin^2\Phi}{2R_2(1-\cos\Phi)} \bigg/ \frac{1}{R_2} = \frac{\sin^2\Phi}{2(1-\cos\Phi)} = \cos^2\frac{\Phi}{2}. \quad (193)$$

With Eq. 80, the ratio of the intensities of the clean absorption mode signal obtained by $(c_{+1},c_{-1})$-PMS, and the absorptive Lorentzian signal is given by $$\Re^{PMS} = \frac{I_0^{States}(0)\cos\Phi}{I_0^{States}(0)} = \cos\Phi. \quad (194)$$

FIG. 2 shows the reduction (in %) of the signal maximum, as $(1-\Re)\times 100$ for both 'States' and $(c_{+1},c_{-1})$-PMS versus $\Phi$.

Implementation and Product Operator Formalism of Mirrored Sampling for 'Non-Constant Time' Evolution Periods Another aspect of the present invention relates to implementation and product operator formalism of mirrored sampling for 'non-constant time' evolution periods.

States' Forward and Backward Sampling for Obtaining $^{13}$C Frequency-Labeled Magnetization (e.g. 2D [$^{13}$C,$^1$H]-HSQC)

A product operator description (Ernst et al., "Principles of Nuclear Magnetic Resonance in One and Two Dimensions," Oxford: Oxford University Press (1987); Jacobsen, N. E., "NMR Spectroscopy Explained," Wiley, New York (2007), which are hereby incorporated by reference in their entirety) for forward and backward sampling of $^{13}$C chemical shifts in non-constant time 2D [$^{13}$C,$^1$H]-HSQC (Cavanagh et al., "Protein NMR Spectroscopy," 2nd Ed., San Diego: Academic Press (2007), which is hereby incorporated by reference in its entirety) (FIG. 3A-B) is provided. The operators representing $^{13}$C and $^1$H are denoted 'C' and 'H', respectively, and only terms yielding detected signal are retained. Before the first 90° pulse on $^{13}$C is applied, the density matrix $\sigma(t_A)$ is proportional to (Cavanagh et al., "Protein NMR Spectroscopy," 2nd Ed., San Diego Academic Press (2007), which is hereby incorporated by reference in its entirety) $H_zC_z$, and after frequency-labeling the density matrix $\sigma(t_B)$ is again proportional to $H_zC_z$. Hence, in all cases the product operator description starts and ends with density matrices which are proportional to $H_zC_z$, while they are modulated differently with the $^{13}$C shift as is required when considering the interferograms introduced in the section above.

Note that backward sampling requires the introduction of an additional 180° pulse on $^{13}C$ (FIGS. 3A-B). To ensure identical duty cycles for forward and backward sampling, a 180° pulse on $^{13}C$ is also introduced for forward sampling.

($c_{+0}, c_{+2}$)-Sampling

The required interferograms are defined in Eq. 2.

$c_{+0}$-Interferogram (FIG. 3A—Forward)

$$\sigma(t_A) \propto H_zC_z \xrightarrow{(90°)_{3\pi/2}} -H_zC_x \xrightarrow{\alpha} -H_zC_x\cos(\alpha t) - H_zC_y\sin(\alpha t) \xrightarrow{(180°)_0} \quad (195)$$
$$-H_zC_x\cos(\alpha t) + H_zC_y\sin(\alpha t) \xrightarrow{(90°)_{\pi/2}} \sigma(t_B) \propto H_zC_z\cos(\alpha t).$$

$c_{+2}$-Interferogram (FIG. 3A—Forward)

$$\sigma(t_A) \propto H_zC_z \xrightarrow{(90°)_0} -H_zC_y \xrightarrow{\alpha} -H_zC_x\cos(\alpha t) + H_zC_y\sin(\alpha t) \xrightarrow{(180°)_0} \quad (196)$$
$$H_zC_x\cos(\alpha t) + H_zC_x\sin(\alpha t) \xrightarrow{(90°)_{\pi/2}} \sigma(t_B) \propto -H_zC_z\sin(\alpha t) =$$
$$H_zC_z\cos\left(\alpha t + \frac{\pi}{2}\right).$$

($c_{-0}, c_{-2}$)-Sampling

The required interferograms are defined in Eq. 6.

$c_{-0}$—Interferogram (FIG. 3B—Backward)

$$\sigma(t_A) \propto H_zC_z \xrightarrow{(90°)_{3\pi/2}} \quad (197)$$
$$-H_zC_x \xrightarrow{(180°)_0} -H_zC_x \xrightarrow{\alpha} -H_zC_x\cos(\alpha t) - H_zC_x\sin(\alpha t) \xrightarrow{(90°)_{\pi/2}}$$
$$\sigma(t_B) \propto H_zC_z\cos(\alpha t) = H_zC_z\cos(\alpha t).$$

$c_{-2}$—Interferogram (FIG. 3B—Backward)

$$\sigma(t_A) \propto H_zC_z \xrightarrow{(90°)_0} \quad (198)$$
$$-H_zC_x \xrightarrow{(180°)_0} H_zC_y \xrightarrow{\alpha} H_zC_y\cos(\alpha t) - H_zC_x\sin(\alpha t) \xrightarrow{(90°)_{\pi/2}}$$
$$\sigma(t_B) \propto H_zC_z\sin(\alpha t) = H_zC_z\cos\left(-\alpha t + \frac{\pi}{2}\right).$$

$\pi/4$ and $3\pi/4$-shifted mirrored sampling for obtaining $^{13}C$ frequency-labeled magnetization (e.g. 2D [$^{13}C$,$^{1}H$]-HSQC)

Note that for obtaining the $c_{+1}$ and $c_{-1}$-interferograms, $\phi=-\pi/4$, and for the $c_{+3}$ or $c_{-3}$-interferograms, $\phi=\pi/4$ (FIGS. 3A-B).

($c_{+1}, c_{-1}$)-Sampling (PMS)

The required interferograms are defined in Eq. 13.

$c_{+1}$—Interferogram (FIG. 3A—Forward)

$$\sigma(t_A) \propto H_zC_z \xrightarrow{(90°)_{-\pi/4}} \quad (199)$$
$$-\frac{1}{\sqrt{2}}(H_zC_x + H_zC_y) \xrightarrow{\alpha} -\frac{1}{\sqrt{2}}(H_zC_x\cos(\alpha t) +$$
$$H_zC_y\sin(\alpha t) + H_zC_y\cos(\alpha t) - H_zC_x\sin(\alpha t)) \xrightarrow{(180°)_0}$$

$$-\frac{1}{\sqrt{2}}(H_zC_x\cos(\alpha t) - H_zC_y\sin(\alpha t) - H_zC_y\cos(\alpha t) -$$
$$H_zC_x\sin(\alpha t)) \xrightarrow{(90°)_{\pi/2}}$$
$$\sigma(t_B) \propto H_zC_z(\cos(\alpha t) - \sin(\alpha t)) = H_zC_z\cos\left(\alpha t + \frac{\pi}{2}\right).$$

$c_{-1}$—Interferogram (FIG. 3B—Backward)

$$\sigma(t_A) \propto H_zC_z \xrightarrow{(90°)_{-\pi/4}} \quad (200)$$
$$-\frac{1}{\sqrt{2}}(H_zC_x + H_zC_y) \xrightarrow{(180°)_0} -\frac{1}{\sqrt{2}}(H_zC_x - H_zC_y) \xrightarrow{\alpha}$$
$$-\frac{1}{\sqrt{2}}(H_zC_x\cos(\alpha t) + H_zC_y\sin(\alpha t) - H_zC_y\cos(\alpha t) +$$
$$H_zC_x\sin(\alpha t)) \xrightarrow{(90°)_{\pi/2}}$$
$$\sigma(t_B) \propto \frac{1}{\sqrt{2}}H_zC_z(\cos(\alpha t) + \sin(\alpha t)) = H_zC_z\cos\left(-\alpha t + \frac{\pi}{2}\right).$$

($c_{+3}, c_{-3}$)-Sampling (PMS)

The required interferograms are defined in Eq. 17.

$c_{+3}$—Interferogram (FIG. 3A—Forward)

$$\sigma(t_A) \propto H_zC_z \xrightarrow{(90°)_{\pi/4}} \quad (201)$$
$$\frac{1}{\sqrt{2}}(H_zC_x - H_zC_y) \xrightarrow{\alpha} \frac{1}{\sqrt{2}}(H_zC_x\cos(\alpha t) + H_zC_y\sin(\alpha t) -$$
$$H_zC_y\cos(\alpha t) + H_zC_x\sin(\alpha t)) \xrightarrow{(180°)_0}$$
$$\frac{1}{\sqrt{2}}(H_zC_x\cos(\alpha t) - H_zC_y\sin(\alpha t) + H_zC_y\cos(\alpha t) +$$
$$H_zC_x\sin(\alpha t)) \xrightarrow{(90°)_{\pi/2}} \sigma(t_B) \propto$$
$$-\frac{1}{\sqrt{2}}H_zC_z(\cos(\alpha t) + \sin(\alpha t)) = H_zC_z\cos\left(\alpha t + \frac{3\pi}{4}\right).$$

$c_{-3}$—Interferogram (FIG. 3B—Backward)

$$\sigma(t_A) \propto H_zC_z \xrightarrow{(90°)_{\pi/4}} \quad (202)$$
$$\frac{1}{\sqrt{2}}(H_zC_x - H_zC_y) \xrightarrow{(180°)_0} \frac{1}{\sqrt{2}}(H_zC_x + H_zC_y) \xrightarrow{\alpha}$$
$$\frac{1}{\sqrt{2}}(H_zC_x\cos(\alpha t) + H_zC_y\sin(\alpha t) + H_zC_y\cos(\alpha t) -$$
$$H_zC_x\sin(\alpha t)) \xrightarrow{(90°)_{\pi/2}} \sigma(t_B) \propto$$
$$-\frac{1}{\sqrt{2}}H_zC_z(\cos(\alpha t) - \sin(\alpha t)) = H_zC_z\cos\left(-\alpha t + \frac{3\pi}{4}\right).$$

Time-Proportional Phase Incrementation (TPPI)

Inspection of Eq. (B2) shows that, in one embodiment, the cases $\{\psi_j=n\pi/2$ and $\delta_j=m\pi\}$ with n=0, 1, 2, 3 and m=0, 1, need to be excluded to ensure phase-sensitive detection of chemical shifts (see paragraph [0015]). However, for these excluded cases, phase sensitive detection can be accomplished by use of time-proportional phase incrementation (TPPI) of radio-frequency pulse or receiver phases, a well known art in the field to detect chemical shifts phase-sensitively (Ernst et al.

"Principles of Nuclear Magnetic Resonance in One and Two Dimensions," Oxford:

Oxford University Press (1987), which is hereby incorporated by reference in its entirety).

Sensitivity Enhancement

Combined forward and backward time domain sampling as described herein can be employed in conjunction with preservation of equivalent pathways (PEP), an approach commonly used to enhance the sensitivity of NMR data acquisition (Cavanagh et al., "Protein NMR Spectroscopy," 2nd Ed., San Diego: Academic Press (2007), which is hereby incorporated by reference in its entirety).

Transverse Relaxation-Optimized NMR Spectroscopy

Transverse relaxation optimized NMR spectroscopy (TROSY) relies on spin-state selective measurement of chemical shifts to enhance sensitivity (Pervushin et al., *Proc. Natl. Acad. Sci. U.S.A.*, 94:12366-12371 (1997), which is hereby incorporated by reference in its entirety). Combined forward and backward time domain sampling as described herein can be employed for TROSY.

Simultaneous Phase Cycled NMR Spectroscopy

Simultaneous phase cycled NMR spectroscopy is a method of simultaneously conducting more than one step of a radiofrequency phase cycle in a nuclear magnetic resonance experiment (U.S. Pat. No. 7,408,346 to Szyperski et al., which is hereby incorporated by reference in its entirety). Combined forward and backward time domain sampling as described herein can be employed for simultaneous phase cycled NMR spectroscopy.

P- and N-Type Time Domain Data Acquisition

Phase sensitive detection can be accomplished by use of pulsed magnetic field gradients such that the amplitude modulation encoded in the C-vectors is encoded in the signal phase instead, yielding P- and N-type time domain (Cavanagh et al., "Protein NMR Spectroscopy," 2nd Ed., San Diego: Academic Press (2007), which is hereby incorporated by reference in its entirety). Linear combination of P- and N-type time domain yields the amplitude modulated C-vectors. Hence, such P- and N-type time domain data acquisition can be readily combined with combined forward and backward time domain sampling as described herein.

Transformation by Use of Operator

The inventions described herein make use of transforming time domain into frequency domain. Routinely, this is accomplished by use of Fourier Transformation represented by operator F (Ernst et al., "Principles of Nuclear Magnetic Resonance in One and Two Dimensions," Oxford: Oxford University Press (1987), which is hereby incorporated by reference in its entirety) employed after multiplication of the C-vector with D-matrix and Q-vector. Since F is a linear operator, C-vectors can alternatively first be Fourier transformed into frequency domain and then multiplied with D-matrix and Q-vector.

Other approaches relying on operators 0 with distinctly different mathematical properties when compared with F have been established to transform time domain into frequency domain (Hoch et al. "NMR Data Processing", Wiley, New York (1996), which is hereby incorporated by reference in its entirety). For any approach relying on a linear operator L, the operator can be employed as is described for F above. However, for non-linear operators (representing, for example, the 'maximum entropy method'), the transformation from time domain into frequency domain is preferably, or necessarily, performed after multiplication of the C-vector with D-matrix and Q-vector in time domain.

EXAMPLES

The Examples set forth below are for illustrative purposes only and are not intended to limit, in any way, the scope of the present invention.

Example 1

Clean Absorption Mode NMR Data Acquisition for Identical Secondary Phase Shifts

Data Acquisition

NMR spectra were acquired for $^{13}C$, $^{15}N$-labeled 8 kDa protein CaR178. All NMR spectra were acquired at 25° C. for CaR178, a target of the Northeast Structural Genomics Consortium (http://www.nesg.org), on a Varian INOVA 600 spectrometer equipped with a cryogenic $^{1}H\{^{13}C,^{15}N\}$-triple resonance probe. The $^{1}H$ carrier frequency was set to the water line at 4.7 ppm throughout.

Non-constant time 2D $[^{13}C,^{1}H]$-HSQC spectra comprising aliphatic signals (FIGS. 4A-I) were recorded along $t_1(^{13}C)$ and $t_2(^{1}H)$, respectively, with spectral widths of 80.0 ppm and 13.4 ppm and $t_{1,max}(^{13}C)=42$ ms and $t_{2,max}(^{1}H)=64$ ms. The $^{13}C$ carrier frequency was set to 35.0 ppm.

Simultaneous constant time (Cavanagh et al., "Protein NMR Spectroscopy," 2nd Ed., San Diego: Academic Press (2007), which is hereby incorporated by reference in its entirety) 2D $[^{13}C^{aliphatic}/^{13}C^{aromatic}]$-HSQC spectra comprising aliphatic and aromatic signals (FIG. 5) were recorded, respectively, with spectral widths of 68.0 ppm and 13.4 ppm along $t_1(^{13}C)$ and $t_2(^{1}H)$ and $t_{1,max}(^{13}C)=21$ ms and $t_{2,max}(^{1}H)=64$ ms. The $^{13}C$ carrier frequency was set to 43.0 ppm. Hence, aromatic signals were folded once along $\omega_1(^{13}C)$.

3D HC(C)H-TOCSY (Cavanagh et al., "Protein NMR Spectroscopy," 2nd Ed., San Diego: Academic Press (2007); Bax et al., *J. Magn. Reson.* 88:425-431 (1990), which are hereby incorporated by reference in their entirety) spectra comprising aliphatic signals (FIGS. 6A-B) were recorded, respectively, with spectral widths of 13.4 ppm, 80.0 ppm and 13.4 ppm along $t_1(^{1}H)$, $t_2(^{13}C)$ and $t_3(^{1}H)$, and $t_{1,max}(^{1}H)=12$ ms, $t_{2,max}(^{13}C)=11$ ms and $t_{3,max}(^{1}H)=64$ ms. The $^{13}C$ carrier frequency was set to 36.0 ppm.

GFT (4,3)D $C^{\alpha\beta}C^{\beta}(CO)NHN$ spectra (FIG. 7) were recorded, respectively, with spectral widths of 80.0 ppm, 32.0 ppm and 13.4 ppm along $t_1(^{13}C^{\alpha};^{13}C^{\alpha\beta})$, $t_2(^{15}N)$ and $t_3(^{1}HN)$, and $t_{1,max}(^{13}C^{\alpha};^{13}C^{\alpha\beta})=7$ ms, $t_{2,max}(^{15}N)=16$ ms and $t_{3,max}(^{1}HN)=64$ ms. The $^{13}C$ carrier frequency was set to 43.0 ppm during the $^{13}C^{\alpha\beta}$ shift evolution, and to 56.0 ppm during the $^{13}C^{\alpha}$ shift evolution. The $^{15}N$ carrier frequency was set at 118.0 ppm.

D and G matrix transformations were performed using programs written in C. Subsequently, spectra were processed and analyzed using the programs nmrPipe (Delaglio et al., *J. Biomol. NMR*, 6:277-293 (1995), which is hereby incorporated by reference in its entirety) and XEASY (Bartels et al., *J. Biomol. NMR*, 6:1-10 (1995), which is hereby incorporated by reference in its entirety). Prior to FT, time domain data were multiplied by sine square bell window functions shifted by 75° and zero-filled at least twice. To ensure artifact-free signal comparison, no linear prediction (Cavanagh et al., "Protein NMR Spectroscopy," 2nd Ed., San Diego: Academic Press (2007), which is hereby incorporated by reference in its entirety) was applied.

Data Processing

In this section, the data processing of PMS and DPMS spectra presented in Example 1 is described.

The interferograms $$c_{\pm n} := \cos\left(\pm \alpha t + \frac{n\pi}{4} + \Phi\right)$$

were recorded and linearly combined (D matrix transformation) as described above. D matrix transformation was followed by transformation with either Q vector or G matrix (for GFT experiments). Finally, Fourier transformation (FT) generated the desired frequency domain spectrum.

$(c_{+1}, c_{-1})$-PMS Simultaneous 2D $[^{13}C^{aliph}/^{13}C^{arom}, ^{1}H]$-HSQC Time domain data corresponding to $(c_{+1}, c_{-1})$-PMS of $t_1(^{13}C)$ dimension consists of two 1D interferograms:

$$S_{+1,-1}(t_1) \propto \begin{bmatrix} c_{+1}(t_1) \\ c_{-1}(t_1) \end{bmatrix}. \tag{203}$$

The two interferograms recorded for the experiment are listed in Table 2.

TABLE 2

Interferograms recorded for $t_1(^{13}C)$-$(c_{+1}, c_{-1})$ simultaneous 2D $[^{13}C^{aliph}/^{13}C^{arom}, ^{1}H]$-HSQC

| Interferogram | Sampling of $t_1(^{13}C)$ | Modulation of detected signal ($\alpha_1 \equiv {}^{13}C$) |
|---|---|---|
| I1 | $c_{+1}$ | $\cos\left(\alpha_1 t_1 + \frac{\pi}{4} + \Phi_1\right)$ |
| I2 | $c_{-1}$ | $\cos\left(-\alpha_1 t_1 + \frac{\pi}{4} + \Phi_1\right)$ |

With Eq. 92, for $(c_{+1}, c_{-1})$-PMS sampling $D_{+1,-1}$ is given by $$D_{+1,-1} = \begin{bmatrix} 1 & 1 \\ -1 & 1 \end{bmatrix}, \tag{204}$$

yielding, with the interferograms of Table 2, the linear combinations of Table 3.

TABLE 3

Linearly combined interferograms after D matrix transformation

| Combined interferograms | Linear combination | Modulation of detected signal ($\alpha_1 \equiv {}^{13}C$) |
|---|---|---|
| L1 | +I1 +I2 | $\cos\left(\frac{\pi}{4} + \Phi_1\right)\cos(\alpha_1 t_1)$ |

TABLE 3-continued

Linearly combined interferograms after D matrix transformation

| Combined interferograms | Linear combination | Modulation of detected signal ($\alpha_1 \equiv {}^{13}C$) |
|---|---|---|
| L2 | −I1 +I2 | $\sin\left(\frac{\pi}{4} + \Phi_1\right)\sin(\alpha_1 t_1)$ |

The linearly combined interferograms are then transformed with the vector Q=[1 i] to construct the spectrum comprising of complex time domain signal as $S_{+1,-1}(t)=L1+i*L2$. Complex FT yields the desired the frequency domain spectrum as shown in FIG. 5.

$(c_{+1}, c_{-1}, c_{+3}, c_{-3})$-DPMS 3D HC(C)H TOCSY

DPMS of more than one indirect dimension requires all combinations of PMS sampling as described in the sections above. The time domain data resulting from $(c_{+1}, c_{-1}, c_{+3}, c_{-3})$-DPMS of two indirect dimensions consist of 16 interferograms:

$$[S_{+1,-1}(t_2) + S_{+3,-3}(t_2)] \otimes [S_{+1,-1}(t_1) + S_{+3,-3}(t_1)] = \tag{205}$$

$$S_{+1,-1}(t_2) \otimes S_{+1,-1}(t_1) + S_{+1,-1}(t_2) \otimes S_{+3,-3}(t_1) +$$

$$S_{+3,-3}(t_2) \otimes S_{+1,-1}(t_1) + S_{+3,-3}(t_2) \otimes S_{+3,-3}(t_1) \propto$$

$$\begin{bmatrix} c_{+1}(t_2) \\ c_{-1}(t_2) \end{bmatrix} \otimes \begin{bmatrix} c_{+1}(t_1) \\ c_{-1}(t_1) \end{bmatrix} + \begin{bmatrix} c_{+1}(t_2) \\ c_{-1}(t_2) \end{bmatrix} \otimes \begin{bmatrix} c_{+3}(t_1) \\ c_{-3}(t_1) \end{bmatrix} + \begin{bmatrix} c_{+3}(t_2) \\ c_{-3}(t_2) \end{bmatrix} \otimes$$

$$\begin{bmatrix} c_{+1}(t_1) \\ c_{-1}(t_1) \end{bmatrix} + \begin{bmatrix} c_{+3}(t_2) \\ c_{-3}(t_2) \end{bmatrix} \otimes \begin{bmatrix} c_{+3}(t_1) \\ c_{-3}(t_1) \end{bmatrix} = \begin{bmatrix} c_{+1}(t_2)c_{+1}(t_1) \\ c_{+1}(t_2)c_{-1}(t_1) \\ c_{-1}(t_2)c_{+1}(t_1) \\ c_{-1}(t_2)c_{-1}(t_1) \end{bmatrix} +$$

$$\begin{bmatrix} c_{+1}(t_2)c_{+3}(t_1) \\ c_{+1}(t_2)c_{-3}(t_1) \\ c_{-1}(t_2)c_{+3}(t_1) \\ c_{-1}(t_2)c_{-3}(t_1) \end{bmatrix} + \begin{bmatrix} c_{+3}(t_2)c_{+1}(t_1) \\ c_{+3}(t_2)c_{-1}(t_1) \\ c_{-3}(t_2)c_{+1}(t_1) \\ c_{-3}(t_2)c_{-1}(t_1) \end{bmatrix} +$$

$$\begin{bmatrix} c_{+3}(t_2)c_{+3}(t_1) \\ c_{+3}(t_2)c_{-3}(t_1) \\ c_{-3}(t_2)c_{+3}(t_1) \\ c_{-3}(t_2)c_{-3}(t_1) \end{bmatrix}.$$

In $(c_{+1}, c_{-1}, c_{+3}, c_{-3})$-DPMS 3D HC(C)H TOCSY, $^1$H and $^{13}$C are sampled, respectively, in $t_1$ and $t_2$. The 16 interferograms of Eq. 205 were recorded and are listed explicitly in Table 4. The interferograms of the four terms in the last line of Eq. 205 correspond to the four sections separated by dashed line in Table 4.

TABLE 4

2D interferograms recorded for ($c_{+1}$, $c_{-1}$, $c_{+3}$, $c_{-3}$)-DPMS 3D HC(C)H TOCSY

| Interferogram | Sampling of $t_1(^1H)$ | Sampling of $t_2(^{13}C)$ | Modulation of detected signal ($\alpha_1 \equiv {}^1H$, $\alpha_2 \equiv {}^{13}C$) |
|---|---|---|---|
| Set A: | | | |
| I1 | $c_{+1}$ | $c_{+1}$ | $\cos(\alpha_1 t_1 + \frac{\pi}{4} + \Phi_1)\cos(\alpha_2 t_2 + \frac{\pi}{4} + \Phi_2)$ |
| I2 | $c_{+1}$ | $c_{-1}$ | $\cos(\alpha_1 t_1 + \frac{\pi}{4} + \Phi_1)\cos(-\alpha_2 t_2 + \frac{\pi}{4} + \Phi_2)$ |
| I3 | $c_{-1}$ | $c_{+1}$ | $\cos(-\alpha_1 t_1 + \frac{\pi}{4} + \Phi_1)\cos(\alpha_2 t_2 + \frac{\pi}{4} + \Phi_2)$ |
| I4 | $c_{-1}$ | $c_{-1}$ | $\cos(-\alpha_1 t_1 + \frac{\pi}{4} + \Phi_1)\cos(-\alpha_2 t_2 + \frac{\pi}{4} + \Phi_2)$ |
| Set B: | | | |
| I5 | $c_{+1}$ | $c_{+3}$ | $\cos(\alpha_1 t_1 + \frac{\pi}{4} + \Phi_1)\cos(\alpha_2 t_2 + \frac{3\pi}{4} + \Phi_2)$ |
| I6 | $c_{+1}$ | $c_{-3}$ | $\cos(\alpha_1 t_1 + \frac{\pi}{4} + \Phi_1)\cos(-\alpha_2 t_2 + \frac{3\pi}{4} + \Phi_2)$ |
| I7 | $c_{-1}$ | $c_{+3}$ | $\cos(-\alpha_1 t_1 + \frac{\pi}{4} + \Phi_1)\cos(\alpha_2 t_2 + \frac{3\pi}{4} + \Phi_2)$ |
| I8 | $c_{-1}$ | $c_{-3}$ | $\cos(-\alpha_1 t_1 + \frac{\pi}{4} + \Phi_1)\cos(-\alpha_2 t_2 + \frac{3\pi}{4} + \Phi_2)$ |
| Set C: | | | |
| I9 | $c_{+3}$ | $c_{+1}$ | $\cos(\alpha_1 t_1 + \frac{3\pi}{4} + \Phi_1)\cos(\alpha_2 t_2 + \frac{\pi}{4} + \Phi_2)$ |
| I10 | $c_{+3}$ | $c_{-1}$ | $\cos(\alpha_1 t_1 + \frac{3\pi}{4} + \Phi_1)\cos(-\alpha_2 t_2 + \frac{\pi}{4} + \Phi_2)$ |
| I11 | $c_{-3}$ | $c_{+1}$ | $\cos(-\alpha_1 t_1 + \frac{3\pi}{4} + \Phi_1)\cos(\alpha_2 t_2 + \frac{\pi}{4} + \Phi_2)$ |
| I12 | $c_{-3}$ | $c_{-1}$ | $\cos(-\alpha_1 t_1 + \frac{3\pi}{4} + \Phi_1)\cos(-\alpha_2 t_2 + \frac{\pi}{4} + \Phi_2)$ |
| Set D: | | | |
| I13 | $c_{+3}$ | $c_{+3}$ | $\cos(\alpha_1 t_1 + \frac{3\pi}{4} + \Phi_1)\cos(\alpha_2 t_2 + \frac{3\pi}{4} + \Phi_2)$ |
| I14 | $c_{+3}$ | $c_{-3}$ | $\cos(\alpha_1 t_1 + \frac{3\pi}{4} + \Phi_1)\cos(-\alpha_2 t_2 + \frac{3\pi}{4} + \Phi_2)$ |
| I15 | $c_{-3}$ | $c_{+3}$ | $\cos(-\alpha_1 t_1 + \frac{3\pi}{4} + \Phi_1)\cos(\alpha_2 t_2 + \frac{3\pi}{4} + \Phi_2)$ |
| I16 | $c_{-3}$ | $c_{-3}$ | $\cos(-\alpha_1 t_1 + \frac{3\pi}{4} + \Phi_1)\cos(-\alpha_2 t_2 + \frac{3\pi}{4} + \Phi_2)$ |

Set A of four 2D interferograms (I1 to I4) result from $(c_{+1}, c_{-1})$-PMS of two indirect dimensions. With Eq. 92, $D_{t2,t1-(+1,-1)}$ for $(c_{+1}, c_{-1})$-PMS sampling of two indirect dimensions is given by $$D_{t2,t1-(+1,-1)} = \begin{bmatrix} 1 & 1 \\ -1 & 1 \end{bmatrix}_{t2} \otimes \begin{bmatrix} 1 & 1 \\ -1 & 1 \end{bmatrix}_{t1} = \begin{bmatrix} 1 & 1 & 1 & 1 \\ -1 & 1 & -1 & 1 \\ -1 & -1 & 1 & 1 \\ 1 & -1 & -1 & 1 \end{bmatrix}, \quad (206)$$

yielding, with set A of four interferograms of Table 4, linear combinations L1-L4 of Table 5.

The linearly combined interferograms are then transformed by the vector $Q(1)=Q \otimes Q=[1\ i\ i\ -1]$ to construct the spectrum comprising complex time domain signal $S_{t2,t1-(1,-1)}(t)=L1+i*L2+i*L3-L4$. The frequency domain spectrum obtained after FT of the complex signal corresponds to Eq. 100.

Set B of four 2D interferograms (I5 to I8) result from $(c_{+1}, c_{-1})$-PMS for $t_1$ ($^1$H) and $(c_{+3}, c_{-3})$-PMS for $t_2$ ($^{13}$C) and the corresponding D matrix transformation is given by:

$$D_{t2-(+3,-3),t1-(+1,-1)} = \qquad (207)$$
$$\begin{bmatrix} -1 & -1 \\ -1 & 1 \end{bmatrix}_{t2} \otimes \begin{bmatrix} 1 & 1 \\ -1 & 1 \end{bmatrix}_{t1} = \begin{bmatrix} -1 & -1 & -1 & -1 \\ 1 & -1 & 1 & -1 \\ -1 & -1 & 1 & 1 \\ 1 & -1 & -1 & 1 \end{bmatrix},$$

yielding, with set B of four interferograms of Table 4, linear combinations L5-L8 of Table 5.

The linearly combined interferograms are then transformed by the vector $Q(1)=Q \otimes Q=[1\ i\ i\ -1]$ to construct the spectrum comprising complex time domain signal $S_{t2-(3,-3),\ t1-(1,-1)}(t)=L5+i*L6+i*L7-L8$. The frequency domain spectrum obtained after FT of the complex signal corresponds to Eq. 104.

Set C of four 2D interferograms (I9 to I12) result from $(c_{+3}, c_{-3})$—PMS for $t_1$($^1$H) and $(c_{+1}, c_{-1})$—PMS for $t_2$ ($^{13}$C) and the corresponding D matrix transformation is given by:

$$D_{t2-(+1,-1),t1-(+3,-3)} = \qquad (208)$$
$$\begin{bmatrix} 1 & 1 \\ -1 & 1 \end{bmatrix}_{t2} \otimes \begin{bmatrix} -1 & -1 \\ -1 & 1 \end{bmatrix}_{t1} = \begin{bmatrix} -1 & -1 & -1 & -1 \\ -1 & 1 & -1 & 1 \\ 1 & 1 & -1 & -1 \\ 1 & -1 & -1 & 1 \end{bmatrix},$$

yielding, with set C of four interferograms of Table 4, linear combinations L9-L12 of Table 5.

The linearly combined interferograms are then transformed by the vector $Q(1)=Q \otimes Q=[1\ i\ i\ -1]$ to construct the spectrum comprising complex time domain signal $S_{t2-(1,-1),\ t1-(3,-3)}(t)=L9+i*L10+i*L11-L12$. The frequency domain spectrum obtained after FT of the complex signal corresponds to Eq. 108.

Set D of four 2D interferograms (I13 to I16) of Table 4 result from $(c_{+3}, c_{-3})$-PMS for $t_1$ ($^1$H) and $(C_{+3}, c_{-3})$-PMS for $t_2$ ($^{13}$C) and the corresponding D-matrix transformation is given by:

$$D_{t2-(+3,-3),t1-(+3,-3)} = \qquad (209)$$
$$\begin{bmatrix} -1 & -1 \\ -1 & 1 \end{bmatrix}_{t2} \otimes \begin{bmatrix} -1 & -1 \\ -1 & 1 \end{bmatrix}_{t1} = \begin{bmatrix} 1 & 1 & 1 & 1 \\ 1 & -1 & 1 & -1 \\ 1 & 1 & -1 & -1 \\ 1 & -1 & -1 & 1 \end{bmatrix},$$

yielding, with set D of four interferograms of Table 4, linear combinations L13-L16 of Table 5.

The linearly combined interferograms are then transformed by the vector $Q(1)=Q \otimes Q=[1\ i\ i\ -1]$ to construct the spectrum comprising complex time domain signal $S_{t2-(3,-3),t1-(3,-3)}(t)=L13+i*L14+i*L15-L16$. The frequency domain spectrum obtained after FT of the complex signal corresponds to Eq. 111.

TABLE 5

Linearly combined interferograms after D matrix transformation

| Combined interferograms | Linear combination | Modulation of detected signal ($\alpha_1 = {}^1$H, $\alpha_2 = {}^{13}$C) |
|---|---|---|
| L1 | +I1 +I2 +I3 +I4 | $\cos(\frac{\pi}{4}+\Phi_1)\cos(\frac{\pi}{4}+\Phi_2)\cos(\alpha_1 t_1)\cos(\alpha_2 t_2)$ |
| L2 | −I1 +I2 −I3 +I4 | $\cos(\frac{\pi}{4}+\Phi_1)\sin(\frac{\pi}{4}+\Phi_2)\cos(\alpha_1 t_1)\sin(\alpha_2 t_2)$ |
| L3 | −I1 −I2 +I3 +I4 | $\sin(\frac{\pi}{4}+\Phi_1)\cos(\frac{\pi}{4}+\Phi_2)\sin(\alpha_1 t_1)\cos(\alpha_2 t_2)$ |
| L4 | +I1 −I2 −I3 +I4 | $\sin(\frac{\pi}{4}+\Phi_1)\sin(\frac{\pi}{4}+\Phi_2)\sin(\alpha_1 t_1)\sin(\alpha_2 t_2)$ |
| L5 | −I5 −I6 −I7 −I8 | $\cos(\frac{\pi}{4}+\Phi_1)\sin(\frac{\pi}{4}+\Phi_2)\cos(\alpha_1 t_1)\cos(\alpha_2 t_2)$ |
| L6 | +I5 −I6 +I7 −I8 | $\cos(\frac{\pi}{4}+\Phi_1)\cos(\frac{\pi}{4}+\Phi_2)\cos(\alpha_1 t_1)\sin(\alpha_2 t_2)$ |
| L7 | −I5 −I6 +I7 +I8 | $\sin(\frac{\pi}{4}+\Phi_1)\sin(\frac{\pi}{4}+\Phi_2)\sin(\alpha_1 t_1)\cos(\alpha_2 t_2)$ |
| L8 | +I5 −I6 −I7 +I8 | $\sin(\frac{\pi}{4}+\Phi_1)\cos(\frac{\pi}{4}+\Phi_2)\sin(\alpha_1 t_1)\sin(\alpha_2 t_2)$ |
| L9 | −I9 −I10 −I11 −I12 | $\sin(\frac{\pi}{4}+\Phi_1)\cos(\frac{\pi}{4}+\Phi_2)\cos(\alpha_1 t_1)\cos(\alpha_2 t_2)$ |
| L10 | −I9 +I10 −I11 +I12 | $\sin(\frac{\pi}{4}+\Phi_1)\sin(\frac{\pi}{4}+\Phi_2)\cos(\alpha_1 t_1)\sin(\alpha_2 t_2)$ |
| L11 | +I9 +I10 −I11 −I12 | $\cos(\frac{\pi}{4}+\Phi_1)\cos(\frac{\pi}{4}+\Phi_2)\sin(\alpha_1 t_1)\cos(\alpha_2 t_2)$ |
| L12 | +I9 −I10 −I11 +I12 | $\cos(\frac{\pi}{4}+\Phi_1)\sin(\frac{\pi}{4}+\Phi_2)\sin(\alpha_1 t_1)\sin(\alpha_2 t_2)$ |

TABLE 5-continued

Linearly combined interferograms after D matrix transformation

| Combined interferograms | Linear combination | Modulation of detected signal ($\alpha_1 \equiv {}^1H$, $\alpha_2 \equiv {}^{13}C$) |
|---|---|---|
| L13 | +I13 +I14 +I15 +I16 | $\sin(\frac{\pi}{4} + \Phi_1)\sin(\frac{\pi}{4} + \Phi_2)\cos(\alpha_1 t_1)\cos(\alpha_2 t_2)$ |
| L14 | +I13 −I14 +I15 −I16 | $\sin(\frac{\pi}{4} + \Phi_1)\cos(\frac{\pi}{4} + \Phi_2)\cos(\alpha_1 t_1)\sin(\alpha_2 t_2)$ |
| L15 | +I13 +I14 −I15 −I16 | $\cos(\frac{\pi}{4} + \Phi_1)\sin(\frac{\pi}{4} + \Phi_2)\sin(\alpha_1 t_1)\cos(\alpha_2 t_2)$ |
| L16 | +I13 −I14 −I15 +I16 | $\cos(\frac{\pi}{4} + \Phi_1)\cos(\frac{\pi}{4} + \Phi_2)\sin(\alpha_1 t_1)\sin(\alpha_2 t_2)$ |

Addition of the four PMS frequency domain spectra resulting from sets A to D in Table 5, yields cancellation of quad peaks so that solely absorptive peaks remain with intensities being proportional to $\cos \Phi_1 \cos \Phi_2$.

Alternatively, all linear combinations can be performed in the time domain using Eq. 180, or in an explicit form:

$$S \propto \bigotimes_{j=0}^{1} Q \bigotimes_{j=0}^{1} D_{(+1,-1,+3,-3)} \bigotimes_{j=0}^{1} C_{(+1,-1,+3,-3)}(t_j) = [1 \ i \ i \ -1] \cdot \begin{bmatrix} 1 & 1 & 1 & 1 & -1 & -1 & -1 & -1 & -1 & -1 & -1 & -1 & 1 & 1 & 1 & 1 \\ -1 & 1 & -1 & 1 & 1 & -1 & 1 & -1 & -1 & 1 & -1 & 1 & 1 & -1 & 1 & -1 \\ -1 & -1 & 1 & 1 & -1 & -1 & 1 & 1 & 1 & 1 & -1 & -1 & 1 & 1 & -1 & -1 \\ 1 & -1 & -1 & 1 & 1 & -1 & -1 & 1 & 1 & -1 & -1 & 1 & 1 & -1 & -1 & 1 \end{bmatrix} \cdot \begin{bmatrix} I1 \\ I2 \\ I3 \\ I4 \\ I5 \\ I6 \\ I7 \\ I8 \\ I9 \\ I10 \\ I11 \\ I12 \\ I13 \\ I14 \\ I15 \\ I16 \end{bmatrix}. \quad (210)$$

($c_{+1}, c_{-1}, c_{+3}, c_{-3}$)-DPMS (4,3)D $\underline{C^{\alpha\beta}C^{\alpha}}$(CO)NHN Processing of GFT spectra acquired with ($c_{+1}, c_{-1}, c_{+3}, c_{-3}$)-DPMS for two jointly measured chemical shifts is analogous to what is described for ($c_{+1}, c_{-1}, c_{+3}, c_{-3}$)-DMPS 3D HC(C)H TOCSY, except that, prior to FT, a G matrix transformation replaces the Q vector transformation.

In the ($c_{+1}, c_{-1}, c_{+3}, c_{-3}$)-DPMS (4,3)D $\underline{C^{\alpha\beta}C^{\alpha}}$(CO)NHN, $^{13}C^{\alpha}$ and $^{13}C^{\alpha\beta}$ chemical shift evolutions are jointly sampled and the resulting time domain data consist of 16 interferograms.

$$\left[ S_{C^{\alpha\beta}-(+1,-1)}(t_1) + S_{C^{\alpha\beta}-(+3,-3)}(t_1) \right] \otimes \quad (211)$$

$$\left[ S_{C^{\alpha}-(+1,-1)}(t_1) + S_{C^{\alpha}-(+3,-3)}(t_1) \right] =$$

$$S_{C^{\alpha\beta}-(+1,-1)}(t_1) \otimes S_{C^{\alpha}-(+1,-1)}(t_1) +$$

$$S_{C^{\alpha\beta}-(+1,-1)}(t_2) \otimes S_{C^{\alpha}-(+3,-3)}(t_1) + S_{C^{\alpha\beta}-(+3,-3)}(t_2) \otimes$$

-continued $$S_{C^{\alpha}-(+1,-1)}(t_1) + S_{C^{\alpha\beta}-(+3,-3)}(t_2) \otimes S_{C^{\alpha}-(+3,-3)}(t_1) \propto$$

$$\begin{bmatrix} c_{C^{\alpha\beta}-(+1)}(t_1) \\ c_{C^{\alpha\beta}-(-1)}(t_1) \end{bmatrix} \otimes \begin{bmatrix} c_{C^{\alpha}-(+1)}(t_1) \\ c_{C^{\alpha}-(-1)}(t_1) \end{bmatrix} + \begin{bmatrix} c_{C^{\alpha\beta}-(+1)}(t_1) \\ c_{C^{\alpha\beta}-(-1)}(t_1) \end{bmatrix} \otimes$$

$$\begin{bmatrix} c_{C^{\alpha}-(+3)}(t_1) \\ c_{C^{\alpha}-(-3)}(t_1) \end{bmatrix} + \begin{bmatrix} c_{C^{\alpha\beta}-(+3)}(t_1) \\ c_{C^{\alpha\beta}-(-3)}(t_1) \end{bmatrix} \otimes \begin{bmatrix} c_{C^{\alpha}-(+1)}(t_1) \\ c_{C^{\alpha}-(-1)}(t_1) \end{bmatrix} +$$

$$\begin{bmatrix} c_{C^{\alpha\beta}-(+3)}(t_1) \\ c_{C^{\alpha\beta}-(-3)}(t_1) \end{bmatrix} \otimes \begin{bmatrix} c_{C^{\alpha}-(+3)}(t_1) \\ c_{C^{\alpha}-(-3)}(t_1) \end{bmatrix} =$$

$$\begin{bmatrix} c_{C^{\alpha\beta}-(+1)}(t_1) c_{C^{\alpha}-(+1)}(t_1) \\ c_{C^{\alpha\beta}-(+1)}(t_1) c_{C^{\alpha}-(-1)}(t_1) \\ c_{C^{\alpha\beta}-(-1)}(t_1) c_{C^{\alpha}-(+1)}(t_1) \\ c_{C^{\alpha\beta}-(-1)}(t_1) c_{C^{\alpha}-(-1)}(t_1) \end{bmatrix} +$$

$$\begin{bmatrix} c_{C^{\alpha\beta}-(+1)}(t_1) c_{C^{\alpha}-(+3)}(t_1) \\ c_{C^{\alpha\beta}-(+1)}(t_1) c_{C^{\alpha}-(-3)}(t_1) \\ c_{C^{\alpha\beta}-(-1)}(t_1) c_{C^{\alpha}-(+3)}(t_1) \\ c_{C^{\alpha\beta}-(-1)}(t_1) c_{C^{\alpha}-(-3)}(t_1) \end{bmatrix} +$$

-continued $$\begin{bmatrix} c_{C^{\alpha\beta}-(+3)}(t_1) c_{C^{\alpha}-(+1)}(t_1) \\ c_{C^{\alpha\beta}-(+3)}(t_1) c_{C^{\alpha}-(-1)}(t_1) \\ c_{C^{\alpha\beta}-(-3)}(t_1) c_{C^{\alpha}-(+1)}(t_1) \\ c_{C^{\alpha\beta}-(-3)}(t_1) c_{C^{\alpha}-(-1)}(t_1) \end{bmatrix} +$$

$$\begin{bmatrix} c_{C^{\alpha\beta}-(+3)}(t_1) c_{C^{\alpha}-(+3)}(t_1) \\ c_{C^{\alpha\beta}-(+3)}(t_1) c_{C^{\alpha}-(+3)}(t_1) \\ c_{C^{\alpha\beta}-(-3)}(t_1) c_{C^{\alpha}-(+3)}(t_1) \\ c_{C^{\alpha\beta}-(-3)}(t_1) c_{C^{\alpha}-(+3)}(t_1) \end{bmatrix}.$$

The 16 interferograms of Eq. 211 were recorded and are listed explicitly in Table 6. The interferograms of the four terms of Eq. 211 correspond to the four sections separated by dashed line in Table 6.

TABLE 6

2D interferograms recorded for DPMS (4,3)D $\underline{C^{\alpha\beta}}\underline{C^{\alpha}}$(CO)NHN

| Interferogram | Sampling of $t_1(^{13}C^\alpha)$ | Sampling of $t_1(^{13}C^{\alpha\beta})$ | Modulation of detected signal ($\alpha_1 \equiv {}^{13}C^\alpha$, $\alpha_2 \equiv {}^{13}C^{\alpha\beta}$) |
|---|---|---|---|
| Set A: | | | |
| I1 | $c_{+1}$ | $c_{+1}$ | $\cos(\alpha_1 t_1 + \frac{\pi}{4} + \Phi_1)\cos(\alpha_2 t_1 + \frac{\pi}{4} + \Phi_2)$ |
| I2 | $c_{+1}$ | $c_{-1}$ | $\cos(\alpha_1 t_1 + \frac{\pi}{4} + \Phi_1)\cos(-\alpha_2 t_1 + \frac{\pi}{4} + \Phi_2)$ |
| I3 | $c_{-1}$ | $c_{+1}$ | $\cos(-\alpha_1 t_1 + \frac{\pi}{4} + \Phi_1)\cos(\alpha_2 t_1 + \frac{\pi}{4} + \Phi_2)$ |
| I4 | $c_{-1}$ | $c_{-1}$ | $\cos(-\alpha_1 t_1 + \frac{\pi}{4} + \Phi_1)\cos(-\alpha_2 t_1 + \frac{\pi}{4} + \Phi_2)$ |
| Set B: | | | |
| I5 | $c_{+1}$ | $c_{+3}$ | $\cos(\alpha_1 t_1 + \frac{\pi}{4} + \Phi_1)\cos(\alpha_2 t_1 + \frac{3\pi}{4} + \Phi_2)$ |
| I6 | $c_{+1}$ | $c_{-3}$ | $\cos(\alpha_1 t_1 + \frac{\pi}{4} + \Phi_1)\cos(-\alpha_2 t_1 + \frac{3\pi}{4} + \Phi_2)$ |
| I7 | $c_{-1}$ | $c_{+3}$ | $\cos(-\alpha_1 t_1 + \frac{\pi}{4} + \Phi_1)\cos(\alpha_2 t_1 + \frac{3\pi}{4} + \Phi_2)$ |
| I8 | $c_{-1}$ | $c_{-3}$ | $\cos(-\alpha_1 t_1 + \frac{\pi}{4} + \Phi_1)\cos(-\alpha_2 t_1 + \frac{3\pi}{4} + \Phi_2)$ |
| Set C: | | | |
| I9 | $c_{+3}$ | $c_{+1}$ | $\cos(\alpha_1 t_1 + \frac{3\pi}{4} + \Phi_1)\cos(\alpha_2 t_1 + \frac{\pi}{4} + \Phi_2)$ |
| I10 | $c_{+3}$ | $c_{-1}$ | $\cos(\alpha_1 t_1 + \frac{3\pi}{4} + \Phi_1)\cos(-\alpha_2 t_1 + \frac{\pi}{4} + \Phi_2)$ |
| I11 | $c_{-3}$ | $c_{+1}$ | $\cos(-\alpha_1 t_1 + \frac{3\pi}{4} + \Phi_1)\cos(\alpha_2 t + \frac{\pi}{4} + \Phi_2)$ |
| I12 | $c_{-3}$ | $c_{-1}$ | $\cos(-\alpha_1 t_1 + \frac{3\pi}{4} + \Phi_1)\cos(-\alpha_2 t_1 + \frac{\pi}{4} + \Phi_2)$ |
| Set D: | | | |
| I13 | $c_{+3}$ | $c_{+3}$ | $\cos(\alpha_1 t_1 + \frac{3\pi}{4} + \Phi_1)\cos(\alpha_2 t_1 + \frac{3\pi}{4} + \Phi_2)$ |
| I14 | $c_{+3}$ | $c_{-3}$ | $\cos(\alpha_1 t_1 + \frac{3\pi}{4} + \Phi_1)\cos(-\alpha_2 t_1 + \frac{3\pi}{4} + \Phi_2)$ |
| I15 | $c_{-3}$ | $c_{+3}$ | $\cos(-\alpha_1 t_1 + \frac{3\pi}{4} + \Phi_1)\cos(\alpha_2 t_1 + \frac{3\pi}{4} + \Phi_2)$ |
| I16 | $c_{-3}$ | $c_{-3}$ | $\cos(-\alpha_1 t_1 + \frac{3\pi}{4} + \Phi_1)\cos(-\alpha_2 t_1 + \frac{3\pi}{4} + \Phi_2)$ |

Set A of four 2D interferograms (I1 to I4) result from $(c_{+1}, c_{-1})$-PMS of two jointly sampled indirect dimensions. $D_{C^{\alpha\beta}, C^{\alpha}-(+1,-1)}$ for $(c_{+1}, c_{-1})$-PMS sampling of two indirect dimensions is given by $$D_{C^{\alpha\beta}, C^{\alpha}-(+1,-1)} = \begin{bmatrix} 1 & 1 \\ -1 & 1 \end{bmatrix}_{C^{\alpha\beta}} \otimes \begin{bmatrix} 1 & 1 \\ -1 & 1 \end{bmatrix}_{C^{\alpha}} = \begin{bmatrix} 1 & 1 & 1 & 1 \\ -1 & 1 & -1 & 1 \\ -1 & -1 & 1 & 1 \\ 1 & -1 & -1 & 1 \end{bmatrix}. \quad (212)$$

yielding, with set A of four interferograms of Table 6, linear combinations L1-L4 of Table 7.

The linearly combined interferograms are then transformed by the G matrix given by $$G(1) = \begin{bmatrix} Q \\ Q^* \end{bmatrix}_1 \otimes [Q]_0 = \begin{bmatrix} 1 & i \\ 1 & -i \end{bmatrix}_1 \otimes [1 \; i]_0 = \begin{bmatrix} 1 & i & i & -1 \\ 1 & i & -i & 1 \end{bmatrix}. \quad (213)$$

Hence, FT of L1+i*L2+i*L3−L4 gives rise to the sub-spectrum where $\alpha_1+\alpha_2$ is observed (the second column of Table 8), while FT of L1+i*L2−i*L3+L4 gives rise to the sub-spectrum where $\alpha_1-\alpha_2$ is observed (the second column of Table 9).

Set B of four 2D interferograms (I5 to I8) result from $(c_{+1}, c_{-1})$-PMS for $t_1$ ($^{13}C^{\alpha}$) and $(c_{+3}, c_{-3})$-PMS for $t_1$ ($^{13}C^{\alpha\beta}$) and the corresponding D matrix transformation is given by:

$$D_{C^{\alpha\beta}-(+3,-3), C^{\alpha}-(+1,-1)} = \begin{bmatrix} -1 & -1 \\ -1 & 1 \end{bmatrix}_{C^{\alpha\beta}} \otimes \begin{bmatrix} 1 & 1 \\ -1 & 1 \end{bmatrix}_{C^{\alpha}} = \begin{bmatrix} -1 & -1 & -1 & -1 \\ 1 & -1 & 1 & -1 \\ -1 & -1 & 1 & 1 \\ 1 & -1 & -1 & 1 \end{bmatrix}. \quad (214)$$

yielding, with set B of four interferograms of Table 6, linear combinations L5-L8 of Table 7.

The linearly combined interferograms are then transformed by the G matrix described in Eq. 213. Hence, FT of L5+i*L6+i*L7−L8 gives rise to the sub-spectrum where $\alpha_1+\alpha_2$ is observed (the third column of Table 8), while FT of L5+i*L6−i*L7+L8 gives rise to the sub-spectrum where $\alpha_1-\alpha_2$ is observed (the third column of Table 9).

Set C of four 2D interferograms (I9 to I12) result from $((c_{+3}, c_{-3})$-PMS for $t_1$ ($^{13}C^{\alpha}$) and $(c_{+1}, c_{-1})$-PMS for $t_1$ ($^{13}C^{\alpha\beta}$) and the corresponding D matrix transformation is given by:

$$D_{C^{\alpha\beta}-(+1,-1), C^{\alpha}-(+3,-3)} = \begin{bmatrix} 1 & 1 \\ -1 & 1 \end{bmatrix}_{C^{\alpha\beta}} \otimes \begin{bmatrix} -1 & -1 \\ -1 & 1 \end{bmatrix}_{C^{\alpha}} = \begin{bmatrix} -1 & -1 & -1 & -1 \\ -1 & 1 & -1 & 1 \\ 1 & 1 & -1 & -1 \\ 1 & -1 & -1 & 1 \end{bmatrix}. \quad (215)$$

yielding, with set C of four interferograms of Table 6, linear combinations L9-L12 of Table 7.

The linearly combined interferograms are then transformed by the G matrix described in Eq. 213. Hence, FT of L9+i*L10+i*L11−L12 gives rise to the sub-spectrum where $\alpha_1+\alpha_2$ is observed (the fourth column of Table 8), while FT of L9+i*L10−i*L11+L12 gives rise to the sub-spectrum where $\alpha_1-\alpha_2$ is observed (the fourth column of Table 9).

Set D of four 2D interferograms (I13 to I16) of Table 4 result from $(c_{+3}, c_{-3})$-PMS for $t_1$ ($^1H$) and $(c_{+3}, c_{-3})$-PMS for $t_2$ ($^{13}C$) and the corresponding D matrix transformation is given by:

$$D_{C^{\alpha\beta}-(+3,-3), C^{\alpha}-(+3,-3)} = \begin{bmatrix} -1 & -1 \\ -1 & 1 \end{bmatrix}_{C^{\alpha\beta}} \otimes \begin{bmatrix} -1 & -1 \\ -1 & 1 \end{bmatrix}_{C^{\alpha}} = \begin{bmatrix} 1 & 1 & 1 & 1 \\ 1 & -1 & 1 & -1 \\ 1 & 1 & -1 & -1 \\ 1 & -1 & -1 & 1 \end{bmatrix}. \quad (216)$$

yielding, with set D of four interferograms of Table 6, linear combinations L13-L16 of Table 7.

The linearly combined interferograms are then transformed by the G matrix described in Eq. 213. Hence, FT of L13+i*L14+i*L15−L16 gives rise to the sub-spectrum where $\alpha_1+\alpha_2$ is observed (the last column of Table 8), while FT of L13+i*L14−i*L15+L16 gives rise to the sub-spectrum where $\alpha_1-\alpha_2$ is observed (the last column of Table 9).

TABLE 7

Linearly combined interferograms after D matrix transformation

| Combined interferograms | Linear combination | Modulation of detected signal ($\alpha_1 \equiv {}^{13}C^{\alpha}$, $\alpha_2 \equiv {}^{13}C^{\alpha\beta}$) |
|---|---|---|
| L1 | +I1 +I2 +I3 +I4 | $\cos(\frac{\pi}{4}+\Phi_1)\cos(\frac{\pi}{4}+\Phi_2)\cos(\alpha_1 t_1)\cos(\alpha_2 t_1)$ |
| L2 | −I1 +I2 −I3 +I4 | $\cos(\frac{\pi}{4}+\Phi_1)\sin(\frac{\pi}{4}+\Phi_2)\cos(\alpha_1 t_1)\sin(\alpha_2 t_1)$ |
| L3 | −I1 −I2 +I3 +I4 | $\sin(\frac{\pi}{4}+\Phi_1)\cos(\frac{\pi}{4}+\Phi_2)\sin(\alpha_1 t_1)\cos(\alpha_2 t_1)$ |
| L4 | +I1 −I2 −I3 +I4 | $\sin(\frac{\pi}{4}+\Phi_1)\sin(\frac{\pi}{4}+\Phi_2)\sin(\alpha_1 t_1)\sin(\alpha_2 t_1)$ |
| L5 | −I5 −I6 −I7 −I8 | $\cos(\frac{\pi}{4}+\Phi_1)\sin(\frac{\pi}{4}+\Phi_2)\cos(\alpha_1 t_1)\cos(\alpha_2 t_1)$ |
| L6 | +I5 −I6 +I7 −I8 | $\cos(\frac{\pi}{4}+\Phi_1)\cos(\frac{\pi}{4}+\Phi_2)\cos(\alpha_1 t_1)\sin(\alpha_2 t_1)$ |
| L7 | −I5 −I6 +I7 +I8 | $\sin(\frac{\pi}{4}+\Phi_1)\sin(\frac{\pi}{4}+\Phi_2)\sin(\alpha_1 t_1)\cos(\alpha_2 t_1)$ |
| L8 | +I5 −I6 −I7 +I8 | $\sin(\frac{\pi}{4}+\Phi_1)\cos(\frac{\pi}{4}+\Phi_2)\sin(\alpha_1 t_1)\sin(\alpha_2 t_1)$ |

TABLE 7-continued

Linearly combined interferograms after D matrix transformation

| Combined interferograms | Linear combination | Modulation of detected signal ($\alpha_1 \equiv {}^{13}C^\alpha, \alpha_2 \equiv {}^{13}C^{\alpha\beta}$) |
|---|---|---|
| L9  | −I9 −I10 −I11 −I12 | $\sin(\frac{\pi}{4}+\Phi_1)\cos(\frac{\pi}{4}+\Phi_2)\cos(\alpha_1 t_1)\cos(\alpha_2 t_1)$ |
| L10 | −I9 +I10 −I11 +I12 | $\sin(\frac{\pi}{4}+\Phi_1)\sin(\frac{\pi}{4}+\Phi_2)\cos(\alpha_1 t_1)\sin(\alpha_2 t_1)$ |
| L11 | +I9 +I10 −I11 −I12 | $\cos(\frac{\pi}{4}+\Phi_1)\cos(\frac{\pi}{4}+\Phi_2)\sin(\alpha_1 t_1)\cos(\alpha_2 t_1)$ |
| L12 | +I9 −I10 −I11 +I12 | $\cos(\frac{\pi}{4}+\Phi_1)\sin(\frac{\pi}{4}+\Phi_2)\sin(\alpha_1 t_1)\sin(\alpha_2 t_1)$ |
| L13 | +I13 +I14 +I15 +I16 | $\sin(\frac{\pi}{4}+\Phi_1)\sin(\frac{\pi}{4}+\Phi_2)\cos(\alpha_1 t_1)\cos(\alpha_2 t_1)$ |
| L14 | +I13 −I14 +I15 −I16 | $\sin(\frac{\pi}{4}+\Phi_1)\cos(\frac{\pi}{4}+\Phi_2)\cos(\alpha_1 t_1)\sin(\alpha_2 t_1)$ |
| L15 | +I13 +I14 −I15 −I16 | $\cos(\frac{\pi}{4}+\Phi_1)\sin(\frac{\pi}{4}+\Phi_2)\sin(\alpha_1 t_1)\cos(\alpha_2 t_1)$ |
| L16 | +I13 −I14 −I15 +I16 | $\cos(\frac{\pi}{4}+\Phi_1)\cos(\frac{\pi}{4}+\Phi_2)\sin(\alpha_1 t_1)\sin(\alpha_2 t_1)$ |

Table 8 and 9, respectively, list the peak intensities of the sub-spectrum measuring $\alpha_1+\alpha_2$ and sub-spectrum measuring $\alpha_1-\alpha_2$, for all combinations of PMS given in Eq.211.

TABLE 8

Relative peaks intensities in the sub-spectrum measuring $\alpha_1 + \alpha_2$

| Peaks at | $t_1({}^{13}C^\alpha) - (c_{+1}, c_{-1})$, $t_1({}^{13}C^{\alpha\beta}) - (c_{+1}, c_{-1})$ | $t_1({}^{13}C^\alpha) - (c_{+1}, c_{-1})$, $t_1({}^{13}C^{\alpha\beta}) - (c_{+3}, c_{-3})$ | $t_1({}^{13}C^\alpha) - (c_{+3}, c_{-3})$, $t_1({}^{13}C^{\alpha\beta}) - (c_{+1}, c_{-1})$ | $t_1({}^{13}C^\alpha) - (c_{+3}, c_{-3})$, $t_1({}^{13}C^{\alpha\beta}) - (c_{+3}, c_{-3})$ |
|---|---|---|---|---|
| $\alpha_1 + \alpha_2$  | $\cos\Phi_1\cos\Phi_2$  | $\cos\Phi_1\cos\Phi_2$  | $\cos\Phi_1\cos\Phi_2$  | $\cos\Phi_1\cos\Phi_2$ |
| $\alpha_1 - \alpha_2$  | $-\cos\Phi_1\sin\Phi_2$ | $\cos\Phi_1\sin\Phi_2$  | $-\cos\Phi_1\sin\Phi_2$ | $\cos\Phi_1\sin\Phi_2$ |
| $-\alpha_1 + \alpha_2$ | $-\sin\Phi_1\cos\Phi_2$ | $-\sin\Phi_1\cos\Phi_2$ | $\sin\Phi_1\cos\Phi_2$  | $\sin\Phi_1\cos\Phi_2$ |
| $-\alpha_1 - \alpha_2$ | $\sin\Phi_1\sin\Phi_2$  | $-\sin\Phi_1\sin\Phi_2$ | $-\sin\Phi_1\sin\Phi_2$ | $\sin\Phi_1\sin\Phi_2$ |

Inspection of Table 8 shows that the cross-talk peak located at $\alpha_1-\alpha_2$ as well as the quad peaks at $-\alpha_1+\alpha_2$ and $-\alpha_1-\alpha_2$, cancel when all differently sampled sub-spectra are added up. Complex FT yields the desired the frequency domain spectrum as shown in FIG. 7.

TABLE 9

Relative peaks intensities in the sub-spectrum measuring $\alpha_1 - \alpha_2$

| Peaks at | $t_1({}^{13}C^\alpha) - (c_{+1}, c_{-1})$, $t_1({}^{13}C^{\alpha\beta}) - (c_{+1}, c_{-1})$ | $t_1({}^{13}C^\alpha) - (c_{+1}, c_{-1})$, $t_1({}^{13}C^{\alpha\beta}) - (c_{+3}, c_{-3})$ | $t_1({}^{13}C^\alpha) - (c_{+3}, c_{-3})$, $t_1({}^{13}C^{\alpha\beta}) - (c_{+1}, c_{-1})$ | $t_1({}^{13}C^\alpha) - (c_{+3}, c_{-3})$, $t_1({}^{13}C^{\alpha\beta}) - (c_{+3}, c_{-3})$ |
|---|---|---|---|---|
| $\alpha_1 - \alpha_2$  | $\cos\Phi_1\cos\Phi_2$  | $\cos\Phi_1\cos\Phi_2$  | $\cos\Phi_1\cos\Phi_2$  | $\cos\Phi_1\cos\Phi_2$ |
| $\alpha_1 + \alpha_2$  | $-\cos\Phi_1\sin\Phi_2$ | $\cos\Phi_1\sin\Phi_2$  | $-\cos\Phi_1\sin\Phi_2$ | $\cos\Phi_1\sin\Phi_2$ |
| $-\alpha_1 - \alpha_2$ | $-\sin\Phi_1\cos\Phi_2$ | $-\sin\Phi_1\cos\Phi_2$ | $\sin\Phi_1\cos\Phi_2$  | $\sin\Phi_1\cos\Phi_2$ |
| $-\alpha_1 + \alpha_2$ | $\sin\Phi_1\sin\Phi_2$  | $-\sin\Phi_1\sin\Phi_2$ | $-\sin\Phi_1\sin\Phi_2$ | $\sin\Phi_1\sin\Phi_2$ |

Inspection of Table 9 shows that the cross-talk peak located at $\alpha_1+\alpha_2$ as well as the quad peaks at $-\alpha_1+\alpha_2$ and $-\alpha_1-\alpha_2$, cancel when all differently sampled sub-spectra are added up.

Alternatively, all linear combinations can be performed in time domain using Eq. 182, or in an explicit form:

$$T \propto \bigotimes_{j=0}^{1} G \bigotimes_{j=0}^{1} D_{(+1,-1,+3,-3)} \bigotimes_{j=0}^{1} C_{(+1,-1,+3,-3)}(t_j) = \begin{bmatrix} 1 & i & i & -1 \\ 1 & i & -i & 1 \end{bmatrix}. \quad (221)$$

-continued $$\begin{bmatrix} 1 & 1 & 1 & 1 & -1 & -1 & -1 & -1 & -1 & -1 & -1 & -1 & 1 & 1 & 1 & 1 \\ -1 & 1 & -1 & 1 & 1 & -1 & 1 & -1 & -1 & 1 & -1 & 1 & 1 & -1 & 1 & -1 \\ -1 & -1 & 1 & 1 & -1 & -1 & 1 & 1 & 1 & 1 & -1 & -1 & 1 & 1 & -1 & -1 \\ 1 & -1 & -1 & 1 & 1 & -1 & -1 & 1 & 1 & -1 & -1 & 1 & 1 & -1 & -1 & 1 \end{bmatrix}.$$

$$\begin{bmatrix} I1 \\ I2 \\ I3 \\ I4 \\ I5 \\ I6 \\ I7 \\ I8 \\ I9 \\ I10 \\ I11 \\ I12 \\ I13 \\ I14 \\ I15 \\ I16 \end{bmatrix}.$$

Comparative Cross Sections

In order to demonstrate the salient peak detection features of the sampling schemes alluded to in the text, non-constant time 2D [$^{13}$C,$^{1}$H]-HSQC spectra were recorded with delayed acquisition, that is, the first FID was acquired with $t_1(^{13}C)=25$ μs (FIGS. 4A-I). This introduces a large 'phase error' of 1.35°/ppm, with a total of 108° across the 80.0 ppm spectral width. Furthermore, 2D [$^{13}$C, $^{1}$H]-HSQC was employed to exemplify non-constant time forward and backward sampling.

Discussion

First, $(c_{+1},c_{-1})$-, $(c_{+0},c_{-2})$-PMS, and corresponding DPMS was implemented and tested for 2D [$^{13}$C,$^{1}$H]-HSQC (Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994), which are hereby incorporated by reference in their entirety). The implementation of non-constant time (Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994), which are hereby incorporated by reference in their entirety) 'backward-sampling' required introduction of an additional 180° $^{13}$C radio-frequency (r.f) pulse (FIGS. 3A-B). PMS and DPMS remove dispersive components and yield clean absorption mode spectra (FIGS. 4A-I) without a phase correction.

$(c_{+1},c_{-1})$-PMS and $(c_{+1},c_{-1},c_{+3},c_{-3})$-DPMS was then employed for simultaneous constant-time 2D [$^{13}C^{aliphatic}/^{13}C^{aromatic}$,$^{1}$H]-HSQC in which aromatic signals are folded. Since frequency labeling was accomplished in a constant-time manner, (Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994), which are hereby incorporated by reference in their entirety) no r.f. pulses had to be added to the pulse scheme (Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994), which are hereby incorporated by reference in their entirety). The phase errors of the folded aromatic signals cannot be corrected after conventional data acquisition, (Ernst et al., "Principles of Nuclear Magnetic Resonance in One and Two Dimensions," Oxford: Oxford University Press (1987), which is hereby incorporated by reference in its entirety) but are eliminated with PMS (FIG. 5).

Multiple $(c_{+1},c_{-1},c_{+3},c_{-3})$-DPMS was exemplified for 3D HC(C)H total correlation spectroscopy (TOCSY) (Bax et al., J. Magn. Reson. 88:425-431 (1990), which is hereby incorporated by reference in its entirety). The $^{13}$C-$^{13}$C isotropic mixing introduces phase errors along $\omega_1(^{13}C)$ which cannot be entirely removed by prior art techniques. Moreover, in hetero-nuclear resolved NMR spectra comprising $^{1}$H-$^{1}$H planes with intense diagonal peaks [e.g. HC(C)H TOCSY], even small phase errors impede identification of cross peaks close to the diagonal. Since $^{1}$H and $^{13}$C frequency labeling was accomplished in a semi constant-time manner (Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994), which is hereby incorporated by reference in its entirety), no r.f. pulses had to be added to the pulse scheme (Bax et al., J. Magn. Reson. 88:425-431 (1990)). Comparison with the conventionally acquired spectrum shows elimination of dispersive components in both indirect dimensions (FIGS. 6A-B).

To exemplify multiple $(c_{+1},c_{-1},c_{+3},c_{-3})$-DPMS for GFT NMR, (Kim et al., J. Am. Chem. Soc. 125:1385-1393 (2003); Atreya et al., Proc. Natl. Acad. Sci. USA 101:9642-9647 (2004); Xia et al., J. Biomol. NMR 29:467-476 (2004); Eletsky et al., J. Am. Chem. Soc. 127, 14578-14579 (2005); Yang et al., J. Am. Chem. Soc. 127:9085-9099 (2005); Atreya et al., Methods Enzymol. 394:78-108 (2005); Liu et al., Proc. Natl. Acad. Sci. U.S.A. 102:10487-10492 (2005); Atreya et al., J. Am. Chem. Soc. 129:680-692 (2007), which are hereby incorporated by reference in their entirety) it was employed for (4,3)D $C^{\alpha\beta}C^{\alpha}$(CO)NHN (Atreya et al., Proc. Natl. Acad. Sci. USA 101:9642-9647 (2004), which is hereby incorporated by reference in its entirety) in both the $^{13}C^{\alpha\beta}$ and $^{13}C^{\alpha}$ shift evolution periods. Since frequency labeling was accomplished in a constant-time manner (Cavanagh et al., "Protein NMR Spectroscopy," 2nd Ed., San Diego: Academic Press (2007); Schmidt-Rohr et al., "Multidimensional Solid-State NMR and Polymers," New York: Academic Press (1994); Atreya et al., *Proc. Natl. Acad. Sci. USA* 101:9642-9647 (2004), which are hereby incorporated by reference in their entirety), no r.f. pulses had to be added to the pulse scheme (Atreya et al., *Proc. Natl. Acad. Sci. USA* 101:9642-9647 (2004), which is hereby incorporated by reference in its entirety). Comparison with standard GFT NMR shows elimination of dispersive components in the GFT-dimension (FIG. 7). Importantly, only PMS can eliminate entirely dispersive components in GFT-based projection NMR (Kim et al., *J. Am. Chem. Soc.* 125:1385-1393 (2003); Atreya et al., *Proc. Natl. Acad. Sci. USA* 101:9642-9647 (2004); Xia et al., *J. Biomol. NMR* 29:467-476 (2004); Eletsky et al., *J. Am. Chem. Soc.* 127, 14578-14579 (2005); Yang et al., *J. Am. Chem. Soc.* 127:9085-9099 (2005); Atreya et al., *Methods Enzymol.* 394:78-108 (2005); Liu et al., *Proc. Natl. Acad. Sci. U.S.A.* 102:10487-10492 (2005); Atreya et al., *J. Am. Chem. Soc.* 129:680-692 (2007); Szyperski et al., *Magn. Reson. Chem.* 44:51-60 (2006); Kupce et al., *J. Am. Chem. Soc.* 126:6429-6440 (2004); Coggins et al., *J. Am. Chem. Soc.* 126:1000-1001 (2004); Eghbalnia et al., *J. Am. Chem. Soc.* 127:12528-12536 (2005); Hiller et al., *Proc. Natl. Acad. Sci. U.S.A.* 102:10876-10881 (2005), which are hereby incorporated by reference in their entirety).

Dispersive components shift peak maxima. For example, in routinely acquired (4,3)D $C^{\alpha\beta}C^{\alpha}$(CO)NHN (Atreya et al., *Proc. Natl. Acad. Sci. USA* 101:9642-9647 (2004), which is hereby incorporated by reference in its entirety), signals exhibit full widths at half height of $\Delta v_{FWHH}$~140 Hz in the GFT dimension. Since phase errors up to about ±15° are observed, maxima are shifted by up to about ±10 Hz (~±0.07 ppm at 600 MHz $^1$H resonance frequency) and the precision of chemical shift measurements is reduced accordingly.

Example 2

Measurement of Secondary Phase Shifts Using PMS

In this section, the protocol for measurement of secondary phase shifts from PMS spectra is described.
π/4 and 3π/4-Shifted Combined Forward-Backward Sampling
($c_{+1}, c_{-1}$)-Sampling (PMS)

The two interferograms for ($c_{+1}, c_{-1}$)-PMS are given by Eq. 13 and the resulting complex time domain signal $S_{+1,-1}(t)$, according to Eq. 14, is proportional to $$S_{+1,-1}(t) \propto [1 \quad i] D_{+1,-1} C_{+1,-1}(t) = \tag{222}$$

$$\frac{1}{\sqrt{2}} [1 \quad i] \begin{bmatrix} 1 & 1 \\ -1 & 1 \end{bmatrix} \begin{bmatrix} \cos(+\alpha t + \frac{\pi}{4} + \Phi_{+1}) \\ \cos(-\alpha t + \frac{\pi}{4} + \Phi_{-1}) \end{bmatrix} =$$

$$\sqrt{2} \cos\left(\frac{\Phi_{+1} + \Phi_{-1}}{2}\right) e^{\left[i\alpha t + i\frac{\Phi_{+1} - \Phi_{-1}}{2}\right]} -$$

$$\sqrt{2} \sin\left(\frac{\Phi_{+1} + \Phi_{-1}}{2}\right) e^{\left[i\alpha t - i\frac{\Phi_{+1} - \Phi_{-1}}{2}\right]}.$$

FT reveals a superposition of absorptive and dispersive components at both the actual and the quadrature peak positions, with peak intensities proportional to $$\cos\left(\frac{\Phi_{+1} + \Phi_{-1}}{2}\right) \text{ and } \sin\left(\frac{\Phi_{+1} + \Phi_{-1}}{2}\right),$$

respectively. The phase shifts are given by $$\frac{\Phi_{+1} - \Phi_{-1}}{2}.$$

In the following, a protocol is described for obtaining the secondary phase shifts from experimentally measured peak volumes and the phase shifts of actual and quad peaks.

The protocol involves two steps:
Step 1:
Phase correct both the actual and the quad peaks, thereby measuring the associated phase shifts $$\frac{\Phi_{+1} - \Phi_{-1}}{2}.$$

For brevity, $$\Phi_{diff} = \frac{\Phi_{+1} - \Phi_{-1}}{2}$$

in the following.
Step 2:
Perform frequency domain signal integration on the phase corrected actual and the quad peaks to obtain the peak 'volumes' $V_{actual}$ and $V_{quad}$, which are proportional to $$V_{actual} \propto \cos\left(\frac{\Phi_{+1} + \Phi_{-1}}{2}\right) \tag{223}$$

$$V_{quad} \propto \sin\left(\frac{\Phi_{+1} + \Phi_{-1}}{2}\right),$$

so that $$\frac{\Phi_{+1} + \Phi_{-1}}{2} = \arctan\left(\frac{V_{quad}}{V_{actual}}\right) = \Phi_{sum}. \tag{224}$$

The secondary phase shifts are calculated having $\Phi_{sum}$ and $\Phi_{diff}$ as according to $$\Phi_{+1} = \Phi_{sum} + \Phi_{diff}$$

$$\Phi_{-1} = \Phi_{sum} - \Phi_{diff} \tag{225}.$$

With Eq. 16 and Eq.225, the figures of merit $M_{+1,-1}^{D}$, $M_{+1,-1}^{Q}$ and $M_{+1,-1}^{I}$ can be calculated.
($c_{+3}, c_{-3}$)-Sampling (PMS)

The two interferograms for ($c_{+3}, c_{-3}$)-PMS are given by Eq. 17 and the resulting complex time domain signal $S_{+3,-3}(t)$, according to Eq. 18, is proportional to $$S_{+3,-3}(t) \propto [1 \quad i] D_{+3,-3} C_{+3,-3}(t) = \tag{226}$$

$$\frac{1}{\sqrt{2}} [1 \quad i] \begin{bmatrix} -1 & -1 \\ -1 & 1 \end{bmatrix} \begin{bmatrix} c_{+3}(t) \\ c_{-3}(t) \end{bmatrix} =$$

$$\frac{1}{\sqrt{2}}[1 \ \ i]\begin{bmatrix} -1 & -1 \\ -1 & 1 \end{bmatrix}\begin{bmatrix} \cos\left(+\alpha t + \frac{3\pi}{4} + \Phi_{+3}\right) \\ \cos\left(-\alpha t + \frac{3\pi}{4} + \Phi_{-3}\right) \end{bmatrix} =$$

$$\sqrt{2}\cos\left(\frac{\Phi_{+3}+\Phi_{-3}}{2}\right)e^{\left[i\alpha t+i\frac{\Phi_{+3}-\Phi_{-3}}{2}\right]} +$$

$$\sqrt{2}\sin\left(\frac{\Phi_{+3}+\Phi_{-3}}{2}\right)e^{\left[-i\alpha t-i\frac{\Phi_{+3}-\Phi_{-3}}{2}\right]}.$$

FT reveals a superposition of absorptive and dispersive components at both the actual and the quadrature peak positions, with peak intensities proportional to $$\cos\left(\frac{\Phi_{+3}+\Phi_{-3}}{2}\right) \text{ and } \sin\left(\frac{\Phi_{+3}+\Phi_{-3}}{2}\right),$$

respectively. The phase shifts associated with the peaks are given by $$\frac{\Phi_{+3}-\Phi_{-3}}{2}.$$

The protocol for obtaining secondary phase shifts from experimentally measured peak volumes and the phase shifts of actual and quad peaks involves two steps.

Step 1:
Phase correct both the actual and the quad peaks, thereby measuring the associated phase shifts $$\frac{\Phi_{+3}-\Phi_{-3}}{2}.$$

For brevity, we define $$\Phi_{diff} = \frac{\Phi_{+3}-\Phi_{-3}}{2}.$$

Step 2:
Perform integration on the phase corrected actual and the quad peaks to obtain the peak 'volumes' $V_{actual}$ and $V_{quad}$, which are proportional to $$V_{actual} = \cos\left(\frac{\Phi_{+3}+\Phi_{-3}}{2}\right) \quad (227)$$

$$V_{quad} = \sin\left(\frac{\Phi_{+3}+\Phi_{-3}}{2}\right).$$

so that, $$\frac{\Phi_{+3}+\Phi_{-3}}{2} = \arctan\left(\frac{V_{quad}}{V_{actual}}\right) = \Phi_{sum}. \quad (228)$$

The secondary phase shifts are calculated using $\Phi_{sum}$ and $\Phi_{diff}$ according to $$\Phi_{+3} = \Phi_{sum} + \Phi_{diff}$$

$$\Phi_{-3} = \Phi_{sum} - \Phi_{diff}. \quad (229)$$

With Eq.20 and Eq.229, the figures of merit $M_{+3,-3}^D$, $M_{+3,-3}^Q$ and $M_{+3,-3}^I$ can be calculated.

0- and π/2-Shifted Combined Forward-Backward Sampling $(c_{+0},c_{-2})$-Sampling (PMS)

The two interferograms for $(c_{+0},c_{-2})$-PMS are given by Eq. 24 and the resulting complex time domain signal $S_{+0,-2}(t)$, according to Eq. 25, is proportional to $$S_{+0,-2}(t) \propto [1 \ \ i]D_{+0,-2}C_{+0,-2}(t) = [1 \ \ i]\begin{bmatrix} 1 & 0 \\ 0 & 1 \end{bmatrix} \quad (230)$$

$$\begin{bmatrix} c_{+0}(t) \\ c_{-2}(t) \end{bmatrix} = [1 \ \ i]\begin{bmatrix} c_{+0} \\ c_{-2} \end{bmatrix} = [1 \ \ i]\begin{bmatrix} \cos(\alpha t + \Phi_{+0}) \\ \sin(\alpha t - \Phi_{-2}) \end{bmatrix} =$$

$$\sqrt{2}\cos\left(\frac{\Phi_{+0}+\Phi_{-2}}{2}\right)e^{\left[i\alpha t+i\frac{\Phi_{+0}-\Phi_{-2}}{2}\right]} -$$

$$\sqrt{2}\sin\left(\frac{\Phi_{+0}+\Phi_{-2}}{2}\right)e^{\left[-i\alpha t-i\left(\frac{\pi}{2}-\frac{\Phi_{+0}-\Phi_{-2}}{2}\right)\right]}.$$

FT reveals a superposition of absorptive and dispersive components at both the actual and the quadrature peak positions, with peak intensities proportional to $$\cos\left(\frac{\Phi_{+0}+\Phi_{-2}}{2}\right) \text{ and } \sin\left(\frac{\Phi_{+0}+\Phi_{-2}}{2}\right),$$

respectively. The phase shifts associated with the two peaks differ by π/2, and is $$\frac{\Phi_{+0}-\Phi_{-2}}{2}$$

for the actual and by $$\frac{\pi}{2} - \frac{\Phi_{+0}-\Phi_{-2}}{2}$$

for the quad peak. The protocol for obtaining secondary phase shifts from experimentally measured peak volumes and phase shifts of the actual and the quad peaks involves two steps.

Step 1:
Phase correct both the actual and the quad peaks and thereby measure the associated phase shifts $$\frac{\Phi_{+0}-\Phi_{-2}}{2}$$

from the required phase correction of actual peak or quad peak after subtracting π/2. For brevity, we define $$\frac{\Phi_{+0}-\Phi_{-2}}{2} = \Phi_{diff}.$$

Step 2:
Perform integration on the phase corrected actual and quad peaks to obtain the peak 'volumes' $V_{actual}$ and $V_{quad}$ which are proportional to $$V_{actual} \propto \cos\left(\frac{\Phi_{+0} + \Phi_{-2}}{2}\right) \qquad (231)$$

$$V_{quad} \propto \sin\left(\frac{\Phi_{+0} + \Phi_{-2}}{2}\right).$$

so that $$\frac{\Phi_{+0} + \Phi_{-2}}{2} = \arctan g\left(\frac{V_{quad}}{V_{actual}}\right) = \Phi_{sum}. \qquad (232)$$

The secondary phase shifts are calculated using $\Phi_{sum}$ and $\Phi_{diff}$ according to $$\Phi_{+0} = \Phi_{sum} + \Phi_{diff}$$

$$\Phi_{-2} = \Phi_{sum} - \Phi_{diff} \qquad (233).$$

With Eq. 27 and Eq. 233, the figures of merit $M_{+0,-2}^D$, $M_{+0,-2}^Q$ and $M_{+0,-2}^I$ can be calculated.

($c_{-0}$,$c_{+2}$)-Sampling (PMS)

The two interferograms for ($c_{-0}$,$c_{+2}$)-PMS are given by Eq. 28 and the resulting complex time domain signal $S_{-0,+2}(t)$, according to Eq. 29, is proportional to $$S_{-0,+2}(t) \propto [1 \quad i] \quad D_{-0,+2}C_{-0,+2}(t) = [1 \quad i]\begin{bmatrix} 1 & 0 \\ 0 & -1 \end{bmatrix}\begin{bmatrix} c_{-0}(t) \\ c_{+2}(t) \end{bmatrix} = \qquad (234)$$

$$[1 \quad -i]\begin{bmatrix} c_{-0} \\ c_{+2} \end{bmatrix} = [1 \quad -i]\begin{bmatrix} \cos(\alpha t - \Phi_{-0}) \\ -\sin(\alpha t + \Phi_{+2}) \end{bmatrix} =$$

$$\sqrt{2}\cos\left(\frac{\Phi_{+2} + \Phi_{-0}}{2}\right)e^{\left[i\alpha t + i\frac{\Phi_{+2} - \Phi_{-0}}{2}\right]} +$$

$$\sqrt{2}\sin\left(\frac{\Phi_{+2} + \Phi_{-0}}{2}\right)e^{\left[-i\alpha t + i\left(\frac{\pi}{2} - \frac{\Phi_{+2} - \Phi_{-0}}{2}\right)\right]}.$$

FT reveals a superposition of absorptive and dispersive components at both actual and quadrature peak positions, with peak intensities proportional to $$\cos\left(\frac{\Phi_{+2} + \Phi_{-0}}{2}\right) \text{ and } \sin\left(\frac{\Phi_{+2} + \Phi_{-0}}{2}\right),$$

respectively. The phase shifts associated with the peaks differ by $\pi/2$ and are given by $$\frac{\Phi_{+2} - \Phi_{-0}}{2}$$

for the actual and by $$\frac{\pi}{2} - \frac{\Phi_{+2} - \Phi_{-0}}{2}$$

for the quad peak. The protocol for obtaining secondary phase shifts from experimentally measured peak volumes and phase shifts of the actual and the quad peaks involves two steps.

Step 1:

Phase correct both the actual and the quad peaks and thereby measure the associated phase shifts $$\frac{\Phi_{+2} - \Phi_0}{2}$$

from the required phase correction of the actual peak or from the phase correction value of the quad peak after subtracting $\pi/2$. For brevity, we define $$\Phi_{diff} = \frac{\Phi_{+2} - \Phi_0}{2}.$$

Step 2:

Perform integration on the phase corrected actual and quad peaks to obtain the volumes $V_{actual}$ and $V_{quad}$, which are proportional to $$V_{actual} \propto \cos\left(\frac{\Phi_{+2} - \Phi_0}{2}\right) \qquad (235)$$

$$V_{quad} \propto \sin\left(\frac{\Phi_{+2} - \Phi_0}{2}\right).$$

so that $$\frac{\Phi_{+2} - \Phi_0}{2} = \arctan g\left(\frac{V_{quad}}{V_{actual}}\right) = \Phi_{sum}. \qquad (236)$$

The secondary phase shifts are calculated using $\Phi_{sum}$ and $\Phi_{diff}$ according to $$\Phi_{-0} = \Phi_{sum} - \Phi_{diff}$$

$$\Phi_{+2} = \Phi_{sum} + \Phi_{diff} \qquad (237).$$

With Eq. 27 and Eq. 237, the figures of merit $M_{+0,-2}^D$, $M_{+0,-2}^Q$ and $M_{+0,-2}^I$ can be calculated.

Figures 8A, 8B:
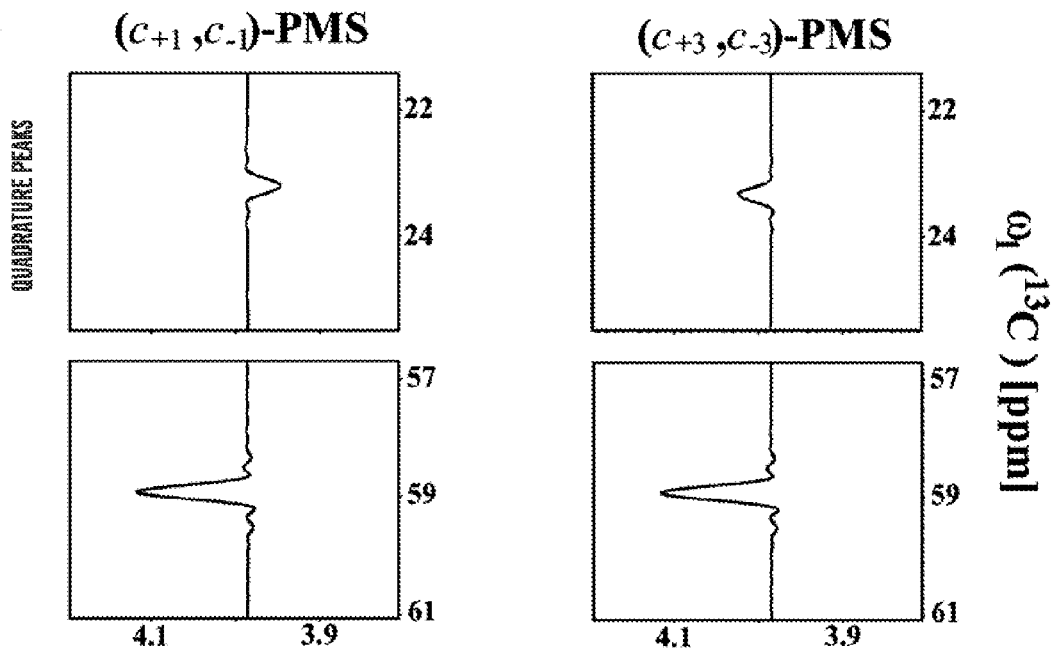
Figures 8C, 8D:
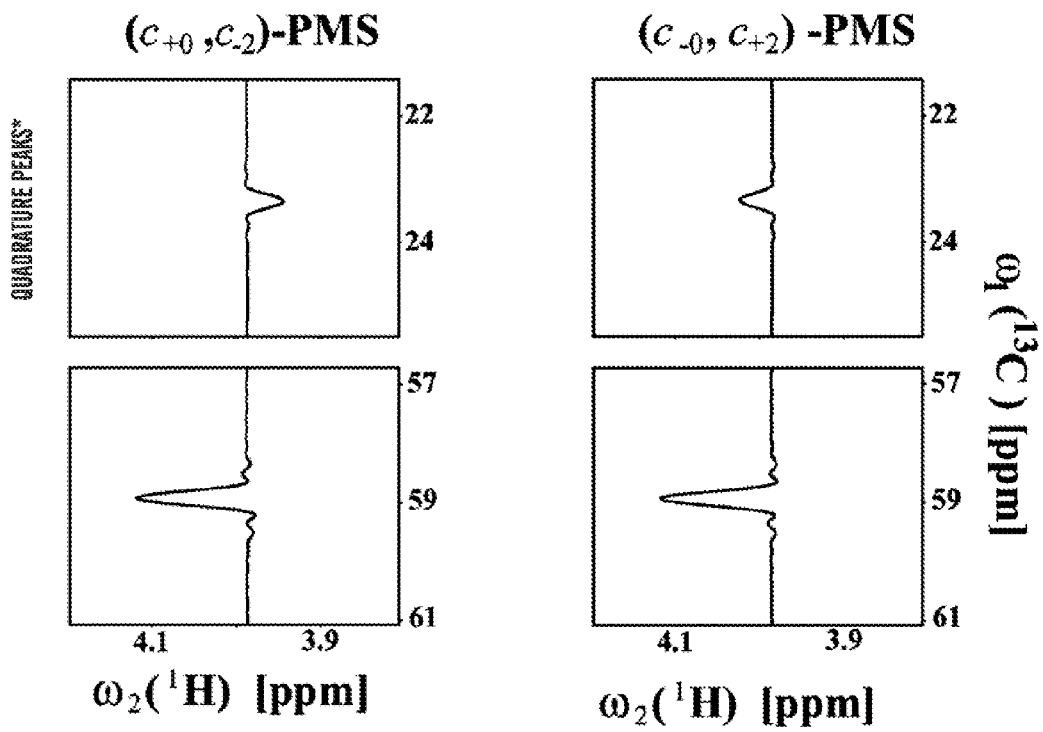

Results ($c_{+1}$,$c_{-1}$)-, ($c_{+3}$,$c_{-3}$)-, ($c_{+0}$,$c_{-2}$)- and ($c_{-0}$,$c_{+2}$)-PMS was employed to acquire aliphatic constant-time 2D [$^{13}$C,$^1$H]-HSQC spectra recorded for a 2 mM solution of $^{15}$N/$^{13}$C-labeled phenylalanine (FIGS. 8A-D). The required interferograms were acquired with different delays for delayed acquisition, so that different secondary phase shifts are obtained for the time domain signals in the interferograms. FIGS. 8A-D show cross sections taken along $\omega_1$($^{13}$C) at the $^1$H-$^{13}$C$^\alpha$ signal from spectra recorded with ($c_{+1}$,$c_{-1}$)-sampling (FIG. 8A), ($c_{+3}$,$c_{-3}$)-sampling (FIG. 8B), ($c_{+0}$,$c_{-2}$)-sampling (FIG. 8C) and ($c_{-0}$,$c_{+2}$)-sampling (FIG. 8D). The peaks exhibit mixed phase due to differences of secondary phase shifts (Table 10). The quad peaks for the ($c_{+0}$,$c_{-2}$)- and ($c_{-0}$,$c_{+2}$)-sampled spectra are shown after a $\pi/2$ zero-order phase correction was applied. The secondary phase shifts were measured using the protocols provided above. Table 10 provides a comparison of predicted and measured secondary phase shifts, revealing the expected agreement between theory and experiment.

TABLE 10

Comparison of predicted and measured secondary phase shifts[a]

| Sampling scheme | Secondary phase shifts | Secondary phase shifts due to delayed acquisition[b] | Measured secondary, phase shifts[c] |
|---|---|---|---|
| $(c_{+1}, c_{-1})$ – (PMS) | $\Phi_{+1}$ | 29.0° | 29.9° |
|  | $\Phi_{-1}$ | 20.9° | 20.7° |
| $(c_{+3}, c_{-3})$ – (PMS) | $\Phi_{+3}$ | 24.9° | 26.5° |
|  | $\Phi_{-3}$ | 16.9° | 16.7° |
| $(c_{+0}, c_{-2})$ – (PMS) | $\Phi_{+0}$ | 29.0° | 28.2° |
|  | $\Phi_{-2}$ | 16.9° | 18.2° |
| $(c_{-0}, c_{+2})$ – (PMS) | $\Phi_{-0}$ | 24.9° | 24.3° |
|  | $\Phi_{+2}$ | 20.9° | 20.8° |

[a]Sample: $^{15}$N, $^{13}$C-labeled phenylalanine (2 mM concentration at pH 6.5). All spectra were recorded at 25° C. on a Varian 500 MHz NMR spectrometer.
[b]Delays Δt for delayed acquisition were set for generating secondary phase shifts according to $\Phi = 2\pi^*(\Omega - \Omega_{carrier})^*\Delta t$, where $(\Omega - \Omega_{carrier})$ represents the offset relative to the carrier frequency in Hz.
[c]Eqs. 225, 229, 233, 237 were used to obtain the secondary phase shifts.

The measurement of the secondary phase shifts enables one to calculate the figures of merit for the different sampling schemes (Table 11) to quantitatively assess the different sampling schemes.

TABLE 11

Figures of merit[a] $M^D$, $M^Q$ and $M^I$ for the sampling schemes of Table 10 corresponding DMPS

| sampling schemes | $M^D$ | $M^Q$ | $M^I$ |
|---|---|---|---|
| $(c_{+1}, c_{-1})$ – (PMS) | 0.92 | 0.68 | 0.90 |
| $(c_{+3}, c_{-3})$ – (PMS) | 0.92 | 0.72 | 0.93 |
| $(c_{+1}, c_{-1}, c_{+3}, c_{-3})$ – (DPMS) | 0.92 | 0.94 | 0.91 |
| $(c_{+0}, c_{-2})$ – (PMS) | 0.92 | 0.70 | 0.92 |
| $(c_{-0}, c_{+2})$ – (PMS) | 0.97 | 0.70 | 0.92 |
| $(c_{+0}, c_{-2}, c_{-0}, c_{+2})$ – (PMS) | 0.94 | 0.97 | 0.92 |

[a]Obtained with Eqs. 16, 20, 27, 31.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of conducting an N-dimensional nuclear magnetic resonance (NMR) experiment in a phase-sensitive manner by use of forward and backward sampling of time domain shifted by a primary phase shift under conditions effective to measure time domain amplitudes and secondary phase shifts, said method comprising:

providing a sample;

applying radiofrequency pulses for an N-dimensional NMR experiment to said sample;

selecting m dimensions of said NMR experiment, wherein m≦N;

sampling a time domain modulation in a phase-sensitive manner in each selected dimension j∈[1,2, . . . , m] arising from time evolution of chemical shift $\alpha_j$ in both a forward and backward manner to obtain two interferograms for each time domain dimension $t_j$ defining the vector $$C_{j,\psi_j}(t_j) := \begin{bmatrix} I^+_{j,\psi_j} c^+_{\psi_j}(t_j) \\ I^-_{j,\psi_j,\delta_j} c^-_{\bar{\psi}_j,\delta_j}(t_j) \end{bmatrix} = \begin{bmatrix} I^+_{j,\psi_j} \cos(\psi_j + \alpha_j t_j + \Phi^+_{j,\psi_j}) \\ I^-_{j,\psi_j,\delta_j} \cos(\psi_j + \delta_j - \alpha_j t_j + \Phi^-_{j,\psi_j,\delta_j}) \end{bmatrix},$$

wherein $I^+_{j,\psi_j}$ and $I^-_{j,\psi_j,\delta_j}$ are amplitudes, $\Psi_j$ and $\Psi_j+\delta_j$ are primary phase shifts with $\Psi_j$, $\delta_j \in [0,2\pi[$ and the cases $\{\psi_j=n\pi/2$ and $\delta_j=m\pi\}$ with n=0, 1, 2, 3 and m=0, 1 being omitted, and $\Phi^+_{j,\psi_j}$ and $\Phi^-_{j,\psi_j,\delta_j}$ are secondary phase shifts;

multiplying each said vectors $C_{j,\psi_j}t_j)$ with a D-matrix defined as $$D_j = \begin{bmatrix} \sin(\psi_j + \delta_j) & \sin(\psi_j) \\ -\cos(\psi_j + \delta_j) & \cos(\psi_j) \end{bmatrix}$$

and a vector Q=[1 i], wherein i=$\sqrt{-1}$, according to $Q \cdot D_j \cdot C_{j,\psi_j}(t_j)$ under conditions effective to create a complex time domain of said selected m dimensions according to $$\bigotimes_j Q \cdot D_j \cdot C_{j,\psi_j}(t_j); \text{ and}$$

transforming said complex time domain into frequency domain by use of an operator O under conditions effective to measure the values of $I^+_{j,\psi_j}$, $I^-_{j,\psi_j,\delta_j}$, $\Phi^+_{j,\psi_j}$ and $\Phi^-_{j,\psi_j,\delta_j}$ in said frequency domain in order to generate NMR spectra comprising frequency domain signals.

2. The method according to claim 1, wherein said operator is a linear operator L.

3. The method according to claim 2, wherein said linear operator is the Fourier transformation operator F.

4. The method according to claim 2, wherein said vectors $C_{j,\psi_j}(t_j)$ are transformed into frequency domain using said linear operator L under conditions effective to yield frequency domain vector L $[C_{j,\psi_j}(t_j)]$, and said multiplying comprises:

multiplying L $[C_{j,\psi_j}(t_j)]$ with said matrix $D_j$ and said vector Q according to $Q \cdot D_j \cdot L[C_{j,\psi_j}(t_j)]$ under conditions effective to generate said frequency domain according to $$\bigotimes_j Q \cdot D_j \cdot L[C_{j,\psi_j}(t_j)].$$

5. The method according to claim 1, wherein for all j: $I^+_{j,\psi_j}=I^-_{j,\psi_j,\delta_j}$, and $\{\Psi_j=\pi/4$ and $\delta_j=0\}$ or $\{\Psi_j=3\pi/4$ and $\delta_j=0\}$.

6. The method according to claim 5, wherein $\Phi^+_{j,\psi_j}=\Phi^-_{j,\psi_j,\delta_j}=\Phi_{j,\psi_j,\delta_j}$, so that signals in said frequency domain are purely absorptive and devoid of dispersive components.

7. The method according to claim 1, wherein for all j: $I^+_{j,\psi_j}=I^-_{j,\psi_j,\delta_j}$, and $\{\Psi_j=0$ and $\delta_j=\pi/2\}$, or $\{\Psi_j=\pi/2$ and $\delta_j=3\pi/2\}$.

8. The method according to claim 7, wherein $\Phi^+_{j,\psi_j}=\Phi^-_{j,\psi_j,\delta_j}=\Phi_{j,\psi_j,\delta_j}$, so that signals in said frequency domain located at $(\alpha_1, \alpha_2, \ldots \alpha_m)$ are purely absorptive and devoid of dispersive components.

9. The method of claim 1, wherein m' dimensions of said selected m dimensions with m'≦m are jointly sampled according to $t=t_1/\kappa_1=t_2/\kappa_2=\ldots=t_{m'}/\kappa_{m'}$, wherein $\kappa_{m'}$ are scaling factors for time evolution in the jointly sampled dimensions, under conditions effective to conduct a G-matrix Fourier Transformation NMR experiment, wherein said multiplication with said vector Q is replaced for K=m'−1 of the m' jointly sampled dimensions by multiplication with matrix G defined as $$G = \begin{bmatrix} 1 & i \\ 1 & -i \end{bmatrix}.$$

10. The method according to claim 9, wherein for all j: $I_{j,\psi_j}^+ = I_{j,\psi_j,\delta_j}^-$, and $\{\Psi_j=\pi/4$ and $\delta_j=0\}$ or $\{\Psi_j=3\pi/4$ and $\delta_j=0\}$.

11. The method according to claim 10, wherein $\Phi_{j,\psi_j}^+ = \Phi_j$, $\Psi_{j,\delta_j}^- = \Phi_{j,\psi_j,\delta_j}$, so that signals in said frequency domain are purely absorptive and devoid of dispersive signal components.

12. The method according to claim 9, wherein for all j: $I_{j,\psi_j}^+ = I_{j,\psi_j,\delta_j}^-$, and $\{\Psi_j=0$ and $\delta_j=\pi/2\}$, or $\{\Psi_j=\pi/2$ and $\delta_j=3\pi/2\}$.

13. The method according to claim 12, wherein $\Phi_{j,\psi_j}^+ = \Phi_j$, $\Psi_{j,\delta_j}^- = \Phi_{j,\psi_j,\delta_j}$, so that signals in said frequency domain located at linear combinations of $(\alpha_1, \alpha_2, \ldots \alpha_m)$ for a given subspectrum of the G-matrix Fourier Transformation NMR experiment are purely absorptive and devoid of dispersive signal components.

14. The method according to claim 1, wherein said secondary phase shifts $\Phi_{j,\psi_j}^+$, and $\Phi_{j,\psi_j,\delta_j}^-$ encode NMR parameters other than said chemical shifts $\alpha_j$.

15. The method according to claim 1, wherein said sampling a time domain modulation is combined with preservation of equivalent pathways for sensitivity enhancement.

16. The method according to claim 1, wherein said NMR experiment is a TROSY NMR experiment.

17. The method according to claim 1, wherein said sampling a time domain modulation is accomplished by use of simultaneous phase cycled NMR.

18. The method according to claim 1, wherein said interferograms are obtained by recording P- and N-type time domain by use of pulsed magnetic field gradients followed by linear combination effective to generate said interferograms.

19. A method of optimizing an N-dimensional nuclear magnetic resonance (NMR) experiment comprising:

measuring values of secondary phase shifts $\Phi_{j,\psi_j}^+$ and $\Phi_{j,\psi_j,\delta_j}^-$ in a first N-dimensional NMR experiment according to the method of claim 1;

identifying an origin of the secondary phase shifts $\Phi_{j,\psi_j}^+$ and $\Phi_{j,\psi_j,\delta_j}^-$ in the first N-dimensional NMR experiment; and modifying a radio frequency pulse scheme of a second N-dimensional NMR experiment under conditions effective to at least partially eliminate the origin of the secondary phase shifts $\Phi_{j,\psi_j}^+$ and $\Phi_{j,\psi_j,\delta_j}^-$ and at least partially eliminate said secondary phase shifts $\Phi_{j,\psi_j}^+$ and $\Phi_{j,\psi_j,\delta_j}^-$.

20. A method of conducting an N-dimensional nuclear magnetic resonance (NMR) experiment in a phase-sensitive manner by use of dual forward and backward sampling of time domain shifted by a primary phase shift under conditions effective to measure secondary phase shifts or at least partially cancel dispersive and quadrature image signal components arising in a frequency domain from secondary phase shifts, said method comprising:

providing a sample;

applying radiofrequency pulses for an N-dimensional NMR experiment to said sample;

selecting m dimensions of said NMR experiment, wherein m≦N;

sampling a time domain modulation in a phase-sensitive manner in each said selected dimension $j \in [1,2,\ldots,m]$ arising from time evolution of chemical shift $\alpha_j$ in both a forward and backward manner to obtain two interferograms for each time domain dimension $t_j$ defining the vector $$C_{j,\psi_j}(t_j) := \begin{bmatrix} I_{j,\psi_j}^+ c_{\psi_j}^+(t_j) \\ I_{j,\psi_j,\delta_j}^- c_{\psi_j,\delta_j}^-(t_j) \end{bmatrix} = \begin{bmatrix} I_{j,\psi_j}^+ \cos(\psi_j + \alpha_j t_j + \Phi_{j,\psi_j}^+) \\ I_{j,\psi_j,\delta_j}^- \cos(\psi_j + \delta_j - \alpha_j t_j + \Phi_{j,\psi_j,\delta_j}^-) \end{bmatrix},$$

wherein $I_{j,\psi_j}^+$ and $I_{j,\psi_j,\delta_j}^-$ are amplitudes, $\Psi_j$ and $\Psi_j+\delta_j$ are primary phase shifts with $\Psi_j$, $\delta_j \in [0,2\pi[$ and the cases $\{\psi_j=n\pi/2$ and $\delta_j=m\pi\}$ with n=0, 1, 2, 3 and m=0, 1 being omitted, and $\Phi_{j,\psi_j}^+$ and $\Phi_{j,\psi_j,\delta_j}^-$ are secondary phase shifts;

multiplying each said vectors $C_{j,\psi_j}(t_j)$ with a D-matrix defined as $$D_j = \begin{bmatrix} \sin(\psi_j + \delta_j) & \sin(\psi_j) \\ -\cos(\psi_j + \delta_j) & \cos(\psi_j) \end{bmatrix}$$

and a vector Q=[1 i], wherein $i=\sqrt{-1}$, according to $Q \cdot D_j \cdot C_{j,\psi_j}(t_j)$ under conditions effective to create a complex time domain of said selected m dimensions according to $$\bigotimes_j Q \cdot D_j \cdot C_{j,\psi_j}(t_j);$$

repeating said selecting, said sampling and said multiplying $(2^m-1)$-times, thereby sampling the m dimensions with all $2^m$ possible permutations resulting from selecting for each dimension j either $\Psi_j$ or $\Psi_j+\pi/2$, with $\delta_j$ being incremented by either 0 or $\pi$, thereby yielding $2^m$ complex time domains;

linearly combining said $2^m$ complex time domains: and transforming said linearly combined complex time domain into frequency domain by use of an operator O, under conditions effective to measure secondary phase shifts or at least partially cancel dispersive and quadrature image peak components arising from $\Phi_{j,\psi_j}^+$ and $\Phi_{j,\psi_j,\delta_j}^-$ in said frequency domain in order to generate NMR spectra comprising frequency domain signals.

21. The method according to claim 20, wherein said transforming comprises measuring the values of $I_{j,\psi_j}^+$, $I_{j,\psi_j,\delta_j}^-$, $\Phi_{j,\psi_j}^+$ and $\Phi_{j,\psi_j,\delta_j}^-$ in said frequency domain.

22. The method according to claim 20, wherein said operator is a linear operator L.

23. The method according to claim 22, wherein said linear operator is the Fourier transformation operator F.

24. The method according to claim 22, wherein said vectors $C_{j,\psi_j}(t_j)$ are transformed into frequency domain using said linear operator L under conditions effective to yield frequency domain vector $L[C_{j,\psi_j}(t_j)]$, and said multiplying comprises:

multiplying $L[C_{j,\psi_j}(t_j)]$ with said matrix $D_j$ and said vector Q according to $Q \cdot D_j \cdot L[C_{j,\psi_j}(t_j)]$ under conditions effective to generate said frequency domain according to $$\bigotimes_j Q \cdot D_j \cdot L[C_{j,\psi_j}(t_j)].$$

25. The method according to claim 20, wherein for all j: $I_{j,\psi_j}{}^+ = I_{j,\psi_j,\delta_j}{}^-$, and $\{\Psi_j=\pi/4 \text{ and } \delta_j=0\}$ or $\{\Psi_j=3\pi/4 \text{ and } \delta_j=0\}$.

26. The method according to claim 25, wherein $\Phi_{j,\psi_j}{}^+ = \Phi_j$, $\Psi_{j,\delta_j}{}^- = \Phi_{j,\psi_j,\delta_j}$, so that signals in said frequency domain are purely absorptive and devoid of dispersive components.

27. The method according to claim 25, wherein $\Phi_{j,\psi_j}{}^+ = \Phi_j$, $\Psi_{j,\delta_j}{}^- = \Phi_j$, so that signals in said frequency domain are purely absorptive and devoid of dispersive components, and quadrature image peaks in said frequency domain are cancelled.

28. The method according to claim 20, wherein for all j: $I_{j,\psi_j}{}^+ = I_{j,\psi_j,\delta_j}{}^-$, and $\{\Psi_j=0 \text{ and } \delta_j=\pi/2\}$, or $\{\Psi_j=\pi/2 \text{ and } \delta_j=3\pi/2\}$.

29. The method according to claim 28, wherein $\Phi_{j,\psi_j}{}^+ = \Phi_j$, $\Psi_{j,\delta_j}{}^- = \Phi_{j,\psi_j,\delta_j}$, so that signals in said frequency domain located at $(\alpha_1, \alpha_2, \ldots \alpha_m)$ are purely absorptive and devoid of dispersive components.

30. The method according to claim 28, wherein $\Phi_{j,\psi_j}{}^+ = \Phi_j$, $\Psi_{j,\delta_j}{}^- = \Phi_j$, so that signals in said frequency domain located at $(\alpha_1, \alpha_2, \ldots, \alpha_m)$ are purely absorptive and devoid of dispersive components, and quadrature image peaks in said frequency domain are cancelled.

31. The method according to claim 20, wherein m' dimensions of said selected m dimensions with m'≦m are jointly sampled according to $t=t_1/\kappa_1=t_2/\kappa_2=\ldots=t_{m'}/\kappa_{m'}$, wherein $\kappa_{m'}$ are scaling factors for the time evolution in the jointly sampled dimensions under conditions effective to conduct a G-matrix Fourier Transformation NMR experiment, wherein said multiplication with said vector Q is replaced for K=m'−1 of the m' jointly sampled dimensions by multiplication with matrix G defined as $$G = \begin{bmatrix} 1 & i \\ 1 & -i \end{bmatrix}.$$

32. The method according to claim 31, wherein for all j: $I_{j,\psi_j}{}^+ = I_{j,\psi_j,\delta_j}{}^-$, and $\{\Psi_j=\pi/4 \text{ and } \delta_j=0\}$ or $\{\Psi_j=3\pi/4 \text{ and } \delta_j=0\}$.

33. The method according to claim 32, wherein $\Phi_{j,\psi_j}{}^+ = \Phi_j$, $\Psi_{j,\delta_j}{}^- = \Phi_{j,\psi_j,\delta_j}$, so that signals in said frequency domain are purely absorptive and devoid of dispersive signal components.

34. The method according to claim 32, wherein $\Phi_{j,\psi_j}{}^+ = \Phi_j$, $\Psi_{j,\delta_j}{}^- = \Phi_j$, so that signals in said frequency domain are purely absorptive and devoid of dispersive signal components, and quadrature image and cross talk peaks in said frequency domain are cancelled.

35. The method according to claim 31, wherein for all j: $I_{j,\psi_j}{}^+ = I_{j,\psi_j,\delta_j}{}^-$, and $\{\Psi_j=0 \text{ and } \delta_j=\pi/2\}$, or $\{\Psi_j=\pi/2 \text{ and } \delta_j=3\pi/2\}$.

36. The method according to claim 35, wherein $\Phi_{j,\psi_j}{}^+ = \Phi_j$, $\Psi_{j,\delta_j}{}^- = \Phi_{j,\psi_j,\delta_j}$, so that signals in said frequency domain located at linear combinations of $(\alpha_1, \alpha_2, \ldots \alpha_m)$ for a given subspectrum of the GFT NMR experiment are purely absorptive and devoid of dispersive signal components.

37. The method according to claim 35, wherein $\Phi_{j,\psi_j}{}^+ = \Phi_j$, $\Psi_{j,\delta_j}{}^- = \Phi_j$, so that signals in said frequency domain located at linear combinations of $(\alpha_1, \alpha_2, \ldots \alpha_m)$ for a given subspectrum of the GFT NMR experiment are purely absorptive and devoid of dispersive signal components, and quadrature image and cross talk peaks in said frequency domain are cancelled.

38. The method according to claim 20, wherein said permutation of said secondary phase shifts is concatenated with execution of a radio-frequency phase cycle.

39. The method according to claim 38, wherein said NMR experiment is conducted under conditions of magic angle spinning of said sample.

40. The method according to claim 38, wherein said phase cycle is executed to suppress signals arising from axial magnetization.

41. The method according to claim 38, wherein said phase cycle is executed to reduce signal arising from solvent.

42. The method according to claim 20, wherein said sampling a time domain modulation is combined with preservation of equivalent pathways for sensitivity enhancement.

43. The method according to claim 20, wherein said NMR experiment is a TROSY NMR experiment.

44. The method according to claim 20, wherein said sampling a time domain modulation is accomplished by use of simultaneous phase cycled NMR.

45. The method according to claim 20, wherein said interferograms are obtained by recording P- and N-type time domain by use of pulsed magnetic field gradients followed by linear combination effective to generate said interferograms.

46. A method of conducting an N-dimensional nuclear magnetic resonance (NMR) experiment in a phase-sensitive manner by use of dual forward and backward sampling of time domain shifted by a primary phase shift under conditions effective to measure secondary phase shifts or at least partially cancel dispersive and quadrature image signal components arising in a frequency domain from secondary phase shifts, said method comprising:

providing a sample;

applying radiofrequency pulses for an N-dimensional NMR experiment to said sample;

selecting m dimensions of said NMR experiment, wherein m≦N;

sampling twice a time domain modulation in a phase-sensitive manner in each said selected dimension j∈[1,2, . . . , m] arising from time evolution of chemical shift $\alpha_j$, once in a forward manner to obtain two interferograms for each time domain dimension $t_j$ defining the vector $$C^+_{j,\psi_j}(t_j) = \begin{bmatrix} I^+_{j,\psi_j} c^+_{\psi_j}(t_j) \\ I^+_{j,\psi_j,\delta_j} c^+_{\psi_j,\delta_j}(t_j) \end{bmatrix} = \begin{bmatrix} I^+_{j,\psi_j} \cos(\psi_j + \alpha_j t_j + \Phi^+_{j,\psi_j}) \\ I^+_{j,\psi_j,\delta_j} \cos(\psi_j + \delta_j + \alpha_j t_j + \Phi^+_{j,\psi_j,\delta_j}) \end{bmatrix},$$

and once in a backward manner to obtain two interferograms for each time domain dimension $t_j$ defining the vector $$C^-_{j,\psi_j}(t_j) := \begin{bmatrix} I^-_{j,\psi_j} c^-_{\psi_j}(t_j) \\ I^-_{j,\psi_j,\delta_j} c^-_{\psi_j,\delta_j}(t_j) \end{bmatrix} = \begin{bmatrix} I^-_{j,\psi_j} \cos(\psi_j - \alpha_j t_j + \Phi^-_{j,\psi_j}) \\ I^-_{j,\psi_j,\delta_j} \cos(\psi_j + \delta_j - \alpha_j t_j + \Phi^-_{j,\psi_j,\delta_j}) \end{bmatrix},$$

wherein $I_{j,\psi_j}{}^+$, $I_{j,\psi_j,\delta_j}{}^+$, $I_{j,\psi_j}{}^-$ and $I_{j,\psi_j,\delta_j}{}^-$ are amplitudes, $\Psi_j$ and $\Psi_j+\delta_j$ are primary phase shifts with $\Psi_j$, $\delta_j \in [0,2\pi[$, and $\Phi_{j,\psi_j}{}^+$, $\Phi_{j,\psi_j,\delta_j}{}^+$, $\Phi_{j,\psi_j}{}^-$ and $\Phi_{j,\psi_j,\delta_j}{}^-$ are secondary phase shifts;

multiplying each said vector $C_{j,\psi_j}^+(t_j)$ with a D-matrix defined as $$D_j^+ = \begin{bmatrix} \sin(\psi_j + \delta_j) & -\sin(\psi_j) \\ \cos(\psi_j + \delta_j) & -\cos(\psi_j) \end{bmatrix}$$

and each said vector $C_{j,\psi_j}^-(t_j)$ with a D-matrix defined as $$D_j^- = \begin{bmatrix} \sin(\psi_j + \delta_j) & -\sin(\psi_j) \\ -\cos(\psi_j + \delta_j) & \cos(\psi_j) \end{bmatrix};$$

multiplying the said products $D_j^+ \cdot C_{j,\psi_j}^+(t_j)$ and $D_j^- \cdot C_{j,\psi_j}^-(t_j)$ with a vector $Q=[1\ i]$, wherein $i=\sqrt{-1}$, according to $Q \cdot D_j^+ \cdot C_{j,\psi_j}^+(t_j)$ and $Q \cdot D_j^- \cdot C_{j,\psi_j}^-(t_j)$ under conditions effective to create a complex time domain of said selected m dimensions according to $$\bigotimes_j Q \cdot D_j^+ \cdot C_{j,\psi_j}^+(t_j) \text{ and } \bigotimes_j Q \cdot D_j^- \cdot C_{j,\psi_j}^-(t_j);$$

repeating said selecting, said phase-sensitive sampling twice and said multiplying $(2^m-2)$-times, thereby sampling said m dimensions with all $2^m$ possible permutations resulting from selecting for each dimension j either phase-sensitive forward or backward sampling according to $C_{j,\psi_j}^+(t_j)$ or $C_{j,\psi_j}^-(t_j)$;

linearly combining said $2^m$ complex time domains; and
transforming said linearly combined complex time domain into frequency domain by use of an operator O, under conditions effective to measure secondary phase shift or at least partially cancel dispersive and quadrature image peak components arising from $\Phi_{j,\psi_j}^+$, $\Phi_{j,\psi_j,\delta_j}^+$, $\Phi_{j,\psi_j}^-$ and $\Phi_{j,\psi_j,\delta_j}^-$ in said frequency domain in order to generate NMR spectra comprising frequency domain signals.

47. The method according to claim 46, wherein said sampling in a phase sensitive manner comprises excluding $\{\psi_j = n\pi/2 \text{ and } \delta_j = m\pi\}$ with n=0, 1, 2, 3 and m=0, 1.

48. The method according to claim 46, wherein said sampling in a phase sensitive manner for $\{\psi_j = n\pi/2 \text{ and } \delta_j = m\pi\}$ with n=0, 1, 2, 3 and m=0, 1 comprises applying time-proportional phase incrementation of radio-frequency pulse or receiver phases.

49. The method according to claim 46, wherein said transforming comprises measuring the values of $I_{j,\psi_j}^+$, $I_{j,\psi_j,\delta_j}^-$, $\Phi_{j,\psi_j}^+$ and $\Phi_{j,\psi_j,\delta_j}^-$ in said frequency domain.

50. The method according to claim 46, wherein said operator is a linear operator L.

51. The method according to claim 50, wherein said linear operator is the Fourier transformation operator F.

52. The method according to claim 50, wherein said vectors $C_{j,\psi_j}^+(t_j)$ and $C_{j,\psi_j}^-(t_j)$ are transformed into frequency domain using said linear operator L under conditions effective to yield frequency domain vectors $L[C_{j,\psi_j}^+(t_j)]$ and $L[C_{j,\psi_j}^-(t_j)]$, and said multiplying comprises:

multiplying said vector $L[C_{j,\psi_j}^+(t_j)]$ with said matrix $D_j^+$ and said vector $L[C_{j,\psi_j}^-(t_j)]$ with said matrix $D_j^-$; and
multiplying said products $D_j^+ \cdot L[C_{j,\psi_j}^+(t_j)]$ and $D_j^- \cdot L[C_{j,\psi_j}^-(t_j)]$ with said vector Q according to $Q \cdot D_j^+ \cdot L[C_{j,\psi_j}^+(t_j)]$ and $Q \cdot D_j^- \cdot L[C_{j,\psi_j}^-(t_j)]$ under conditions effective to generate said frequency domain according to $$\bigotimes_j Q \cdot D_j^+ \cdot L[C_{j,\psi_j}^+(t_j)] \text{ and } \bigotimes_j Q \cdot D_j^- \cdot L[C_{j,\psi_j}^-(t_j)].$$

53. The method according to claim 46, wherein for all j: $I_{j,\psi_j}^+ = I_{j,\psi_j,\delta_j}^+ = I_{j,\psi_j}^- = I_{j,\psi_j,\delta_j}^-$, and $\{\psi_j = 0 \text{ and } \delta_j = \pi/2\}$.

54. The method according to claim 53, wherein $\Phi_{j,\psi_j}^+ = \Phi_j$, $\psi_j^- = \Phi_{j,\psi_j}$ and $\Phi_{j,\psi_j,\delta_j}^+ = \Phi_{j,\psi_j,\delta_j}^- = \Phi_{j,\psi_j,\delta_j}$, so that signals in said frequency domain are purely absorptive and devoid of dispersive components.

55. The method according to claim 53, wherein $\Phi_{j,\psi_j}^+ = \Phi_j$, $\psi_j^- = \Phi_{j,\psi_j,\delta_j}^+ = \Phi_{j,\psi_j,\delta_j}^- = \Phi_j$, so that signals in said frequency domain are purely absorptive and devoid of dispersive components, and quadrature image peaks in said frequency domain are entirely cancelled.

56. The method according to claim 46, wherein m' dimensions of said selected m dimensions with $m' \leq m$ are jointly sampled according to $t=t_1/\kappa_1=t_2/\kappa_2=\ldots=t_{m'}/\kappa_{m'}$, wherein $\kappa_{m'}$ are the scaling factors for the time evolution in the jointly sampled dimensions, effective to conduct a G-matrix Fourier Transformation NMR experiment, wherein said multiplication with said vector Q is replaced for $K=m'-1$ of the m' jointly sampled dimensions by multiplication with matrix G defined as $$G = \begin{bmatrix} 1 & i \\ 1 & -i \end{bmatrix}.$$

57. The method according to claim 56, wherein for all j: $I_{j,\psi_j}^+ = I_{j,\psi_j,\delta_j}^+ = I_{j,\psi_j}^- = I_{j,\psi_j,\delta_j}^-$, and $\{\psi_j = 0 \text{ and } \delta_j = \pi/2\}$.

58. The method according to claim 57, wherein $\Phi_{j,\psi_j}^+ = \Phi_j$, $\psi_j^- = \Phi_{j,\psi_j}$ and $\Phi_{j,\psi_j,\delta_j}^+ = \Phi_{j,\psi_j,\delta_j}^- = \Phi_{j,\psi_j,\delta_j}$, so that signals in said frequency domain are purely absorptive and devoid of dispersive signal components.

59. The method according to claim 57, wherein $\Phi_{j,\psi_j}^+ = \Phi_j$, $\psi_j^- = \Phi_{j,\psi_j,\delta_j}^+ = \Phi_{j,\psi_j,\delta_j}^- = \Phi_j$, so that signals in said frequency domain are purely absorptive and devoid of dispersive signal components, and quadrature image and cross talk peaks in said frequency domain are entirely cancelled.

60. The method according to claim 46, wherein said permutation of said secondary phase shifts is concatenated with execution of a radio-frequency phase cycle.

61. The method according to claim 60, wherein said NMR experiment is conducted under conditions of magic angle spinning of said sample.

62. The method according to claim 60, wherein said phase cycle is executed to suppress signals arising from axial magnetization.

63. The method according to claim 60, wherein said phase cycle is executed to reduce signal arising from solvent.

64. The method according to claim 46, wherein said sampling a time domain modulation is combined with preservation of equivalent pathways for sensitivity enhancement.

65. The method according to claim 46, wherein said NMR experiment is a TROSY NMR experiment.

66. The method according to claim 46, wherein said sampling a time domain modulation is accomplished by use of simultaneous phase cycled NMR.

67. The method according to claim 46, wherein said interferograms are obtained by recording P- and N-type time domain by use of pulsed magnetic field gradients followed by linear combination effective to generate said interferograms.

* * * * *